United States Patent [19]

Kanojia et al.

[11] 4,176,188

[45] Nov. 27, 1979

[54] UTERO-EVACUANTS

[75] Inventors: Ramesh M. Kanojia, Somerville; Michael P. Wachter, Bloomsbury; Robert H. K. Chen, Belle Mead, all of N.J.

[73] Assignee: Ortho Pharmaceutical Corp., Raritan, N.J.

[21] Appl. No.: 903,456

[22] Filed: May 8, 1978

Related U.S. Application Data

[62] Division of Ser. No. 742,940, Nov. 18, 1976, Pat. No. 4,102,895.

[51] Int. Cl.$^2$ .............................................. A61K 31/335
[52] U.S. Cl. ................................... 424/270; 424/275; 424/276
[58] Field of Search ........... 260/333, 306.7 R, 327 M; 424/278, 270

[56] References Cited

U.S. PATENT DOCUMENTS

| 3,573,283 | 3/1971 | Merijan et al. .................. 260/293.89 |
| 4,086,358 | 4/1978 | Wachter et al. ...................... 424/278 |
| 4,112,079 | 9/1978 | Chen ................................. 424/278 X |

OTHER PUBLICATIONS

Chem. Abstracts 67:63102p.
Chem. Abstracts 69:67917x.
Chem. Abstracts 72:132091b.

*Primary Examiner*—Ethel G. Love
*Attorney, Agent, or Firm*—Benjamin F. Lambert

[57] ABSTRACT

Chemical compounds having a substituted oxepane ring and methods of preparing such compounds are described. The compounds are active as utero-evacuant agents.

19 Claims, No Drawings

UTERO-EVACUANTS

This is a division of application Ser. No. 742,940, filed Nov. 18, 1976, now U.S. Pat. No. 4,102,895.

The present invention relates to pharmacologically-active compounds and to processes for preparing them. The compounds which are the subject of this invention are represented by the formulae:

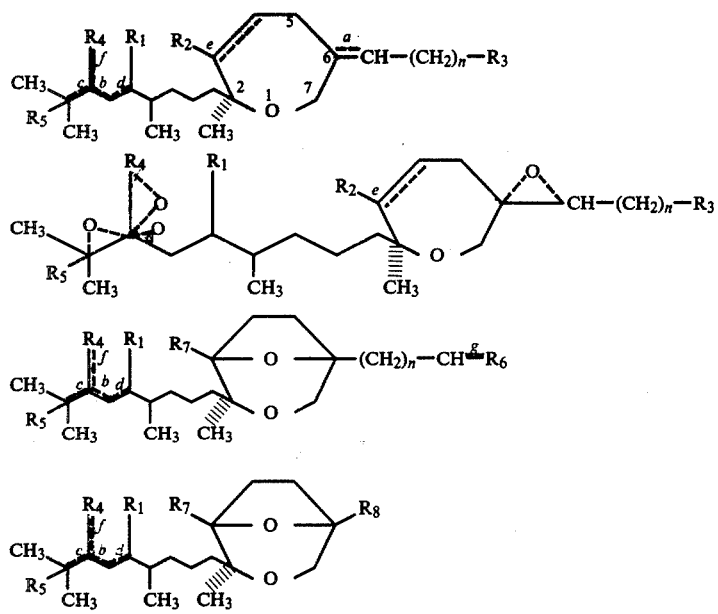

I

II

III and
IV wherein $R_1$ and $R_2$ are each —XY wherein X is hydrogen or hydroxy provided that when X is hydrogen Y is hydrogen; methyl; hydroxy; lower alkoxy wherein the alkoxy group is straight or branched chain and contains 1–8 carbon atoms; cycloalkoxy wherein the cycloalkyl group contains 3–6 carbon atoms; phenoxy; substituted phenoxy wherein the substituent is nitro, halo or lower alkyl having 1–5 carbon atoms; trialkylsilyloxy wherein the alkyl group contains 1–5 carbon atoms; heterocycloalkyloxy wherein the hetero atom is nitrogen, oxygen or sulfur and the cycloalkyl group contains 4–5 carbon atoms; —OCOR' wherein R' is straight or branched chain lower alkyl containing 1–8 carbon atoms, cycloalkyl containing 3–6 carbon atoms, phenyl, substituted phenyl wherein the substituent is nitro, halo, lower alkyl wherein the alkyl group contains 1–5 carbon atoms, hydroxy, lower alkoxy wherein the alkoxy group contains 1–5 carbon atoms, aryl such as phenyl and substituted phenyl wherein the substituent is nitro, halo or lower alkyl having 1–5 carbon atoms, and aryloxy such as phenoxy and substituted phenoxy wherein the substituent is nitro, halo or lower alkyl having 1–5 carbon atoms, provided that no more than three substituents are present on the phenyl ring at any one time; a sulfate, nitrate or phosphate radical; thiol; alkylthio wherein the alkyl group contains 1–8 carbon atoms; arylthio such as phenylthio or substituted phenylthio wherein the substituent on the phenyl group is as defined above; halo; amino; alkylamino wherein the alkyl group contains 1–8 carbon atoms; dialkylamino wherein the alkyl group contains 1–8 carbon atoms; arylamino such as phenylamino or substituted phenylamino wherein the substituent is as defined above; —NH—CO—Q wherein Q is hydrogen, lower alkyl containing 1–8 carbon atoms, phenyl or substituted phenyl wherein the substituent is nitro, halo or lower alkyl having 1–5 carbon atoms; —OCONHR wherein R is hydrogen or an alkyl group containing 1–8 carbon atoms; and when X is hydroxy, Y is cyano; straight or branched chain lower alkyl, lower alkenyl or lower alkynyl wherein the alkyl group contains 1–8 carbon atoms and the alkenyl and alkynyl groups contain 2–8 carbon atoms; propadienyl; benzyl; substituted benzyl wherein the substituent is nitro, halo or lower alkyl having 1–5 carbon atoms; phenyl; substituted phenyl wherein the substituent on the phenyl group is as defined above; provided that when d or e is unsaturated, $R_1$ and $R_2$ are either X or Y; also within the scope of the invention are the quaternary ammonium salts and the pharmaceutically acceptable acid addition salts thereof such as the hydrochlorides or hydrobromides, for example.

$R_1$ and/or $R_2$ are oxo; thioxo; hydroxyimino; alkoxyimino wherein the alkoxy group containing 1–8 carbon atoms; aryloxyimino such as phenyloxyimino or substituted phenyloxyimino wherein the substituent on the phenyl group is as defined above; acyloxyimino wherein the acyl group is derived from a lower alkanoic acid having 1–8 carbon atoms or an aromatic acid such as benzoic acid or substituted benzoic acid wherein the substituent is nitro, halo or a lower alkyl group having 1–5 carbon atoms, for example; hydrazono; alkylhydrazono, or dialkylhydrazono wherein the alkyl group contains 1–8 carbon atoms; arylhydrazono such as phenylhydrazono or substituted phenylhydrazono wherein the substituent on the phenyl group is as defined above; arylsulfonylhydrazono such as phenylsulfonylhydrazono or substituted phenylsulfonylhydrazono wherein the substituent on the phenyl group is as defined above, carbamoylhydrazono; ethylenedioxy; ethylenedithio; ethylenethiooxy; dialkoxy such as dimethoxy, diethoxy, dibutoxy and the like; thiazolidinyl; methylenyl; alkylidenyl wherein the alkyl group contains 2-8 carbon atoms; alkylimino wherein the alkyl group contains 1-8 carbon atoms; or arylimino such as phenylimino and substituted phenylimino wherein the substituent on the phenyl group is as defined above;

$R_3$ is —CHXY wherein X is hydrogen or hydroxy provided that when X is hydrogen Y is hydrogen; methyl; hydroxy; lower alkoxy wherein the alkoxy group is straight or branched chain and contains 1-8 carbon atoms; cycloalkoxy wherein the cycloalkyl group contains 3-6 carbon atoms; phenoxy, substituted phenoxy wherein the substituent is nitro, halo or lower alkyl having 1-5 carbon atoms; trialkylsilyloxy wherein the alkyl group contains 1-5 carbon atoms; heterocycloalkyloxy wherein the hetero atom is nitrogen, oxygen or sulfur and the cycloalkyl group contains 4-5 carbon atoms; —OCOR' wherein R' is straight or branched chain lower alkyl containing 1-8 carbon atoms, cycloalkyl containing 3-6 carbon atoms, phenyl or substituted phenyl wherein the substituent on the phenyl group is as defined above; a sulfate, nitrate or phosphate radical; thiol; alkylthio wherein the alkyl group contains 1-8 carbon atoms; arylthio such as phenylthio or substituted phenylthio wherein the substituent on the phenyl group is as defined above; halo; amino; alkylamino wherein the alkyl group contains 1-8 carbon atoms; dialkylamino wherein the alkyl group contains 1-8 carbon atoms; arylamino such as phenylamino or substituted phenylamino wherein the substituent on the phenyl group is as defined above; —NH—CO—Z wherein Q is hydrogen, lower alkyl containing 1-8 carbon atoms, phenyl or substituted phenyl wherein the substituent is nitro, halo or lower alkyl having 1-5 carbon atoms; —OCONHR wherein R is hydrogen or an alkyl group containing 1-8 carbon atoms; and the quaternary ammonium salts and the pharmaceutically acceptable acid addition salts thereof; and when X is hydroxy, Y is cyano; straight or branched chain lower alkyl, lower alkenyl or lower alkynyl wherein the alkyl group contains 1-8 carbon atoms and the alkenyl and alkynyl groups contain 2-8 carbon atoms; propadienyl; benzyl; phenyl; substituted phenyl wherein the substituent on the phenyl group is as defined above; and $R_3$ is —CHZ wherein Z is oxo; thioxo; hydroxyimino; alkoxyimino wherein the alkoxy group contains 1-8 carbon atoms; aryloxyimino such as phenyloxyimino or substituted phenyloxyimino wherein the substituent on the phenyl group is as defined above; acyloxyimino wherein the acyl group is derived from a lower alkanoic acid or an aromatic acid; hydrazono; alkylhydrazono or dialkylhydrazono wherein the alkyl group contains 1-8 carbon atoms; arylhydrazono such as phenylhydrazono or substituted phenylhydrazono wherein the substituent on the phenyl group is as defined above; arylsulfonylhydrazono such as phenylsulfonylhydrazono or substituted phenylsulfonylhydrazono wherein the substituent on the phenyl group is as defined above; carbamoylhydrazono; ethylenedioxy; ethylenedithio; ethylenethiooxy; dialkoxy such as dimethoxy, diethoxy, dibutoxy and the like; thiazolidinyl; methylenyl; alkylidenyl wherein the alkyl group contains 2-8 carbon atoms; alkylimino wherein the alkyl group contains 1-8 carbon atoms; or arylimino such as phenylimino and substituted phenylimino wherein the substituent on the phenyl group is as defined above; and $R_3$ is carboxy; —COOR' wherein R' is as defined above; —COR" wherein R" is amino, alkylamino, or dialkylamino wherein the alkyl group contains 1-8 carbon atoms or arylamino such as benzamino or substituted benzamino wherein the substituent on the phenyl group is as defined above, halo, hydrazino, alkylhydrazino or dialkylhydrazino wherein the alkyl group contains 1-8 carbon atoms, arylhydrazino such as phenylhydrazino or substituted phenylhydrazino wherein the substituent on the phenyl group is as defined above, arylsulfonylhydrazino such as phenylsulfonylhydrazino for example, or substituted phenylsulfonylhydrazino wherein the substituent is as defined above; cyano; and ammonium, alkali metal and alkaline earth metal salts thereof where $R_3$ is carboxy;

$R_4$ is hydrogen, methyl or methylenyl;

$R_5$ is hydrogen, hydroxy, hydroperoxy or —OCOR''' wherein R''' is lower alkyl containing 1-8 carbon atoms;

$R_6$ is methylenyl when g is unsaturated, and when g is saturated $R_6$ is —CHXY wherein X is hydrogen or hydroxy, provided that when X is hydrogen Y is hydrogen; methyl; hydroxy; lower alkoxy wherein the alkoxy group is straight or branched chain and contains 1-8 carbon atoms; cycloalkoxy wherein the cycloalkyl group contains 3-6 carbon atoms; phenoxy, substituted phenoxy wherein the substituent is nitro, halo or lower alkyl having 1-5 carbon atoms; trialkylsilyloxy wherein the alkyl group contains 1-5 carbon atoms; heterocycloalkyloxy wherein the hetero atom is nitrogen, oxygen or sulfur and the cycloalkyl group contains 4-5 carbon atoms; —OCOR' wherein R' is straight or branched chain lower alkyl containing 1-8 carbon atoms, cycloalkyl containing 3-6 carbon atoms, phenyl, substituted phenyl wherein the substituent on the phenyl group is as defined above for $R_1$ and $R_2$ equals —XY; a sulfate, nitrate or phosphate radical; thiol; alkylthio wherein the alkyl group contains 1-8 carbon atoms; arylthio such as phenylthio or substituted phenylthio wherein the substituent on the phenyl group is as defined above; halo; amino; alkylamino wherein the alkyl group contains 1-8 carbon atoms; dialkylamino wherein the alkyl group contains 1-8 carbon atoms; arylamino such as phenylamino or substituted phenylamino wherein the substituent on the phenyl group is as defined above, and the quaternary ammonium and acid addition salts thereof; —NH—CO—Q wherein Q is hydrogen, lower alkyl containing 1-8 carbon atoms, phenyl or substituted phenyl; —OCONHR wherein R is hydrogen or an alkyl group containing 1-8 carbon atoms; and when X is hydroxy, Y is cyano; straight or branched chain lower alkyl, lower alkenyl or lower alkynyl wherein the alkyl group contains 1-8 carbon atoms and the alkenyl or alkynyl groups contain 2-8 carbon atoms; propadienyl; benzyl; substituted benzyl wherein the substituent on the benzyl group is as defined above; phenyl; substituted phenyl wherein the substituent on the phenyl group is as defined above; and $R_6$ is —CHZ wherein Z is oxo; thioxo; hydroxyimino; alkoxyimino wherein the alkoxy group contains 1-8 carbon atoms; aryloxyimino such as phenyloxyimino or substituted phenyloxyimino wherein the substituent on the phenyl group is as defined above; acyloxyimino wherein the acyl group is derived from a lower alkanoic acid having 1-8 carbon atoms or an aromatic acid such as benzoic acid, or a substituted benzoic acid, for example; hydrazono; alkylhydrazono wherein the alkyl group contains 1-8 carbon atoms; arylhydrazono such as phenylhydrazono or substituted phenylhydrazono wherein the substituent on the phenyl group is as defined above; arylsulfonylhydrazono such as phenylsulfonylhydrazono or substituted phenylsulfonylhydrazono wherein the substituent on the phenyl group is as defined above; carbamoylhydrazono; ethylenedioxy; dialkoxy such as dimethoxy; diethoxy, dibutoxy and the like; ethylenedithio; ethylenethiooxy; thiazolidinyl; methylenyl; alkylidenyl wherein the alkyl group contains 2-8 carbon atoms; alkylimino wherein the alkyl group contains 1-8 carbon atoms; or arylimino such as phenylimino and substituted phenylimino wherein the substituent on the phenyl group is as defined above; and $R_6$ is carboxy; —COOR' wherein R' is as defined above; —COR" wherein R" is amino, alkylamino or dialkylamino wherein the alkyl group contains 1-8 carbon atoms; arylamino such as benzamino or substituted benzamino wherein the substituent on the phenyl group is as defined above, halo, hydrazino, alkylhydrazino or dialkylhydrazino wherein the alkyl group contains 1-8 carbon atoms, arylhydrazino such as phenylhydrazino or substituted phenylhydrazino wherein the substituent on the phenyl group is as defined above, arylsulfonylhydrazino such as phenylsulfonylhydrazino, and substituted phenylsulfonylhydrazino, for example; cyano; and ammonium, alkali metal and alkaline earth metal salts thereof where $R_6$ is carboxy;

$R_7$ is hydrogen, hydroxy, lower alkoxy wherein the alkoxy group contains 1-8 carbons or —OCOR''' wherein R''' is lower alkyl containing 1-8 carbon atoms; and $R_8$ is —COOH and the ammonium, alkali metal and alkaline earth metal salts thereof; —CH$_2$OH; —CHO; cyano; —COOR' wherein R' is as defined above; —COCl or —CONH$_2$; and n is an integer from 0-5.

Excluded from Formula I are those compounds wherein n is 0 and a and c are unsaturated, b, d, e and f are saturated, $R_1$ is oxo, $R_2$ is —XY wherein X and Y are hydrogen and hydroxy, $R_3$ is —CH$_2$OH and $R_4$ is hydrogen and those compounds wherein n is 0, a and b are unsaturated, c, d, e and f are saturated, $R_1$ is oxo, $R_2$ is —XY wherein X and Y are hydrogen and hydroxy, $R_3$ is —CH$_2$OH, $R_4$ is methyl and $R_5$ is hydrogen when the carbon at the 3 position has the R configuration and the orientation at the a double bond has the E configuration.

Preferred among the compounds of the present invention are those compounds of the formulae:

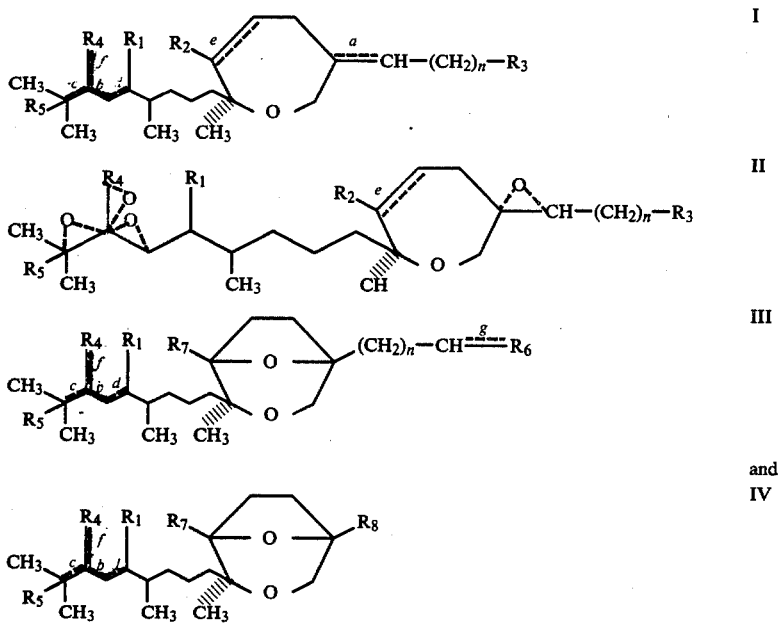

wherein $R_1$ and $R_2$ are each —XY wherein X is hydrogen or hydroxy provided that when X is hydrogen, Y is hydrogen; methyl; hydroxy; lower alkoxy; cycloalkoxy; heterocycloalkoxy; phenoxy; substituted phenoxy; —OCOR' wherein R' is lower alkyl, cycloalkyl, phenyl and substituted phenyl; halo; amino; alkylamino; dialkylamino; and when X is hydroxy, Y is lower alkyl; lower alkenyl; lower alkynyl; benzyl; substituted benzyl; phenyl; substituted phenyl; provided that when d or e is unsaturated $R_1$ and $R_2$ are either X or Y; and $R_1$ and/or $R_2$ are oxo; hydroxyimino or dialkoxy;

$R_3$ is —CHXY wherein X is hydrogen or hydroxy provided that when X is hydrogen, Y is hydrogen; methyl; hydroxy; lower alkoxy; cycloalkoxy; heterocycloalkoxy; phenoxy; substituted phenoxy; —OCOR' wherein R' is lower alkyl, cycloalkyl, phenyl or substituted phenyl; halo; amino; alkylamino; dialkylamino; and when X is hydroxy, Y is lower alkyl; lower alkenyl; lower alkynyl; benzyl; substituted benzyl; phenyl; substituted phenyl; and $R_3$ is —CHZ, wherein Z is oxo, hydroxyimino or dialkoxy; and $R_3$ is carboxy; —COOR' wherein R' is as defined above; and ammonium, alkali metal and alkaline earth metal salts thereof where $R_3$ is carboxy;

$R_4$ is hydrogen, methyl or methylenyl;

$R_5$ is hydrogen; hydroxy; hydroperoxy; or —OCOR''' wherein R''' is lower alkyl;

$R_6$ is methylenyl when g is unsaturated, and when g is saturated $R_6$ is —CHXY wherein X is hydrogen, or hydroxy, provided that when X is hydrogen, Y is hydrogen; methyl; hydroxy; lower alkoxy; cycloalkoxy; phenoxy; substituted phenoxy; —OCOR' wherein R' is as defined above; halo; amino; alkylamino; dialkylamino; and when X is hydroxy, Y is lower alkyl; lower alkenyl; lower alkynyl; benzyl; substituted benzyl; phenyl; substituted phenyl; and $R_6$ is —CHZ wherein Z is oxo, hydroxyimino or dialkoxy; or $R_6$ is carboxy; —COOR' wherein R' is as defined above; and ammonium, alkali metal and alkaline earth metal salts thereof where $R_6$ is carboxy;

$R_7$ is hydrogen; hydroxy; lower alkoxy; or —OCOR''' wherein R''' is lower alkyl;

$R_8$ is —COOR' wherein R' is as defined above or —COOH and the ammonium and alkali metal and alkaline earth metal salts thereof; and n is an integer from 0–5, provided that in formula I $C_3$ does not have the R configuration and the double bond at a does not have the E configuration when n=0, a and c are unsaturated, b, d, e and f are saturated, $R_1$ is oxo, $R_2$ is —XY wherein X and Y are hydrogen and hydroxy, $R_3$ is —CH$_2$OH and $R_4$ is hydrogen and when n=0, a and b are unsaturated, c, d, e and f are saturated, $R_1$ is oxo, $R_2$ is —XY wherein X and Y are hydrogen and hydroxy, $R_3$ is —CH$_2$OH, $R_4$ is methyl and $R_5$ is hydrogen.

As can be seen from the above structures, the side chains extending from the 2 and 6 positions of the oxepane ring may be either saturated or unsaturated. In addition, the bond between carbons 3 and 4 of the ring may also be saturated or unsaturated. The points of unsaturation on the ring and side chains are indicated by the letters a, b, c, d, e, f and g. However, when there is a double bond at b, there is no double bond at c, d and f. When a is unsaturated, the configuration around the a double bond may be either E or Z. It is understood therefore, unless otherwise stated, that when the starting material in a given example has a 6E configuration, the product will have a 6E configuration and when the starting material has a 6Z configuration, the product will also have a 6Z configuration. The carbon at the 3 position may have either the R or the S configuration.

Also within the scope of the invention are those compounds having an epoxide ring in either side chain as illustrated in Formula II. Although several epoxide rings are illustrated in Formula II, at no time is there more than one epoxide bridge in the side chain at the 2 position of the oxepane ring. Those compounds having an oxygen bridge between carbons 3 and 6 (Formula III) are also part of the present invention.

In U.S. Ser. No. 672,918, a method is described for obtaining discrete compounds from the zoapatle plant. The zoapatle plant is a bush about 2 meters high that grows wild in Mexico. Botanically it is known as *Montanoa tomentosa* according to Cervantes, Fam. Compositae, Tribe Heliantheae; another variety of the species is *Montanoa floribunda*. The plant is described in great detail in *Las Plantas Medicinales de Mexico*, third edition, Ediciones Botas (1944).

The plant has been used for centuries in the form of a "tea" or other crude aqueous preparations primarily as a labor inducer for humans. Its use as a utero-evacuant agent has been documented in the literature, but definitive chemical and pharmacological studies have not been described. By utero-evacuant is meant an agent which causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated.

As a result of the purification steps described in Ser. No. 672,918, two discrete compounds are isolated. One of the compounds is 2S,3R-6E-(2-hydroxyethylidene)-2-methyl-2-(4,8-dimethyl-5-oxo-7-nonenyl)-oxepan-3-ol and the other is 2S,3R-6E-(2-hydroxyethylidene)-2-methyl-2-(5-oxo-4,7,8-trimethyl-6E-nonenyl)-oxepan-3-ol. These compounds are the starting materials for the novel compounds of this invention and are not part of the present invention.

The following schematic diagram illustrates general methods for preparing the monocyclic and bicyclic compounds of the present invention from the naturally occurring substances. The starting materials are designated by the numbers 1 and 25 while the other numbers refer to specific examples which are fully illustrated below. The letters designate the specific reagent or reagents employed in the reaction. Although a compound having an E configuration at the 6 position may be prepared by a given example, it should be understood that the same process may be employed for compounds having a Z configuration at the 6 position. As can be seen from the diagram, the intermediate compounds formed by the illustrated processes may be used as starting materials for other compounds. However, the end products and the intermediates both possess useful activity.

PREPARATION OF BICYCLIC AND MONOCYCLIC COMPOUNDS

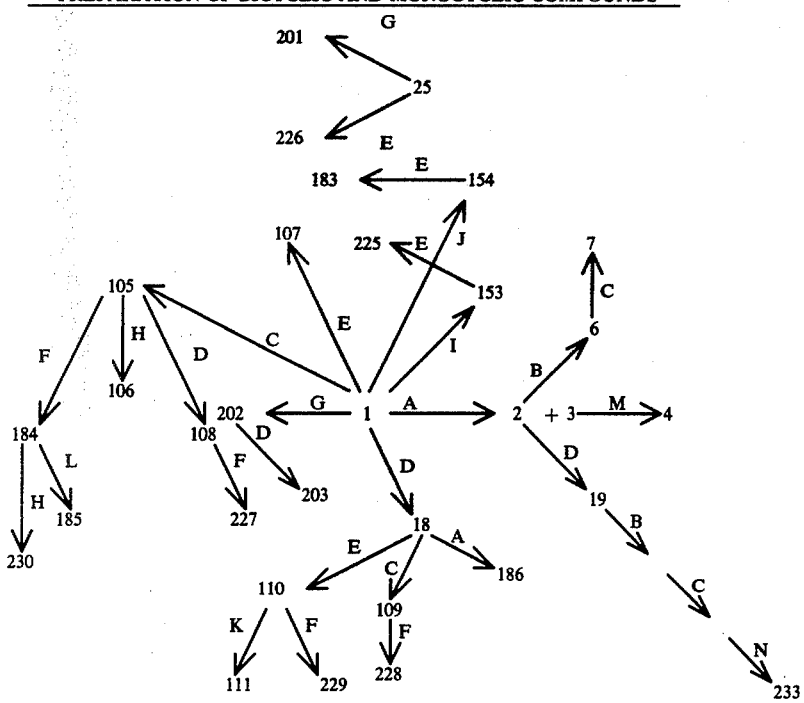

A = Ac₂O/Pyridine
B = K₂CO₃
C = MnO₂
D = NaBH₄
E = PtO₂, NaHCO₃, O₂
F = 10 5PD/C, H₂
G = Jones Reagent
H = NaBH(OAc)₃
I = CH₃Li
J = HC≡CLi·H₂NCH₂CH₂NH₂
K = CH₂N₂
L = AgNO₃, NaOH, NH₄OH M = 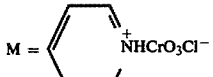

N = MnO₂, NaCN, HOAc, MeOH

The compounds of this invention are prepared by using the naturally occurring compounds as the starting material. The compounds that are prepared for a given series are generally employed as the starting materials for all of the other compounds in that series.

Those compounds wherein n is equal to or greater than 1 are prepared by reacting an appropriately substituted compound having an acyl halide grouping in the 6 position with diazomethane in an appropriate solvent. Suitable solvents include diethyl ether, tetrahydrofuran, dioxane and the like. The resulting diazoketone is then rearranged to the homologous acid. The length of the side chain can be further increased by converting the acid thus obtained to the acid halide and reacting the acid halide with diazomethane as described above. In this way the length of the side chain can be increased to the desired length.

Those compounds of Formula II having an epoxide ring on either of the side chains are prepared by reacting the unsaturated compound with a peracid such as, for example, m-chloroperoxybenzoic acid, or by reaction with vanadylacetylacetonate/t-butyl hydroperoxide or hydrogen peroxide/sodium hydroxide.

Those compounds of Formula IV are prepared by reacting the appropriately substituted compound of Formula I having an unsaturated double bond at a with an oxidizing reagent such as, for example, Jones reagent in an appropriate solvent. Suitable solvents include acetone, 2-butanone and the like.

Those compounds of Formula III having an oxygen bridge between carbons 3 and 6 are prepared by reacting those compounds of Formula I wherein R₂ or R₃ is hydroxy or oxo, a is unsaturated, n=0 with an appropriate agent such as p-toluenesulfonic acid, manganese dioxide and platinum oxide/sodium bicarbonate, for example. These reactions are carried out in a suitable solvent, such as benzene, toluene, xylene and the like. The reactions are generally carried out at room temperature although elevated temperatures may be employed in some cases.

The initial extract from which the purified materials are obtained is prepared from the zoapatle plant through a series of extraction and purification steps. These procedures are described in detail in Ser. No. 672,918. The material obtained as a result of this purification procedure is a mixture containing at least three components as evidenced by gas chromatography. The presence of utero-evacuant materials in the mixture is determined through the use of procedures employed for the detection of uterine contractions and interruption of pregnancy in female animals.

The compounds of the present invention have also been found to possess utero-evacuant properties. They are effective in inducing uterine contractions when administered in doses ranging from about 0.25 mg./kg. to about 100 mg./kg. The compounds are effective in interrupting pregnancy at dosage levels between about 2.5 mg./kg. and 400 mg./kg. The actual dosage employed will depend upon the species of animal to which the compound is administered. The compounds can be administered in formulations prepared according to acceptable pharamceutical practices. Suitable formulations include solutions, suspensions and solid dosage forms in pharmaceutically acceptable carriers. They can be administered perorally or intravenously or in any conventional manner in accordance with acceptable pharmaceutical practices.

In addition to their activity as utero-evacuants, many of the compounds of the present invention have been found to possess useful activity as central nervous system depressants. Activity at doses as low as 3.7 mg./kg. has been observed.

The following describes the invention in greater particularity and is intended to be a way of illustrating but not limiting the invention.

EXAMPLE 1

2S,3R-6E-(2-Hydroxyethylidene)-2-methyl-2-(4,8-dimethyl-5-oxo-7-nonenyl)-oxepan-3-ol

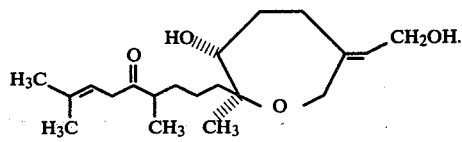

The crude extract obtained by extracting the leaves of the zoapatle plant (50 g.) is dissolved in ether (5 l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in.×4 ft.) of 2.5 kg. of neutral silicic acid packed in chloroform. The column is eluted with chloroform, chloform-isopropanol mixtures, and fractions are collected. The fractions are evaporated to dryness in vacuo at a temperature below 40° C. The column is eluted as follows:

| Fraction | Volume/Fraction (ml.) | Eluent |
|---|---|---|
| 1-7 | 650 | CHCl$_3$ |
| 8-30 | 500 | isopropanol:CHCl$_3$(1:41.7) |
| 31-60 | 500 | isopropanol:CHCl$_3$(1:33.3) |

-continued

| Fraction | Volume/Fraction (ml.) | Eluent |
|---|---|---|
| 61-105 | 500 | isopropanol:CHCl$_3$(1:28.6) |

The composition of the fractions is monitored by thin layer chromatography [silica gel, isopropanol-chloroform (1:12.5)] and by gas chromatography—3% OV17 [methyl silicone - phenyl silicone (1:1)] column using a programmed run (150°–250°). Fractions Nos. 78–84 are combined and the solvent removed in vacuo to afford an oily residue (5.1 g.) which contains at least three components as indicated by gas chromatography.

A portion of the residue (3.2 g.) is then dissolved in benzene (50 ml.) and the solution added to a column (4 in.×35 in.) packed with 2 kg. of OR-PVA Merck-O-Gel 2000* prepared in benzene. The column is eluted with benzene. Thin layer chromatography and gas chromatography are used to monitor the composition of the fractions.

*A vinyl acetate copolymer which swells in organic solvents, produced by E. M. Merck, Inc.

| Fraction | Volume/Fraction (ml.) |
|---|---|
| 1-7 | 1000 |
| 8-45 | 300 |

Fractions 23–33 contain 1.73 g. (54%) of the applied material.

Fraction 31 is evaporated to give 2S,3R-6E-(2-hydroxyethylidene)-2-methyl-2-(4,8-dimethyl-5-oxo-7-nonenyl)-oxepan-3-ol as an oil (0.326 g.) having the following spectral characteristics:

I.R. (Neat)μ: 2.91 and 5.88;

N.M.R. $\frac{CDCl_3}{TMS}$ δ: 5.41 (m, 2, $>$C=CH—CH$_2$OH and $>$C=CH—CH$_2$—$\overset{O}{\overset{\|}{C}}$—); 4.20 (d, 2,C=CH—CH$_2$OH);

4.15 (s, 2, C—O—CH$_2$—$\overset{|}{C}$=); 3.58 [broad t, 1, $>$CH(OH)]; 3.18 (d, 2, C=CH—CH$_2$—$\overset{O}{\overset{\|}{C}}$—); 1.71

[d, 6, C=C—(CH$_3$)$_2$]; 1.15 (s, 3,

C—O—$\overset{|}{\underset{|}{C}}$—CH$_3$);

Mass Spec. [m/e]: 320 [M-18], 251, 233, 221, 171, 143, 141, 137, 125, 113, 97, 95, 81, 69;

Chemical Ionization: M$^+$+H=339;

M.W.=338

EXAMPLE 2

2S,3R-3-Acetoxy-6-(2-acetoxyethylidene)-2-methyl-2-(4,8-dimethyl-5-oxo-7-nonenyl)-oxepane A solution of 2S,3R-6-(2-hydroxyethylidene)-2-methyl-2-(4,8-dimethyl-5-oxo-7-nonenyl)-oxepan-3-ol (500 mg.) in dry pyridine (6 ml.) is treated, while stirring at room temperature under nitrogen, with acetic anhydride (3 ml.). After stirring 18 hrs. at room temperature, the mixture is evaporated to dryness in vacuo, treated with methanol (1 ml.) and again evaporated in dryness in vacuo. The residue is chromatographed on a SilicAR column, using ethyl acetatecyclohexane (1:20) as the eluting solvent. The less polar fraction is eluted to afford 2S,3R-3-acetoxy-6-(2-acetoxyethylidene)-2-methyl-2-(4,8-dimethyl-5-oxo-7-nonenyl)-oxepane (200 mg.):

I.R. (Neat)μ, 5.75, 5.83 and 6.2;

NMR$_{TMS}^{CDCl_3}$ δ: 1.06 (d, J=7Hz, 3H,—CH—C$\underline{H}_3$); 1.14 (s, 3H,—O—C—C$\underline{H}_3$); 1.60 and 1.70 [each s, 3H, HC=C—(C$\underline{H}_3$)$_2$]; 2.03 (s, 6H,—OCO—C$\underline{H}_3$; 3.11 (d, J= 8Hz, 2H,—C$\underline{H}_2$—C);
 ‖
 O 4.08 (s, 2H, C$\underline{H}_2$—O—C), 4.60 (d, J=8Hz, 2H, C=CH—C$\underline{H}_2$—OAc); 4.80 (m, 1H, C$\underline{H}$—OAc); 5.1–5.5(m, 2H, (CH$_3$)$_2$—C=C$\underline{H}$, C=C$\underline{H}$—CH$_2$—OAc).

When in the above procedure propionic anhydride and benzoic anhydride are employed in place of acetic anhydride, the corresponding propionate and benzoate esters are obtained.

The following compounds are prepared according to the procedure of Example 2 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

| R$_1$ | R$_2$ | R$_3$ | R$_4$ | R$_5$ | a | b | c |
|---|---|---|---|---|---|---|---|
| =O | —OCO—C$_6$H$_4$pNO$_2$ | —CH$_2$—O—COC$_6$H$_4$pNO$_2$ | H | — | u | s | u |
| =O | =O | —CH$_2$—OCOC$_6$H$_5$ | H | — | u | s | u |
| —OCOC$_3$H$_7$ | =O | —CHO | H | — | u | s | u |
| —OCOC$_6$H$_4$pBr | =O | CH$_2$—O—COC$_6$H$_4$pBr | H | — | u | s | u |
| —OCOC$_6$H$_5$ | —OCOC$_6$H$_5$ | —CH$_2$—OCOC$_6$H$_5$ | H | — | u | s | u |
| =O | —OCOC$_5$H$_{11}$ | —CH$_2$OCOC$_5$H$_{11}$ | CH$_3$ | H | u | u | s |
| =O | OAc | —CH$_2$OAc | H | H | s | s | u |
| =O | OCOC$_6$H$_5$ | —CH$_2$—O—COC$_6$H$_5$ | CH$_3$ | H | s | s | s |
| =O | OAc | CH$_2$OAc | H | — | s | s | u |
| =O | OAc | —CH$_2$OAc | H | H | u | s | s |
| =O | OAc | CH$_2$OAc | CH$_3$ | H | s | u | s |
| =O | OCOC$_3$H$_7$ | —CH$_2$OCOC$_3$H$_7$ | CH$_3$ | H | u | s | s |
| =O | OAc | CH$_2$OAc | H | H | u | u | s |
| =O | OAc | CH$_2$—OAc | CH$_3$ | — | u | s | u |
| =O | OAc | CH$_2$—OAc | =CH$_2$ | H | u | s | s |
| =O | OAc | CH$_2$—OAc | CH$_3$ | — | s | s | u |
| =O | OCOC$_6$H$_5$ | CH$_2$—Br | H | — | u | s | u |
| =O | OAc | CH$_2$—SH | H | — | u | s | u |
| /O\ \O/ | OAc | CH$_2$OAc | H | — | u | s | u |
| =O | OH | CH$_2$OCOC$_6$H$_5$ | H | — | u | s | u |
| /S\ \S/ | OAc | CH$_2$—OAc | H | — | u | s | u |
| CH$_3$ / \ OH | OAc | CH$_2$—OAc | H | — | u | s | u |
| =O | OAc | CH$_2$—OAc | H | OH | u | u | s |
| =O | OAc | CH$_2$OTHP | H | — | u | s | u |
| OCOC$_6$H$_5$ | OCOC$_6$H$_5$ | —CH$_2$OAc | H | — | u | s | u |
| OCOC$_6$H$_5$ | OCOC$_6$H$_5$ | CO$_2$H | H | — | s | s | u |
| OCOC$_6$H$_5$ | OCOC$_6$H$_5$ | CO$_2$CH$_3$ | H | — | s | s | u |
| OCOC$_6$H$_5$ | OCOC$_6$H$_5$ | CO$_2$Na | H | — | s | s | u |
| OCOC$_6$H$_5$ | OCOC$_6$H$_5$ | CONH$_2$ | H | — | s | s | u |
| OCOC$_6$H$_5$ | OCOC$_6$H$_5$ | CONHNH$_2$ | H | — | s | s | u |
| OCOC$_6$H$_5$ | OCOC$_6$H$_5$ | C≡N | H | — | s | s | u | u - unsaturated
s - saturated

The following compounds are prepared according to the procedure of Example 2 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

| $R_1$ | $R_2$ | $R_3$ | $R_4$ | b | c |
|---|---|---|---|---|---|
| —OAc | =CH$_2$ | —H | — | s | u |
| —OCOC$_6$H$_5$ | =CH$_2$ | —CH$_3$ | H | u | s |
| —OCOC$_6$H$_4$pNO$_2$ | —CH$_3$ | —H | H | s | s |
| —OCO—⟨phenyl⟩ | CH$_3$ | —CH$_3$ | H | s | s |
| —OCOC$_6$H$_{13}$ | =CH$_2$ | —H | H | u | s |
| —OCO—C(CH$_3$)$_3$ | =CH$_2$ | =CH$_2$ | H | s | s |
| —OAc | =CH$_2$ | —CH$_3$ | — | s | u |
| —OCO—C$_6$H$_4$pBr | CH$_3$ | —H | — | s | u |
| —OCO—CH$_2$—C$_6$H$_5$ | =CH$_2$ | H | H | s | s |
| —OCO—C$_4$H$_9$ | CH$_3$ | H | H | u | s |
| —OCO—C$_3$H$_7$ | CH$_3$ | =CH$_2$ | H | s | s |
| —OCO—C$_5$H$_{11}$ | CH$_3$ | —CH$_3$ | — | s | u |
| —OCO—C$_2$H$_5$ | =CH$_2$ | CH$_3$ | H | s | s |
| —OAc | CH$_3$ | CH$_3$ | H | u | s |
| =O | CH$_2$—OAc | H | — | s | u |
| —OAc | CH$_2$—OAc | H | — | s | u |
| —OAc | CHO | H | — | s | u |
| —OAc | CO$_2$H | H | — | s | u |
| OCOC$_6$H$_5$ | CO$_2$CH$_3$ | H | — | s | u |
| —OAc | C≡N | H | — | s | u |
| —OAc | CONH$_2$ | H | — | s | u |
| —OAc | CONH$_2$ | H | —H | s | s |
| —OAc | CONH—C$_6$H$_5$ | H | — | s | u |
| CH$_3$ | CH$_2$OAc | H | — | s | u |
| <OH | | | | | | u - unsaturated
s - saturated

EXAMPLE 3

2S,3R-6-(2-Acetoxyethylidene)-2-methyl-2-(4,8-dimethyl-5-oxo-7-nonenyl)-oxepan-3-ol A sample of 2S,3R-6-(2-hydroxyethylidene)-2-methyl-2-(4,8-dimethyl-5-oxo-7-nonenyl)-oxepan-3-ol (2.6 g.) is dissolved in benzene (200 ml.) and pyridine (20 ml.). The solution is cooled to 0° under nitrogen and treated with an excess of acetyl chloride (15 ml.) during a 15 min. period. The mixture is allowed to stir for 2 hrs. followed by the addition of ether (300 ml.). The organic layer is washed with saturated cupric sulfate solution (3×200 ml.), dried (MgSO$_4$) and evaporated in vacuo to give a brown oil.

The oil is chromatographed on a SilicAR column using ether:petroleum ether (2:3) as the eluting solvent. The less polar fraction is eluted to afford 2S,3R-3-acetoxy-6-(2-acetoxyethylidene)-2-methyl-2-(4,8-dimethyl-5-oxo-7-nonenyl)-oxepane (1.3 g.) and the more polar fraction is eluted to afford 2S,3R-6-(2-acetoxyethylidene)-2-methyl-2-(4,8-dimethyl-5-oxo-7-nonenyl)-oxepan-3-ol (1.1 g.):

I.R. (Neat) 2.86 (br), 5.76 (s), 5.83 (s), 8.0μ(s);

N.M.R.$_{TMS}^{CDCl_3}$ δ: 5.3 [m, 2H, (CH$_3$)$_2$C=C$\underline{H}$, C=C$\underline{H}$-CH$_2$OAc], 4.6 (d, J=7Hz, 2H, C=CH—C$\underline{H}$$_2$OAc), 4.05 (bs, 2H, OC$\underline{H}$$_2$C=C), 3.5 (m, 1H, HOC$\underline{H}$—CO), 3.1 [bd, J=7Hz, 2H, (CH$_3$)$_2$C=CC$\underline{H}$$_2$CO].

When in the above procedure benzoyl chloride, propionyl chloride and pentanoyl chloride are employed in place of acetyl chloride, the corresponding benzoate, propionate and pentanoate esters are obtained.

EXAMPLE 4

2S-6-(2-Acetoxyethylidene)-2-methyl-2-(4,8-dimethyl-5-oxo-7-nonenyl)-oxepan-3-one A solution of 2S,3R-6-(2-acetoxyethylidene)-2-methyl-2-(4,8-dimethyl-5-oxo-7-nonenyl)-oxepan-3-ol (350 mg) in methylene chloride (2 ml) is added to a solution of pyridinium chlorochromate (338 mg) in methylene chloride (1.5 ml) at room temperature. The mixture is stirred for 2 hours and treated with ether (100 ml). The resulting mixture is filtered through a pad of celite and the solvent removed in vacuo to give an oily residue which is purified on preparative tlc plates (2:5, ethyl acetate:chloroform) to give 2S-6-(2-acetoxyethylidene)-2-methyl-2-(4,8-dimethyl-5-oxo-7-nonenyl)-oxepan-3-one (0.195 g):

IR (neat) μ: 5.74 (OCOCH$_3$) and 5.85 (C=O); NMR (CDCl$_3$—TMS) δ: 1.06 (d, J=7Hz, 3H, C$\underline{H}$$_3$—CH), 1.23 (s, 3H, C$\underline{H}$$_3$—C—), 2.03 (s, 3H, OCOC$\underline{H}$$_3$), 3.09 (d, J=7Hz, 2H, C$\underline{H}$$_2$CO—), 4.03 (s, 2H, O—C$\underline{H}$$_2$—), 4.56 (d, J=7Hz, 2H, C$\underline{H}$$_2$—OAc).

EXAMPLE 5

2S,6-(2-Hydroxyethylidene)-2-methyl-2-(4,8-dimethyl-5-oxo-7-nonenyl)-oxepan-3-one A solution of 2S,6-(2-acetoxyethylidene)-2-methyl-2-(4,8-dimethyl-5-oxo-7-nonenyl)-oxepan-3-one (378 mg.) in methanol (10 ml.) is treated at 0° with potassium carbonate (200 mg.) in water (10 ml.) for 2.5 hrs. The reaction mixture is diluted with water and extracted with ether. Removal of the solvent in vacuo affords 2S,6-(2-hydroxyethylidene)-2-methyl-2-(4,8-dimethyl-5-oxo-7-nonenyl)-oxepan-3-one.

The following compounds are prepared by the method of Example 5 by substituting an equivalent amount of the appropriate starting material for 2S,6-(2-acetoxyethylidene)-2-methyl-2-(4,8-dimethyl-5-oxo-7-nonenyl)-oxepan-3-one.

| $R_4$ | $R_5$ | a | b | c |
|---|---|---|---|---|
| CH$_3$ | H | u | u | s |
| H | H | s | s | s |
| CH$_3$ | H | s | s | s |
| H | — | s | s | u |
| H | H | u | s | s |

-continued

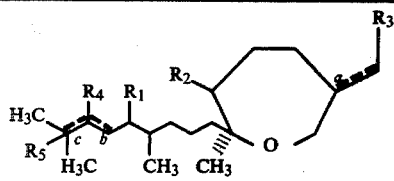

| R4 | R5 | a | b | c |
| --- | --- | --- | --- | --- |
| CH3 | H | s | u | s |
| CH3 | H | u | s | s |
| H | H | u | u | s |
| =CH2 | H | u | s | s |
| CH3 | — | u | s | u |
| H | H | s | u | s |
| =CH2 | H | s | s | s |
| CH3 | — | s | s | u |
| H | —OH | u | u | s |
| H | —OH | s | s | s |
| H | OH | s | u | s |

R₁ - =O
R₂ - =O
R₃ - —CH₂OH
u - unsaturated
s - saturated

EXAMPLE 6

2S,3R-3-Acetoxy-6-(2-hydroxyethylidene)-2-methyl-2-(4,8-dimethyl-5-oxo-7-nonenyl)-oxepane A solution of 2S,3R-3-acetoxy-6-(2-acetoxyethylidene)-2-methyl-2-(4,8-dimethyl-5-oxo-7-nonenyl)-oxepane (300 mg.) in methanol (8 ml.) is treated at 0° C. with potassium carbonate (160 mg.) in water (8 ml.) for 4 hrs. The reaction mixture is diluted with water (160 ml.) and extracted with ether (240 ml.). The organic layer is dried and the solvent removed in vacuo to give an oily residue (~260 mg.).

The residue is plate chromatographed on silica gel, using ethyl acetate-hexane (1:1) as the developing solvent. The major band is eluted with ethyl acetate to afford 2S,3R-3-acetoxy-6-(2-hydroxyethylidene)-2-methyl-2-(4,8-dimethyl-5-oxo-7-nonenyl)-oxepane (144 mg.)

I.R. (Neat) μ: 2.9, 5.75 and 5.85;

N.M.R. $_{TMS}{}^{CDCl_3}$ δ: 1.05 (d, J=7 Hz, 3H, CH—CH₃), 1.11 (s, 3H, —O—C—CH₃), 1.61 and 1.73 [each s, each 3H, (CH₃)₂—C=CH], 2.01 (s, 3H, —O—CO—CH₃), 3.09 (d, J=7 Hz, 2H, —CH₂—CO), 4.06 (s, 2H,

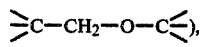

4.13 (d, J=8 Hz, 2H, =CH—CH₂—OH), 4.61–4.83 (m, 1H, CH—OAc), 5.23–5.50 [m, 2H, (CH₃)₂—C=CH and =CH-CH₂OH].

EXAMPLE 7

2S,3R-3-Acetoxy-6-(2-oxoethylidene)-2-methyl-2-(4,8-dimethyl-5-oxo-7-nonenyl)-oxepane A. A solution of 2S,3R-3-acetoxy-6-(2-hydroxyethylidene)-2-methyl-2-(4,8-dimethyl-5-oxo-7-nonenyl)-oxepane (400 mg.) in methylene chloride (100 ml.) is treated with manganese dioxide (1.2 g.) at room temperature under nitrogen for 17 hrs. The manganese dioxide is filtered and washed with methylene chloride and the solvent is removed in vacuo to give an oil (400 mg.).

This oil is plate chromatographed on silica gel, using ethyl acetate-hexane (2:3) as the developing solvent. The major band is eluted with ethyl acetate to afford 2S,3R-3-acetoxy-6-(2-oxoethylidene)-2-methyl-2-(4,8-dimethyl-5-oxo-7-nonenyl)-oxepane (230 mg.):

I.R. (Neat) μ: 5.75, 5.80 and 5.97;

N.M.R. $_{TMS}{}^{CDCl_3}$ δ: 1.06 (d, J=7 Hz, 3H, CH—CH₃); 1.11 (s, 3H, C—O—C—CH₃); 1.60 (s, 3H, CH₃—C=CH); 1.71 (s, 3H, CH₃—C=CH); 2.06 (s, 3H, CO—CH₃); 3.09 (d, J=7 Hz, 2H, CH₂—CO); 4.25 (s, 2H, —C—CH₂—O—C); 4.74 (m, 1H, CH—OAc); 5.11–5.45 [m, 1H, (CH₃)₂—C=CH]; 5.81 (d, J=8 Hz, 1H,=CH—CHO); 9.95 [d, J=8 Hz, 1H, (CHO)]; UV (EtOH); 238 nm. (ε=10288)

B. Following the procedure of Example 4 but substituting an equivalent amount of 2S,3R-3-acetoxy-6-(2-hydroxyethylidene)-2-methyl-2-(4,8-dimethyl-5-oxo-7-nonenyl)-oxepane for 2S,3R-6-(2-acetoxyethylidene)-2-methyl-2-(4,8-dimethyl-5-oxo-7-nonenyl)-oxepane-3-ol, 2S,3R-3-acetoxy-6-(2-oxoethylidene)-2-methyl-2-(4,8-dimethyl-5-oxo-7-nonenyl)-oxepane is obtained.

The following compounds are prepared by method A of Example 7 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

| R4 | R5 | a | b | c |
| --- | --- | --- | --- | --- |
| CH3 | H | u | u | s |
| H | H | u | s | s |
| CH3 | H | u | s | s |
| H | H | u | u | s |
| =CH2 | H | u | s | s |
| CH3 | — | u | s | u |
| H | OH | u | u | s |

R₁ - =O
R₂ - —OAc
R₃ - CHO
u - unsaturated
s - saturated

The following compounds are prepared by method B of Example 7 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

| R4 | R5 | a | b | c |
| --- | --- | --- | --- | --- |
| H | H | s | s | s |
| CH3 | H | s | s | s |
| H | — | s | s | u |
| CH3 | H | s | u | s |
| H | H | s | u | s |
| =CH2 | H | s | s | s |
| CH3 | — | s | s | u |
| H | —OH | s | s | s |

-continued

| R4 | R5 | a | b | c |
|----|----|---|---|---|
| H  | —OH | s | u | s |

EXAMPLE 8

2S,3R-3-Acetoxy-6-(2-hydroxyethylidene)-2-methyl-2-(4,8-dimethyl-5-hydroxy-7-nonenyl)-oxepane A solution of 2S,3R-3-acetoxy-6-(2-hydroxyethylidene)-2-methyl-2-(4,8-dimethyl-5-oxo-7-nonenyl)-oxepane (380 mg.) in absolute ethanol (10 ml.) is treated with sodium borohydride (60 mg.) at room temperature for 18 hrs. The solution is diluted with water (5 ml.) followed by 5% hydrochloric acid until the solution is neutral. The aqueous phase is extracted with methylene chloride and the organic phase is washed with saturated salt solution, dried and evaporated to give 2S,3R-3-acetoxy-6-(2-hydroxyethylidene)-2-methyl-2-(4,8-dimethyl-5-hydroxy-7-nonenyl)-oxepane.

EXAMPLE 9

2S,3R-3-Acetoxy-6-[2-(tetrahydropyran-2-yloxy)ethylidene]-2-methyl-2-[4,8-dimethyl-5-(tetrahydropyran-2-yloxy)-7-nonenyl]-oxepane A solution of 2S,3R-3-acetoxy-6-(2-hydroxyethylidene)-2-methyl-2-(4,8-dimethyl-5-hydroxy-7-nonenyl)-oxepane (382 mg.) in anhydrous benzene (3 ml.) is treated with dihydropyran (4.5 ml.) and p-toluenesulfonic acid (2 mg.) under nitrogen. After 2 hrs. at 25° C., the reaction mixture is washed with 10% sodium bicarbonate solution, dried and evaporated to give 2S,3R-3-acetoxy-6-[2-(tetrahydropyran-2-yloxy)ethylidene]-2-methyl-2-[4,8-dimethyl-5-(tetrahydropyran-2-yloxy)-7-nonenyl]-oxepane.

EXAMPLE 10

2S,3R-6-[2-(Tetrahydropyran-2-yloxy)-ethylidene]-2-methyl-2-[4,8-dimethyl-5-(tetraydropyran-2-yloxy)-7-nonenyl]-oxepan-3-ol A solution of 2S,3R-3-acetoxy-6-[2-(tetrahydropyran-2-yloxy)-ethylidene]-2-methyl-2-[4,8-dimethyl-5-(tetrahydropyran-2-yloxy)-7-nonenyl]-oxepane (550 mg.) in methanol (10 ml.) is treated with potassium carbonate (210 mg.) in water (10 ml.) for 18 hrs. at 25° C. The reaction mixture is diluted with water (150 ml.) and extracted with ether. The organic phase is dried and evaporated to give 2S,3R-6-[2-(tetrahydropyran-2-yloxy)ethylidene]-2-methyl-2-[4,8-dimethyl-5-(tetrahydropyran-2-yloxy)-7-nonenyl]-oxepan-3-ol.

EXAMPLE 11

2S-6-[2-(Tetrahydropyran-2-yloxy)-ethylidene]-2-methyl-2-[4,8-dimethyl-5-(tetrahydropyran-2-yloxy)-7-nonenyl]-oxepan-3-one A solution of 2S,3R-6-[2-(tetrahydropyran-2-yloxy)ethylidene]-2-methyl-2-[4,8-dimethyl-5-(tetrahydropyran-2-yloxy)-7-nonenyl]-oxepan-3-ol (508 mg.) in methylene chloride (35 ml.) and pyridine (1 ml.) is treated with chromium trioxide (625 mg.) and celite (1.5 g.). The resulting suspension is stirred for 4 hrs. and filtered. The filter cake is washed with methylene chloride and the filtrate evaporated. The filter cake is then washed with ether, the filtrate is added to the residue obtained from the evaporation of the methylene chloride, filtered through additional celite and the organic phase is treated with 10% sodium bicarbonate solution and washed with a saturated salt solution, dried and evaporated to give 2S-6-[2-tetrahydropyran-2-yloxy)-ethylidene]-2-methyl-2-[4,8-dimethyl-5-(tetrahydropyran-2-yloxy)-7-nonenyl]-oxepan-3-one.

EXAMPLE 12

2S-6-(2-Hydroxyethylidene)-2-methyl-2-(4,8-dimethyl-5-hydroxy-7-nonenyl)-oxepan-3-one A solution of 2S-6-[2-(tetrahydropyran-2-yloxy)ethylidene]-2-methyl-2-[4,8-dimethyl-5-(tetrahydropyran-2-yloxy)-7-nonenyl]-oxepan-3-one (500 mg.) in 70% acetic acid (100 ml.) is warmed on a steam bath for 2 hrs. and then stirred at room temperature for 18 hrs. The solution is evaporated to dryness and the residue is dissolved in ether and treated with 5% sodium bicarbonate solution, washed with saturated salt solution, dried and evaporated to give 2S-6-(2-hydroxyethylidene)-2-methyl-2-(4,8-dimethyl-5-hydroxy-7-nonenyl)-oxepan-3-one.

The following compounds are prepared by the method of Example 12 by substituting an equivalent amount of the appropriate starting material for 2S-6-[2-(tetrahydropyran-2-yloxy)-ethylidene]-2-methyl-2-[4,8-dimethyl-5-(tetrahydropyran-2-yloxy)-7-nonenyl]-oxepan-3-one.

| R4   | R5 | a | b | c |
|------|----|---|---|---|
| CH3  | H  | u | u | s |
| H    | H  | s | s | s |
| CH3  | H  | s | s | s |
| H    | —  | s | s | u |
| H    | H  | u | s | s |
| CH3  | H  | s | u | s |
| CH3  | H  | u | s | s |
| H    | H  | u | u | s |
| =CH2 | H  | u | s | s |
| CH3  | —  | u | s | u |
| H    | H  | s | u | s |
| =CH2 | H  | s | s | s |
| CH3  | —  | s | s | u |
| H    | OH | u | u | s |
| H    | OH | s | s | s |
| H    | OH | s | u | s |

R1 - —OH
R2 - =O
R3 - —CH2OH
u - unsaturated
s - saturated

EXAMPLE 13

2S-6-(2-Oxoethylidene)-2-methyl-2-(4,8-dimethyl-5-hydroxy-7-nonenyl)-oxepan-3-one A solution of 2S-6-(2-hydroxyethylidene)-2-methyl-2-(4,8-dimethyl-5-hydroxy-7-nonenyl)-oxepan-3-one (338 mg.) in methylene chloride (30 ml.) is treated with manganese dioxide (150 mg.). After stirring at 25° C. for 18 hrs. under nitrogen, the resulting suspension is filtered, the filter cake washed with methylene chloride and the combined filtrate and washings evaporated to give 2-S-6-(2-oxoethylidene)-2-methyl-2-(4,8-dimethyl-5-hydroxy-7-nonenyl)-oxepan-3-one.

The following compounds are prepared by the method of Example 13 by substituting an equivalent amount of the appropriate starting material for 2S-6-(2-hydroxyethylidene)-2-methyl-2-(4,8-dimethyl-5-hydroxy-7-nonenyl)-oxepan-3-one.

| $R_4$ | $R_5$ | a | b | c |
|---|---|---|---|---|
| H | H | u | s | s |
| $CH_3$ | H | u | s | s |
| $=CH_2$ | H | u | s | s |
| $CH_3$ | — | u | s | u |

$R_1$ - —OH
$R_2$ - =O
$R_3$ - —CHO
u - unsaturated
s - saturated

EXAMPLE 14

2S-6-(2-t-Butyldimethylsiloxyethylidene)-2-methyl-2-(4,8-dimethyl-5-hydroxy-7-nonenyl)oxepan-3-one To a solution of 2S-6-(2-hydroxyethylidene)-2-methyl-2-(4,8-dimethyl-5-hydroxy-7-nonenyl)-oxepan-3-one (338 mg.), pyridine (1 ml.) and ether (10 ml.) is added t-butyldimethylsilyl chloride (170 mg.) at 0° under nitrogen. The mixture is allowed to warm to 25° C. and is stirred for 1 hr. The resulting mixture is treated with ether (25 ml.) and water (20 ml.). The organic phase is separated, washed with saturated cupric sulfate (3×25 ml.), dried and evaporated to afford 2S-6-(2-t-butyldimethylsiloxyethylidene)-2-methyl-2-(4,8-dimethyl-5-hydroxy-7-nonenyl)-oxepan-3-one.

EXAMPLE 15

2S-6-(2-t-Butyldimethylsiloxyethylidene)-2-methyl-2-(5-acetoxy-4,8-dimethyl-7-nonenyl)oxepan-3-one Following the procedure of Example 2 but substituting an equivalent amount of 2S-6-(2-t-butyldimetylsiloxyethylidene)-2-methyl-2-(4,8-dimethyl-5-hydroxy-7-nonenyl)oxepan-3-one for 2S,3R-6E-(2-hydroxyethylidene)-2-methyl-2-(4,8-dimethyl-5-oxo-7-nonenyl)-oxepan-3-ol, 2S-6-(2-t-butyldimethylsiloxyethylidene)-2-methyl-2-(5-acetoxy-4,8-dimethyl-7-nonenyl)-oxepan-3-one is obtained.

EXAMPLE 16

2S-6-(2-Hydroxyethylidene)-2-methyl-2-(5-acetoxy-4,8-dimethyl-7-nonenyl)-oxepan-3-one A solution of 2S-6-(2-t-butyldimethylsiloxyethylidene)-2-methyl-2-(5-acetoxy-4,8-dimethyl-7-nonenyl)-oxepan-3-one (597 mg.) in 9:1 tetrahydrofuran:water (15 ml.) is treated with 80% acetic acid (10 ml.) at 25° C. for 2 hrs. The resulting solution is evaporated in vacuo and the residue is partitioned between ether and water. The organic phase is washed with saturated salt solution, dried and evaporated to afford 2S-6-(2-hydroxyethylidene)-2-methyl-2-(5-acetoxy-4,8-dimethyl-7-nonenyl)-oxepan-3-one.

EXAMPLE 17

2S-6-(2-Oxoethylidene)-2-methyl-2-(5-acetoxy-4,8-dimethyl-7-nonenyl)-oxepan-3-one Following the procedure of Example 11 but substituting an equivalent amount of 2S-6-(2-hydroxyethylidene)-2-methyl-2-(5-acetoxy-4,8-dimethyl-7-nonenyl)-oxepan-3-one for 2S,3R-6-[2-(tetrahydropyran-2-yloxy)-ethylidene]-3-hydroxy-2-methyl-2-[4,8-dimethyl-5-(tetrahydropyran-2-yloxy)-7-nonenyl]-oxepane, 2S-6-(2-oxoethylidene)-2-methyl-2-(5-acetoxy-4,8-dimethyl-7-nonenyl)-oxepan-3-one is obtained.

Following the procedure of Example 10 but substituting an equivalent amount of 2S-6-(2-oxoethylidene)-2-methyl-2-(5-acetoxy-4,8-dimethyl-7-nonenyl)-oxepan-3-one for 2S,3R-3-acetoxy-6-[2-(tetrahydropyran-2-yloxy)-ethylidene]-2-methyl-2-[4,8-dimethyl-5-(tetrahydropyran-2-yloxy)-7-nonenyl]-oxepane, 2S-6-(2-oxoethylidene)-2-methyl-2-(4,8-dimethyl-5-hydroxy-7-nonenyl)-oxepan-3-one is obtained.

The following compounds are obtained by the sequence outlined in Examples 14 through 17 by substituting an equivalent amount of the appropriate starting material for 2S-6-(2-hydroxyethylidene)-2-methyl-2-(4,8-dimethyl-5-hydroxy-7-nonenyl)-oxepan-3-one.

| $R_4$ | $R_5$ | a | b | c |
|---|---|---|---|---|
| $CH_3$ | H | u | u | s |
| H | H | s | s | s |
| $CH_3$ | H | s | s | s |
| H | — | s | s | u |
| $CH_3$ | H | s | u | s |
| H | H | u | u | s |
| H | H | s | u | s |
| $=CH_2$ | H | s | s | s |
| $CH_3$ | — | s | s | u |
| H | OH | u | u | s |
| H | OH | s | s | s |
| H | OH | s | u | s |

$R_1$ - —OH
$R_2$ - =O
$R_3$ - —CHO
u - unsaturated
s - saturated

EXAMPLE 18

2S,3R-6-(2-Hydroxyethylidene)-2-methyl-2-(4,8-dimethyl-5-hydroxy-7-nonenyl)-oxepan-3-ol 2S,3R-6-(2-Hydroxyethylidene)-2-methyl-2-(4,8-dimethyl-5-oxo-7-nonenyl)-oxepan-3-ol (700 mg.) is dissolved in absolute ethanol (20 ml.); sodium borohydride (115 mg.) is added slowly with stirring and the reaction mixture is stirred at room temperature for 18 hrs. The reaction is quenched by adding water (10 ml.) followed by 5% hydrochloric acid (~3-5 ml.) until the solution is neutral. The aqueous phase is extracted with methylene chloride, filtered through phase-separating paper and the solvent removed in vacuo. The residue (660 mg.) is plate chromatographed on silica gel using isopropanol-chloroform (1:9) as the developing solvent. The major band is eluted with isopropanol-chloroform (1:1) to afford 2S,3R-6-(2-hydroxyethylidene)-2-methyl-2-(4,8-dimethyl-5-hydroxy-7-nonenyl)-oxepan-3-ol (424 mg.):

I.R. (Neat) μ: 2.95 and 6.0;

N.M.R.$_{CDCl_3}{}^{TMS}$ δ: 0.91 (d, J=5 Hz, 3H, —CH—C$\underline{H}_3$); 1.14 (s, 3H, —O—C—C$\underline{H}_3$); 1.65 and 1.71 [each s, 6H, HC=C—(C$\underline{H}_3$)$_2$]; 3.33—3.63 (m, 2H, —C$\underline{H}$—OH); 4.15 (d, J=6 Hz, 4H, C=CH—C$\underline{H}_2$—OH, -CH$_2$—O—R); 5.13–5.56 [multiplet, 2H, C=C$\underline{H}$—CH$_2$OH; (CH$_3$)$_2$—C=C$\underline{H}$].

The following compounds are prepared by the method of Example 18 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

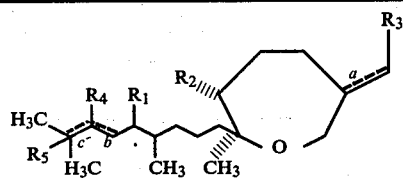

| R$_4$ | R$_5$ | a | b | c |
|---|---|---|---|---|
| CH$_3$ | H | u | u | s |
| H | H | s | s | s |
| CH$_3$ | H | s | s | s |
| H | — | s | s | u |
| H | H | u | s | s |
| CH$_3$ | H | s | u | s |
| CH$_3$ | H | u | s | s |
| H | H | u | u | s |
| =CH$_2$ | H | u | s | s |
| CH$_3$ | — | u | s | u |
| H | H | s | u | s |
| =CH$_2$ | H | s | s | s |
| CH$_3$ | — | s | s | u |
| H | OH | u | u | s |
| H | OH | s | s | s |
| H | OH | u | s | s |
| H | OH | s | u | s |

R$_1$ - —OH
R$_2$ - —OH
R$_3$ - —CH$_2$OH
u - unsaturated
s - saturated

The following compounds are prepared by the method of Example 18 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

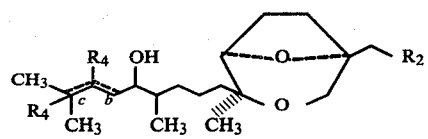

| R$_2$ | R$_3$ | R$_4$ | b | c |
|---|---|---|---|---|
| =CH$_2$ | H | — | s | u |
| =CH$_2$ | CH$_3$ | H | u | s |
| CH$_3$ | H | H | s | s |
| CH$_3$ | CH$_3$ | H | s | s |
| =CH$_2$ | H | H | u | s |
| =CH$_2$ | =CH$_2$ | H | s | s |
| =CH$_2$ | CH$_3$ | — | s | u |
| CH$_3$ | H | — | s | u |
| =CH$_2$ | H | H | s | s |
| CH$_3$ | H | H | u | s |
| CH$_3$ | =CH$_2$ | H | s | s |
| CH$_3$ | CH$_3$ | — | s | u |
| =CH$_2$ | CH$_3$ | H | s | s |
| CH$_3$ | CH$_3$ | H | u | s |
| =CH$_2$ | H | OH | u | s |
| CH$_3$ | H | OH | s | s | u - unsaturated
s - saturated

EXAMPLE 19

2S,3R-3Acetoxy-6-(2-acetoxyethylidene)-2-methyl-2-(4,8-dimethyl-5-hydroxy-7-nonenyl)-oxepane To a mixture of 2S,3R-3-acetoxy-6-(2-acetoxyethylidene)-2-methyl-2-(4,8-dimethyl-5-oxo-7-nonenyl)-oxepane (400 mg.) and methanol (10 ml.), an excess of sodium borohydride (100 mg.) is added at 0° under nitrogen. The mixture is stirred for 2 hrs. and then treated with saturated ammonium chloride (20 ml.) and ether (100 ml.). The organic layer is dried and evaporated to give a brown oily residue which is chromatographed on a SilicAR column using ether-petroleum ether (1:1) as the eluting solvent. The major fraction is eluted to afford 2S,3R-3-acetoxy-6-(2-acetoxyethylidene)-2-methyl-2-(4,8-dimethyl-5-hydroxy-7-nonenyl)-oxepane (356 mg.):

I.R. (Neat) μ: 2.86 and 5.78;

N.M.R.$_{TMS}{}^{CDCl_3}$ δ: 5.3 (m, 2H, =C$\underline{H}$—CH$_2$OAc, C$\underline{H}$=C(CH$_3$)$_2$, 4.7 (m, 3H, OC$\underline{H}_2$, $\underline{H}$C—OAc, 4.1 (bs, 2H, =CH—C$\underline{H}_2$OAc), 3.45 (m, 1H, $\underline{H}$COH), 2.03 (s, 6H, C$\underline{H}_3$—C=O).

EXAMPLE 20

2S,3R-3-Acetoxy-6-(2-acetoxyethylidene)-2-methyl-2-(5-acetoxy-4,8-dimethyl-7-nonenyl)-oxepane Following the procedure of Example 2 but substituting an equivalent amount of 2S,3R-6-(2-hydroxyethylidene)-2-methyl-2-(4,8-dimethyl-5-hydroxy-7-nonenyl)-oxepane-3-ol for 2S,3R-6-(2-hydroxyethylidene)-2-methyl-2-(4,8-dimethyl-5-oxo-7-nonenyl)-oxepan-3-ol, there is obtained 2S,3R-3-acetoxy-6-(2-acetoxyethylidene)-2-methyl-2-(5-acetoxy-4,8-dimethyl-7-nonenyl)-oxepane.

EXAMPLE 21

2S,3R-3-Acetoxy-6-(2-hydroxyethylidene)-2-methyl-2-(5-acetoxy-4,8-dimethyl-7-nonenyl)-oxepane Following the procedure of Example 6 but substituting an equivalent amount of 2S,3R-3-acetoxy-6-(2-acetoxyethylidene)-2-methyl-2-(5-acetoxy-4,8-dimethyl-7-nonenyl)-oxepane for 2S,3R-acetoxy-6-(2-acetoxyethylidene)-2-methyl-2-(4,8-dimethyl-5-oxo-7-nonenyl)-oxepane, there is obtained 2S,3R-3-acetoxy-6-(2-hydroxyethylidene)-2-methyl-2-(5-acetoxy-4,8-dimethyl-7-nonenyl)-oxepane.

EXAMPLE 22

2S,3R-3-Acetoxy-6-(2-oxoethylidene)-2-methyl-2-(5-acetoxy-4,8-dimethyl-7-nonenyl)-oxepane A. A solution of 2S,3R-3-acetoxy-6-(2-hydroxyethylidene)-2-methyl-2-(5-acetoxy-4,8-dimethyl-7-nonenyl)-oxepane (422 mg.) in methylene chloride (80 ml.) is stirred with manganese dioxide (840 mg.) at room temperature under nitrogen for 17 hrs. Removal of the manganese dioxide by filtration followed by removal of the solvent from the filtrate and washings in vacuo affords 2S,3R-3-acetoxy-6-(2-oxoethylidene)-2-methyl-2-(5-acetoxy-4,8-dimethyl-7-nonenyl)-oxepane.

B. Following the procedure of Example 11 but substituting an equivalent amount of 2S,3R-3-acetoxy-6-(2-hydroxyethylidene)-2-methyl-2-(5-acetoxy-4,8-dimethyl-7-nonenyl)-oxepane for 2S,3R-6-[2-(tetrahydropyran-2-yloxy)-ethylidene]-2-methyl-2-(4,8-dimethyl-5-(tetrahydropyran-2-yloxy)-7-nonenyl)-oxepan-3-ol, 2S,3R-3-acetoxy-6-(2-oxoethylidene)-2-methyl-2-(5-acetoxy-4,8-dimethyl-7-nonenyl)-oxepane is obtained.

The following compounds are prepared by the method of Example 22B by substituting an equivalent amount of the appropriate starting material for 2S,3R-6-[2-(tetrahydropyran-2-yloxy)-ethylidene]-2-methyl-2-[4,8-dimethyl-5-(tetrahydropyran-2-yloxy)-7-nonenyl)]-oxepan-3-ol.

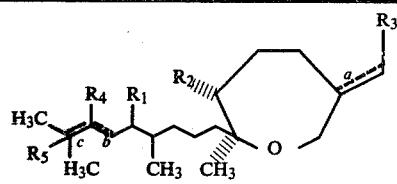

| $R_4$ | $R_5$ | a | b | c |
|---|---|---|---|---|
| CH₃ | H | u | u | s |
| H | H | s | s | s |
| CH₃ | H | s | s | s |
| H | — | s | s | u |
| H | H | u | s | s |
| CH₃ | H | s | u | s |
| CH₃ | H | u | s | s |
| H | H | u | u | s |
| =CH₂ | H | u | s | s |
| CH₃ | — | u | s | u |
| H | H | s | u | s |
| =CH₂ | H | s | s | s |
| CH₃ | — | s | s | u |
| H | OH | u | u | s |
| H | OH | s | s | s |
| H | OH | s | u | s |

$R_1$ - —OAc
$R_2$ - —OAc
$R_3$ - —CHO
u - unsaturated
s - saturated

EXAMPLE 23

2S-6-(2-Oxoethylidene)-2-methyl-2-(4,8-dimethyl-5-oxo-7-nonenyl)-oxepan-3-one

Following the procedure of Example 11 but substituting an equivalent amount of 2S-6-(2-hydroxyethylidene)-2-methyl-2-(4,8-dimethyl-5-oxo-7-nonenyl)-oxepan-3-one for 2S,3R-6-[2-(tetrahydropyran-2-yloxy)-ethylidene]-2-methyl-2-(4,8-dimethyl-5-(tetrahydropyran-2-yloxy)-7-nonenyl)-oxepan-3-ol. 2S-6-(2-oxoethylidene)-2-methyl-2-(4,8-dimethyl-5-oxo-7-nonenyl)-oxepan-3-one is obtained.

The following compounds are prepared by the method of Example 23 by substituting an equivalent amount of the appropriate starting material for 2S-6-(2-hydroxyethylidene)-2-methyl-2-(4,8-dimethyl-5-oxo-7-nonenyl)-oxepan-3-one.

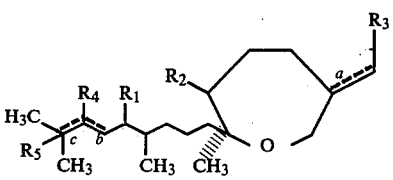

| $R_4$ | $R_5$ | a | b | c |
|---|---|---|---|---|
| CH₃ | H | u | u | s |
| H | H | s | s | s |
| CH₃ | H | s | s | s |
| H | — | s | s | u |
| H | H | u | s | s |
| CH₃ | H | s | u | s |
| CH₃ | H | u | s | s |
| H | H | u | u | s |
| =CH₂ | H | u | s | s |
| CH₃ | — | u | s | u |
| H | H | s | u | s |
| =CH₂ | H | s | s | s |
| CH₃ | — | s | s | u |
| H | OH | u | u | s |
| H | OH | s | s | s |
| H | OH | s | u | s |
| H | OH | u | s | s |

$R_1$ - =O
$R_2$ - =O
$R_3$ - —CHO
u - unsaturated
s - saturated

EXAMPLE 24

2S,3R-6ξ-(2-Hydroxyethyl)-2-methyl-2-(4,8-dimethyl-5-oxo-7-nonyl)-oxepan-3-ol (Isomer A and B)

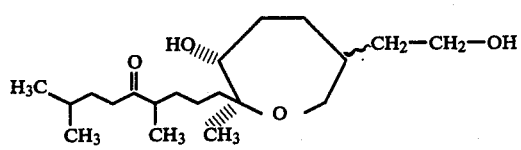

A mixture of 2S,3R-6-(2-hydroxyethylidene)-2-methyl-2-(4,8-dimethyl-5-oxo-7-nonenyl)-oxepan-3-ol (821 mg.), platinum oxide (100 mg.), sodium nitrite (1.5 mg. in one drop of water) and absolute ethanol (100 ml.) is hydrogenated at atmospheric pressure for 1.3 hrs. The reaction mixture is filtered through celite and the solvent is evaporated in vacuo. The residue is chromatographed on a SilicAR column using ethyl acetate:cyclohexane (2:3) as the eluting solvent. The less polar fraction is eluted to afford Isomer A, 2S,3R-6ξ-(2-hydroxyethyl)-2-methyl-2-(4,8-dimethyl-5-oxo-7-nonyl)-oxepan-3-ol (283 mg.):

I.R. (Neat) μ: 2.90 and 5.87;
N.M.R.$_{TMS}^{CDCl_3}$ δ: 0.9 [d, J=5 Hz, 6 H, (C$\underline{H}_3$)$_2$—CH—]; 1.10

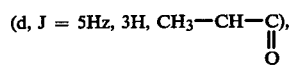
(d, J = 5Hz, 3H, CH$_3$—CH—C̲), 1.15 (s, 3 H, C$\underline{H}_3$—C—O); 2.4

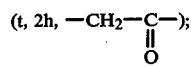
(t, 2h, —CH$_2$—C̲—);

3.4–3.8 (m, 5 H, —C$\underline{H}_2$OH, —C$\underline{H}_2$OR, >C$\underline{H}$OH) Further elution with ethyl acetate-cyclohexane (1:1) affords Isomer B, 2S,3R-6-(2-hydroxyethyl)-2-methyl-2-(4,8-dimethyl-5-oxo-7-nonyl)-oxepan-3-ol (263 mg.):

I.R. (Neat) μ: 2.90 and 5.87;
N.M.R.$_{TMS}^{CDCl_3}$ δ: 0.9 [d, J=5 Hz, 6 H, (C$\underline{H}_3$)$_2$—CH], 1.05 (d, J=5 Hz, 3 H, C$\underline{H}_3$—C—H); 1.07 (s, 3 H, C$\underline{H}_3$—C—O), 2.42 (t, 2 H, C$\underline{H}_2$—C=O); 3.3 (d, J=7 Hz, 1 H, >C$\underline{H}$OH); 3.5 (bs, 2 H, —C$\underline{H}_2$—O—R); 3.7 (d, J=5 Hz, 2 H, —C$\underline{H}_2$OH).

EXAMPLE 25

2S,3R-6E-(2-Hydroxyethylidene)-2-methyl-2-(5-oxo-4,7,8-trimethyl-6E-nonenyl)-oxepan-3-ol

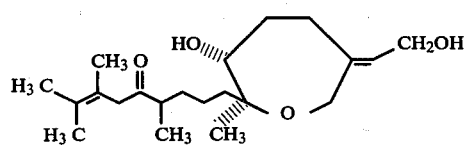

The crude extract obtained by extracting the leaves of the zoapatle plant (50 g.) is dissolved in ether (5 l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in.×4 ft.) of 2.5 kg. of neutral silicic acid packed in chloroform. The column is eluted with chloroform, chloroform-isopropanol mixtures, and fractions are collected. The fractions are evaporated to dryness in vacuo at a temperature below 40° C. The column is eluted as follows:

| Fraction | Volume/Fraction (ml.) | Eluent |
|---|---|---|
| 1–7 | 650 | CHCl$_3$ |
| 8–30 | 500 | isopropanol:CHCl$_3$ (1:41.7) |
| 31–60 | 500 | isopropanol:CHCl$_3$ (1:33.3) |
| 61–105 | 500 | isopropanol:CHCl$_3$ (1:28.6) |

The composition of the fractions is monitored by thin layer chromatography [silica gel, isopropanol-chloroform (1:12.5)] and by gas chromatography—3% OV17 [methyl silicone - phenyl silicone (1:1)] column using a programmed run (150°–250°). Fractions Nos. 78–84 are combined and the solvent removed in vacuo to afford an oily residue (5.1 g.) which contains at least three components as indicated by gas chromatography.

A portion of the residue (3.2 g.) is then dissolved in benzene (50 ml.) and the solution added to a column (4 in.×35 in.) packed with 2 kg. of OR-PVA Merck-O-Gel 2000 prepared in benzene. The column is eluted with benzene and thin layer chromatography and gas chromatography are used to monitor the composition of the fractions.

| Fraction | Volume/Fraction (ml.) |
|---|---|
| 1–7 | 1000 |
| 8–45 | 300 |
| 46–47 | 1000 |

Fractions 23–33 contain 1.73 g. (54%) of the applied material.

Fractions 24–25 are evaporated to give 2S,3R-6E-(2-hydroxyethylidene)-2-methyl-2-(5-oxo-4,7,8-trimethyl-6E-nonenyl)-oxepan-3-ol as an oil (0.251 g.) having the following spectral characteristics:

I.R. (Neat) μ: 2.90, 5.96 and 6.21;

N.M.R. TMS$^{CDCL_3}$ δ: 6.11 (broad s, 1, —C̲—CH=C);

5.48 (m, 1, C=CH—CH$_2$OH); 4.19 (d, 2,

C=CH—CH$_2$OH); 4.13 (s, 2, C—O—CH$_2$—C̲=);

3.56 [broad t, 1, —C$\underline{H}$(OH)]; 2.10 (d, 3,

H$_3$C—C̲=C); 1.13 (s, 3, C—O—C̲—CH$_3$); 1.07 [d, 6, C=C̲—CH(CH$_3$)$_2$];

Mass Spec. [m/e]: 334 [M-18], 225, 140, 111, 95, 81, 69;

U.V.—λ max (EtOH): ~239 nm [ε=8500]

Chemical Ionization: M++H=353; M.W.=352

EXAMPLE 26

2S,3R-6ξ-(2-Hydroxyethyl)-2-methyl-2-(5-oxo-4,7,8-trimethylnonyl)-oxepan-3-ol

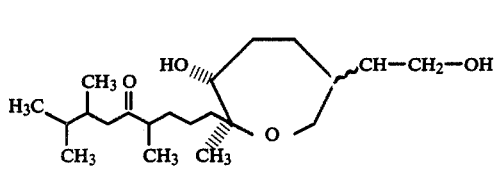

Following the hydrogenation procedure described in Example 24 but substituting an equivalent amount of 2S,3R-6E-(2-hydroxyethylidene)-2-methyl-2-(5-oxo-4,7,8-trimethyl-6E-nonenyl)-oxepan-3-ol for 2S,3R-6E-(2-hydroxy ethylidene)-2-methyl-2-(4,8-dimethyl-5-oxo-7-nonenyl)-oxepan-3-ol, a mixture of isomers of 2S,3R-6ξ-(2-hydroxyethyl)-2-methyl-2-(5-oxo-4,7,8-trimethylnonyl)-oxepan-3-ol is obtained.

EXAMPLE 27

2S,3R-3-Acetoxy-6-(2-acetoxyethylidene)-2-methyl-2-(4,8-dimethyl-7,8-oxide-5-oxononyl)-oxepane A solution of m-chloroperoxybenzoic acid (85%, 80 mg.) in methylene chloride (2 ml.) is slowly added to a cooled (0°–5°) solution of 2S,3R-3-acetoxy-6-(2-acetoxyethylidene)-2-methyl-2-(4,8-dimethyl-5-oxo-7-nonenyl)-oxepane (139 mg.) in methylene chloride (2 ml.). The reaction mixture is stirred at 0°–5° for 1 hr. and then at room temperature for 2 hrs. The mixture is treated with 5% aqueous sodium bisulfite solution, and the organic layer is washed with 5% aqueous sodium bicarbonate solution (2×25 ml.), and brine (2×25 ml.). The mixture is dried, concentrated in vacuo and purified by preparative thin layer chromatography to afford 2S,3R-3-acetoxy-6-(2-acetoxyethylidene)-2-methyl-2-(4,8-dimethyl-7,8-oxido-5-oxononyl)-oxepane.

EXAMPLE 28

2S,3R-3-Acetoxy-6ξ-(2-acetoxyethyl)-2-methyl-2-(4,8-dimethyl-7,8-oxido-5-oxononyl)-oxepane

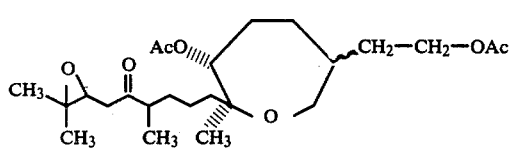

A mixture of 2S,3R-3-acetoxy-6-(2-acetoxyethylidene)-2-methyl-2-(4,8-dimethyl-7,8-oxido-5-oxononyl)-oxepane. (438 mg.), platinum oxide (50 mg.), and sodium nitrite (0.5 mg. in one drop of water) in absolute ethanol (50 ml.) is hydrogenated at atmospheric pressure until one molar equivalent of hydrogen is taken up. The catalyst is removed by filtration and the filtrate evaporated in vacuo to afford a mixture of isomers of 2S,3R-3-acetoxy-6ξ-(2-acetoxyethyl)-2-methyl-2-(4,8-dimethyl-7,8-oxido-5-oxononyl)-oxepane.

EXAMPLE 29

2S,3R-3-Acetoxy-6-(2-acetoxyethyl)-2-methyl-2-(4,8-dimethyl-5-oxo-7-nonenyl)-oxepane

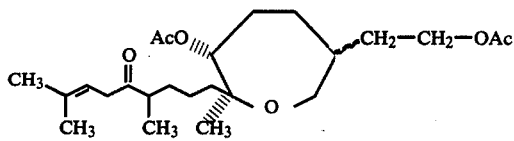

A solution of 2S,3R-3-acetoxy-6ξ-(2-acetoxyethyl)-2-methyl-2-(4,8-dimethyl-7,8-oxido-5-oxononyl)-oxepane (440 mg.) in absolute ethanol (200 ml.) containing zinc-copper couple (10 g.) is refluxed for 48 hrs. Removal of the metal by filtration followed by evaporation of the solvent in vacuo affords a mixture of isomers of 2S,3R-3-acetoxy-6ξ-(2-acetoxyethyl)-2-methyl-2-(4,8-dimethyl-5-oxo-7-nonenyl)-oxepane.

EXAMPLE 30

2S,3R-6ξ-(2-Hydroxyethyl)-2-methyl-2-(4,8-dimethyl-5-oxo-7-nonenyl)-oxepan-3-ol

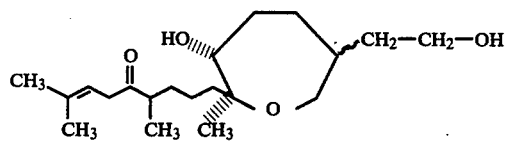

A solution of 2S,3R-3-acetoxy-6-(2-acetoxyethyl)-2-methyl-2-(4,8-dimethyl-5-oxo-7-nonenyl)-oxepane (426 mg.) in methanol (100 ml.) is stirred at room temperature under nitrogen with potassium carbonate (332 mg.) in water (30 ml.) for 19 hrs. The mixture is evaporated in vacuo, and the residue extracted with methylene chloride. The extracts are dried and evaporated to afford a mixture of isomers of 2S,3R-6ξ-(2-hydroxyethyl)-2-methyl-2-(4,8-dimethyl-5-oxo-7-nonenyl)-oxepan-3-ol.

EXAMPLE 31

2S,3R-6-[2'-Hydroxy-(6,1'-oxido)-ethyl]-2-methyl-2-(4,8-dimethyl-5-oxo-7-nonenyl)-oxepan-3-ol To a stirred solution of 2S,3R-6-(2-hydroxyethylidene)-2-methyl-2-(4,8-dimethyl-5-oxo-7-nonenyl)-oxepan-3-ol (338 mg.) and vanadyl acetylacetonate (10 mg.) in benzene (10 ml.) at room temperature is added dropwise over a period of 10 mins. t-butylhydroperoxide (~94%, 152 mg.). After six hrs., the resulting solution is washed with 10% aqueous sodium bisulfite solution, water and dried. Removal of the solvent, in vacuo, and purification of the residue by chromatography affords 2S,3R-6-[2'-hydroxy-(6,1'-oxido)-ethyl]-2-methyl-2-(4,8-dimethyl-5-oxo-7-nonenyl)-oxepan-3-ol.

EXAMPLE 32

2S,3R-6-[2'-Hydroxy-(6,1'-oxido)-ethyl]-2-methyl-2-(4,8-dimethyl-5-oxononyl)-oxepan-3-ol Following the hydrogenation procedure of Example 28 but substituting an equivalent amount of 2S,3R-6-[2'-hydroxy-(6,1'-oxido)-ethyl]-2-methyl-2-(4,8-dimethyl- 5-oxo-7-nonenyl)-oxepan-3-ol for 2S,3R-3-acetoxy-6-(2-acetoxyethylidene)-2-methyl-2-(4,8-dimethyl-7,8-oxido-5-oxononyl)-oxepane, there is obtained 2S,3R-6-[2′-hydroxy-(6,1′-oxido)-ethyl]-2-methyl-2-(4,8-dimethyl-5-oxononyl)-oxepan-3-ol.

EXAMPLE 33

2S,3R-6-(2-Hydroxyethylidene)-2-methyl-2-(4,8-dimethyl-5-oxononyl)-oxepan-3-ol

Following the procedure of Example 29 but substituting an equivalent amount of 2S,3R-6-[2′-hydroxy-(6,1′-oxido)-ethyl]-2-methyl-2-(4,8-dimethyl-5-oxononyl)-oxepan-3-ol for 2S,3R-3-acetoxy-6-(2-acetoxyethyl)-2-methyl-2-(4,8-dimethyl-7,8-oxido-5-oxononyl)-oxepane, there is obtained 2S,3R-6-(2-hydroxyethylidene)-2-methyl-2-(4,8-dimethyl-5-oxononyl)-oxepan-3-ol.

EXAMPLE 34

2S,3R-6-(2-Hydroxyethylidene)-2-methyl-2-(6,7-oxido-5-oxo-4,7,8-trimethylnonyl)-oxepan-3-ol A solution of 2S,3R-6-(2-hydroxyethylidene)-2-methyl-2-(5-oxo-4,7,8-trimethyl-6E-nonenyl)-oxepan-3-ol (352 mg.) in methanol (10 ml.) is treated with 30% aqueous hydrogen peroxide (0.5 ml.) and 6 N aqueous sodium hydroxide (1 ml.). The resulting mixture is stirred for 3 hrs. at room temperature and then treated with water (50 ml.) and ether (100 ml.). The organic layer is dried and evaporated to give 2S,3R-6-(2-hydroxyethylidene)-2-methyl-2-(6,7-oxido-5-oxo-4,7,8-trimethylnonyl)-oxepan-3-ol.

EXAMPLE 35

2S,3R-6ξ-(2-Hydroxyethyl)-2-methyl-2-(6,7-oxido-5-oxo-4,7,8-trimethylnonyl)-oxepan-3-ol

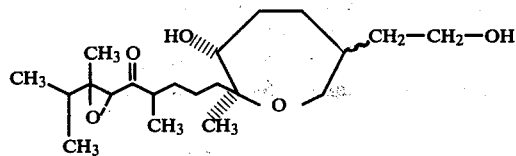

A mixture of 2S,3R-6-(2-hydroxyethylidene)-2-methyl-2-(6,7-oxido-5-oxo-4,7,8-trimethylnonyl)-oxepan-3-ol (368 mg.), platinum oxide (30 mg.), sodium nitrite (1 mg.) and absolute ethanol (50 ml.) is hydrogenated at atmospheric pressure for 1.5 hr. The resulting mixture is filtered through celite and the solvent is evaporated to give a mixture of isomers of 2S,3R-6ξ-(2-hydroxyethyl)-2-methyl-2-(6,7-oxido-5-oxo-4,7,8-trimethylnonyl)-oxepan-3-ol.

EXAMPLE 36

2S,3R-6ξ-(2-Hydroxyethyl)-2-methyl-2-(5-oxo-4,7,8-trimethyl-6-nonenyl)-oxepan-3-ol

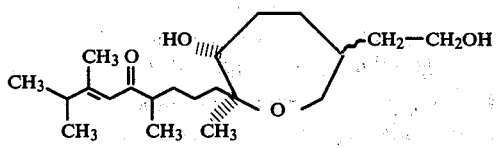

Following the procedure of Example 29 but substituting an equivalent amount of 2S,3R-6ξ-(2-hydroxyethyl)-2-methyl-2-(6,7-oxido-5-oxo-4,7,8-trimethylnonyl)-oxepan-3-ol for 2S,3R-3-acetoxy-6-(2-acetoxyethyl)-2-methyl-2-(4,8-dimethyl-7,8-oxido-5-oxononyl)-oxepane, a mixture of isomers of 2S,3R-6ξ-(2-hydroxyethyl)-2-methyl-2-(5-oxo-4,7,8-trimethyl-6-nonenyl)-oxepan-3-ol is obtained.

EXAMPLE 37

2S,3R-6-[2′-Hydroxy-(6,1′-oxido)-ethyl]-2-methyl-2-(5-oxo-4,7,8-trimethyl-6-nonenyl)-oxepan-3-ol Following the procedure of Example 31 but substituting an equivalent amount of 2S,3R-6-(2-hydroxyethylidene)-2-methyl-2-(5-oxo-4,7,8-trimethyl-6E-nonenyl)-oxepan-3-ol for 2S,3R-6-(2-hydroxyethylidene)-2-methyl-2-(4,8-dimethyl-5-oxo-7-nonenyl)-oxepan-3-ol, 2S,3R-6-[2′-hydroxy-(6,1′-oxido)ethyl]-2-methyl-2-(5-oxo-4,7,8-trimethyl-6-nonenyl)-oxepan-3-ol is obtained.

EXAMPLE 38

2S,3R-6-[2′-Hydroxy-(6,1′-oxido)-ethyl]-2-methyl-2-(5-oxo-4,7,8-trimethylnonyl)-oxepan-3-ol Following the procedure of Example 32 but substituting an equivalent amount of 2S,3R-6-[2′-hydroxy-(6,1′-oxido)-ethyl]-2-methyl-2-(5-oxo-4,7,8-trimethyl-6-nonenyl)-oxepan-3-ol for 2S,3R-6-[2′-hydroxy-(6,1′-oxido)-ethyl]-2-methyl-2-(4,8-dimethyl-5-oxo-7-nonenyl)-oxepan-3-ol, 2S,3R-6-[2′-hydroxy-(6,1′-oxido)ethyl]-2-methyl-2-(5-oxo-4,7,8-trimethylnonyl)-oxepan-3-ol is obtained.

EXAMPLE 39

2S,3R-6-(2-Hydroxyethylidene)-2-methyl-2-(5-oxo-4,7,8-trimethylnonyl)-oxepan-3-ol Following the procedure of Example 33 but substituting an equivalent amount of 2S-3R-6-[2′-hydroxy-(6,1′-oxido)-ethyl]-2-methyl-2-(5-oxo-4,7,8-trimethylnonyl)-oxepan-3-ol for 2S,3R-6-[2′-hydroxy-(6,1′-oxido)-ethyl]-2-methyl-2-(4,8-dimethyl-5-oxononyl)-oxepan-3-ol, 2S,3R-6-(2-hydroxyethylidene)-2-methyl-2-(5-oxo-4,7,8-trimethylnonyl)-oxepan-3-ol is obtained.

EXAMPLE 40

2S,3R-6-(2-Hydroxyethylidene)-2-methyl-2-(4,8-dimethyl-5-oxo-6-nonenyl)-oxepan-3-ol A solution of 2S,3R-6-(2-hydroxyethylidene)-2-methyl-2-(4,8-dimethyl-5-oxo-7-nonenyl)-oxepan-3-ol (338 mg.) in anhydrous ethanol (5 ml.) is treated with sodium (230 mg.) in ethanol (10 ml.) and the resulting solution is allowed to stand for 14 hours. The solution is then diluted with cold water and quickly extracted with ether. The organic layer is washed with saturated salt solution, dried and evaporated to give 2S,3R-6-(2-hydroxyethylidene)-2-methyl-2-(4,8-dimethyl-5-oxo-6-nonenyl)-oxepan-3-ol.

EXAMPLES 41 and 42

2S,3R-6-(2-Hydroxyethylidene)-2-methyl-2-(4,8-dimethyl-7-methylene-5-oxononyl)-oxepan-3-ol and 2S,3R-6-(2-Hydroxyethylidene)-2-methyl-2-(5-oxo-4,7,8-trimethyl-7-nonenyl)-oxepan-3-ol A solution of 2S,3R-6-(2-hydroxyethylidene)-2-methyl-2-(5-oxo-4,7,8-trimethyl-6E-nonenyl)-oxepan-3-ol (352 mg.) in t-butanol (5 ml.) is treated with a solution of potassium t-butoxide (1.12 g.) in t-butanol (50 ml.). The resulting solution is stirred at 25° for 16 hrs., then poured into 10% acetic acid (50 ml.). The reaction mixture is then treated with dilute sodium bicarbonate solution and extracted with ether. The ether extract is washed with saturated salt solution, dried and evaporated to give a mixture of 2S,3R-6-(2-hydroxyethylidene)-2-methyl-2-(4,8-dimethyl-7-methylene-5-oxononyl)-oxepan-3-ol and 2S,3R-6-(2-hydroxyethylidene)-2-methyl-2-(5-oxo-4,7,8-trimethyl-7-nonenyl)-oxepan-3-ol, which are separated by chromatography.

EXAMPLE 43

2S,3R-6-(2-Hydroxyethylidene)-2-methyl-2-(4,8-dimethyl-6,7-oxido-5-oxononyl)-oxepan-3-ol Following the procedure of Example 3, but substituting an equivalent amount of 2S,3R-6-(2-hydroxyethylidene)-2-methyl-2-(4,8-dimethyl-5-oxo-6-nonenyl)-oxepan-3-ol for 2S,3R-6-(2-hydroxyethylidene)-2-methyl-2-(5-oxo-4,7,8-trimethyl-6E-nonenyl)-oxepan-3-ol, 2S,3R-6-(2-hydroxyethylidene)-2-methyl-2-(4,8-dimethyl-6,7-oxido-5-oxononyl)-oxepan-3-ol is obtained.

EXAMPLE 44

2S,3R-6ξ-(2-Hydroxyethyl)-2-methyl-2-(4,8-dimethyl-6,7-oxido-5-oxononyl)-oxepan-3-ol

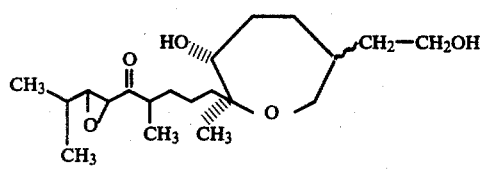

Following the procedure of Example 35 but substituting an equivalent amount of 2S,3R-6-(2-hydroxyethylidene)-2-methyl-2-(4,8-dimethyl-6,7-oxido-5-oxononyl)-oxepan-3-ol for 2S,3R-6-(2-hydroxyethylidene)-2-methyl-2-(6,7-oxido-5-oxo-4,7,8-trimethylnonyl)-oxepan-3-ol, a mixture of isomers of 2S,3R-b 6ξ-(2-hydroxyethyl)-2-methyl-2-(4,8-dimethyl-6,7-oxido-5-oxononyl)-oxepan-3-ol is obtained.

EXAMPLE 45

2S,3R-6ξ-(2-Hydroxyethyl)-2-methyl-2-(4,8-dimethyl-5-oxo-6-nonenyl)-oxepan-3-ol

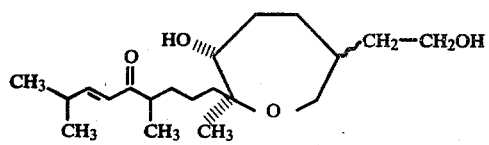

Following the procedure of Example 36 but substituting an equivalent amount of 2S,3R-6ξ-(2-hydroxyethyl)-2-methyl-2-(4,8-dimethyl-6,7-oxido-5-oxononyl)-oxepan-3-ol for 2S,3R-6-(2-hydroxyethyl)-2-methyl-2-(6,7-oxido-5-oxo-4,7,8-trimethylnonyl)-oxepan-3-ol, an isomeric mixture of 2S,3R-6ξ-(2-hydroxyethyl)-2-methyl-2-(4,8-dimethyl-5-oxo-6-nonenyl)-oxepan-3-ol is obtained.

EXAMPLE 46

2S,3R-3-Acetoxy-b 6-(2-acetoxyethylidene)-2-methyl-2-(4,8-dimethyl-7-methylene-5-oxononyl)-oxepane Following the procedure of Example 2 but substituting an equivalent amount of 2S,3R-6-(2-hydroxyethylidene)-2-methyl-2-(4,8-dimethyl-7-methylene-5-oxononyl)-oxepan-3-ol for 2S,3R-6-(2-hydroxyethylidene)-2-methyl-2-(4,8-dimethyl-5-oxo-7-nonenyl)-oxepan-3-ol, 2S,3R-3-acetoxy-6-(2-acetoxyethylidene)-2-methyl-2-(4,8-dimethyl-7-methylene-5-oxononyl)-oxepane is obtained.

EXAMPLE 47

2S,3R-3-Acetoxy-6-(2-acetoxyethylidene)-2-methyl-2-(4,8-dimethyl-7,1'-oxidomethylene-5-oxononyl)-oxepane Following the procedure of Example 27 but substituting an equivalent amount of 2S,3R-3-acetoxy-6-(2-acetoxyethylidene)-2-methyl-2-(4,8-dimethyl-7-methylene-5-oxononyl)-oxepane for 2S,3R-3-acetoxy-6-(2-acetoxyethylidene)-2-methyl-2-(4,8-dimethyl-5-oxo-7-nonenyl)-oxepane, 2S,3R-3-acetoxy-b 6-(2-acetoxyethylidene)-2-methyl-2-(4,8-dimethyl-7,1'-oxidomethylene-5-oxononyl)-oxepane is obtained.

EXAMPLE 48

2S,3R-3-Acetoxy-6ξ-(2-acetoxyethyl)-2-methyl-2-(4,8-dimethyl-7,1'-oxidomethylene-5-oxononyl)-oxepane

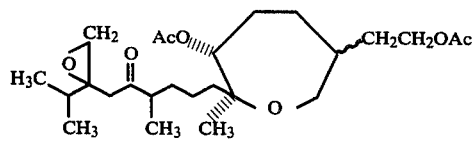

Following the procedure of Example 28 but substituting an equivalent amount of 2S,3R-3-acetoxy-6-(2-acetoxyethylidene)-2-methyl-2-(4,8-dimethyl-7,1'-oxidomethylene-5-oxononyl)-oxepane for 2S,3R-3-acetoxy-6-(2-acetoxyethylidene)-2-methyl-2-(4,8-dimethyl-7,8-oxido-5-oxononyl)-oxepane, a mixture of isomers of 2S,3R-3-acetoxy-6ξ-(2-acetoxyethyl)-2-methyl-2-(4,8-dimethyl-7,1'-oxidomethylene-5-oxononyl)-oxepane is obtained.

EXAMPLE 49

2S,3R-3-Acetoxy-6ξ-(2-acetoxyethyl)-2-methyl-2-(4,8-dimethyl-7-methylene-5-oxononyl)-oxepane

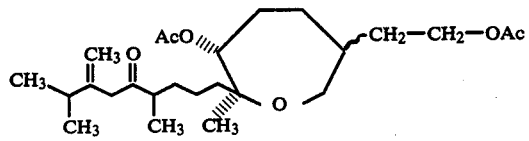

Following the procedure of Example 29 but substituting an equivalent amount of the isomeric mixture of 2S,3R-3-acetoxy-6ξ-(2-acetoxyethyl)-2-methyl-2-(4,8-dimethyl-7,1'-oxidomethylene-5-oxononyl)-oxepane for 2S,3R-3-acetoxy-6-(2-acetoxyethyl)-2-methyl-2-(4,8-dimethyl-7,8-oxido-5-oxononyl)-oxepane, a mixture of isomers of 2S,3R-3-acetoxy-6ξ-(2 -acetoxyethyl)-2-methyl-2-(4,8-dimethyl-7-methylene-5-oxononyl)-oxepane is obtained.

EXAMPLE 50

2S,3R-6ξ-(2-Hydroxyethyl)-2-methyl-2-(4,8-dimethyl-7-methylene-5-oxononyl)-oxepan-3-ol

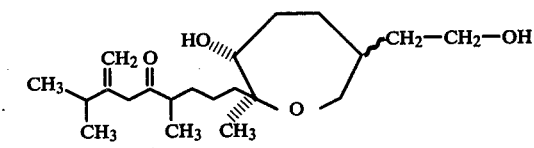

Following the procedure of Example 30 but substituting an equivalent amount of the isomeric mixture of 2S,3R-3-acetoxy-6ξ-(2-acetoxyethyl)-2-methyl-2-(4,8-dimethyl-7-methylene-5-oxononyl)-oxepane for 2S,3R-3-acetoxy-6ξ-(2-acetoxyethyl)-2-methyl-2-(4,8-dimethyl-5-oxo-7-nonenyl)-oxepane, a mixture of isomers of 2S,3R-6ξ-(2-hydroxyethyl)-2-methyl-2-(4,8-dimethyl-7-methylene-5-oxononyl)-oxepan-3-ol is obtained.

EXAMPLE 51

2S,3R-3-Acetoxy-6-(2-acetoxyethylidene)-2-methyl-2-(5-oxo-4,7,8-trimethyl-7-nonenyl)-oxepane Following the procedure of Example 2 but substituting an equivalent amount of 2S,3R-6-(2-hydroxyethylidene)-2-methyl-2-(5-oxo-4,7,8-trimethyl-7-nonenyl)-oxepan-3-ol for 2S,3R-6E-(2-hydroxyethylidene)-2-methyl-2-(4,8-dimethyl-5-oxo-7-nonenyl)-oxepan-3-ol, 2S,3R-3-acetoxy-6-(2-acetoxyethylidene)-2-methyl-2-(5-oxo-4,7,8-trimethyl-7-nonenyl)-oxepane is obtained.

EXAMPLE 52

2S,3R-3-Acetoxy-6-(2-acetoxyethylidene)-2-methyl-2-(7,8-oxido-5-oxo-4,7,8-trimethylnonyl)-oxepane Following the procedure of Example 27 but substituting an equivalent amount of 2S,3R-3-acetoxy-6-(2-acetoxyethylidene)-2-methyl-2-(5-oxo-4,7,8-trimethyl-7-nonenyl)-oxepane for 2S,3R-3-acetoxy-6-(2-acetoxyethylidene)-2-methyl-2-(4,8-dimethyl-5-oxo-7-nonenyl)-oxepane, 2S,3R-3-acetoxy-6-(2-acetoxyethylidene)-2-(7,8-oxido-5-oxo-4,7,8-trimethylnonyl)-oxepane is obtained.

EXAMPLE 53

2S,3R-3-Acetoxy-6ξ-(2-acetoxyethyl)-2-methyl-2-(7,8-oxido-5-oxo-4,7,8-trimethylnonyl)-oxepane

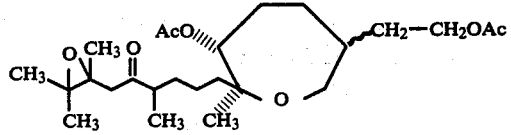

Following the procedure of Example 28 but substituting an equivalent amount of 2S,3R-3-acetoxy-6-(2-acetoxyethylidene)-2-methyl-2-(7,8-oxido-5-oxo-4,7,8-trimethylnonyl)-oxepane for 2S,3R-3-acetoxy-6-(2-acetoxyethylidene)-2-methyl-2-(4,8-dimethyl-7,8-oxido-5-oxononyl)-oxepane a mixture of isomers of 2S,3R-3-acetoxy-6ξ-(2-acetoxyethyl)-2-methyl-2-(7,8-oxido-5-oxo-4,7,8-trimethylnonyl)-oxepane is obtained.

EXAMPLE 54

2S,3R-3-Acetoxy-6ξ-(2-acetoxyethyl)-2-methyl-2-(5-oxo-4,7,8-trimethyl-7-nonenyl)-oxepane

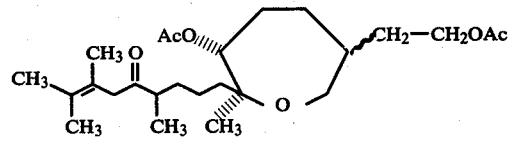

Following the procedure of Example 29 but substituting an equivalent amount of 2S,3R-3-acetoxy-6-(2-acetoxyethyl)-2-methyl-2-(7,8-oxido-5-oxo-4,7,8-trimethylnonyl)-oxepane (53a, 53b) for 2S,3R-3-acetoxy-6-(2-acetoxyethyl)-2-methyl-2-(4,8-dimethyl-7,8-oxido-5-oxononyl)-oxepane, a mixture of isomers of 2S,3R-3-acetoxy-6ξ-(2-acetoxyethyl)-2-methyl-2-(5-oxo-4,7,8-trimethyl-7-nonenyl)-oxepane is obtained.

EXAMPLE 55

2S,3R-6ξ-(2-Hydroxyethyl)-2-methyl-2-(5-oxo-4,7,8-trimethyl-7-nonenyl)-oxepan-3-ol

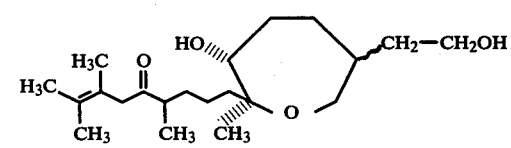

Following the procedure of Example 30 but substituting an equivalent amount of 2S,3R-3-acetoxy-6-(2-acetoxyethyl)-2-methyl-2-(5-oxo-4,7,8-trimethyl-7-nonenyl)-oxepane for 2S,3R-3-acetoxy-6-(2-acetoxyethyl)-2-methyl-2-(4,8-dimethyl-5-oxo-7-nonenyl)-oxepane, a mixture of isomers of 2S,3R-6ξ-(2-hydroxyethyl)-2-methyl-2-(5-oxo-4,7,8-trimethyl-7-nonenyl)-oxepan-3-ol is obtained.

EXAMPLE 56

2S-2-Methyl-6-carboxymethylene-2-(4,8-dimethyl-5-oxo-7-nonenyl)-oxepan-3-one A solution of 2S-6-(2-oxoethylidene)-2-methyl-2-(4,8-dimethyl-5-oxo-7-nonenyl)-oxepan-3-one (334 mg) in tetrahydrofuran:water (9:1) (10 ml.) is treated with argentic oxide (460 mg.) with vigorous stirring. After 14 hrs. the suspension is filtered, and the filtrate is evaporated to dryness. The residue is treated with dilute sodium bicarbonate solution and extracted with ether. The aqueous layer is acidified to pH 3 with dilute hydrochloric acid and extracted with ether. The ether extracts are dried and evaporated to give 2S-2-methyl-6-carboxymethylene-2-(4,8-dimethyl-5-oxo-7-nonenyl)-oxepan-3-one.

The following compounds are prepared by the method of Example 56 by substituting an equivalent amount of the appropriate starting material for 2S-6-(2-oxoethylidene)-2-methyl-2-(4,8-dimethyl-5-oxo-7-nonenyl)-oxepan-3-one.

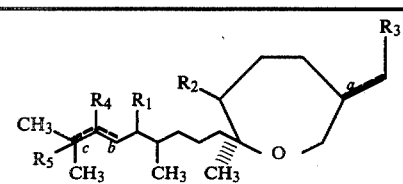

| $R_4$ | $R_5$ | a | b | c |
|---|---|---|---|---|
| $CH_3$ | H | u | u | s |
| H | H | s | s | s |
| $CH_3$ | H | s | s | s |
| H | — | s | s | u |
| H | H | u | s | s |
| $CH_3$ | H | s | u | s |
| $CH_3$ | H | u | s | s |
| H | H | u | u | s |
| $=CH_2$ | H | u | s | s |
| $CH_3$ | — | u | s | u |
| H | H | s | u | s |
| $=CH_2$ | H | s | s | s |
| $CH_3$ | — | s | s | u |
| H | OH | u | u | s |
| H | OH | s | s | s |
| H | OH | s | u | s |
| H | OH | u | s | s |

$R_1$ - =O
$R_2$ - =O
$R_3$ - —COOH
u - unsaturated
s - saturated

EXAMPLE 57

2S,3R-3-Acetoxy-2-methyl-6-carboxymethylene-2-(4,8-dimethyl-5-oxo-7-nonenyl)-oxepane Following the procedure of Example 56 but substituting an equivalent amount of 2S,3R-3-acetoxy-6-(2-oxoethylidene)-2-methyl-2-(4,8-dimethyl-5-oxo-7-nonenyl)-oxepane for 2S-6-(2-oxoethylidene)-2-methyl-2-(4,8-dimethyl-5-oxo-7-nonenyl)-oxepan-3-one, 2S,3R-3-acetoxy-2-methyl-6-carboxymethylene-2-(4,8-dimethyl-6-oxo-7-nonenyl)-oxepane is obtained.

The following compounds are prepared by the method of Example 57 by substituting an equivalent amount of the appropriate starting material for 2S,3R-3-acetoxy-6-(2-oxoethylidene)-2-methyl-2-(4,8-dimethyl-5-oxo-7-nonenyl)-oxepane.

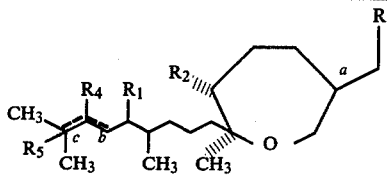

| $R_4$ | $R_5$ | a | b | c |
|---|---|---|---|---|
| $CH_3$ | H | u | u | s |
| H | H | s | s | s |
| $CH_3$ | H | s | s | s |
| H | — | s | s | u |
| H | H | u | s | s |
| $CH_3$ | H | s | u | s |
| $CH_3$ | H | u | s | s |
| H | H | u | u | s |
| $=CH_2$ | H | u | s | s |
| $CH_3$ | — | u | s | u |
| H | H | s | u | s |
| $=CH_2$ | H | s | s | s |
| $CH_3$ | — | s | s | u |
| H | OH | u | u | s |
| H | OH | s | s | s |
| H | OH | s | u | s |
| H | OH | u | s | s |

$R_1$ - =O
$R_2$ - —OAc
$R_3$ - —COOH
u - unsaturated
s - saturated

EXAMPLE 58

2S-2-Methyl-6-carboxymethylene-2-(4,8-dimethyl-5-hydroxy-7-nonenyl)-oxepan-3-one Following the procedure of Example 56 but substituting an equivalent amount of 2S-6-(2-oxoethylidene)-2-methyl-2-(4,8-dimethyl-5-hydroxy-7-nonenyl)-oxepan-3-one for 2S-6-(2-oxoethylidene)-2-methyl-2-(4,8-dimethyl-5-oxo-7-nonenyl)-oxepan-3-one, 2S-2-methyl-6-carboxymethylene-2-(4,8-dimethyl-5-hydroxy-7-nonenyl)-oxepan-3-one is obtained.

The following compounds are prepared by the method of Example 58 by substituting an equivalent amount of the appropriate starting material for 2S-6-(2-oxoethylidene)-2-methyl-2-(4,8-dimethyl-5-hydroxy-7-nonenyl)-oxepan-3-one.

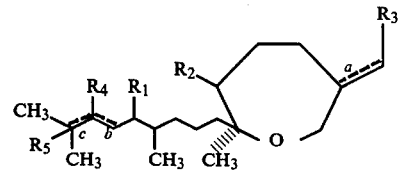

-continued

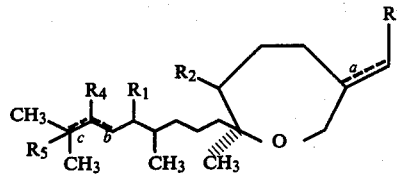

| R$_4$ | R$_5$ | a | b | c |
|---|---|---|---|---|
| =CH$_2$ | H | s | s | s |
| CH$_3$ | — | s | s | u |

R$_1$ - —OH
R$_2$ - =O
R$_3$ - —COOH
u - unsaturated
s - saturated

EXAMPLE 59

2S,3R-3-Acetoxy-2-methyl-6-carboxymethylene-2-(5-acetoxy-4,8-dimethyl-7-nonenyl)-oxepane Following the procedure of Example 56 but substituting an equivalent amount of 2S,3R-3-acetoxy-6-(2-oxoethylidene)-2-methyl-2-(5-acetoxy-4,8-dimethyl-7-nonenyl)-oxepane for 2S-6-(2-oxoethylidene)-2-methyl-2-(4,8-dimethyl-5-oxo-7-nonenyl)-oxepan-3-one, 2S,3R-3-acetoxy-2-methyl-6-carboxymethylene-2-(5-acetoxy-4,8-dimethyl-7-nonenyl)-oxepane is obtained.

The following compounds are prepared by the method of Example 59 by substituting an equivalent amount of the appropriate starting material for 2S,3R-3-acetoxy-6-(2-oxoethylidene)-2-methyl-2-(5-acetoxy-4,8-dimethyl-7-nonenyl)-oxepane.

EXAMPLE 60

2S-2-Methyl-6-carbmethoxymethylene-2-(4,8-dimethyl-5-oxo-7-nonenyl)-oxepan-3-one Method A. An excess of diazomethane is added at 0° to a mixture of 2S-2-methyl-6-carboxymethylene-2-(4,8-dimethyl-5-oxo-7-nonenyl)-oxepan-3-one (350 mg.) and ether (20 ml.). The resulting mixture is treated with glacial acetic acid (10 ml.) and then washed with 10% aqueous sodium bicarbonate solution. The organic layer is dried and evaporated to give 2S-2-methyl-6-carbmethoxymethylene-2-(4,8-dimethyl-5-oxo-7-nonenyl)-oxepan-3-one.

Method B. A mixture of 2S-2-methyl-6-carboxymethylene-2-(4,8-dimethyl-5-oxo-7-nonenyl)-oxepan-3-one (350 mg.), methanol (10 ml.) and concentrated sulfuric acid (0.1 ml.) is refluxed for 5 hrs. under nitrogen, then treated with water (50 ml.) at 0°. Most of the methanol is removed in vacuo and the residue is extracted with ether. The organic layer is dried and evaporated to give 2S-2-methyl-6-carbmethoxymethylene-2-(4,8-dimethyl-5-oxo-7-nonenyl)-oxepan-3-one.

The following compounds are prepared by the methods of Example 60 by substituting an equivalent amount of the appropriate starting material for 2S-2-methyl-6-carboxymethylene-2-(4,8-dimethyl-5-oxo-7-nonenyl)-oxepan-3-one.

Similarly, by substituting an appropriate alcohol for methanol in the procedure of Example 60, (Method B), the corresponding esters are formed. Thus, for example, ethanol, propanol, t-butanol and benzyl alcohol afford the ethyl, propyl, t-butyl and benzyl esters respectively.

| R$_4$ | R$_5$ | a | b | c |
|---|---|---|---|---|
| CH$_3$ | H | u | u | s |
| H | H | s | s | s |
| CH$_3$ | H | s | s | s |
| H | — | s | s | u |
| H | H | u | s | s |
| CH$_3$ | H | s | u | s |
| CH$_3$ | H | u | s | s |
| H | H | u | u | s |
| =CH$_2$ | H | u | s | s |
| CH$_3$ | — | u | s | u |
| H | H | s | u | s |
| =CH$_2$ | H | s | s | s |
| CH$_3$ | — | s | s | u |
| H | OH | u | u | s |
| H | OH | s | s | s |
| H | OH | s | u | s |
| H | OH | u | s | s |

R$_1$ - —OAc
R$_2$ - —OAc
R$_3$ - —COOH
u - unsaturated
s - saturated

| R$_4$ | R$_5$ | R$_6$ | a | b | c | Method |
|---|---|---|---|---|---|---|
| CH$_3$ | H | CH$_3$ | u | u | s | A |
| H | H | C$_2$H$_5$ | s | s | s | B |
| CH$_3$ | H | C$_4$H$_9$ | s | s | s | B |
| H | — | C$_3$H$_7$ | s | s | u | B |
| H | H | CH$_3$ | u | s | s | A |
| CH$_3$ | H | C$_2$H$_5$ | s | u | s | B |
| CH$_3$ | H | CH$_3$ | u | s | s | A |
| H | H | CH$_3$ | u | u | s | A |
| =CH$_2$ | H | CH$_3$ | u | s | s | A |
| CH$_3$ | — | CH$_3$ | u | s | u | A |
| H | H | C$_3$H$_7$ | s | u | s | B |
| =CH$_2$ | H | C$_2$H$_5$ | s | s | s | B |
| CH$_3$ | — | C$_3$H$_7$ | s | s | u | B |
| H | OH | CH$_3$ | u | u | s· | A |
| H | OH | C$_3$H$_7$ | s | s | s | B |
| H | OH | C$_2$H$_5$ | s | u | s | B |
| H | OH | C$_3$H$_7$ | u | s | s | B |

R$_1$ - =O
R$_2$ - =O
R$_3$ - —COOR$_6$
u - unsaturated
s - saturated

The following compounds are prepared by the methods of Example 60 by substituting an equivalent amount of the appropriate starting material for 2S-2-methyl-6-carboxymethylene-2-(4,8-dimethyl-5-oxo-7-nonenyl)-oxepan-3-one.

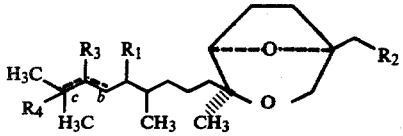

| $R_3$ | $R_4$ | $R_5$ | b | c | Method |
|---|---|---|---|---|---|
| $CH_3$ | H | $CH_3$ | u | s | A |
| H | H | $C_4H_9$ | s | s | B |
| $CH_3$ | H | $CH_3$ | s | s | A |
| H | H | $-CH_2-C_6H_5$ | u | s | B |
| $=CH_2$ | H | $C_6H_5$ | s | s | B |
| $CH_3$ | — | $C_2H_5$ | s | u | B |
| H | OH | $CH_3$ | u | s | A |
| H | OH | $CH_3$ | s | s | A |

$R_1$ - —OH
$R_2$ - —COOR$_5$
u - unsaturated
s - saturated

The following compounds are prepared by the methods of Example 60 by substituting an equivalent amount of the appropriate starting material for 2S-2-methyl-6-carboxymethylene-2-(4,8-dimethyl-5-oxo-7-nonenyl)-oxepan-3-one.

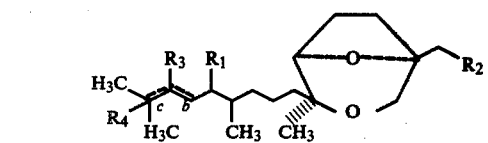

| $R_3$ | $R_4$ | $R_5$ | b | c | Method |
|---|---|---|---|---|---|
| $CH_3$ | H | $CH_3$ | u | s | A |
| H | H | $C_2H_5$ | s | s | B |
| $CH_3$ | H | $C_4H_9$ | s | s | B |
| H | H | $C_3H_7$ | u | s | B |
| $=CH_2$ | H | $C_3H_7$ | s | s | B |
| $CH_3$ | — | $C_2H_5$ | s | u | B |
| H | OH | $CH_3$ | u | s | A |
| H | OH | $CH_3$ | s | s | A |

$R_1$ - =O
$R_2$ - —COOR$_5$
u - unsaturated
s - saturated

EXAMPLE 61

2S,3R-3-Acetoxy-2-methyl-6-carbmethoxymethylene-2-(4,8-dimethyl-5-oxo-7-nonenyl)-oxepane Following the procedures of Example 60 but substituting an equivalent amount of 2S,3R-3-acetoxy-2-methyl-6-carboxymethylene-2-(4,8-dimethyl-5-oxo-7-nonenyl)-oxepane for 2S-2-methyl-6-carboxymethylene-2-(4,8-dimethyl-5-oxo-7-nonenyl)-oxepan-3-one, 2S,3R-3-acetoxy-2-methyl-6-carbmethoxymethylene-2-(4,8-dimethyl-5-oxo-7-nonenyl)-oxepane is obtained.

The following compounds are prepared by the methods of Example 61 by substituting an equivalent amount of the appropriate starting material for 2S,3R-3-acetoxy-2-methyl-6-carboxymethylene-2-(4,8-dimethyl-5-oxo-7-nonenyl)-oxepane.

Similarly, by substituting an appropriate alcohol for methanol in the procedure of Example 61, (Method B), the corresponding esters are formed. Thus, for example, ethanol, propanol, t-butanol and benzyl alcohol afford the ethyl, propyl, t-butyl and benzyl esters respectively.

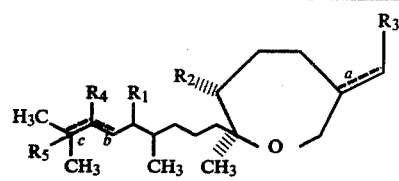

| $R_4$ | $R_5$ | $R_6$ | a | b | c | Method |
|---|---|---|---|---|---|---|
| $CH_3$ | H | $CH_3$ | u | u | s | A |
| H | H | $-C_4H_9$ | s | s | s | B |
| $CH_3$ | H | $-C_2H_5$ | s | s | s | B |
| H | — | $-CH_2-C_6H_5$ | s | s | u | B |
| H | H | $CH_3$ | u | s | s | A |
| $CH_3$ | H | $C_3H_7$ | s | u | s | B |
| $CH_3$ | H | $CH_3$ | u | s | s | A |
| H | H | $CH_3$ | u | u | s | A |
| $=CH_2$ | H | $CH_3$ | u | s | s | A |
| $CH_3$ | — | $CH_3$ | u | s | u | A |
| H | H | $C_3H_7$ | s | u | s | B |
| $=CH_2$ | H | $C_2H_5$ | s | s | s | B |
| $CH_3$ | — | $C_4H_9$ | s | s | u | B |
| H | OH | $CH_3$ | u | u | s | A |
| H | OH | $C_2H_5$ | s | s | s | B |
| H | OH | $C_3H_7$ | s | u | s | B |
| H | OH | $C_4H_9$ | u | s | s | B |

$R_1$ - =O
$R_2$ - —OAc
$R_3$ - —COOR$_6$
u - unsaturated
s - saturated

EXAMPLE 62

2S-2-Methyl-6-carbmethoxymethylene-2-(4,8-dimethyl-5-hydroxy-7-nonenyl)-oxepan-3-one Following the procedure of Example 60 but substituting an equivalent amount of 2S-2-methyl-6-carboxymethylene-2-(4,8-dimethyl-5-hydroxy-7-nonenyl)-oxepan-3-one for 2S-2-methyl-6-carboxymethylene-2-(4,8-dimethyl-5-oxo-7-nonenyl)-oxepan-3-one, 2S-2-methyl-6-carbmethoxymethylene-2-(4,8-dimethyl-5-hydroxy-7-nonenyl)-oxepan-3-one is obtained.

The following compounds are prepared by the methods of Example 62 by substituting an equivalent amount of the appropriate starting material for 2S-2-methyl-6-carboxymethylene-2-(4,8-dimethyl-5-hydroxy-7-nonenyl)-oxepan-3-one.

Similarly, by substituting an appropriate alcohol for methanol in the procedure of Example 62, (Method B), the corresponding esters are formed. Thus, for example, ethanol, propanol, t-butanol and benzyl alcohol afford the ethyl, propyl, t-butyl and benzyl esters respectively.

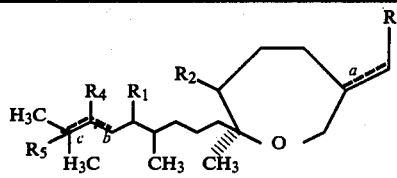

| R4 | R5 | R6 | a | b | c | Method |
|---|---|---|---|---|---|---|
| CH3 | H | CH3 | u | u | s | A |
| H | H | —CH2—C6H5 | s | s | s | B |
| CH3 | H | C3H7 | s | s | s | B |
| H | — | —C4H9 | s | s | u | B |
| H | H | CH3 | u | s | s | A |
| CH3 | H | —C2H5 | s | u | s | B |
| CH3 | H | CH3 | u | s | s | A |
| H | H | CH3 | u | u | s | A |
| =CH2 | H | CH3 | u | s | s | A |
| CH3 | — | CH3 | u | s | u | A |
| H | H | —C3H7 | s | u | s | B |
| =CH2 | H | —C2H5 | s | s | s | B |
| CH3 | — | CH3 | s | s | u | B |

R1 - —OH
R2 - =O
R3 - —COOR6
u - unsaturated
s - saturated

EXAMPLE 63

2S,3R-3-Acetoxy-2-methyl-6-carbmethoxymethylene-2-(5-acetoxy-4,8-dimethyl-7-nonenyl)-oxepane Following the procedure of Example 60 but substituting an equivalent amount of 2S,3R-3-acetoxy-2-methyl-6-carboxymethylene-2-(5-acetoxy-4,8-dimethyl-7-nonenyl)-oxepane for 2S-2-methyl-6-carboxymethylene-2-(4,8-dimethyl-5-oxo-7-nonenyl)-oxepan-3-one affords 2S,3R-3-acetoxy-2-methyl-6-carbmethoxymethylene-2-(5-acetoxy-4,8-dimethyl-7-nonenyl)-oxepane.

Similarly, by substituting an appropriate alcohol for methanol in the procedure of Example 63 (Method B), the corresponding esters are formed. Thus, for example, ethanol, propanol, t-butanol and benzyl alcohol afford the ethyl, propyl, t-butyl and benzyl esters respectively.

The following compounds are prepared by the method of Example 63 by substituting an equivalent amount of the appropriate starting material for 2S,3R-3-acetoxy-2-methyl-6-carboxymethylene-2-(5-acetoxy-4,8-dimethyl-7-nonenyl)-oxepane.

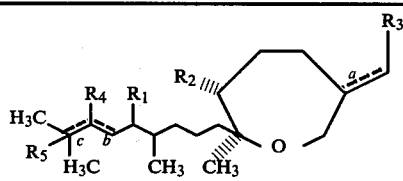

| R4 | R5 | R6 | a | b | c | Method |
|---|---|---|---|---|---|---|
| CH3 | H | CH3 | u | u | s | A |
| H | H | C2H5 | s | s | s | B |
| CH3 | H | C3H7 | s | s | s | B |
| H | — | C3H7 | s | s | u | B |
| H | H | CH3 | u | s | s | A |
| CH3 | H | —C4H9 | s | u | s | B |
| CH3 | H | CH3 | u | s | s | A |
| H | H | CH3 | u | u | s | A |
| =CH2 | H | CH3 | u | s | s | A |
| CH3 | — | CH3 | u | s | u | A |

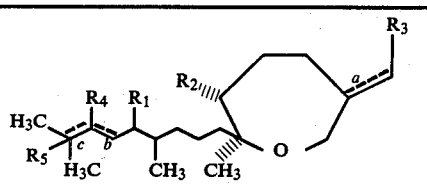

| R4 | R5 | R6 | a | b | c | Method |
|---|---|---|---|---|---|---|
| H | H | —CH2—C6H5 | s | u | s | B |
| =CH2 | H | C2H5 | s | s | s | B |
| CH3 | — | CH3 | s | s | u | B |
| H | OH | CH3 | u | u | s | A |
| H | OH | —C3H7 | s | s | s | B |
| H | OH | C2H5 | s | u | s | B |
| H | OH | C4H9 | u | s | s | B |

R1 - —OAc
R2 - —OAc
R3 - —COOR6
u - unsaturated
s - saturated

EXAMPLE 64

2S-2-Methyl-6-carboxymethylene-2-(4,8-dimethyl-5-oxo-7-nonenyl)-oxepan-3-one, sodium salt A solution of 2S-2-methyl-6-carboxymethylene-2-(4,8-dimethyl-5-oxo-7-nonenyl)-oxepan-3-one (350 mg.) in 1:1 tetrahydrofuran:water (10 ml.) is titrated with an equivalent amount of 1 N sodium hydroxide solution. The resulting solution is evaporated to afford 2S-2-methyl-6-carboxymethylene-2-(4,8-dimethyl-5-oxo-7-nonenyl)-oxepan-3-one, sodium salt.

Similarly, by substituting other basic hydroxides for sodium hydroxide in the procedure of Example 64, the corresponding salts are formed. Thus, for example, potassium hydroxide and ammonium hydroxide afford the potassium and ammonium salts respectively.

The following compounds are prepared by the method of Example 64 by substituting an equivalent amount of the appropriate starting material for 2S-2-methyl-6-carboxymethylene-2-(4,8-dimethyl-5-oxo-7-nonenyl)-oxepan-3-one.

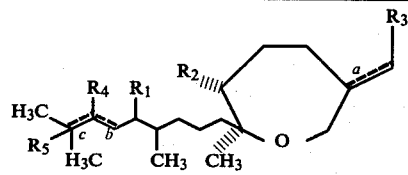

| R4 | R5 | R6 | a | b | c |
|---|---|---|---|---|---|
| CH3 | H | Na | u | u | s |
| H | H | K | s | s | s |
| CH3 | H | Li | s | s | s |
| H | — | Na | s | s | u |
| H | H | (½ Ca) | u | s | s |
| CH3 | H | K | s | u | s |
| CH3 | H | (½ Mg) | u | s | s |
| H | H | Na | u | u | s |
| =CH2 | H | Li | u | s | s |
| CH3 | — | Na | u | s | u |
| H | H | Na | s | u | s |
| =CH2 | H | NH4 | s | s | s |
| CH3 | — | Na | s | s | u |
| H | OH | NH4 | u | u | s |
| H | OH | Li | s | s | s |
| H | OH | (½ Ca) | s | u | s |

-continued

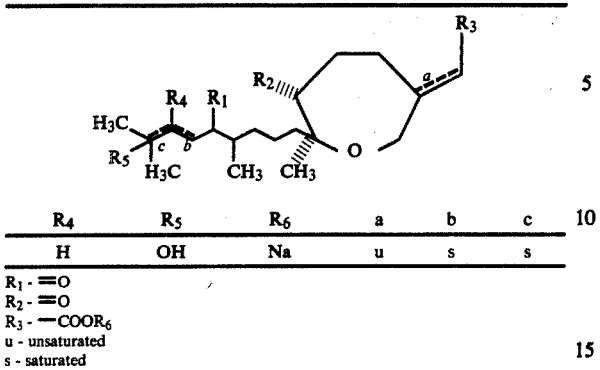

| R4 | R5 | R6 | a | b | c |
|---|---|---|---|---|---|
| H | OH | Na | u | s | s |

$R_1$ - =O
$R_2$ - =O
$R_3$ - —$COOR_6$
u - unsaturated
s - saturated

EXAMPLE 65

2S,3R-3-Acetoxy-2-methyl-6-chloroformylmethylene-2-(4,8-dimethyl-5-oxo-7-nonenyl)-oxepane A solution of oxalyl chloride (1.65 ml.) in dry benzene (5 ml.) is slowly added to a stirred solution of 2S,3R-3-acetoxy-2-methyl-6-carboxymethylene-2-(4,8-dimethyl-5-oxo-7-nonenyl)-oxepane (394 mg.) in dry benzene (15 ml.) at 0°, and the mixture stirred at 0° for 1 hr. The solvent and excess of oxalyl chloride are removed in vacuo to afford 2S,3R-3-acetoxy-2-methyl-6-chloroformylmethylene-2-(4,8-dimethyl-5-oxo-7-nonenyl)-oxepane.

EXAMPLE 66

2S,3R-3-Acetoxy-2-methyl-6-carbamoylmethylene-2-(4,8-dimethyl-5-oxo-7-nonenyl)-oxepane To a well chilled (−30°) and stirred solution of anhydrous ammonia (34 mg.) in dry methylene chloride (25 ml.) is slowly added a solution of freshly prepared 2S,3R-3-acetoxy-2-methyl-6-chloroformylmethylene-2-(4,8-dimethyl-5-oxo-7-nonenyl)-oxepane (413 mg.) in dry methylene chloride (25 ml.) over a period of 3 hrs. while maintaining the reaction temperature below 0°. The solvent is evaporated in vacuo to afford 2S,3R-3-acetoxy-2-methyl-6-carbamoylmethylene-2-(4,8-dimethyl-5-oxo-7-nonenyl)-oxepane.

Similarly, by substituting appropriate amines for ammonia in the procedure of Example 66, the corresponding amides are prepared. Thus, for example, dimethylamine, ethylamine, benzylamine and diphenylamine afford the dimethylamide, ethylamide, benzylamide and diphenylamide respectively.

Similarly, by substituting hydrazines and substituted hydrazides for ammonia in the procedure of Example 66, the corresponding acylhydrazides are formed. Thus, for example, hydrazine, dimethylhydrazine, phenylhydrazine and p-toluenesulfonylhydrazide afford the corresponding hydrazide, dimethylhydrazide, phenylhydrazide and p-toluenesulfonylhydrazides respectively.

The following compounds are prepared by the method of Example 66 by substituting an equivalent amount of the appropriate starting material for 2S,3R-3-acetoxy-2-methyl-6-chloroformylmethylene-2-(4,8-dimethyl-5-oxo-7-nonenyl)-oxepane and the appropriate amino compound.

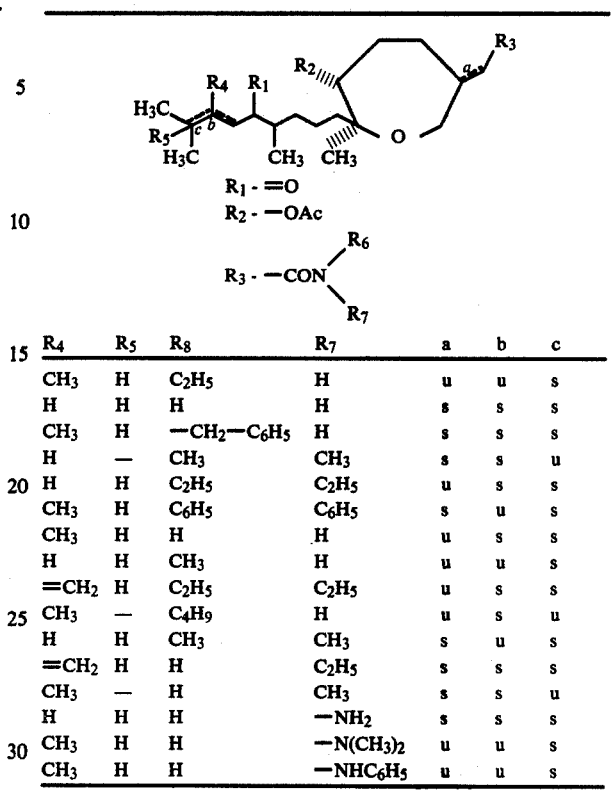

$R_1$ - =O
$R_2$ - —OAc
$R_3$ - —CON$\begin{smallmatrix}R_6\\R_7\end{smallmatrix}$

| R4 | R5 | R8 | R7 | a | b | c |
|---|---|---|---|---|---|---|
| CH3 | H | C2H5 | H | u | u | s |
| H | H | H | H | s | s | s |
| CH3 | H | —CH2—C6H5 | H | s | s | s |
| H | — | CH3 | CH3 | s | s | u |
| H | H | C2H5 | C2H5 | u | s | s |
| CH3 | H | C6H5 | C6H5 | s | u | s |
| CH3 | H | H | H | u | s | s |
| H | H | CH3 | H | u | u | s |
| =CH2 | H | C2H5 | C2H5 | u | s | s |
| CH3 | — | C4H9 | H | u | s | u |
| H | H | CH3 | CH3 | s | u | s |
| =CH2 | H | H | C2H5 | s | s | s |
| CH3 | — | H | CH3 | s | s | u |
| H | H | H | —NH2 | s | s | s |
| CH3 | H | H | —N(CH3)2 | u | u | s |
| CH3 | H | H | —NHC6H5 | u | u | s | u - unsaturated
s - saturated

EXAMPLE 67

2S,3R-3-Acetoxy-2-methyl-6-carbamoylmethylene-2-(4,8-dimethyl-5-hydroxy-7-nonenyl)-oxepane To a solution of 2S,3R-3-acetoxy-2-methyl-6-carbamoylmethylene-2-(4,8-dimethyl-5-oxo-7-nonenyl)-oxepane (381 mg.) in ethanol (20 ml.) at 0° is slowly added sodium borohydride (40 mg.) and the mixture stirred at 0° for 5 minutes. The mixture is then quickly treated with saturated aqueous ammonium chloride solution and extracted with chloroform. The chloroform extract is washed with brine, dried and evaporated to dryness in vacuo to afford 2S,3R-3-acetoxy-2-methyl-6-carbamoylmethylene-2-(4,8-dimethyl-5-hydroxy-7-nonenyl)-oxepane.

Similarly, by substituting appropriate keto amides for 2S,3R-3-acetoxy-2-methyl-6-carbamoylmethylene-2-(4,8-dimethyl-5-oxo-7-nonenyl)-oxepane in the procedure of Example 67, the corresponding hydroxy amides are formed. Thus, for example, the dimethylamide and ethylamide of Example 66 afford the corresponding hydroxyamides.

The following compounds are prepared by the method of Example 67 by substituting an equivalent amount of the appropriate starting material for 2S,3R-3-acetoxy-2-methyl-6-carbamoylmethylene-2-(4,8-dimethyl-5-oxo-7-nonenyl)-oxepane.

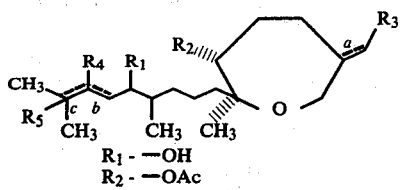

| R$_4$ | R$_5$ | R$_6$ | R$_7$ | a | b | c |
|---|---|---|---|---|---|---|
| CH$_3$ | H | C$_2$H$_5$ | H | u | u | s |
| H | H | H | H | s | s | s |
| CH$_3$ | H | —CH$_2$—C$_6$H$_5$ | H | s | s | s |
| H | — | CH$_3$ | CH$_3$ | s | s | u |
| H | H | C$_2$H$_5$ | C$_2$H$_5$ | u | s | s |
| CH$_3$ | H | —C$_6$H$_5$ | C$_6$H$_5$ | s | u | s |
| CH$_3$ | H | H | H | u | s | s |
| H | H | CH$_3$ | H | u | u | s |
| =CH$_2$ | H | C$_2$H$_5$ | C$_2$H$_5$ | u | s | s |
| CH$_3$ | — | C$_4$H$_9$ | H | u | s | u |
| H | H | CH$_3$ | CH$_3$ | s | u | s |
| =CH$_2$ | H | H | C$_2$H$_5$ | s | s | s |
| CH$_3$ | — | H | CH$_3$ | s | s | u | u - unsaturated
s - saturated

EXAMPLE 68

2S-2-Methyl-6-carboxymethylene-2-(5-acetoxy-4,8-dimethyl-7-nonenyl)-oxepan-3-one Following the procedure of Example 2 but substituting an equivalent amount of 2S-2-methyl-6-carboxymethylene-2-(4,8-dimethyl-5-hydroxy-7-nonenyl)-oxepan-3-one for 2S,3R-6-(2-hydroxyethylidene)-2-methyl-2-(4,8-dimethyl-5-oxo-7-nonenyl)-oxepan-3-ol, there is obtained 2S-2-methyl-6-carboxymethylene-2-(5-acetoxy-4,8-dimethyl-7-nonenyl)-oxepan-3-one.

EXAMPLE 69

2S-2-Methyl-6-chloroformylmethylene-2-(5-acetoxy-4,8-dimethyl-7-nonenyl)-oxepan-3-one Following the procedure of Example 65 but substituting an equivalent amount of 2S-2-methyl-6-carboxymethylene-2-(5-acetoxy-4,8-dimethyl-7-nonenyl)-oxepan-3-one for 2S,3R-3-acetoxy-2-methyl-6-carboxymethylene-2-(4,8-dimethyl-5-oxo-7-nonenyl)-oxepane, there is obtained 2S-2-methyl-6-chloroformylmethylene-2-(5-acetoxy-4,8-dimethyl-7-nonenyl)-oxepan-3-one.

EXAMPLE 70

2S-2-Methyl-6-carbamoylmethylene-2-(5-acetoxy-4,8-dimethyl-7-nonenyl)-oxepan-3-one Following the procedure of Example 66 but substituting an equivalent amount of 2S-2-methyl-6-chloroformylmethylene-2-(5-acetoxy-4,8-dimethyl-7-nonenyl)-oxepan-3-one for 2S,3R-3-acetoxy-2-methyl-6-chloroformylmethylene-2-(4,8-dimethyl-5-oxo-7-nonenyl)-oxepane, there is obtained 2S-2-methyl-6-carbamoylmethylene-2-(5-acetoxy-4,8-dimethyl-7-nonenyl)-oxepan-3-one.

Similarly by substituting appropriate amines for ammonia in the procedure of Example 70, the corresponding amides are formed. Thus, for example, diethylamine, methylamine and diphenylamine afford the diethylamide, methylamide and diphenylamide respectively.

EXAMPLE 71

2S-2-Methyl-6-carbamoylmethylene-2-(4,8-dimethyl-5-hydroxy-7-nonenyl)-oxepan-3-one Following the procedure of Example 10 but substituting an equivalent amount of 2S-2-methyl-6-carbamoylmethylene-2-(5-acetoxy-4,8-dimethyl-7-nonenyl)-oxepan-3-one for 2S,3R-3-acetoxy-6-[2-(tetrahydropyran-2-yloxy)-ethylidene]-2-methyl-2-[4,8-dimethyl-5-(tetrahydropyran-2-yloxy)-7-nonenyl]-oxepane, there is obtained 2S-2-methyl-6-carbamoylmethylene-2-(4,8-dimethyl-5-hydroxy-7-nonenyl)-oxepan-3-one.

Similarly, by substituting appropriate N-substituted acetoxy amides from Example 70 for 2S-2-methyl-6-carbamoylmethylene-2-(5-acetoxy-4,8-dimethyl-7-nonenyl)-oxepan-3-one in the procedure of Example 71, the corresponding hydroxy amides are obtained.

The following compounds are prepared by the method of Example 71 by substituting an equivalent amount of the appropriate starting material for 2S-2-methyl-6-carbamoylmethylene 2-(5-acetoxy-4,8-dimethyl-7-nonenyl)-oxepan-3-one.

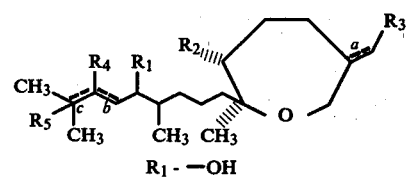

| R$_4$ | R$_5$ | R$_6$ | R$_7$ | a | b | c |
|---|---|---|---|---|---|---|
| CH$_3$ | H | C$_2$H$_5$ | H | u | u | s |
| H | H | H | H | s | s | s |
| CH$_3$ | H | —CH$_2$—C$_6$H$_5$ | H | s | s | s |
| H | — | CH$_3$ | CH$_3$ | s | s | u |
| H | H | C$_2$H$_5$ | C$_2$H$_5$ | u | s | s |
| CH$_3$ | H | C$_6$H$_5$ | C$_6$H$_5$ | s | u | s |
| CH$_3$ | H | H | H | u | s | s |
| H | H | CH$_3$ | H | u | u | s |
| =CH$_2$ | H | C$_2$H$_5$ | C$_2$H$_5$ | u | s | s |
| CH$_3$ | — | C$_4$H$_9$ | H | u | s | u |
| H | H | CH$_3$ | CH$_3$ | s | u | s |
| =CH$_2$ | H | H | C$_2$H$_5$ | s | s | s |
| CH$_3$ | — | H | CH$_3$ | s | s | u | u - unsaturated
s - saturated

EXAMPLE 72

2S-2-Methyl-6-chloroformylmethylene-2-(4,8-dimethyl-5-oxo-7-nonenyl)-oxepan-3-one Following the procedure of Example 65 but substituting an equivalent amount of 2S-2-methyl-6-carboxymethylene-2-(4,8-dimethyl-5-oxo-7-nonenyl)oxepan-3-one for 2S,3R-3-acetoxy-2-methyl-6-carboxymethylene-2-(4,8-dimethyl-5-oxo-7-nonenyl)-oxepane, there is obtained 2S-2-methyl-6-chloroformylmethylene-2-(4,8-dimethyl-5-oxo-7-nonenyl)-oxepan-3-one.

EXAMPLE 73

2S-2-Methyl-6-carbamoylmethylene-2-(4,8-dimethyl-5-oxo-7-nonenyl)-oxepan-3-one

Following the procedure of Example 66 but substituting an equivalent amount of 2S-2-methyl-6-chloroformylmethylene-2-(4,8-dimethyl-5-oxo-7-nonenyl)-oxepan-3-one for 2S,3R-3-acetoxy-2-methyl-6-chloroformylmethylene-2-(4,8-dimethyl-5-oxo-7-nonenyl)-oxepane, there is obtained 2S-2-methyl-6-carbamoylmethylene-2-(4,8-dimethyl-5-oxo-7-nonenyl)-oxepan-3-one.

Similarly, by substituting appropriate amines for ammonia in the procedure of Example 73, the corresponding amides are formed. Thus, for example, butylamine, dipropylamine and dibenzylamine afford the butylamide, dipropylamide and dibenzylamide respectively.

The following compounds are prepared by the method of Example 73 by substituting an equivalent amount of the appropriate starting material for 2S-2-methyl-6-chloroformylmethylene-2-(4,8-dimethyl-5-oxo-7-nonenyl)-oxepan-3-one.

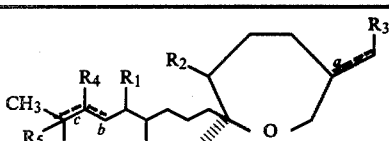

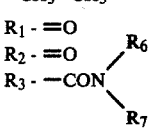

| $R_4$ | $R_5$ | $R_6$ | $R_7$ | a | b | c |
|---|---|---|---|---|---|---|
| $CH_3$ | H | H | H | u | u | s |
| H | H | $CH_3$ | $CH_3$ | s | s | s |
| $CH_3$ | H | $CH_3$ | H | s | s | s |
| H | — | H | $-CH_2-C_6H_5$ | s | s | u |
| H | H | $-CH_2-C_6H_5$ | $-CH_2-C_6H_5$ | u | s | s |
| $CH_3$ | H | $C_2H_5$ | $C_2H_5$ | s | u | s |
| $CH_3$ | H | $C_3H_7$ | H | u | s | s |
| H | H | H | H | u | u | s |
| $=CH_2$ | H | $CH_3$ | $CH_3$ | u | s | s |
| $CH_3$ | — | $CH_3$ | $-CH_2-C_6H_5$ | u | s | u |
| H | H | $C_6H_5$ | $-C_2H_5$ | s | u | s |
| $=CH_2$ | H | $-CH_3$ | $-H$ | s | s | s |
| $CH_3$ | — | $-H$ | $-H$ | s | s | u | u - unsaturated
s - saturated

EXAMPLE 74

2S-3,3-Dimethoxy-6-(2-hydroxyethylidene)-2-methyl-2-(5,5-dimethoxy-4,8-dimethyl-7-nonenyl)-oxepane A solution of 2S-6-(2-hydroxyethylidene)-2-methyl-2-(4,8-dimethyl-5-oxo-7-nonenyl)-oxepan-3-one (336 mg.) in absolute methanol (2 ml.) and trimethyl orthoformate (1 ml.) is treated with one drop of 4.4 N methylsulfuric acid. After stirring for 24 hrs. at room temperature, the solution is made basic with cold 5% sodium hydroxide in methanol, diluted with cold water and extracted with ether. The ether extract is washed with water, dried and evaporated to give 2S-3,3-dimethoxy-6-(2-hydroxyethylidene)-2-methyl-2-(5,5-dimethoxy-4,8-dimethyl-7-nonenyl)-oxepane.

EXAMPLE 75

2S-3,3-Dimethoxy-6-(2-oxoethylidene)-2-methyl-2-(5,5-dimethoxy-4,8-dimethyl-7-nonenyl)-oxepane Following the procedure of Example 11, but substituting an equivalent amount of 2S-3,3-dimethoxy-6-(2-hydroxyethylidene)-2-methyl-2-(5,5-dimethoxy-4,8-dimethyl-7-nonenyl)-oxepane for 2S,3R-6-([2-(tetrahydropyran-2-yloxy)-ethyliene]-2-methyl-2-[4,8-dimethyl-5-(tetrahydropyran-2-yloxy)-7-nonenyl]-oxepan-3-ol affords 2S-3,3-dimethoxy-6-(2-oxoethylidene)-2-methyl-2-(5,5-dimethoxy-4,8-dimethyl-7-nonenyl)-oxepane.

EXAMPLE 76

2S-3,3-Dimethoxy-6-[2-(hydroxyimino)-ethylidene]-2-methyl-2-(5,5-dimethoxy-4,8-dimethyl-7-nonenyl)oxepane A solution of 2S-3,3-dimethoxy-6-(2-oxoethylidene)-2-methyl-2-(5,5-dimethoxy-4,8-dimethyl-7-nonenyl)-oxepane (426 mg.) in anhydrous pyridine (5 ml.) is treated with a solution of hydroxylamine hydrochloride (200 mg.) in pyridine (2 ml.). After standing at 25° C. for 24 hrs., the pyridine is evaporated and the residue is partitioned between ether and water. The aqueous layer is further extracted with ether and the combined organic extract is dried and evaporated to give 2S-3,3-dimethoxy-6-[2-(hydroxyimino)-ethylidene]-2-methyl-2-(5,5-dimethoxy-4,8-dimethyl-7-nonenyl)-oxepane.

EXAMPLE 77

2S-3,3-Dimethoxy-2-methyl-6-cyanomethylene-2-(5,5-dimethoxy-4,8-dimethyl-7-nonenyl)-oxepane A solution of 2S-3,3-dimethoxy-6-[2-(hydroxyimino)ethylidene]-2-methyl-2-(5,5-dimethoxy-4,8-dimethyl-7-nonenyl)-oxepane (441 mg.) in acetic anhydride (1 ml.) is treated with anhydrous sodium acetate (3 mg.) at reflux for 5 hrs. The reaction mixture is poured into cold water (10 ml.) and extracted with ether. The combined ether extracts are dried and evaporated to give 2S-3,3-dimethoxy-2-methyl-6-cyanomethylene-2-(5,5-dimethoxy-4,8-dimethyl-7-nonenyl)-oxepane.

EXAMPLE 78

2S-2-Methyl-6-cyanomethylene-2-(4,8-dimethyl-5-oxo-7-nonenyl)-oxepan-3-one

A solution of 2S-3,3-dimethoxy-2-methyl-6-cyanomethylene-2-(5,5-dimethoxy-4,8-dimethyl-7-nonenyl)-oxepane (423 mg.) in a 2:1 mixture of chloroform:5% aqueous trifluoroacetic acid (30 ml.) is stirred at 25° C. for 2 hrs. The organic and aqueous phases are separated, the aqueous phase is extracted with additional chloroform, and the organic extracts are combined, dried and evaporated to give 2S-2-methyl-6-cyanomethylene-2-(4,8-dimethyl-5-oxo-7-nonenyl)-oxepan-3-one.

The following compounds are prepared by the method of Example 78 by substituting an equivalent amount of the appropriate starting material for 2S-3,3-dimethoxy-2-methyl-6-cyanomethylene-2-(5,5-dimethoxy-4,8-dimethyl-7-nonenyl)-oxepane.

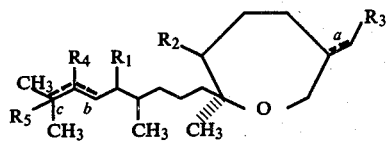

R₁ - =O
R₂ - =O
R₃ - —C≡N

| R₄ | R₅ | a | b | c |
|---|---|---|---|---|
| CH₃ | H | u | u | s |
| H | H | s | s | s |
| CH₃ | H | s | s | s |
| H | — | s | s | u |
| H | H | u | s | s |
| CH₃ | H | s | u | s |
| CH₃ | H | u | s | s |
| H | H | u | u | s |
| =CH₂ | H | u | s | s |
| CH₃ | — | u | s | u |
| H | H | s | u | s |
| =CH₂ | H | s | s | s |
| CH₃ | — | s | s | u | u - unsaturated
s - saturated

EXAMPLE 79

2S,3R-3-Acetoxy-6-[2-(hydroxyimino)-ethylidene]-2-methyl-2-(5-acetoxy-4,8-dimethyl-7-nonenyl)oxepane Following the procedure of Example 76, but substituting an equivalent amount of 2S,3R-3-acetoxy-6-(2-oxoethylidene)-2-methyl-2-(5-acetoxy-4,8-dimethyl-7-nonenyl)-oxepane for 2S-3,3-dimethoxy-6-(2-oxoethylidene)-2-methyl-2-(5,5-dimethyl-7-nonenyl)-oxepane, 2S,3R-3-acetoxy-6-[2-(hydroxyimino)-ethylidene]-2-methyl-2-(5-acetoxy-4,8-dimethyl-7-nonenyl)-oxepane is obtained.

EXAMPLE 80

2S,3R-3-Acetoxy-2-methyl-6-cyanomethylene-2-(5-acetoxy-4,8-dimethyl-7-nonenyl)-oxepane Following the procedure of Example 77, but substituting an equivalent amount of 2S,3R-3-acetoxy-6-[2-(hydroxyimino)-ethylidene]-2-methyl-2-(5-acetoxy-4,8-dimethyl-7-nonenyl)-oxepane for 2S-3,3-dimethoxy-6-[2-(hydroxyimino)-ethylidene]-2-methyl-2-(5,5-dimethoxy-4,8-dimethyl-7-nonenyl)-oxepane, 2S,3R-3-acetoxy-2-methyl-6-cyanomethylene-2-(5-acetoxy-4,8-dimethyl-7-nonenyl)-oxepane is obtained.

The following compounds are prepared by the method of Example 80 by substituting an equivalent amount of the appropriate starting material for 2S,3R-3-acetoxy-6-[2-(hydroxyimino)-ethylidene]-2-methyl-2-(5-acetoxy-4,8-dimethyl-7-nonenyl)-oxepane.

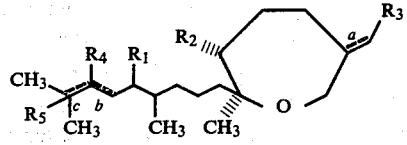

R₁ - —OAc
R₂ - —OAc
R₃ - C≡N

| EXAMPLE | R₄ | R₅ | a | b | c |
|---|---|---|---|---|---|
| | CH₃ | H | u | u | s |
| | H | H | s | s | s |
| | CH₃ | H | s | s | s |
| | H | — | s | s | u |
| | H | H | u | s | s |
| | CH₃ | H | s | u | s |
| | CH₃ | H | u | s | s |
| | H | H | u | u | s |
| | =CH₂ | H | u | s | s |
| | CH₃ | — | u | s | u |
| | H | H | s | u | s |
| | =CH₂ | H | s | s | s |
| | CH₃ | — | s | s | u | u - unsaturated
s - saturated

EXAMPLE 81

2S-3,3-Dimethoxy-6-(2-hydroxyethylidene)-2-methyl-2-(5-acetoxy-4,8-dimethyl-7-nonenyl)oxepane Following the procedure of Example 74, but substituting an equivalent amount of 2S-6-(2-hydroxyethylidene)-2-methyl-2-(5-acetoxy-4,8-dimethyl-7-nonenyl)-oxepan-3-one for 2S-6-(2-hydroxyethylidene)-2-methyl-2-(4,8-dimethyl-5-oxo-7-nonenyl)-oxepan-3one, 2S-3,3-dimethoxy-6-(2-hydroxyethylidene)-2-methyl-2-(5-acetoxy-4,8-dimethyl-7-nonenyl)oxepane is obtained.

EXAMPLE 82

2S-3,3-Dimethoxy-6-(2-oxoethylidene)-2-methyl-2-(5-acetoxy-4,8-dimethyl-7-nonenyl)-oxepane Following the procedure of Example 11, but substituting an equivalent amount of 2S-3,3-dimethoxy-6-(2-hydroxyethylidene)-2-methyl-2-(5-acetoxy-4,8-dimethyl-7-nonenyl)-oxepane for 2S,3R-6-[2-(tetrahydropyran-2-yloxy)ethylidene]-2-methyl-2-[4,8-dimethyl-5-(tetrahydropyran-2-yloxy)-7-nonenyl]-oxepan-3-ol, 2S-3,3-dimethoxy-6-(2-oxoethylidene)-2-methyl-2-(5-acetoxy-4,8-dimethyl-7-nononyl)-oxepane is obtained.

EXAMPLE 83

2S-3,3-Dimethoxy-6-[2-(hydroxyimino)-ethyidene]-2-methyl-2-(5-acetoxy-4,8-dimethyl-7-nonenyl)oxepane Following the procedure of Example 76, but substituting an equivalent amount of 2S-3,3-dimethoxy-6-(2-oxoethylidene)-2-methyl-2-(5-acetoxy-4,8-dimethyl-7-nonenyl)-oxepane for 2S-3,3-dimethoxy-6-(2-oxoethylidene)2-methyl-2-(5,5-dimethoxy-4,8-dimethyl-7-nonenyl)-oxepane, 2S-3,3-dimethoxy-6-[2-(hydroxyimino)-ethylidene]-2-methyl-2-(5-acetoxy-4,8-dimethyl-7-nonenyl)-oxepane is obtained.

EXAMPLE 84

2S-3,3-Dimethoxy-2-methyl-6-cyanomethylene-2-(5-acetoxy-4,8-dimethyl-7-nonenyl)-oxepane Following the procedure of Example 77, but substituting an equivalent amount of 2S-3,3-dimethoxy-6-[2-(hydroximino)-ethylidene]-2-methyl-2-(5-acetoxy-4,8-dimethyl-7-nonenyl)-oxepane for 2S-3,3-dimethoxy-6-[2-(hydroxyimino)-ethylidene]-2-methyl-2-(5,5-dimethoxy-4,8-dimethyl-7-nonenyl)-oxepane, 2S-3,3-dimethoxy-2-methyl-6-cyanomethylene-2-(5-acetoxy-4,8-dimethyl-7-nonenyl)-oxepane is obtained.

EXAMPLE 85

2S-2-Methyl-6-cyanomethylene-2-(5-acetoxy-4,8-dimethyl-7-nonenyl)-oxepan-3-one

Following the procedure of Example 78, but substituting an equivalent amount of 2S-3,3-dimethoxy-2-methyl-6-cyanomethylene-2-(5-acetoxy-4,8-dimethyl-7-nonenyl)oxepane for 2S-3,3-dimethoxy-2-methyl-6-cyanomethylene-2-(5,5-dimethoxy-4,8-dimethyl-7-nonenyl)-oxepane, 2S-2-methyl-6-cyanomethylene-2-(5-acetoxy-4,8-dimethyl-7-nonenyl)-oxepan-3-one is obtained.

EXAMPLE 86

2S-2-Methyl-6-cyanomethylene-2-(4,8-dimethyl-5-hydroxy-7-nonenyl)-oxepane

Following the procedure of Example 10, but substituting an equivalent amount of 2S-2-methyl-6-cyanomethylene-2-(5-acetoxy-4,8-dimethyl-7-nonenyl)-oxepan-3-one for 2S,3R-3-acetoxy-6-[2-(tetrahydropyran-2-yloxy)ethylidene]-2-methyl-2-[4,8-dimethyl-5-(tetrahydropyran-2-yloxy)-7-nonenyl]-oxepane, 2S-2-methyl-6-cyanomethylene-2-(4,8-dimethyl-5-hydroxy-7-nonenyl)-oxepane is obtained.

The following compounds are prepared by the method of Example 86 by substituting an equivalent amount of the appropriate starting material for 2S-2-methyl-6-cyanomethylene-2-(5-acetoxy-4,8-dimethyl-7-nonenyl)-oxepan-3-one.

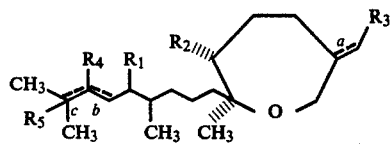

$R_1$ - OH
$R_2$ - =O
$R_3$ - C≡N

| $R_4$ | $R_5$ | a | b | c |
|---|---|---|---|---|
| $CH_3$ | H | u | u | s |
| H | H | s | s | s |
| $CH_3$ | H | s | s | s |
| H | — | s | s | u |
| H | H | u | s | s |
| $CH_3$ | H | s | u | s |
| $CH_3$ | H | u | s | s |
| H | H | u | u | s |
| =$CH_2$ | H | u | s | s |
| $CH_3$ | — | u | s | u |
| H | H | s | u | s |
| =$CH_2$ | H | s | s | s |

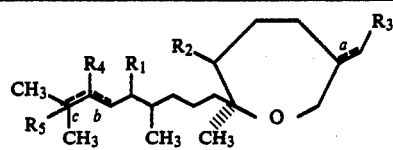

$R_1$ - OH
$R_2$ - =O
$R_3$ - C≡N

| $R_4$ | $R_5$ | a | b | c |
|---|---|---|---|---|
| $CH_3$ | — | s | s | u | u - unsaturated
s - saturated

EXAMPLE 87

2S,3R-3-Acetoxy-6-[2-(hydroxyimino)-ethylidene]-2-methyl-2-(4,8-dimethyl-5-oxo-7-nonenyl)-oxepane Following the procedure of Example 76, but substituting an equivalent amount of 2S,3R-3-acetoxy-6-(2-oxoethylidene)-2-methyl-2-(4,8-dimethyl-5-oxo-7-nonenyl)-oxepane for 2S-3,3-dimethoxy-6-(2-oxoethylidene)-2-methyl-2-(5,5-dimethoxy-4,8-dimethyl-7-nonenyl)-oxepane and employing one equivalent of hydroxylamine hydrochloride, 2S,3R-3-acetoxy-6-[2-(hydroxyimino)-ethylidene]-2-methyl-2-(4,8-dimethyl-5-oxo-7-nonenyl)-oxepane is obtained.

EXAMPLE 88

2S,3R-3-Acetoxy-2-methyl-6-cyanomethylene-2-(4,8-dimethyl-5-oxo-7-nonenyl)-oxepane Following the procedure of Example 77 but substituting an equivalent amount of 2S,3R-3-acetoxy-6-[2-(hydroxyimino)-ethylidene]-2-methyl-2-(4,8-dimethyl-5-oxo-7-nonenyl)-oxepane for 2S-3,3-dimethoxy-6-[2-(hydroxyimino)-ethylidene]-2-methyl-2-(5,5-dimethoxy-4,8-dimethyl-7-nonenyl)-oxepane, 2S,3R-3-acetoxy-2-methyl-6-cyanomethylene-2-(4,8-dimethyl-5-oxo-7-nonenyl)-oxepane is obtained.

The following compounds are prepared by the method of Example 88 by substituting an equivalent amount of the appropriate starting material for 2S,3R-3-acetoxy-6-[2-(hydroxyimino)-ethylidene-]-2-methyl-2-(4,8-dimethyl-5-oxo-7-nonenyl)-oxepane.

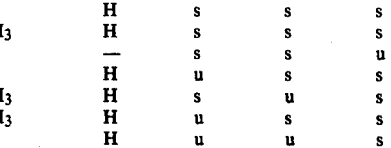

$R_1$ - =O
$R_2$ - —OAc
$R_3$ - C≡N

| $R_4$ | $R_5$ | a | b | c |
|---|---|---|---|---|
| $CH_3$ | H | u | u | s |
| H | H | s | s | s |
| $CH_3$ | H | s | s | s |
| H | — | s | s | u |
| H | H | u | s | s |
| $CH_3$ | H | s | u | s |
| $CH_3$ | H | u | s | s |
| H | H | u | u | s |
| =$CH_2$ | H | u | s | s |
| $CH_3$ | — | u | s | u |
| H | H | s | u | s |
| =$CH_2$ | H | s | s | s |

-continued

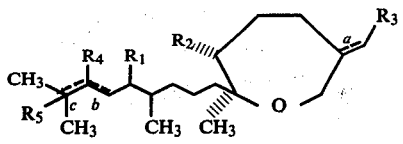

R₁ - =O
R₂ - —OAc
R₃ - C≡N

| R₄ | R₅ | a | b | c |
|---|---|---|---|---|
| CH₃ | — | s | s | u | u - unsaturated
s - saturated

EXAMPLE 89

2S,3R,6R-6-Ethenyl-2-methyl-2-(4,8-dimethyl-5-oxo-7-nonenyl)-3,6-oxidooxepane 2S,3R-6-(2-hydroxyethylidene)-2-methyl-2-(4,8-dimethyl-5-oxo-7-nonenyl)-oxepan-3-ol is dissolved in benzene (40 ml.); p-toluenesulfonic acid (181 mg.) is added and the resulting suspension is stirred at room temperature for 24 hrs. The benzene solution is decanted, the residue washed with benzene (3X) and the combined benzene layers evaporated to dryness in vacuo at 35°. The resulting reddish-brown residue (605 mg.) is chromatographed on a Silicar column using chloroform as the eluting solvent. The major non-polar fraction is eluted to afford 2S,3R,6R-6-ethenyl-2-methyl-2-(4,8-dimethyl-5-oxo-7-nonenyl)-3,6-oxidooxepane (235 mg.).

IR -(neat) 5.85μ; NMR (CDCl₃( δ 1.04, 1.31, 1.63 and 1.76 (CH₃); AB q centered at 3.51; 5.0–6.2 (vinyl H).

EXAMPLE 90

2S,3R,6R-6-Ethenyl-2-methyl-2-(5-oxo-4,7,8-trimethyl-6-nonenyl)-3,6-oxidooxepane Following the procedure of Example 89, but substituting an equivalent amount of 2S,3R-6-(2-hydroxyethylidene)-2-methyl-2-(5-oxo-4,7,8-trimethyl-6E-nonenyl)oxepan-3-ol for 2S,3R-6-(2-hydroxyethylidene)-2-methyl-2-(4,8-dimethyl-5-oxo-7-nonenyl)-oxepan-3-ol, 2S,3R,6R-6-ethenyl-2-methyl-2-(5-oxo-4,7,8-trimethyl-6-nonenyl)-3, 6-oxidooxepane is obtained.

EXAMPLE 91

2S,3R,6S-6-Ethyl-2-methyl-2-(4,8-dimethyl-5-oxononyl)-3,6-oxidooxepane 2S,3R,6R-6-ethenyl-2-methyl-2-(4,8-dimethyl-5-oxo-7-nonenyl)-3,6-oxiddoxepane (235 mg.) is dissolved in absolute ethanol (200 ml.), 10% palladium/carbon (200 mg.) is added and the resulting suspension hydrogenated at 25 psi for 1 hr. The palladium/carbon is filtered, and the filtrate is evaporated to dryness to give 2S,3R,6S-6-ethyl-2-methyl-2-(4,8-dimethyl-5-oxononyl)-3,6-oxidooxepane (237 mg.)

IR (neat) 5.85μ; NMR (CDCl₃) 0.8–1.35 (CH₃); AB q centered at 3.5; no vinyl H.

EXAMPLE 92

2S,3R,6S-6-Ethyl-2-methyl-2-(5-oxo-4,7,8-trimethylnonyl)-3,6-oxidooxepane

Following the procedure of Example 91, but substituting an equivalent amount of 2S,3R,6R-6-ethenyl-2-methyl-2-(5-oxo-4,7,8-trimethyl-6-nonenyl)-3,6-oxidooxepane for 2S,3R,6R-6-ethenyl-2-methyl-2-(4,8-dimethyl-5-oxo-7-nonenyl)-3,6-oxidooxepane, 2S,3R,6S-6-ethyl-2-methyl-2-(5-oxo-4,7,8-trimethylnonyl)-3,6-oxidooxepane is obtained.

EXAMPLE 93

2S,3R,6R-6-Ethenyl-2-methyl-2-(4,8-dimethyl-5-oxo-6-nonenyl)-3,6-oxidooxepane

Following the procedure of Example 40, but substituting an equivalent amount of 2S,3R,6R-6-ethenyl-2-methyl-2-(4,8-dimethyl-5-oxo-7-nonenyl)-3,6-oxidooxepane for 2S,3R-6-(2-hydroxyethylidene)-2-methyl-2-(4,8-dimethyl-5-oxo-7-nonenyl)-oxepane-3-ol, 2S,3R,6R-6-ethenyl-2-methyl-2-(4,8-dimethyl-5-oxo-6-nonenyl)-3,6-oxidooxepane is obtained.

EXAMPLES 94 and 95

2S,3R,6R-6-Ethenyl-2-methyl-2-(4,8-dimethyl-7-methylene-5-oxononyl)-3,6-oxidooxepane and 2S,3R,6R-6-Ethenyl-2-methyl-2-(5-oxo-4,7,8-trimethyl-7-nonenyl)-3,6-oxidooxepane Following the procedure of Examples 41 and 42 but substituting an equivalent amount of 2S,3R,6R-6-ethenyl-2-methyl-2-(5-oxo-4,7,8-trimethyl-6-nonenyl)-3,6-oxidooxepane for 2S,3R-6-(2-hydroxyethylidene)-2-methyl-2-(5-oxo-4,7,8-trimethyl-6E-nonenyl)-oxepan-3-ol, 2S,3R,6R-6-ethenyl-2-methyl-2-(4,8-dimethyl-7-methylene-5-oxononyl)-3,6-oxidooxepane and 2S,3R,6R-6-ethenyl-2-methyl-2-(5-oxo-4,7,8-trimethyl-7-nonenyl)-3,6-oxidooxepane are obtained. The compounds are separated by chromatography.

EXAMPLE 96

2S,3R,6S-6-Ethyl-2-methyl-2-(4,8-dimethyl-5-oxo-7-nonenyl)-3,6-oxidooxepane

Following the procedure of Example 35 but substituting an equivalent amount of 2S,3R,6R-6-ethenyl-2-methyl-2-(4,8-dimethyl-5-oxo-7-nonenyl)-3,6-oxidooxepane for 2S,3R-6-(2-hydroxyethylidene)-2-methyl-2-(6,7-oxido-5-oxo-4,7,8-trimethylnonyl)-oxepan-3-ol, 2S,3R,6S-6-ethyl-2-methyl-2-(4,8-dimethyl-5-oxo-7-nonenyl)-3,6-oxidooxepane is obtained. The reaction is stopped after an equivalent of hydrogen is absorbed.

EXAMPLE 97

2S,3R,6S-6-(1,2-Dibromoethyl)-2-methyl-2-(4,8-dimethyl-5-oxo-6-nonenyl)-3,6-oxidooxepane Bromine (160 mg.) is added to a mixture of 2S,3R,6R-6-ethenyl-2-methyl-2-(4,8-dimethyl-5-oxo-6-nonenyl)-3,6-oxidooxepane (320 mg.) and methylene chloride (20 ml.) at 0°. The resulting mixture is stirred for 5 mins., then treated with water (30 ml.) and methylene chloride (30 ml.). The organic layer is dried and evaporated to give 2S,3R,6S-6-(1,2-dibromoethyl)-2-methyl-2-(4,8-dimethyl-5-oxo-6-nonenyl)-3,6-oxidooxepane.

EXAMPLE 98

2S,3R6S-6-(1,2-Dibromoethyl)-2-methyl-2-(4,8-dimethyl-5-oxononyl)-3,6-oxidooxepane A mixture of 2S,3R,6S-6-(1,2-dibromoethyl)-2-methyl-2-(4,8-dimethyl-5-oxo-6-nonenyl)-3,6-oxidooxepane (470 mg.), palladium on carbon (5%, 20 mg.) and glacial acetic acid (30 ml.) is hydrogenated at atmospheric pressure for 16 hrs. The resulting mixture is filtered through Celite and the filtrate is treated with water (50 ml.) and ether (100 ml.). The organic phase is washed with 10% sodium carbonate solution (3×100 ml.) dried and evaporated to give 2S,3R,6S-6-(1,2-dibromoethyl)-2-methyl-2-(4,8-dimethyl-5-oxononyl)-3,6-oxidooxepane.

EXAMPLE 99

2S,3R,6R-6-ethenyl-2-methyl-2-(4,8-dimethyl-5-oxononyl)-3,6-oxidooxepane

To a mixture of 2S,3R,6S-6-(1,2-dibromoethyl)-2-methyl-2-(4,8-dimethyl-5-oxononyl)-3,6-oxidooxepane (470 mg.) and glacial acetic acid (20 ml.) is added an excess of zinc dust (200 mg.) at 0° and the resulting mixture is stirred for 1 hour. The reaction mixture is filtered through a pad of Celite and the filtrate is treated with water (50 ml.) and ether (100 ml.). The organic phase is washed with 10% sodium carbonate solution (3×100 ml.), dried and evaporated to give 2S,3R,6R-6-ethenyl-2-methyl-2-(4,8-dimethyl-5-oxononyl)-3,6-oxidooxepane.

EXAMPLE 100

2S,3R,6S-6-Ethyl-2-methyl-2-(4,8-dimethyl-5-oxo-6-nonenyl)-3,6-oxidooxepane

Following the procedure of Example 93 but substituting 2S,3R,6S-6-ethyl-2-methyl-2-(4,8-dimethyl-5-oxo-7-nonenyl)-3,6-oxidooxepane for an equivalent amount of 2S,3R,6R-6-ethenyl-2-methyl-2-(4,8-dimethyl-5-oxo-7-nonenyl)-3,6-oxidooxepane, 2S,3R,6S-6-ethyl-2-methyl-2-(4,8-dimethyl-5-oxo-6-nonenyl)-3,6-oxidooxepane is obtained.

EXAMPLE 101

2S,3R,6R-6-Ethenyl-2-methyl-2-(5-oxo-4,7,8-trimethylnonyl)-3,6-oxidooxepane

Following the procedure of Example 98 but substituting an equivalent amount of 2S,3R,6R-6-ethenyl-2-methyl-2-(5-oxo-4,7,8-trimethyl-6-nonenyl)-3,6-oxidooxepane for 2S,3R,6R-6-ethenyl-2-methyl-2-(4,8-dimethyl-5-oxo-6-nonenyl)-3,6-oxidooxepane, 2S,3R,6R-6-ethenyl-2-methyl-2-(5-oxo-4,7,8-trimethylnonyl)-3,6-oxidooxepane is obtained.

EXAMPLE 102

2S,3R,6S-6-Ethyl-2-methyl-2-(5-oxo-4,7,8-trimethyl-6-nonenyl)-3,6-oxidooxepane

Following the procedure of Example 96 but substituting an equivalent amount of 2S,3R,6R-6-ethenyl-2-methyl-2-(5-oxo-4,7,8-trimethyl-6-nonenyl)-3,6-oxidooxepane for 2S,3R,6R-6-ethenyl-2-methyl-2-(4,8-dimethyl-5-oxo-7-nonenyl)-3,6-oxidooxepane, 2S,3R,6S-6-ethyl-2-methyl-2-(5-oxo-4,7,8-trimethyl-6-nonenyl)-3,6-oxidooxepane is obtained.

EXAMPLES 103 and 104

2S,3R,6S-6-Ethyl-2-methyl-2-(4,8-dimethyl-7-methylene-5-oxononyl)-3,6-oxidooxepane and 2S,3R,6S-6-Ethyl-2-methyl-2-(5-oxo-4,7,8-trimethyl-7-nonenyl)-3,6-oxidooxepane Following the procedure of Examples 41 and 42 but substituting an equivalent amount of 2S,3R,6S-6-ethyl-2-methyl 2-(5-oxo-4,7,8-trimethyl-6-nonenyl)-3,6-oxidooxepane for 2S,3R-6-(2-hydroxyethylidene)-2-methyl-2-(5-oxo-4,7,8-trimethyl-6E-nonenyl)-oxepane-3-ol affords 2S,3R,6S-6-ethyl-2-methyl-2-(4,8-dimethyl-7-methylene-5-oxononyl)-3,6-oxidooxepane and 2S,3R,6S-6-ethyl-2-methyl-2-(5-oxo-4,7,8-trimethyl-7-nonenyl)-3,6-oxidooxepane. The compounds are separated by chromatography.

EXAMPLE 105

2S,3R,6R-6-(2-Oxoethyl)-2-methyl-2-(4,8-dimethyl-5-oxo-7-nonenyl)-3,6-oxidooxepane A solution of 2S,3R-6-(2-hydroxyethylidene)-2-methyl-2-(4,8-dimethyl-5-oxo-7-nonenyl)-oxepan-3-ol (1.0 g.) in methylene chloride (250 ml.) is stirred with manganese dioxide (2.2 g.) at room temperature under nitrogen for 17 hours. The manganese dioxide is filtered, washed with methylene chloride and the solvent is removed in vacuo.

The residue is plate chromatographed on silica gel, using ethyl acetate-chloroform (4:1) as the developing solvent. The less polar UV absorbing band is eluted with ethyl acetate-chloroform (4:1) to afford 2S,3R,6R-6-(2-oxoethyl)-2-methyl-2-(4,8-dimethyl-5-oxo-7-nonenyl)-3,6-oxidooxepane (850 mg.):

IR (neat) μ: 3.63 (CHO), 5.80 (>C=O, H—C=O);

NMR (CDCl$_3$) δ: 1.06 (d, J=7 Hz, 3H, (CH—C$\underline{H}_3$), 1.30 (s, 3H, —O—COC$\underline{H}_3$), 1.63 and 1.75 [each s, each 3H, C=C—(C$\underline{H}_3$)$_2$], 2.60 (d, J=2 Hz, 2H, —C$\underline{H}_2$—CHO), 3.13 (d, J=8 Hz, 2H, —C$\underline{H}_2$—CO); 3.29 and 3.73

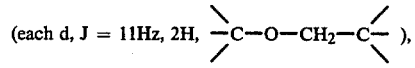

(each d, J = 11Hz, 2H,

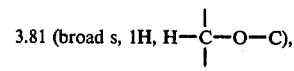

3.81 (broad s, 1H, H—C—O—C), 5.25 [m, 1H, H$\underline{C}$—C=(CH$_3$)$_2$], 9.78 (t, J=2 Hz, 1H, —CH$_2$—C$\underline{H}$O).

The following compounds are prepared by the method of Example 105 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

| R3 | R4 | b | c |
|---|---|---|---|
| CH3 | H | u | s |
| CH3 | H | s | s |
| H | H | u | s |
| =CH2 | H | s | s |
| CH3 | — | s | u |
| H | OH | u | s |
| H | OH | s | s | u - unsaturated
s - saturated

EXAMPLE 106

2S,3R,6R-6-(2-Hydroxyethyl)-2-methyl-2-(4,8-dimethyl-5-oxo-7-nonenyl)-3,6-oxidooxepane A suspension of sodium borohydride (69.8 mg.) in benzene (15 ml.) is treated with acetic acid (92 mg.) and refluxed for 1 hour under nitrogen to afford a clear solution of sodium triacetoxyborohydride. To this solution is added a solution of 2S,3R,6R-6-(2-oxoethyl)-2-methyl-2-(4,8-dimethyl-5-oxo-7-nonenyl)-3,6-oxidooxepane (158 mg.) in benzene (5 ml.) and the mixture refluxed for 5 hours under nitrogen. The solvent is removed in vacuo, the residue diluted with water and extracted with methylene chloride. Removal of the solvent from the dried organic phase affords a residue which is plate chromatographed on silica gel, using ethyl acetate:chloroform (4:1) as the developing solvent. The major band is eluted with ethyl acetate to afford 2S,3R-6-(2-hydroxyethyl)-2-methyl-2-(4,8-dimethyl-5-oxo-7-nonenyl)-3,6-oxidooxepane (121 mg.):

IR (neat) μ: 2.85 (OH), 5.82 (C=O); NMR (CDCl$_3$) δ: 1.06 (d, J=6 Hz, 3H, C$\underline{H}_3$—CH), 1.27 (s, 3H, 2—C$\underline{H}_3$), 1.60 and 1.73 [each s, each 3H, (C$\underline{H}_3$)$_2$—C=C], 3.09 (d, J=7 Hz, 2H, C$\underline{H}_2$—CO), 3.17 and 3.75 (each d, J=11 Hz, each 1H, 7—C$\underline{H}_2$), 3.75 (t, 3H, C$\underline{H}_2$—OH and 3—$\underline{H}$), 5.06–5.43 (broad m, 1H, H$\underline{C}$—C=(CH$_3$)$_2$ The following compounds are prepared by the method of Example 106 by substituting an equivalent amount of the appropriate starting material for 2S,3R,6R-6-(2-oxoethyl)-2-methyl-2-(4,8-dimethyl-5-oxo-7-nonenyl)-3,6-oxidooxepane.

| EXAMPLE | R3 | R4 | b | c |
|---|---|---|---|---|
| | CH3 | H | u | s |
| | H | H | s | s |
| | CH3 | H | s | s |
| | H | H | u | s |
| | =CH2 | H | s | s |
| | CH3 | — | s | u |
| | H | OH | u | s |
| | H | OH | s | s | u - unsaturated
s - saturated

EXAMPLE 107

2S,3R,6R-2-methyl-6-carboxymethyl-2-(4,8-dimethyl-5-oxo-7-nonenyl)-3,6-oxidooxepane To a stirred suspension of pre-reduced platinum oxide (500 mg.) in water (75 ml.) is added sodium bicarbonate (1.58 g.), 2S,3R-6-(2-hydroxyethylidene)-2-methyl-2-(4,8-dimethyl-5-oxo-7-nonenyl)-oxepan-3-ol (600 mg.) in acetone (48 ml.) and water (117 ml.). The mixture is stirred briskly at room temperature protected from light under an oxygen atmosphere (in an atmospheric pressure hydrogenation apparatus for 24 hours). Platinum metal is removed by filtration on a pad of Celite and washed with 10% acetone in water. The combined filtrate and washings are evaporated to dryness in vacuo. The residue is dissolved in water (~125 ml.) and extracted with ethyl acetate (2×100 ml.). The aqueous layer is acidified to pH 3 with dil. hydrochloric acid and quickly extracted with ethyl acetate (2×100 ml.). The organic layer is washed with brine, dried and evaporated in vacuo to afford an oily residue (0.681 g.) which is plate chromatographed on silica gel, using isopropanol-chloroform-acetic acid (36:363:1) as the eluting solvent. The least polar band is eluted with isopropanol-chloroform (1:6) to afford 2,S,3R-6R-2-methyl-(6-carboxymethyl)-2-(4,8-dimethyl-5-oxo-7-nonenyl)-3,6-oxidooxepane (170 mg):

IR (neat) μ: 2.8–3.3 (broad, OH), 5.8 (shoulder) 5.85 (C=O and COOH); NMR (CDCl$_3$) δ: 1.03 (d, J=7 Hz, 3H, C$\underline{H}_3$—CH), 1.27

(s, 3H, CH$_3$—C$\diagdown^{\diagup O}_{\diagdown}$), 1.60 and 1.70 (each s, each 3H, (C$\underline{H}_3$)$_2$—C=C), 2.57

(s, 2H $\diagdown$CH$_2$—COOH), 3.10 (d, J=7 Hz, 2H, CH—C$\underline{H}_2$—CO), 3.40 and 3.73

(each d, J = 11Hz, 2H, $\diagdown$C—O—CH$_2$—C$\diagup$),

-continued 3.85 (broad s, 1H, H—C(—O—C), 5.23 (m, 1H, CH=C), 6.83 (broad s, 1H, COOH).

The following compounds are prepared by the method of Example 107 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

$R_1$ - =O
$R_2$ - —$CO_2H$

| EXAMPLE | $R_3$ | $R_4$ | b | c |
|---|---|---|---|---|
| | $CH_3$ | H | u | s |
| | $CH_3$ | H | s | s |
| | H | H | u | s |
| | =$CH_2$ | H | s | s |
| | $CH_3$ | — | s | u |
| | H | OH | s | s | u - unsaturated
s - saturated

EXAMPLE 108

2S,3R,6R-6-(2-Hydroxyethyl)-2-methyl-2-(4,8-dimethyl-5-hydroxy-7-nonenyl)-3,6-oxidooxepane A solution of 2S,3R,6R-6-(oxoethyl)-2-methyl-2-(4,8-dimethyl-5-oxo-7-nonenyl)-3,6-oxidooxepane (200 mg.) in ethanol (10 ml.) is treated with sodium borohydride (55 mg) at room temperature under nitrogen for 18 hours. Ethanol is removed in vacuo, the residue diluted with water (5 ml.) and neutralized with 5% hydrochloric acid. The aqueous solution is extracted with methylene chloride (2×50 ml.) and the organic layer dried and the solvent removed in vacuo. The residue is plate chromatographed on silica gel using isopropanol chloroform (1:9) as the developing solvent. The major band is eluted with isopropanol-chloroform (1:1) to afford 2S,3R,6R-6-(2-hydroxyethyl)-2-methyl-2-(4,8-dimethyl-5-hydroxy-7-nonenyl)-3,6-oxidooxepane (152 mg.):

IR (neat) μ: 2.90 (OH); NMR (CDCl$_3$) δ: 0.88 (d, J=6 Hz, 3H, C$\underline{H}_3$—CH—CH—C—OH), 1.32 (s, 3H, —O—C—CH$_3$), 1.63 and 1.72 [each s, each 3H, (C$\underline{H}_3$)$_2$—C=CH], 3.08–3.70

(total 6H, H—C(—O) of which 3.18 and 3.60 (each d, J =

12Hz, each 1H, —C—O—CH$_2$—C—), 3.60 (t, J = 6Hz, 3H,

H—C—O—C and CH$_2$—CH$_2$—OH)

are clearly visible and 3.20–3.40 (broad m, 1H, $\underline{H}$—C—OH) is diffused; 5.12 [m, 1H, (CH$_3$)$_2$—C=C$\underline{H}$].

The following compounds are prepared by the method of Example 108 by substituting an equivalent amount of the appropriate starting material for 2S,3R,6R-6-(oxoethyl)-2-methyl-2-(4,8-dimethyl-5-oxo-7-nonenyl)-3,6-oxidooxepane.

$R_1$ - OH
$R_2$ - CH$_2$OH

| $R_3$ | $R_4$ | b | c |
|---|---|---|---|
| $CH_3$ | H | u | s |
| H | H | s | s |
| $CH_3$ | H | s | s |
| H | H | u | s |
| =$CH_2$ | H | s | s |
| $CH_3$ | — | s | u |
| H | OH | u | s |
| H | OH | s | s | u - unsaturated
s - saturated

EXAMPLE 109

2S,3R,6R-6-(2-Oxoethyl)-2-methyl-2-(4,8-dimethyl-5-hydroxy-7-nonenyl)-3,6-oxidooxepane (A) Following the procedure of Example 105 but substituting an equivalent amount of 2S,3R-6-(2-hydroxyethylidene)-2-methyl-2-(4,8-dimethyl-5-hydroxy-7-nonenyl)oxepan-3-ol for 2S,3R-6-(2-hydroxyethylidene)-2-methyl-2-(4,8-dimethyl-5-oxo-7-nonenyl)-oxepan-3-ol, 2S,3R,6R-6-(2-oxoethyl)-2-methyl-2-(4,8-dimethyl-5-hydroxy-7-nonenyl)-3,6-oxidooxepane (81% yield) is obtained.

IR (neat) μ: 2.86 (OH), 3.64 (CHO) and 5.81 (C=O); NMR (CDCl$_3$—TMS) δ: 0.90 (d, J=6 Hz, 3H, C$\underline{H}_3$—CH), 1.33 (s, 3H, C$\underline{H}_3$—C—), 1.65 and 1.73 [both s, 3H each, (C$\underline{H}_3$)$_2$C=CH], 2.60 (d, J=2 Hz, 2H, C$\underline{H}_2$—CHO), 3.29 and 3.74 (each d, J=11 Hz, each 1H, O—C$\underline{H}_2$—C), 9.80 (t, J=2 Hz, 1H, C$\underline{H}$O).

(B) A solution of 2S,3R-6-(2-hydroxyethylidene)-2-methyl-2-(4,8-dimethyl-5-hydroxy-7-nonenyl)-oxepan-3-ol (340 mg.) in t-butanol (20 ml.) is treated with 2,3-dichloro-5,6-dicyano-1,4-benzoquinone (340 mg.) and the mixture heated to reflux for 124 hours. Removal of the solvent followed by chromatography affords 2S,3R,6R-6-(2-oxoethyl)-2-methyl-2-(4,8-dimethyl-5-hydroxy-7-nonenyl)-3,6-oxidooxepane.

The following compounds are prepared by the methods of Example 109 by substituting an equivalent amount of the appropriate starting material for 2S,3R-6-(2-hydroxyethylidene)-2-methyl-2-(4,8-dimethyl-5-hydroxy-7-nonenyl)-oxepan-3-ol.

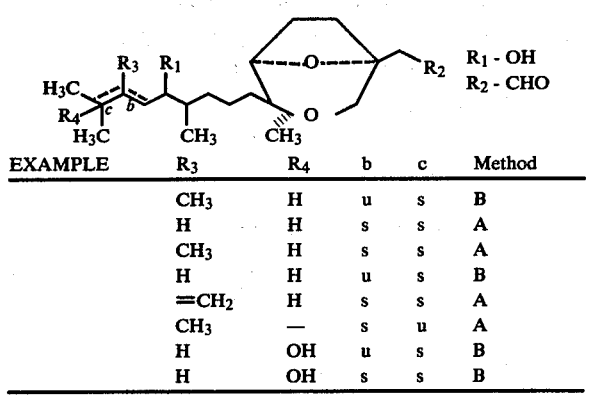

| EXAMPLE | R3 | R4 | b | c | Method |
|---------|-----|-----|---|---|--------|
|         | CH3 | H   | u | s | B      |
|         | H   | H   | s | s | A      |
|         | CH3 | H   | s | s | A      |
|         | H   | H   | u | s | B      |
|         | =CH2| H   | s | s | A      |
|         | CH3 | —   | s | u | A      |
|         | H   | OH  | u | s | B      |
|         | H   | OH  | s | s | B      | u - unsaturated
s - saturated

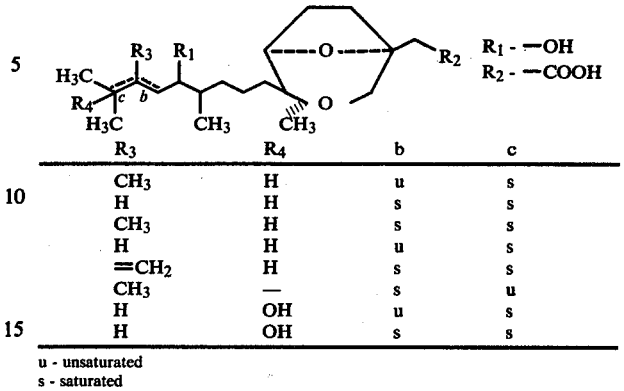

| R3   | R4 | b | c |
|------|----|----|---|
| CH3  | H  | u | s |
| H    | H  | s | s |
| CH3  | H  | s | s |
| H    | H  | u | s |
| =CH2 | H  | s | s |
| CH3  | —  | s | u |
| H    | OH | u | s |
| H    | OH | s | s | u - unsaturated
s - saturated

EXAMPLE 110

2S,3R,6R-2-Methyl-6-carboxymethyl-2-(4,8-dimethyl-5-hydroxy-7-nonenyl)-3,6-oxidooxepane To a stirred suspension of pre-reduced platinum oxide (400 mg.) in water (28 ml.) is added sodium bicarbonate (650 mg. and 2S,3R-6-(2-hydroxyethylidene)-2-methyl-2-(4,8-dimethyl-5-hydroxy-7-nonenyl)-oxepan-3-ol (260 mg.) in acetone (12 ml.) and water (20 ml.). The mixture is stirred briskly at room temperature under an oxygen atmosphere for 20 hrs. Platinum metal is removed by filtration on a pad of Celite and washed with 10% acetone/water. The combined filtrate and washings are evaporated to dryness in vacuo. The residue is dissolved in water (150 ml.) and extracted with ethyl acetate (2×175 ml.). The aqueous layer is acidified to pH 3 with dilute hydrochloric acid and quickly extracted with ethyl acetate (2×150 ml.). The ethyl acetate layer is washed with brine, dried and evaporated in vacuo to afford an oily residue (0.240 g.) which is plate chromatographed on silica gel using isopropanol:chloroform (1:8) with a drop of acetic acid as the eluting solvent. The major band is eluted with isopropanol:chloroform (1:1) to afford 2S,3R,6R-2-methyl-6-carboxymethyl-2-(4,8-dimethyl-5-hydroxy-7-nonenyl)-3,6-oxidooxepane (192 mg.):

IR (neat) $\mu$: 2.89 (OH), 5.8 (C=O and COOH); NMR (CDCl$_3$) $\delta$: 0.88 (d, J=7 Hz, 3$\underline{H}$, CH$_3$—CH—CH—OH), 1.31 (s, 3H, C$\underline{H}_3$—C—O), 1.63 and 1.71 [each s, each 3H, (C$\underline{H}_3$)$_2$—C=CH)], 2.60 (s, 2H, C$\underline{H}_2$—CO$_2$H), 3.39 and 3.76 (each d, J=11 Hz, 2H, —C—C$\underline{H}_2$—O—C), 3.85 (m, 1H, $\underline{H}$—C—O—C) 4.91, 5.16 [m, 1H, (CH$_3$)$_2$—C=C$\underline{H}$) and 6.03 (broad s, 1H, COO$\underline{H}$)].

The following compounds are prepared by the method of Example 110 by substituting an equivalent amount of the appropriate starting material for 2S,3R-6-(2-hydroxyethylidene)-2-methyl-2-(4,8-dimethyl-5-hydroxy-7-nonenyl)oxepan-3-ol.

EXAMPLE 111

2S,3R,6R-2-Methyl-6-carbmethoxymethyl-2-(4,8-dimethyl-5-hydroxy-7-nonenyl)-3,6-oxidooxepane N-methylnitrosourea (1 g.) is slowly added (3 mins.) to a well shaken, cold (0°–5°) mixture of 40% aqueous potassium hydroxide (3 ml.) and ether (10 ml.). When all the solid is dissolved (~15 min.), the ethereal solution of diazomethane is decanted, dried (potassium hydroxide pellets) and added to a solution of 2S,3R,6R-2-methyl-6-carboxymethyl-2-(4,8-dimethyl-5-hydroxy-7-nonenyl)-3,6-oxidooxepane (77 mg.) in ether (5 ml.). After all the excess diazomethane is evaporated, the ether solution is washed with water, dried and the ether removed under a stream of nitrogen to afford 2S,3R,6R-2-methyl-6-carbmethoxymethyl-2-(4,8-dimethyl-5-hydroxy-7-nonenyl)-3,6-oxidooxepane (74 mg.):

IR (neat)$\mu$: 2.85 (OH), 5.75 (COOMe); NMR (CDCl$_3$) $\delta$: 0.85 (d, J=7 Hz, 3H, C$\underline{H}_3$—CH), 1.30 (s, 3H, CH$_3$—C—O—), 1.63 and 1.73 [each s, each 3H, (CH$_3$)$_2$C=CH], 2.58 (s, 2H, —C—CH$_2$—COOCH$_3$), 3.65 (s, 3H, CH$_3$OCO—), 3.40 and 3.77 (each d, J=11Hz, each 1H, —C—CH$_2$—O—C—), ~3.23 (m, 2H, HC—C—OH and HC—O—C), 5.15 (m, 1H C=CH).

EXAMPLE 112

2S,3R,6R-2-Methyl-6-carbmethoxymethyl-2-(4,8-dimethyl-5-oxo-7-nonenyl)-3,6-oxidooxepane Following the procedure of Example 111 but substituting an equivalent amount of 2S,3R,6R-2-methyl-6-carboxymethyl-2-(4,8-dimethyl-5-oxo-7-nonenyl)-3,6-oxidooxepane for 2S,3R,6R-2-methyl-6-carboxymethyl-2-(4,8-dimethyl-5-hydroxy-7-nonenyl)-3,6-oxidooxepane, 2S,3R,6R-2-methyl-6-carbmethoxymethyl-2-(4,8- dimethyl-5-oxo-7-nonenyl)-3,6-oxidooxepane is obtained.

EXAMPLE 113

2S,3R,6R-2-Methyl-6-cyanomethyl-2-(4,8-dimethyl-5-oxo-7-nonenyl)-3,6-oxidooxepane Following the procedure for the synthesis of 2S,3R-3-acetoxy-2-methyl-6-cyanomethylene-2-(4,8-dimethyl-5-oxo-7-nonenyl)-oxepane from 2S,3R-3-acetoxy-6-(2-oxoethylidene)-2-methyl-2-(4,8-dimethyl-5-oxo-7-nonenyl)-oxepane but substituting an equivalent amount of 2S,3R,6R-6-(2-oxoethyl)-2-methyl-2-(4,8-dimethyl-5-oxo-7-nonenyl)-3,6-oxidooxepane for 2S,3R-3-acetoxy-6-(2-oxoethylidene)-2-methyl-2-(4,8-dimethyl-5-oxo-7-nonenyl)-oxepane in Example 87 affords the corresponding oxime which is dehydrated as described in Example 88.

The following compounds are prepared by the method of Example 113 by substituting an equivalent amount of the appropriate starting material for 2S,3R,6R-6-(2-oxoethyl)-2-methyl-2-(4,8-dimethyl-5-oxo-7-nonenyl)-3,6-oxidooxepane.

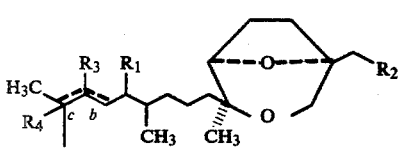

$R_1 - =O$
$R_2 - C≡N$

| $R_3$ | $R_4$ | b | c |
|-------|-------|---|---|
| $CH_3$ | H | u | s |
| H | H | s | s |
| $CH_3$ | H | s | s |
| H | H | u | s |
| $=CH_2$ | H | s | s |
| $CH_3$ | — | s | u | u - unsaturated
s - saturated

EXAMPLE 114

2S,3R,6R-2-Methyl-6-cyanomethyl-2-(4,8-dimethyl-5-hydroxy-7-nonenyl)-3,6-oxidooxepane Following the procedure of Example 18 but substituting an equivalent amount of 2S,3R,6R-2-methyl-6-cyanomethyl-2-(4,8-dimethyl-5-oxo-7-nonenyl)-3,6-oxidooxepane for 2S,3R-6-(2-hydroxyethylidene)-2-methyl-2-(4,8-dimethyl-5-oxo-7-nonenyl)-oxepan-3-ol affords 2S,3R,6R-2-methyl-6-cyanomethyl-2-(4,8-dimethyl-5-hydroxy-7-nonenyl)-3,6-oxidooxepane.

The following compounds are prepared by the method of Example 114 by substituting an equivalent amount of the appropriate starting material for 2S,3R,6R-2-methyl-6-cyanomethyl-2-(4,8-dimethyl-5-oxo-7-nonenyl)-3,6-oxidooxepane.

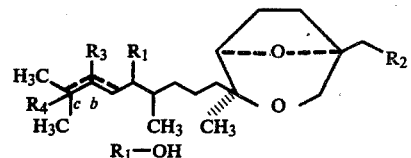

$R_1—OH$
$R_2—C≡N$

| $R_3$ | $R_4$ | b | c |
|-------|-------|---|---|
| $CH_3$ | H | u | s |
| H | H | s | s |
| $CH_3$ | H | s | s |
| H | H | u | s |
| $=CH_2$ | H | s | s |
| $CH_3$ | — | s | u | u - unsaturated
s - saturated

EXAMPLE 115

2S,3R,6R-2-Methyl-6-carbamoylmethyl-2-(4,8-dimethyl-5-oxo-7-nonenyl)-3,6-oxidooxepane Following the procedures of Examples 65 and 66 for the synthesis of 2S,3R-3-acetoxy-2-methyl-6-carbamoylmethylene-2-(4,8-dimethyl-5-oxo-7-nonenyl)-oxepane from 2S,3R-3-acetoxy-2-methyl-6-carboxymethylene-2-(4,8-dimethyl-5-oxo-7-nonenyl)-oxepane but substituting an equivalent amount of 2S,3R,6R-2-methyl-6-carboxymethyl-2-(4,8-dimethyl-5-oxo-7-nonenyl)-3,6-oxidooxepane for 2S,3R-3-acetoxy-2-methyl-6-carboxymethylene-2-(4,8-dimethyl-5-oxo-7-nonenyl)-oxepane in Example 65, 2S,3R,6R-2-methyl-6-carbamoylmethyl-2-(4,8-dimethyl-5-oxo-7-nonenyl)-3,6-oxidooxepane is obtained.

The following compounds are prepared by the method of Example 115 by substituting an equivalent amount of the appropriate starting material for 2S,3R,6R-2-methyl-6-carboxymethyl-2-(4,8-dimethyl-5-oxo-7-nonenyl)-3,6-oxidooxepane.

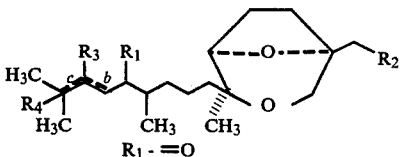

$R_1 - =O$ $R_2 - —CON\begin{matrix}R_5\\R_6\end{matrix}$

| $R_3$ | $R_4$ | $R_5$ | $R_6$ | b | c |
|-------|-------|-------|-------|---|---|
| $CH_3$ | H | H | H | u | s |
| H | H | $CH_3$ | $CH_3$ | s | s |
| $CH_3$ | H | $C_2H_5$ | H | s | s |
| H | H | $C_6H_5$ | $C_6H_5$ | u | s |
| $=CH_2$ | H | $—CH_2C_6H_5$ | H | s | s |
| $CH_3$ | — | $CH_3$ | H | s | u | u - unsaturated
s - saturated

EXAMPLE 116

2S,3R,6R-2-Methyl-6-carbamoylmethyl-2-(4,8-dimethyl-5-hydroxy-7-nonenyl)-3,6-oxidooxepane Following the procedure of Example 114 but substituting an equivalent amount of 2S,3R,6R-2-methyl-6- carbamoylmethyl-2-(4,8-dimethyl-5-oxo-7-nonenyl)-3,6-oxidooxepane for 2S,3R,6S-2-methyl-6-cyanomethyl-2-(4,8-dimethyl-5-oxo-7-nonenyl)-3,6-oxidooxepane, 2S,3R,6R-2-methyl-6-carbamoylmethyl-2-(4,8-dimethyl-5-hydroxy-7-nonenyl)-3,6-oxidooxepane is obtained.

The following compounds are prepared by the method of Example 116 by substituting an equivalent amount of the appropriate starting material for 2S,3R,6R-2-methyl-6-carbamoylmethyl-2-(4,8-dimethyl-5-oxo-7-nonenyl)-3,6-oxidooxepane.

thylidene)-2-methyl-2-(4,8-dimethyl-5-hydroxyimino-7-nonenyl)-oxepane is obtained.

The following examples are prepared by the procedure of Example 117 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| R₁ | R₂ | R₃ | R₄ | R₅ | a | b | c |
|---|---|---|---|---|---|---|---|
| =N—OH | —OH | —CH₂OH | H | — | u | s | u |
| —OH | =N—OH | —CH₂OH | H | — | u | s | u |
| —OAc | OAc | —CH=N—OH | H | — | u | s | u |
| =N—OH | =N—OH | —CH=N—OH | H | — | u | s | u |
| =N—OH | OH | —CH₂OH | CH₃ | H | u | u | s |
| =N—OH | OH | —CH₂OH | H | H | s | s | s |
| =N—OH | OH | —CH₂OH | CH₃ | H | s | s | s |
| =N—OH | OH | —CH₂OH | H | — | s | s | u |
| =N—OH | OH | —CH₂OH | CH₃ | H | s | u | s |
| =N—OH | OH | —CH₂OH | CH₃ | — | u | s | u |
| =N—OH | OH | —CH₂OH | =CH₂ | H | u | s | s |
| =N—OH | OH | —CH₂OH | CH₃ | — | s | s | u |
| ⟩CH₃/OH | OAc | CH=N—OH | H | — | u | s | u | u - unsaturated
s - saturated

| R₃ | R₄ | R₅ | R₆ | b | c |
|---|---|---|---|---|---|
| CH₃ | H | H | H | u | s |
| H | H | CH₃ | CH₃ | s | s |
| CH₃ | H | C₂H₅ | H | s | s |
| H | H | C₆H₅ | C₆H₅ | u | s |
| =CH₂ | H | —CH₂C₆H₅ | H | s | s |
| CH₃ | — | CH₃ | H | s | u | u - unsaturated
s - saturated

EXAMPLE 117

2S,3R-3-Acetoxy-6-(2-acetoxyethylidene)-2-methyl-2-(4,8-dimethyl-5-hydroxyimino-7-nonenyl)-oxepane Following the procedure of Example 76 but substituting an equivalent amount of 2S,3R-3-acetoxy-6-(2-acetoxyethylidene)-2-methyl-(4,8-dimethyl-5-oxo-7-nonenyl)-oxepane for 2S-3,3-dimethoxy-6-(2-oxoethylidene)-2-methyl-2-(5,5-dimethoxy-4,8-dimethyl-7-nonenyl)-oxepane, 2S,3R-3-acetoxy-6-(2-acetoxye- The following compounds are prepared by the procedure of Example 117 by substituting an equivalent amount of the appropriate starting material for 2S, 3R-3-acetoxy-6-(2-acetoxyethylidene)-2-methyl-2-(4,8-dimethyl-5-oxo-7-nonenyl)oxepane.

| R₁ | R₂ | R₃ | R₄ | b | c |
|---|---|---|---|---|---|
| =N—OH | =CH₂ | H | — | s | u |
| =N—OH | =CH₂ | =CH₂ | H | s | s |
| =N—OH | =CH₂ | —CH₃ | — | s | u |
| =N—OH | —CH₃ | —H | — | s | u |
| =N—OH | =CH₂ | —H | H | s | s |
| =N—OH | =CH₂ | —CH₃ | H | s | s |
| =N—OH | —CH₂OH | H | — | s | u |
| =O | CH=NOH | H | — | s | u |
| —OH | —CH=NOH | H | — | s | u |
| =N—OH | CO₂CH₃ | H | — | s | u |
| =N—OH | C≡N | H | — | s | u |
| =N—OH | CONH—NH₂ | H | — | s | u |
| =N—OH | CONH—N(CH₃)₂ | H | — | s | u |
| ⟩CH₃/OH | CH=NOH | H | — | s | u | u - unsaturated
s - saturated

EXAMPLE 118

2S,3R-3-Acetoxy-6-(2-acetoxyethylidene)-2-methyl-2-[4,8-dimethyl-5-(p-nitrophenoxy)imino-7-nonenyl]-oxepane A solution of 2S,3R-3-acetoxy-6-(2-acetoxyethylidene)-2-methyl-2-(4,8-dimethyl-5-oxo-7-nonenyl)-oxepane (422 mg) in absolute ethanol (15 ml) is treated with p-nitrophenylhydroxylamine (250 mg) and a trace of hydrochloric acid. After stirring for 72 hrs at 25° C., the ethanol is evaporated and the mixture is purified by chromatography to afford 2S,3R-3-acetoxy-6-(2-acetoxyethylidene)-2-methyl-2-[4,8-dimethyl-5-(p-nitrophenoxy)imino-7-nonenyl]-oxepane.

Similarly, by substituting other aromatic hydroxylamines for p-nitrophenylhydroxylamine in the above procedure, the corresponding oximes are formed. Thus, phenylhydroxylamine and dinitrophenylhydroxylamine afford the phenoxyimino and dinitrophenoxyimino compounds respectively.

The following compound is prepared according to the method of Example 118 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

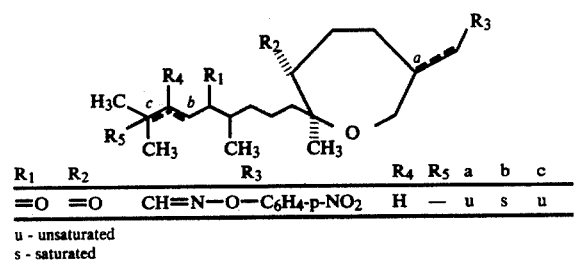

| $R_1$ | $R_2$ | $R_3$ | $R_4$ | $R_5$ | a | b | c |
|---|---|---|---|---|---|---|---|
| =O | =O | CH=N—O—$C_6H_4$-p-$NO_2$ | H | — | u | s | u | u - unsaturated
s - saturated

The following compounds are prepared by the procedure of Example 118 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

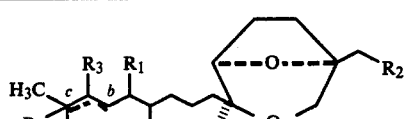

| $R_1$ | $R_2$ | $R_3$ | $R_4$ | b | c |
|---|---|---|---|---|---|
| =N—O—$C_6H_5$ | =$CH_2$ | H | H | u | s |
| =N—O—$C_6H_4$-p-$NO_2$ | —$CH_3$ | —$CH_3$ | — | s | u | u - unsaturated
s - saturated

EXAMPLE 119

2S,3R-3-Acetoxy-6-(2-acetoxyethylidene)-2-methyl-2-(4,8-dimethyl-5-methoxyimino-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg) in anhydrous pyridine (2 ml) is treated with methoxylamine hydrochloride (105 mg) under nitrogen. After standing for 24 hours at 25° C., the reaction mixture is poured into water and extracted with chloroform. The chloroform extract is washed with dilute aqueous sodium bicarbonate and saturated salt solution, dried and evaporated to afford 2S,3R-3-acetoxy-6-(2-acetoxyethylidene)-2-methyl-2-(4,8-dimethyl-5-methoxyimino-7-nonenyl)-oxepane.

Similarly by substituting other alkoxyamine hydrochlorides for methoxylamine hydrochloride in the procedure of Example 119, the corresponding oximes are formed. Thus, ethoxylamine hydrochloride, butoxylamine hydrochloride and O-phenoxy hydroxylamine hydrochloride afford the ethoxyimino, butoxyimino and phenoxyimino compounds respectively.

The following compounds are prepared by the procedure of Example 119 by substituting an equivalent amount of the appropriate starting material for 2S,3R-3-acetoxy-6-(2-acetoxyethylidene)-2-methyl-(4,8-dimethyl-5-oxo-7-nonenyl)-oxepane.

| $R_1$ | $R_2$ | $R_3$ | $R_4$ | $R_5$ | a | b | c |
|---|---|---|---|---|---|---|---|
| =N—$OCH_3$ | =N—$OCH_3$ | —$CH_2OH$ | H | — | u | s | u |
| =N—$OCH_2C_6H_5$ | OH | —$CH_2OH$ | H | H | u | s | s |
| =N—$OCH_2C_6H_5$ | OH | —$CH_2OH$ | $CH_3$ | H | u | s | s |
| =N—$OCH_3$ | OH | —$CH_2OH$ | H | H | u | u | s |
| =N—$OCH_3$ | OAc | —$CO_2H$ | H | — | u | s | u |
| =N—$OCH_3$ | OAc | —$CO_2CH_3$ | H | — | u | s | u |
| =N—$OCH_3$ | OAc | $CONHCH_3$ | H | — | u | s | u |
| =N—$OCH_3$ | OAc | $CONH_2$ | H | — | u | s | u |
| =N—$OCH_3$ | OAc | $CONHNH_2$ | H | — | u | s | u |
| =N—$OCH_3$ | OAc | C≡N | H | — | u | s | u |
| =N—$OCH_3$ | OTHP | $CH_2OTHP$ | H | — | u | s | u |
| =N—$OCH_3$ | OAc | $CH_2ONO_2$ | H | — | u | s | u |
| =N—$OCH_3$ | OAc | $CH_2$—OPO$(OCH_3)_2$ | H | — | u | s | u |
| =N—$OCH_3$ | OAc | $CH_2$—$OCH_3$ | H | — | u | s | u |
| =N—$OCH_3$ | OAc | $CH_2$—Br | H | — | u | s | u |
| =N—$OCH_3$ | OAc | $CH_2SH$ | H | — | u | s | u |

-continued

| R₁ | R₂ | R₃ | R₄ | R₅ | a | b | c |
|---|---|---|---|---|---|---|---|
| (dioxolane) | OAc | CH=N—OCH₃ | H | — | u | s | u |
| (dithiolane) | OAc | CH=N—OCH₃ | H | — | u | s | u |
| =N—OCH₃ | OH | CH₂OH | H | OH | u | u | s | u - unsaturated
s - saturated

The following compounds are prepared according to the procedure of Example 119 by substituting an equivalent amount of the appropriate starting material for 2S,3R-3-acetoxy-6-(2-acetoxyethylidene)-2-methyl-(4,8-dimethyl-5-oxo-7-nonenyl)-oxepane.

| R₁ | R₂ | R₃ | R₄ | b | c |
|---|---|---|---|---|---|
| =N—OCH₃ | =CH₂ | CH₃ | H | u | s |
| =N—OCH₂C₆H₅ | CH₃ | CH₃ | H | s | s |
| =N—OCH₃ | CH₃ | H | H | u | s |
|  | CH₃ | CH₃ | H | u | s |
| =N—O—(cyclopentyl) |  |  |  |  |  |
| =N—OCH₃ | CO₂H | H | — | s | u |
| =N—OC₂H₅ | CH₂OH | H | — | s | u |
| =N—OCH₂C₆H₅ | CONH₂ | H | — | s | u | u - unsaturated
s - saturated

EXAMPLE 120

2S,3R-3-Acetoxy-6-(2-acetoxyethylidene)-2-methyl-2-(4,8-dimethyl-5-benzoyloxyimino-7-nonenyl)-oxepane A solution of 2S,3R-3-acetoxy-6-(2-acetoxyethylidene)-2-methyl-2-(4,8-dimethyl-5-hydroxyimino-7-nonenyl)-oxepane (437 mg) in anhydrous benzene (3 ml) and anhydrous pyridine (72 mg) is treated with benzoyl chloride (140 mg). The mixture is refluxed for 3 hrs, cooled, additional benzene is added and the reaction mixture is washed with water. The organic phase is dried over potassium carbonate and evaporated to afford 2S,3R-3-acetoxy-6-(2-acetoxyethylidene)-2-methyl-2-(4,8-dimethyl-5-benzoyloxyimino-7-nonenyl)-oxepane.

Similarly, by substituting other acyl chlorides for benzoyl chloride, in the procedure of Example 120, the corresponding acyloximes are formed. Thus acetyl chloride and butyryl chloride afford the acetoxyimino and butyryloxymino compounds respectively.

The following compounds are prepared according to the procedure of Example 120 by substituting an equivalent amount of the appropriate starting material for 2S,3R-3-acetoxy-6-(2-acetoxyethylidene)-2-methyl-2-(4,8-dimethyl-5-hydroxyimino-7-nonenyl)-oxepane and employing the appropriate acylating agent.

| R₁ | R₂ | R₃ | R₄ | R₅ | a | b | c |
|---|---|---|---|---|---|---|---|
| =O | OAc | —CH=N—OAc | H | — | u | s | u |
| =O | OAc | —CH=N—OBz | H | — | u | s | u | u - unsaturated
s - saturated
Bz - benzoyl

The following compounds are prepared according to the procedure of Example 120 by substituting an equivalent amount of the appropriate starting material for 2S,3R-3-acetoxy-6-(2-acetoxyethylidene)-2-methyl-2-(4,8-dimethyl-5-hydroxyimino-7-nonenyl)-oxepane.

| R₁ | R₂ | R₃ | R₄ | b | c |
|---|---|---|---|---|---|
| =N—OAc | CH₃ | H | H | s | s |
| =N—OAc | CH₃ | =CH₂ | H | s | s |
| =N—OBz | CH₃ | H | H | s | s | u - unsaturated
s - saturated
Bz - benzoyl

EXAMPLE 121

2S,3R-3-Acetoxy-6-(2-acetoxyethylidene)-2-methyl-2-(4,8-dimethyl-5-dimethylhydrazono-7-nonenyl)-oxepane A mixture of 2S,3R-3-acetoxy-6-(2-acetoxyethylidene)-2-methyl-2-(4,8-dimethyl-5-oxo-7-nonenyl)-oxepane (422 mg) and N,N-dimethylhydrazine (85 mg) is heated for 4 hrs at 70° C. and then at room temperature for 48 hrs. Ether and water are added and the layers separated. The organic layer is dried and evaporated to afford 2S,3R-3-acetoxy-6-(2-acetoxyethylidene)-2-methyl-2-(4,8-dimethyl-5-dimethylhydrazono-7-nonenyl)-oxepane.

Similarly by substituting other hydrazines for N,N-dimethylhydrazine in the procedure of Example 121, the corresponding hydrazones are formed. Thus, hydrazine and N,N-dibutylhydrazine afford the corresponding hydrazono and dibutylhydrazono compounds respectively.

The following compounds are prepared according to the procedure of Example 121 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

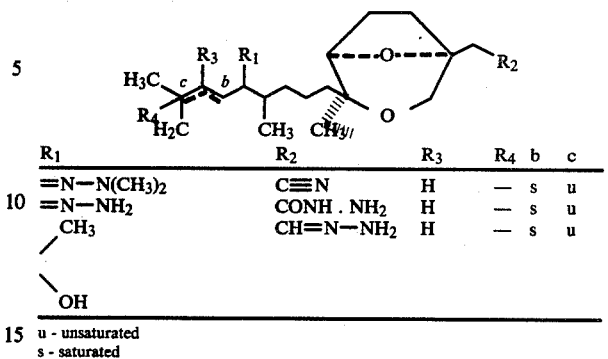

| R₁ | R₂ | R₃ | R₄ | b | c |
|---|---|---|---|---|---|
| =N—N(CH₃)₂ | C≡N | H | — | s | u |
| =N—NH₂ | CONH.NH₂ | H | — | s | u |
| /CH₃ \OH | CH=N—NH₂ | H | — | s | u | u - unsaturated
s - saturated

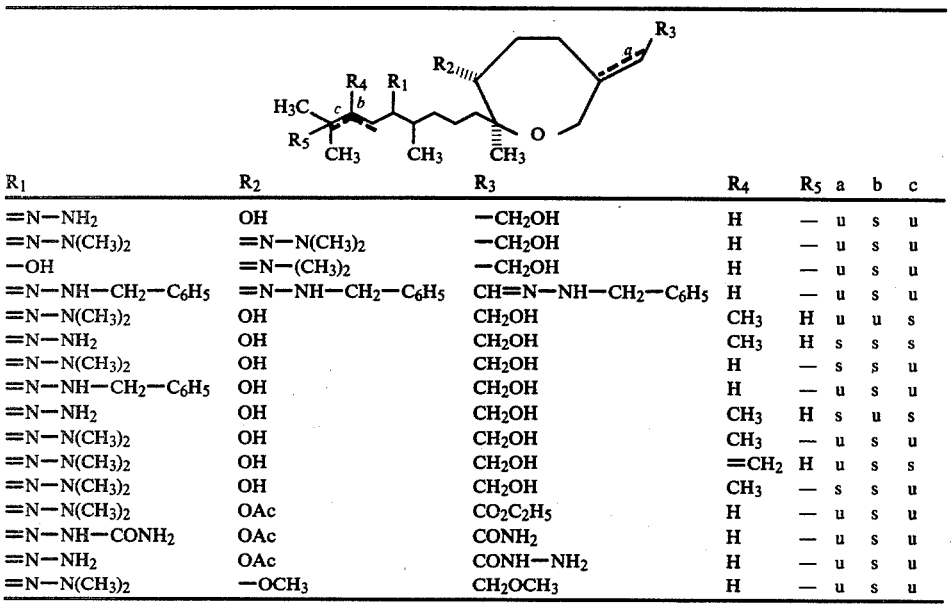

| R₁ | R₂ | R₃ | R₄ | R₅ | a | b | c |
|---|---|---|---|---|---|---|---|
| =N—NH₂ | OH | —CH₂OH | H | — | u | s | u |
| =N—N(CH₃)₂ | =N—N(CH₃)₂ | —CH₂OH | H | — | u | s | u |
| —OH | =N—(CH₃)₂ | —CH₂OH | H | — | u | s | u |
| =N—NH—CH₂—C₆H₅ | =N—NH—CH₂—C₆H₅ | CH=N—NH—CH₂—C₆H₅ | H | — | u | s | u |
| =N—N(CH₃)₂ | OH | CH₂OH | CH₃ | H | u | u | s |
| =N—NH₂ | OH | CH₂OH | CH₃ | H | s | s | s |
| =N—N(CH₃)₂ | OH | CH₂OH | H | — | s | s | u |
| =N—NH—CH₂—C₆H₅ | OH | CH₂OH | H | — | u | s | u |
| =N—NH₂ | OH | CH₂OH | CH₃ | H | s | u | s |
| =N—N(CH₃)₂ | OH | CH₂OH | CH₃ | — | u | s | u |
| =N—N(CH₃)₂ | OH | CH₂OH | =CH₂ | H | u | s | s |
| =N—N(CH₃)₂ | OH | CH₂OH | CH₃ | — | s | s | u |
| =N—N(CH₃)₂ | OAc | CO₂C₂H₅ | H | — | u | s | u |
| =N—NH—CONH₂ | OAc | CONH₂ | H | — | u | s | u |
| =N—NH₂ | OAc | CONH—NH₂ | H | — | u | s | u |
| =N—N(CH₃)₂ | —OCH₃ | CH₂OCH₃ | H | — | u | s | u | u - unsaturated
s - saturated

The following compounds are prepared according to the procedure of Example 121 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

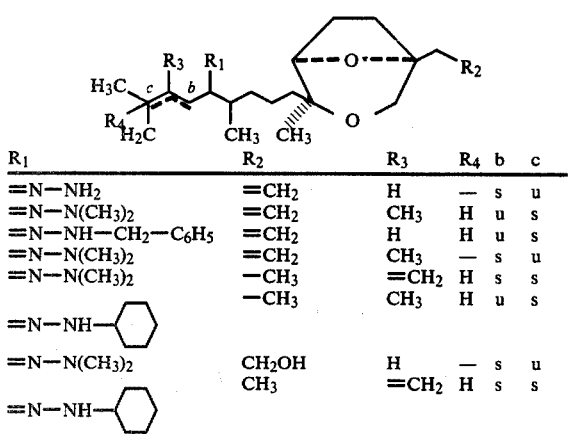

| R₁ | R₂ | R₃ | R₄ | b | c |
|---|---|---|---|---|---|
| =N—NH₂ | =CH₂ | H | — | s | u |
| =N—N(CH₃)₂ | =CH₂ | CH₃ | H | u | s |
| =N—NH—CH₂—C₆H₅ | =CH₂ | H | H | u | s |
| =N—N(CH₃)₂ | =CH₂ | CH₃ | — | s | u |
| =N—N(CH₃)₂ | —CH₃ | =CH₂ | H | s | s |
| =N—NH—⟨phenyl⟩ | —CH₃ | CH₃ | H | u | s |
| =N—N(CH₃)₂ | CH₂OH | H | — | s | u |
| =N—NH—⟨phenyl⟩ | CH₃ | =CH₂ | H | s | s |

EXAMPLE 122

2S,3R-3-Acetoxy-6-(2-acetoxyethylidene)-2-methyl-2-(4,8-dimethyl-5-carbamoylhydrazono-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg) in methanol (1 ml) is treated with a solution of semicarbazide (17 ml) prepared by dissolving semicarbazide hydrochloride (2.5 g) and pyridine (1.8 ml) in water (15 ml) and methanol (60 ml). The mixture is refluxed for 18 hrs. The methanol is evaporated in vacuo and the residue partitioned between ether and water. The organic extract is dried and evaporated to aford 2S,3R-3-acetoxy-6-(2-acetoxyethylidene)-2-methyl-2-(4,8-dimethyl-5-carbamoylhydrazono-7-nonenyl)-oxepane.

The following compounds are prepared according to the procedure of Example 122 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| $R_1$ | $R_2$ | $R_3$ | $R_4$ | $R_5$ | a | b | c |
|---|---|---|---|---|---|---|---|
| =N—NH—CONH$_2$ | OH | CH$_2$OH | CH$_3$ | H | u | s | s |
| =N—NH—CONH$_2$ | OH | CH$_2$OH | H | H | u | u | s |
| =N—NH—CONH$_2$ | OAc | CONH$_2$ | H | — | u | s | u |
| =N—NH—CONH$_2$ | OAc | C≡N | H | — | u | s | u |
| =N—NH—CONH$_2$ | OAc | CH$_2$—ONO$_2$ | H | — | u | s | u |
| =N—NH—CONH$_2$ | OAc | CH$_2$—O—PO(OCH$_3$)$_2$ | H | — | u | s | u |
| =N—NH—CONH$_2$ | OAc | CH$_2$—O—CH$_3$ | H | — | u | s | u |
| =N—NH—CONH$_2$ | OAc | CH$_2$—N(CH$_3$)$_2$ | H | — | u | s | u |
| =N—NH—CONH$_2$ | OAc | CH$_2$—SH | H | — | u | s | u |
| (dioxolane O-O ring) | OAc | CH=N—NHCONH$_2$ | H | — | u | s | u |
| =CH$_2$ | OAc | CH=N—NHCONH$_2$ | H | — | u | s | u |
| (dithiolane S-S ring) | OAc | CH=N—NHCONH$_2$ | H | — | u | s | u |
| (CH$_3$, OH substituents) | OAc | CH=N—NHCONH$_2$ | H | — | u | s | u |
| =N—NH—CONH$_2$ | OH | CH$_2$OH | H | OH | u | u | s | u - unsaturated
s - saturated

The following compounds are prepared according to the procedure of Example 122 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

residue is then dissolved in methylene chloride, washed with saturated salt solution, dried and evaporated to give 2S,3R-3-acetoxy-6-(2-acetoxyethylidene)-2-methyl-2-[4,8-dimethyl-5-(2,4-dinitrophenylhydrazono)-7-nonenyl]-oxepane.

| $R_1$ | $R_2$ | $R_3$ | $R_4$ | b | c |
|---|---|---|---|---|---|
| =N—NH—CONH$_2$ | =CH$_2$ | =CH$_2$ | H | s | s |
| =N—NH—CONH$_2$ | CH$_3$ | H | — | s | u |
| =N—NH—CONH$_2$ | =CH$_2$ | H | H | s | s |
| =N—NH—CONH$_2$ | CH$_3$ | H | H | u | s |
| =O | CH=N—NH—CONH$_2$ | H | — | s | u |
| =N—NH—CONH$_2$ | CO$_2$H | H | — | s | u |
| =N—NH—CONH$_2$ | CH$_2$OH | H | — | s | u |
| =N—NH—CONH$_2$ | CO$_2$CH$_3$ | H | — | s | u | u - unsaturated
s - saturated

EXAMPLE 123

2S,3R-3-Acetoxy-6-(2-acetoxyethylidene)-2-methyl-2-[4,8-dimethyl-5-(2,4-dinitrophenylhydrazono)-7-nonenyl]-oxepane A solution of 2S,3R-3-acetoxy-6-(2-acetoxyethylidene)-2-methyl-2-(4,8-dimethyl-5-oxo-7-nonenyl)-oxepane (422 mg) in ethanol (10 ml) is treated with a standard acidic solution of 2,4-dinitrophenylhydrazine in aqueous ethanol at 50° C. for 3 hrs. The reaction mixture is cooled to room temperature and water (35 ml) is added. The solvent is decanted and the residue washed with additional water until it is neutral. The Similarly, by substituting other aromatic hydrazines for 2,4-dinitrophenylhydrazine in the procedure of Example 123, the corresponding aromatic hydrazones are formed. Thus phenylhydrazine and p-bromophenylhydrazine afford the corresponding phenylhydrazone and p-bromophenylhydrazone compounds respectively.

The following compounds are prepared according to the procedure of Example 123 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| R₁ | R₂ | R₃ | R₄ | R₅ | a | b | c |
|---|---|---|---|---|---|---|---|
| —OH | OAc | CH=N—NH—C₆H₅ | H | — | u | s | u |
| =N—NH—C₆H₃(NO₂)₂ | OAc | CO₂H | H | — | u | s | u |
| =N—NH—C₆H₃(NO₂)₂ | OAc | CO₂CH₃ | H | — | u | s | u |
| =O | OAc | CH=N—NH—C₆H₃(NO₂)₂ | H | — | u | s | u | u - unsaturated
s - saturated

The following compounds are prepared according to the procedure of Example 123 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| R₁ | R₂ | R₃ | R₄ | b | c |
|---|---|---|---|---|---|
| =N—NH—C₆H₃(NO₂)₂ | CH₃ | H | —H | s | s |
| =N—NH—C₆H₅ | CH₃ | CH₃ | — | s | u |
| =N—NH—C₆H₄-p-NO₂ | =CH₂ | CH₃ | —H | s | s |
| =N—NH—C₆H₃(NO₂)₂ | CONH—CH₃ | H | — | s | u | u - unsaturated
s - saturated

EXAMPLE 124

2S,3R-3-Acetoxy-6-(2-acetoxyethylidene)-2-methyl-2-(4,8-dimethyl-5-p-bromobenzenesulfonylhydrazono-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg) in absolute ethanol (20 ml) is treated with p-bromobenzenesulfonylhydrazide (427 mg) and a trace of hydrochloric acid. After stirring at room temperature for 18 hr, the solution is evaporated, the residue taken up in methylene chloride, filtered and evaporated to afford 2S,3R-3-acetoxy-6-(2-acetoxyethylidene)-2-methyl-2-(4,8-dimethyl-5-p-bromobenzenesulfonylhydrazono-7-nonenyl)-oxepane.

Similarly, by substituting other sulfonylhydrazides for p-bromobenzenesulfonylhydrazide in the procedure of Example 124, the corresponding sulfonylhydrazones are formed. Thus, benzenesulfonylhydrazide and p-toluenesulfonylhydrazide afford the benzenesulfonylhydrazono and toluenesulfonylhydrazono compounds respectively.

The following compounds are prepared according to the method of Example 124 by substituting an equivalent amount of the appropriate starting material for 2S,3R-3-acetoxy-6-(2-acetoxyethylidene-2-methyl-2-(4,8-dimethyl-5-oxo-7-nonenyl)-oxepane and employing the appropriate sulfonylhydrazide.

| R₁ | R₂ | R₃ | R₄ | R₅ | a | b | c |
|---|---|---|---|---|---|---|---|
| —OH | =O | CH=N—NH—SO₂—C₆H₅ | H | — | u | s | u |
| =N—NH—SO₂—C₆H₄-p-CH₃ | OH | CH₂OH | H | H | s | s | s | u - unsaturated
s - saturated

The following compounds are prepared according to the procedure of Example 124 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| R₁ | R₂ | R₃ | R₄ | b | c |
|---|---|---|---|---|---|
| =N—NH—SO₂—C₆H₄-p-CH₃ | CH₃ | CH₃ | H | s | s |
| =N—NH—SO₂—C₆H₄-p-CH₃ | —CONH₂ | H | — | s | u |

EXAMPLE 125

2S,3R-3-Acetoxy-6-(2-acetoxyethylidene)-2-methyl-2-(5-amino-4,8-dimethyl-7-nonenyl) oxepane A solution of 2S,3R-3-acetoxy-6-(2-acetoxyethylidene)-2-methyl-2-(4,8-dimethyl-5-oxo-7-nonenyl)-oxepane (422 mg.) and ammonium acetate (770 mg.) in methanol (3 ml.) is treated with lithium cyanohydridoborate (33 mg.). After stirring for 48 hrs. at 25°, concentrated hydrochloric acid is added until a pH <2 is reached and the methanol is evaporated. The residue is dissolved in water and extracted with ether. The aqueous solution is cooled, made basic with sodium carbonate and quickly extracted with ether. The ethereal extract is dried and evaporated to give 2S,3R-3-acetoxy-6-(2-acetoxyethylidene)-2-methyl-2-(5-amino-4,8-dimethyl-7-nonenyl)-oxepane.

The following compounds are prepared by the procedure of Example 125 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| $R_1$ | $R_2$ | $R_3$ | $R_4$ | $R_5$ | a | b | c |
|---|---|---|---|---|---|---|---|
| —NH$_2$ | —OH | CH$_2$—OH | —H | — | u | s | u |
| —NH$_2$ | —NH$_2$ | CH$_2$—OAc | —H | — | u | s | u |
| —OH | —OAc | CH$_2$—NH$_2$ | —H | — | u | s | u |
| —NH$_2$ | —NH$_2$ | CH$_2$—NH$_2$ | —H | — | u | s | u |
| —NH$_2$ | —OH | CH$_2$—OH | —CH$_3$ | H | u | u | s |
| —NH$_2$ | —OAc | CH$_2$—OAc | —H | — | s | s | u |
| —NH$_2$ | —OH | CH$_2$—OH | —CH$_3$ | H | s | u | s |
| —NH$_2$ | —OH | CH$_2$—OH | —CH$_3$ | H | u | s | s |
| —NH$_2$ | —OH | CH$_2$—OH | —CH$_3$ | — | u | s | u |
| —NH$_2$ | —OH | CH$_2$—OH | =CH$_2$ | H | u | s | s |
| —NH$_2$ | —OAc | CH$_2$—OAc | —CH$_3$ | — | s | s | u |
| —NH$_2$ | —OH | CH$_2$—OH | =CH$_2$ | H | s | s | s |
| —NH$_2$ | —OAc | CO$_2$H | —CH$_3$ | H | u | u | s |
| —NH$_2$ | —OAc | CO$_2$C$_2$H$_5$ | —CH$_3$ | H | u | u | s |
| —NH$_2$ | —OAc | CO$_2$C$_2$H$_5$ | —CH$_3$ | H | s | u | s |
| —NH$_2$ | —OAc | CONH$_2$ | —CH$_3$ | H | u | u | s |
| —NH$_2$ | —OAc | C≡N | —CH$_3$ | H | u | u | s |
| —NH$_2$ | —OAc | C≡N | —CH$_3$ | H | s | u | s |
| —NH$_2$ | —OH | CH$_2$—OH | —H | OH | u | u | s |
| S–S | —NH$_2$ | CH$_2$—OAc | —H | — | u | s | u |
| S–S | —OAc | CH$_2$—NH$_2$ | —H | — | u | s | u |
| —NH$_2$ | —OAc | CH$_2$—Br | —H | — | u | s | u |
| =CH$_2$ | —OAc | CH$_2$NH$_2$ | —H | — | u | s | u |
| CH$_3$/\OH | —OAc | CH$_2$—NH$_2$ | —H | — | u | s | u | u - unsaturated
s - saturated

The following compounds are prepared by the method of Example 125 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| $R_1$ | $R_2$ | $R_3$ | $R_4$ | b | c |
|---|---|---|---|---|---|
| —NH$_2$ | CH$_2$—NH$_2$ | —H | — | s | u |
| —OAc | CH$_2$—NH$_2$ | —H | — | s | u |
| —NH$_2$ | CO$_2$C$_2$H$_5$ | —H | — | s | u |
| —NH$_2$ | CO$_2$CH$_3$ | —H | — | s | u |
| —NH$_2$ | CO$_2$C$_4$H$_9$ | —H | — | s | u |
| —NH$_2$ | CONH$_2$ | —H | — | s | u |
| —NH$_2$ | =CH$_2$ | —CH$_3$ | H | u | s |
| —NH$_2$ | =CH$_2$ | —CH$_3$ | — | s | u |
| —NH$_2$ | —CH$_2$NH$_2$ | —CH$_3$ | H | u | s |
| —NH$_2$ | =CH$_2$ | —H | OH | u | s |
| —NH$_2$ | CONHC$_2$H$_5$ | —H | — | s | u |
| =CH$_2$ | CH$_2$—NH$_2$ | —H | — | s | u |
| CH$_3$/\OH | CH$_2$—NH$_2$ | —H | — | s | u |
| —NH$_2$ | CH$_2$—SCH$_3$ | —H | — | s | u | u - unsaturated
s - saturated

EXAMPLE 126

2S,3R-3-Acetoxy-6-(2-acetoxyethylidene)-2-methyl-2-(5-benzoylamino-4,8-dimethyl-7-nonenyl)-oxepane To a mixture of 2S,3R-3-acetoxy-6-(2-acetoxyethylidene)-2-methyl-2-(5-amino-4,8-dimethyl-7-nonenyl)-oxepane (422 mg.) and N,N-dimethylaniline (0.14 ml.) is added benzoyl chloride (0.155 ml.). The mixture is heated and stirred at 90° for 3 hrs., cooled and poured into dilute hydrochloric acid and extracted with ether. The ethereal extract is dried and evaporated to give 2S,3R-3-acetoxy-6-(2-acetoxyethylidene)-2-methyl-2-(5-benzoylamino-4,8-dimethyl-7-nonenyl)-oxepane.

Similarly, by substituting other acyl chlorides for benzoyl chloride in the procedure of Example 126, the corresponding acylamines are obtained. Thus acetyl chloride and butyryl chloride afford the 5-acetoxy and 5-butyryloxy compounds respectively.

EXAMPLE 127

2S,3R-3-Acetoxy-6-(2-acetoxyethylidene)-2-methyl-2-(4,8-dimethyl-5-methylamino-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg.) and anhydrous methylamine (190 mg.) in methanol (2.5 ml.) is treated with 5 N hydrochloric acid (0.4 ml.) in methanol and lithium cyanohydridoborate (30 mg.). The solution is stirred at 25° for 72 hrs., then worked-up as described in Example 125 to give 2S,3R-3-acetoxy-6-(2-acetoxyethylidene)-2-methyl-2-(4,8-dimethyl-5-methylamino-7-nonenyl)-oxepane.

Similarly, by substituting other primary amines for methylamine in the procedure of Example 127, the corresponding primary amines are formed. Thus ethylamine and phenylamine afford the 5-ethylamino and 5-phenylamino compounds respectively.

The following examples are prepared by the method of Example 127 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane and employing the appropriate primary amine.

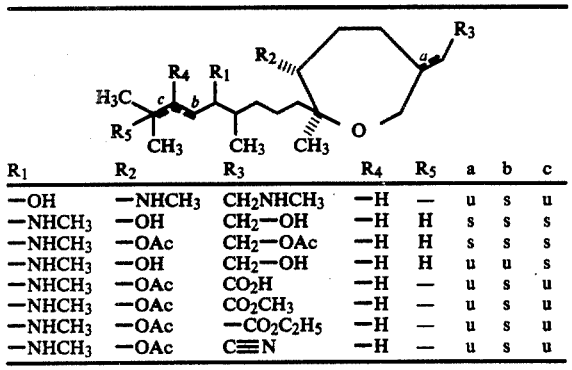

| $R_1$ | $R_2$ | $R_3$ | $R_4$ | $R_5$ | a | b | c |
|---|---|---|---|---|---|---|---|
| —OH | —NHCH$_3$ | CH$_2$NHCH$_3$ | —H | — | u | s | u |
| —NHCH$_3$ | —OH | CH$_2$—OH | —H | H | s | s | s |
| —NHCH$_3$ | —OAc | CH$_2$—OAc | —H | H | s | s | s |
| —NHCH$_3$ | —OH | CH$_2$—OH | —H | H | u | u | s |
| —NHCH$_3$ | —OAc | CO$_2$H | —H | — | u | s | u |
| —NHCH$_3$ | —OAc | CO$_2$CH$_3$ | —H | — | u | s | u |
| —NHCH$_3$ | —OAc | —CO$_2$C$_2$H$_5$ | —H | — | u | s | u |
| —NHCH$_3$ | —OAc | C≡N | —H | — | u | s | u | u - unsaturated
s - saturated

The following compounds are prepared by the procedure of Example 127 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane and employing the appropriate primary amine.

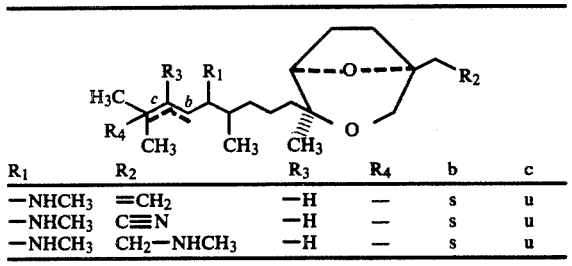

| $R_1$ | $R_2$ | $R_3$ | $R_4$ | b | c |
|---|---|---|---|---|---|
| —NHCH$_3$ | =CH$_2$ | —H | — | s | u |
| —NHCH$_3$ | C≡N | —H | — | s | u |
| —NHCH$_3$ | CH$_2$—NHCH$_3$ | —H | — | s | u | u - unsaturated
s - saturated

EXAMPLE 128

2S,3R-3-Acetoxy-6-(2-acetoxyethylidene)-2-methyl-2-(4,8-dimethyl-5-dimethylamino-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg.) and anhydrous dimethylamine (270 mg.) in absolute methanol (2.5 ml.) is treated with 5 N hydrochloric acid (0.4 ml.) in methanol and lithium cyanohydridoborate (33 mg.). The solution is stirred for 72 hrs. then worked-up as in Example 125 to give 2S,3R-3-acetoxy-6-(2-acetoxyethylidene)-2-methyl-2-(4,8-dimethyl-5-dimethylamino-7-nonenyl)-oxepane.

Similarly, by substituting other secondary amines for dimethylamine in the procedure of Example 128, the corresponding secondary amines are obtained. Thus dipropylamine and dibenzylamine afford the 5-dipropylamino and 5-dibenzylamino compounds respectively.

The following compounds are prepared by the procedure of Example 128 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane and employing the appropriate secondary amine.

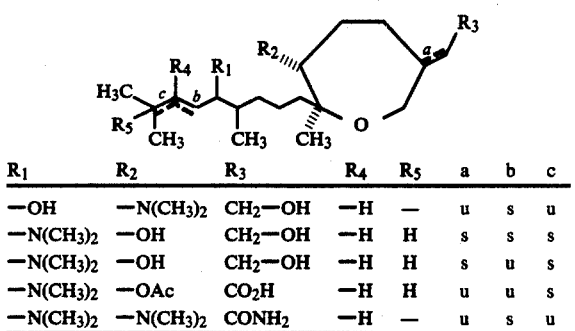

| $R_1$ | $R_2$ | $R_3$ | $R_4$ | $R_5$ | a | b | c |
|---|---|---|---|---|---|---|---|
| —OH | —N(CH$_3$)$_2$ | CH$_2$—OH | —H | — | u | s | u |
| —N(CH$_3$)$_2$ | —OH | CH$_2$—OH | —H | H | s | s | s |
| —N(CH$_3$)$_2$ | —OH | CH$_2$—OH | —H | H | s | u | s |
| —N(CH$_3$)$_2$ | —OAc | CO$_2$H | —H | H | u | u | s |
| —N(CH$_3$)$_2$ | —N(CH$_3$)$_2$ | CONH$_2$ | —H | — | u | s | u | u - unsaturated
s - saturated

The following compounds are prepared by the procedure of Example 128 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane and employing the appropriate secondary amine.

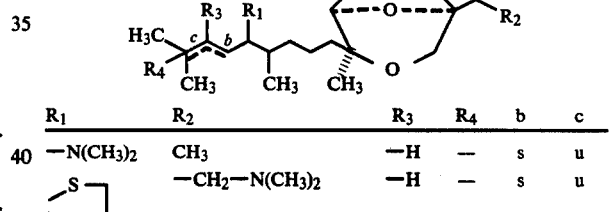

| $R_1$ | $R_2$ | $R_3$ | $R_4$ | b | c |
|---|---|---|---|---|---|
| —N(CH$_3$)$_2$ | CH$_3$ | —H | — | s | u |
| S–S (cyclic) | —CH$_2$—N(CH$_3$)$_2$ | —H | — | s | u | u - unsaturated
s - saturated

EXAMPLE 129

2S,3R-3-Acetoxy-6-(2-acetoxyethylidene)-2-methyl-2-(4,8-dimethyl-5-trimethylammonio-7-nonenyl)-oxepane iodide A solution of 2S,3R-3-acetoxy-6-(2-acetoxyethylidene)-2-methyl-2-(4,8-dimethyl-5-dimethylamino-7-nonenyl)-oxepane (450 mg.) in methyl iodide (3 ml.) is allowed to stand at 40° C. for 48 hrs. The excess methyl iodide is evaporated in vacuo to give 2S,3R-3-acetoxy-6-(2-acetoxyethylidene)-2-methyl-2-(4,8-dimethyl-5-trimethylammonio-7-nonenyl)-oxepane iodide.

The following compounds are prepared by the procedure of Example 129 by substituting an equivalent amount of the appropriate starting material for 2S,3R-3-acetoxy-6-(2-acetoxyethylidene)-2-methyl-2-(4,8-dimethyl-5-dimethylamino-7-nonenyl)-oxepane.

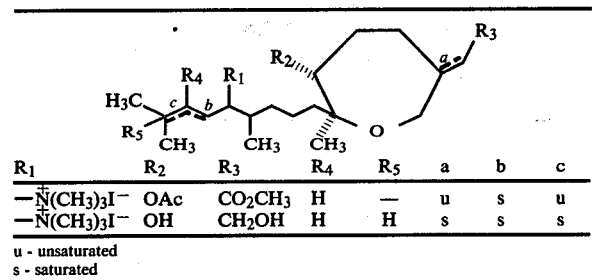

| $R_1$ | $R_2$ | $R_3$ | $R_4$ | $R_5$ | a | b | c |
|---|---|---|---|---|---|---|---|
| $-\overset{+}{N}(CH_3)_3I^-$ | OAc | $CO_2CH_3$ | H | — | u | s | u |
| $-\overset{+}{N}(CH_3)_3I^-$ | OH | $CH_2OH$ | H | H | s | s | s | u - unsaturated
s - saturated

The following compound is prepared by the procedure of Example 129 by substituting an equivalent amount of the appropriate starting material for 2S,3R-3-acetoxy-6-(2-acetoxyethylidene)-2-methyl-2-(4,8-dimethyl-5-dimethylamino-7-nonenyl-oxepane.

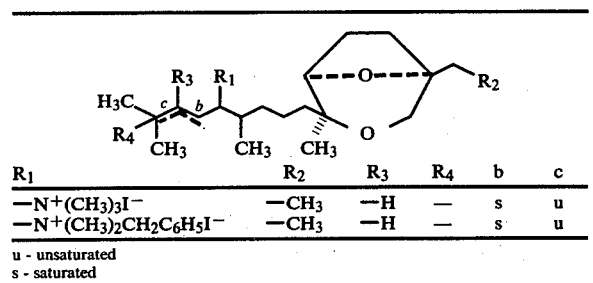

| $R_1$ | $R_2$ | $R_3$ | $R_4$ | b | c |
|---|---|---|---|---|---|
| $-N^+(CH_3)_3I^-$ | | $-CH_3$ | $-H$ | — | s | u |
| $-N^+(CH_3)_2CH_2C_6H_5I^-$ | | $-CH_3$ | $-H$ | — | s | u | u - unsaturated
s - saturated

EXAMPLE 130

2S-3-(Azacyclohex-1-yl)-6-(2-hydroxyethylidene)-2-methyl-2-(4,8-dimethyl-5-hydroxy-7-nonenyl)-3-oxepene A solution of 2S-6-(2-hydroxyethylidene)-2-methyl-2-(4,8-dimethyl-5-hydroxy-7-nonenyl)-oxepane-3-one (338 mg) and piperidine (170 mg) in anhydrous benzene (25 ml) is refluxed for 12 hrs employing a Dean-Stark water separator. The benzene and excess piperidine are evaporated in vacuo to give 2S-3-(azacyclohex-1-yl)-6-(2-hydroxyethylidene)-2-methyl-2-(4,8-dimethyl-5-hydroxy-7-nonenyl)-3-oxepene.

EXAMPLE 131

2S,3R-3-Acetoxy-6-(2-acetoxyethylidene)-2-methyl-2-(4,8-dimethyl-5-isopropylimino-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg) and isopropylamine (60 mg) in benzene (20 ml) is treated with one drop of concentrated hydrochloric acid and the reaction mixture refluxed with a water separator for 12 hrs. The benzene is evaporated to give 2S,3R-3-acetoxy-6-(2-acetoxyethylidene)-2-methyl-2-(4,8-dimethyl-5-isopropylimino-7-nonenyl)-oxepane.

EXAMPLE 132

2S,3R-6-(2-Trimethylsiloxyethylidene)-2-methyl-2-(4,8-dimethyl-5-oxo-7-nonenyl)-3-trimethylsiloxyoxepane To a mixture of 2S,3R-6-(2-hydroxyethylidene)-2-methyl-2-(4,8-dimethyl-5-oxo-7-nonenyl)-oxepan-3-ol (338 mg), pyridine (1 ml) and ether (10 ml) is added trimethylsilyl chloride (224 mg) at 0° under nitrogen. After the addition is completed, the mixture is allowed to warm to room temperature and stirred for 10 mins. The resulting mixture is then treated with ether (30 ml) and water (20 ml). The organic layer is washed with saturated cupric sulfate (3×20 ml), dried and evaporated in vacuo to give 2S,3R-6-(2-trimethylsiloxyethylidene)-2-methyl-2-(4,8-dimethyl-5-oxo-7-nonenyl)-3-trimethylsiloxyoxepane.

The following compounds are prepared according to the procedure of Example 132 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

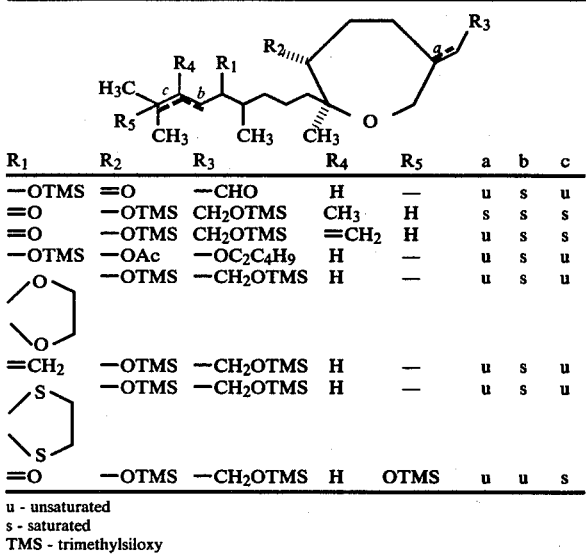

| $R_1$ | $R_2$ | $R_3$ | $R_4$ | $R_5$ | a | b | c |
|---|---|---|---|---|---|---|---|
| —OTMS | =O | —CHO | H | — | u | s | u |
| =O | —OTMS | $CH_2OTMS$ | $CH_3$ | H | s | s | s |
| =O | —OTMS | $CH_2OTMS$ | $=CH_2$ | H | u | s | s |
| —OTMS | —OAc | $-OC_2C_4H_9$ | H | — | u | s | u |
| ⟨O-O⟩ | —OTMS | $-CH_2OTMS$ | H | — | u | s | u |
| $=CH_2$ | —OTMS | $-CH_2OTMS$ | H | — | u | s | u |
| ⟨S-S⟩ | —OTMS | $-CH_2OTMS$ | H | — | u | s | u |
| =O | —OTMS | $-CH_2OTMS$ | H | OTMS | u | u | s | u - unsaturated
s - saturated
TMS - trimethylsiloxy

The folowing compounds are prepared according to the procedure of Example 132 by substituting an equivalent amount of the appropriate starting material for 2S,3R-6-(2-hydroxyethylidene)-2-methyl-2-(4,8-dimethyl-5-oxo-7-nonenyl)oxepan-3-ol.

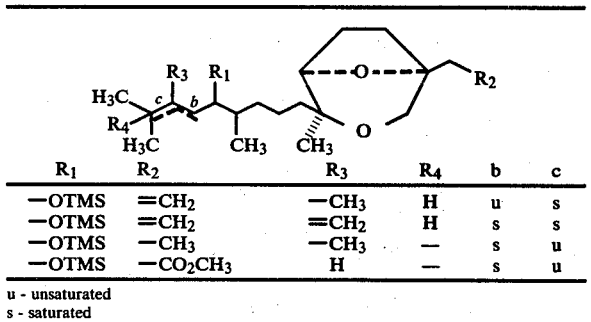

| $R_1$ | $R_2$ | $R_3$ | $R_4$ | b | c |
|---|---|---|---|---|---|
| —OTMS | $=CH_2$ | $-CH_3$ | H | u | s |
| —OTMS | $=CH_2$ | $=CH_2$ | H | s | s |
| —OTMS | $-CH_3$ | $-CH_3$ | — | s | u |
| —OTMS | $-CO_2CH_3$ | H | — | s | u | u - unsaturated
s - saturated

EXAMPLE 133

2S,3R-Acetoxy-6-(2-methoxyethylidene)-2-methyl-2-(5-acetoxy-4,8-dimethyl-7-nonenyl)-oxepane (A) Following the procedure of Example 141, but substituting an equivalent amount of 2S,3R-3-acetoxy-6-(2-hydroxyethylidene)-2-methyl-2-(5-acetoxy-4,8-dimethyl-7-nonenyl)oxepane for 2S,3R-3-acetoxy-6-(2-hydroxyethylidene)-2-methyl-2-(4,8-dimethyl-5-oxo-7- nonenyl)-oxepane the 2-bromoethylidene derivative is obtained. A mixture of sodium amide (39 mg) and tetrahydrofuran (10 ml) is treated with dry methanol (32 mg) in tetrahydrofuran (1 ml) at 0° under argon. The 2-bromoethylidene derivative (450 mg) is added and the resulting mixture is refluxed for 2 hrs. The mixture is treated with water (20 ml) and ether (50 ml) and the organic layer dried and evaporated to afford 2S,3R-3-acetoxy-6-(2-methoxyethylidene)-2-methyl-2-(5-acetoxy-4,8-dimethyl-7-nonenyl)-oxepane.

Similarly, by substituting other alcohols for methanol in the above procedure, the corresponding ethers are formed. Thus, phenol, ethanol and cyclohexanol afford the phenyl ether, ethyl ether and cyclohexyl ether respectively.

(B) To a mixture of sodium amide (39 mg) and tetrahydrofuran (20 ml) is added 2S,3R-3-acetoxy-6-(2-hydroxyethylidene)-2-methyl-2-(5-acetoxy-4,8-dimethyl-7-nonenyl)-oxepane (400 mg) in tetrahydrofuran (1 ml) at 0° under argon. The mixture is allowed to warm to room temperature and is treated with an excess of methyl iodide (1 ml). The resulting mixture is stirred overnight and then treated with water (30 ml) and ether (50 ml). The organic layer is dried and evaporated to afford 2S,3R-3-acetoxy-6-(2-methoxyethylidene)-2-methyl-2-(5-acetoxy-4,8-dimethyl-7-nonenyl)-oxepane.

Similarly by substituting other halides for methyl iodide in this procedure, the corresponding ethers are formed. Thus, allyl bromide, benzyl bromide and ethyl iodide afford the allyl ether, benzyl ether and ethyl ether respectively.

The following compounds are prepared according to the procedure of Example 133 by substituting an equivalent amount of the appropriate starting material for 2S,3R-3-acetoxy-6-(2-hydroxyethylidene)-2-methyl-2-(5-acetoxy-4,8-dimethyl-7-nonenyl)-oxepane and employing the appropriated alkyl halide.

| $R_1$ | $R_2$ | $R_3$ | $R_4$ | $R_5$ | a | b | c |
|---|---|---|---|---|---|---|---|
| —OCH$_3$ | —OAc | —CHO | H | — | u | s | u |
| —OC$_5$H$_{11}$ | —OC$_5$H$_{11}$ | —CH$_2$—OC$_5$H$_{11}$ | H | — | u | s | u |
| =O | —OCH$_3$ | —CH$_2$—OCH$_3$ | H | H | s | s | s |
| =O | —OC$_3$H$_7$ | —CH$_2$OC$_3$H$_7$ | H | H | u | s | s |
| =O | —OC$_2$H$_5$ | —CH$_2$—OC$_2$H$_5$ | CH$_3$ | H | s | u | s |
| =O | —OCH$_3$ | —CH$_2$OCH$_3$ | CH$_3$ | H | s | s | s |
| =O | —OCH$_3$ | —CH$_2$OCH$_3$ | CH$_3$ | — | u | s | u |
| —OCH$_3$ | —OAc | —CO$_2$CH$_3$ | H | — | u | s | u |
| —OCH$_3$ | —OAc | C≡N | H | — | u | s | u |
| —OCH$_2$C$_6$H$_5$ | —OAc | —CHO | H | — | u | s | u |
| ⟨O–O⟩ | —OAc | —CH$_2$OC$_6$H$_5$ | H | — | u | s | u | u - unsaturated
s - saturated

The following compounds are prepared according to the procedure of Example 133 by substituting an equivalent amount of the appropriate starting material for 2S,3R-3-acetoxy-6-(2-hydroxyethylidene)-2-methyl-2-(5-acetoxy-4,8-dimethyl-7-nonenyl)-oxepane and employing the appropriate alkyl halide.

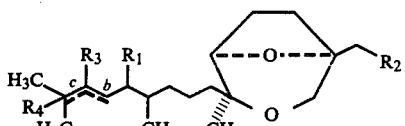

| $R_1$ | $R_2$ | $R_3$ | $R_4$ | b | c |
|---|---|---|---|---|---|
| —OCH$_3$ | —CH$_3$ | —H | H | s | s |
| —OCH$_3$ | —CH$_3$ | —CH$_3$ | H | s | s |
| —OC$_2$H$_5$ | =CH$_2$ | H | H | u | s |
| —O—C$_3$H$_7$ | —CH$_3$ | H | — | s | u |
| —OCH$_2$—C$_6$H$_5$ | =CH$_2$ | H | H | s | s |
| —OC$_6$H$_5$ | CH$_3$ | =CH$_2$ | H | s | s |
| —OC$_2$H$_5$ | =CH$_2$ | —CH$_3$ | H | s | s |
| —OC$_4$H$_9$ | —CH$_3$ | —CH$_3$ | H | u | s |
| —OCH$_3$ | —CO$_2$CH$_3$ | H | — | s | u |
| —OCH$_3$ | —CONH$_2$ | H | — | s | u |
| —OCH$_3$ | —CONH—NH$_2$ | H | — | s | u | u - unsaturated
s - saturated

EXAMPLE 134

2S,3R-6-[2-(Tetrahydropyran-2-yloxy)-ethylidene]-2-methyl-2-(4,8-dimethyl-5-oxo-7-nonenyl)-3-(tetrahydropyran-2-yloxy)-oxepane A solution of 2S,3R-6-(2-hydroxyethylidene)-2-methyl-2-(4,8-dimethyl-5-oxo-7-nonenyl)-oxepan-3-ol (600 mg) in benzene (5 ml) is treated, while stirring, with dihydropyran (7.8 ml) and p-toluenesulfonic acid monohydrate (3 mg) at room temperature under nitrogen for 1.2 hrs. The benzene solution is washed with 10% aqueous sodium carbonate solution, dried and the solvent removed in vacuo to afford the crude product (871 mg) which is chromatographed on a SilicAR column using ethyl acetate-hexane (1:20) as the eluting solvent. The major fraction is eluted to afford 2S,3R-6-[2-(tetrahydropyran-2-yloxy)-ethylidene]-2-methyl-2-(4,8-dimethyl-5-oxo-7-nonenyl)-3-(tetrahydropyran-2-yloxy)-oxepane (395 mg).

IR (neat) very weak OH at 2.95μ, C=O at 5.81μ
NMR$_{TMS}^{CDCl_3}$ δ 1.05 (d, J=7 Hz, 3H, CH—C$\underline{H}_3$); 1.10 (s, 3H, O—C—C$\underline{H}_3$); 1.23 (s, 3H, unassigned); 2.60 (s, 2H, unassigned); 3.11 (d, J=7 Hz, C$\underline{H}_2$—CO); 4.05 (s, 2H, C$\underline{H}_2$—O—R); 4.58 (m, C=CH—CH$_2$—OTHP); 5.10–5.20 [m,2H, (CH$_3$)$_2$—C=C$\underline{H}$ and C=C$\underline{H}$—CH$_2$—OTHP].

The following compounds are prepared according to the procedure of Example 134 by substituting an equivalent amount of the starting material for 2S,3R-6-(2-hydroxyethylidene)-2-methyl-2-(4,8-dimethyl-5-oxo-7-nonenyl)-oxepan-3-ol.

| R₁ | R₂ | R₃ | R₄ | R₅ | a | b | c |
|---|---|---|---|---|---|---|---|
| =O | =O | CH₂OTHP | H | — | u | s | u |
| —OTHP | =O | CH₂OTHP | H | — | s | s | u |
| =O | —OTHP | CH₂OTHP | CH₃ | H | u | u | s |
| =O | OTHP | CH₂OTHP | H | — | s | s | u |
| =O | OTHP | CH₂OTHP | H | H | u | u | s |
| =O | OTHP | CH₂OTHP | CH₃ | — | u | s | u |
| —OTHP | OAc | CONH₂ | H | — | u | s | u |
| —OTHP | —OAc | CON(CH₃)₂ | H | — | u | s | u |
| =O | OH | CH₂OTHP | H | — | u | s | u |
| =O | OTHP | CH₂Br | H | — | u | s | u |
| =O | OTHP | CH₂SCH₃ | H | — | u | s | u |
| CH₃/\OH | OTHP | CH₂OTHP | H | — | u | s | u | u - unsaturated
s - saturated
THP - tetrahydropyran-2-yloxy

The following compounds are prepared according to the procedure of Example 134 by substituting an equivalent amount of the appropriate starting material for 2S,3R-6-(2-hydroxyethylidene)-2-methyl-2-(4,8-dimethyl-5-oxo-7-nonenyl)-oxepan-3ol.

| R₁ | R₂ | R₃ | R₄ | b | c |
|---|---|---|---|---|---|
| —OTHP | =CH₂ | H | — | s | u |
| —OTHP | =CH₂ | CH₃ | — | s | u |
| —OTHP | —CH₃ | H | H | u | s |
| =O | CH₂OTHP | H | — | s | u |
| —OCH₂C₆H₅ | CH₂OTHP | H | — | s | u |
| —OTHP | —CHO | H | — | s | u |
| —OTHP | C≡N | H | — | s | u |
| —OTHP | CONH₂ | H | — | s | u |
| CH₃/\OH | CH₂OTHP | H | — | s | u | u - unsaturated
s - saturated
THP - tetrahydropyran-2-yloxy

EXAMPLE 134'

2S,3R-6-[2-(Tetrahydropyran-2-yloxy)-ethylidene]-2-methyl-2-(4,8-dimethyl-5-tetrahydropyran-2-yloxy-7-nonenyl)-3-(tetrahydropyran -2-yloxy)-oxepane To a mixture of 2S,3R-6-(2-hydroxyethylidene)-2-methyl-2-(4,8-dimethyl-5-hydroxy-7-nonenyl)-oxepan-3-ol (450 mg) and methylene chloride (10 ml) is added dihydropyran (2.25 ml) and p-toluenesulfonic acid (5.0 mg) at room temperature under nitrogen for 1.2 hr. The organic phase is washed with 10% sodium bicarbonate solution (3×15 ml) and dried. The solvent is removed in vacuo to give a brown oily residue which is plate chromatographed on silica gel, using ethyl acetate-cyclohexane (1:4) as the developing solvent. The major band is eluted with ethyl acetate-cyclohexane (1:1) to afford 2S,3R-6-[2-(tetrahydropyran-2-yloxy)-ethylidene]-2-methyl-2-(4,8-dimethyl-5-tetrahydropyran-2-yloxy-7-nonenyl)-3(tetrahydropyran-2-yloxy)oxepane (329 mg): ir (neat); 9.3μ (C—O); nmr (CDCl₃,δ): 4.03 (m, 2H, C$\underline{H}_2$—O—R), 4.56 (m, 2H, C=CH—C$\underline{H}_2$—OTHP), 5.1 to 5.5 [m, 2H, (CH₃)₂—C=CH and C=CH—C$\underline{H}$₂—OTHP].

EXAMPLE 135

2S,3R-3-Acetoxy-6-(2-sulfooxyethylidene)-2-methyl-2-(4,8-dimethyl-5-oxo-7-nonenyl)-oxepane A solution of 2S,3R-3-acetoxy-6-(2-hydroxyethylidene)-2-methyl-2-(4,8-dimethyl-5-oxo-7-nonenyl)-oxepane (380 mg) and N-cyclohexylsulfamic acid (600 mg) in anhydrous pyridine (20 ml) is heated at 60° C. for 4 hours. The reaction mixture is diluted with water (1.0 ml) and heated to 100° for 10 minutes to decompose excess N-cyclohexylsulfamic acid. The pyridine is evaporated, the residue is dissolved in water (10 ml) and passed through Dowex 50 H³⁰ resin to afford 2S,3R-3-acetoxy-6-(2-sulfooxyethylidene)-2-methyl-2-(4,8-dimethyl-5-oxo-7-nonenyl)oxepane.

The following compound is prepared according to the procedure of Example 135 by substituting an equivalent amount of the appropriate starting material for 2S,3R-3-acetoxy-6-(2-hydroxyethylidene)-2-methyl-2-(4,8-dimethyl-5-oxo-7-nonenyl)oxepane.

| R₁ | R₂ | R₃ | R₄ | R₅ | a | b | c |
|---|---|---|---|---|---|---|---|
| =O | =O | CH₂OSO₃H | H | — | u | s | u | u - unsaturated
s - saturated

The following compounds are prepared according to the procedure of Example 135 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

| EXAMPLE | R₁ | R₂ | R₃ | R₄ | b | c |
|---|---|---|---|---|---|---|
| | —OSO₃H | =CH₂ | CH₃ | H | u | s |
| | —OSO₃H | =CH₃ | =CH₂ | H | s | s |
| | —OSO₃H | CH₃ | H | H | u | s |
| | —OSO₃H | CONH(CH₃)₂ | H | — | s | u | u - unsaturated
s - saturated

EXAMPLE 136

2S,3R-3-Acetoxy-6-(2-sulfooxyethylidene)-2-methyl-2-(4,8-dimethyl-5-oxo-7-nonenyl)-oxepane, triethylammonium salt A solution of 2S,3R-3-acetoxy-6-(2-hydroxyethylidene)-2-methyl-2-(4,8-dimethyl-5-oxo-7-nonenyl)-oxepane (380 mg) and purified triethylamine sulfur trioxide complex (210 mg) in pyridine (2 ml) is heated at 75° for 12 hours. After cooling, anhydrous ether (50 ml) is added to the reaction mixture and the resulting solution is allowed to stand in the cold for 1 hour. The ether is decanted and the residue is chromatographed on silica gel to give 2S,3R-3-acetoxy-6-(2-sulfooxyethylidene)-2-methyl-2-(4,8-dimethyl-5-oxo-7-nonenyl)-oxepane, triethylammonium salt.

The following compounds are prepared according to the procedure of Example 136 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

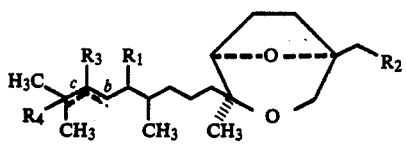

| $R_1$ | $R_2$ | $R_3$ | $R_4$ | b | c |
|---|---|---|---|---|---|
| $OSO_3NH(C_2H_5)_3$ | $CH_3$ | H | H | s | s |
| $OSO_3NH(C_2H_5)_3$ | $CH_3$ | $=CH_2$ | H | s | s |
| $OSO_3NH(C_2H_5)_3$ | CHO | H | — | s | u |
| $OSO_3NH(C_2H_5)_3$ | $CONH_2$ | H | — | s | u |
| $OSO_2NH(C_2H_5)_3$ | $CONH-NH_2$ | H | — | s | u | u - unsaturated
s - saturated

EXAMPLE 137

2S,3R-3-Acetoxy-6-(2-nitrooxyethylidene)-2-methyl-2-(4,8-dimethyl-5-oxo-7-nonenyl)-oxepane Nitric acid (95%, 0.65 ml) is slowly added to acetic anhydride (1.98 ml) at −25° C. followed by the addition of 2S,3R-3-acetoxy-6-(2-hydroxyethylidene)-2-methyl-2-(4,8-dimethyl-5-oxo-7-nonenyl)-oxepane (380 mg) at −20° C. The stirred mixture is slowly warmed to 0°–5° C. within 20 minutes. The mixture is then poured over ice, neutralized with sodium bicarbonate and extracted with ether. The ether extract is evaporated in vacuo to afford 2S,3R-3-acetoxy-6-(2-nitrooxyethylidene)-2-methyl-2-(4,8-dimethyl-5-oxo-7-nonenyl)-oxepane.

The following compounds are prepared according to the procedure of Example 136 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

| $R_1$ | $R_2$ | $R_3$ | $R_4$ | $R_5$ | a | b | c |
|---|---|---|---|---|---|---|---|
| =O | $OSO_3NH(C_2H_5)_3$ | $CH_2-OSO_3NH(C_2H_5)_3$ | H | — | u | s | u |
| $-OSO_3NH(C_2H_5)_3$ | =O | CHO | H | — | u | s | u |
| $-OSO_3NH(C_2H_5)_3$ | OAc | CHO | H | — | u | s | u |
| $-OSO_3NH(C_2H_5)_3$ | $OSO_3NH(C_2H_5)_3$ | $CH_2-OSO_3NH(C_2H_5)_3$ | H | — | u | s | u |
| =O | $OSO_3NH(C_2H_5)_3$ | $CH_2-OSO_3NH(C_2H_5)_3$ | $CH_3$ | H | u | u | s |
| =O | $OSO_3NH(C_2H_5)_3$ | $CH_2-OSO_3NH(C_2H_5)_3$ | H | H | u | s | s |
| =O | $OSO_3NH(C_2H_5)_3$ | $CH_2-OSO_3NH(C_2H_5)_3$ | $CH_3$ | H | u | s | s |
| =O | $OSO_3NH(C_2H_5)_3$ | $CH_2-OSO_3NH(C_2H_5)_3$ | H | H | u | u | s |
| =O | $OSO_3NH(C_2H_5)_3$ | $CH_2-OSO_3NH(C_2H_5)_3$ | $=CH_2$ | H | u | s | s |
| =O | $OSO_3NH(C_2H_5)_3$ | $CH_2-OSO_3NH(C_2H_5)_3$ | $CH_3$ | — | u | s | u |
| =O | $OSO_3NHCH_3$ | $CH_2-OTHP$ | H | — | u | s | u |
| /O\O\ (dioxane ring) | $OSO_3NH(C_2H_5)_3$ | $CH_2-OSO_3NH(C_2H_5)_3$ | H | — | u | s | u |
| /N\S\ | $OSO_3NH(C_2H_5)_3$ | $CH_2-OSO_3NH(C_2H_5)_3$ | H | — | u | s | u |
| /S\S\ | $OSO_3NH(C_2H_5)_3$ | $CH_2-OSO_3NH(C_2H_5)_3$ | H | — | u | s | u |
| /CH_3 \OH | $OSO_3NH(C_2H_5)_3$ | $CH_2-OSO_3NH(C_2H_5)_3$ | H | — | u | s | u | u - unsaturated
s - saturated
THP - tetrahydropyran-2-yloxy

The following compounds are prepared according to the procedure of Example 137 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

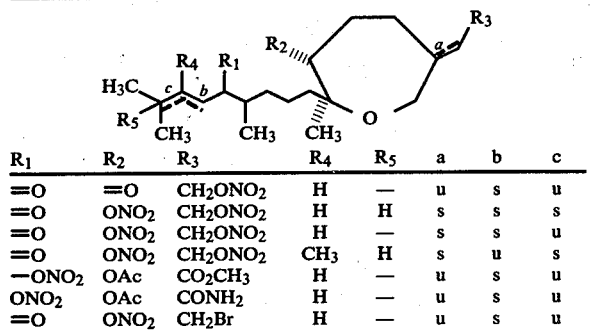

| R₁ | R₂ | R₃ | R₄ | R₅ | a | b | c |
|---|---|---|---|---|---|---|---|
| =O | =O | CH₂ONO₂ | H | — | u | s | u |
| =O | ONO₂ | CH₂ONO₂ | H | H | s | s | s |
| =O | ONO₂ | CH₂ONO₂ | H | — | s | s | u |
| =O | ONO₂ | CH₂ONO₂ | CH₃ | H | s | u | s |
| —ONO₂ | OAc | CO₂CH₃ | H | — | u | s | u |
| ONO₂ | OAc | CONH₂ | H | — | u | s | u |
| =O | ONO₂ | CH₂Br | H | — | u | s | u | u - unsaturated
s - saturated

The following compounds are prepared according to the procedure of Example 137 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

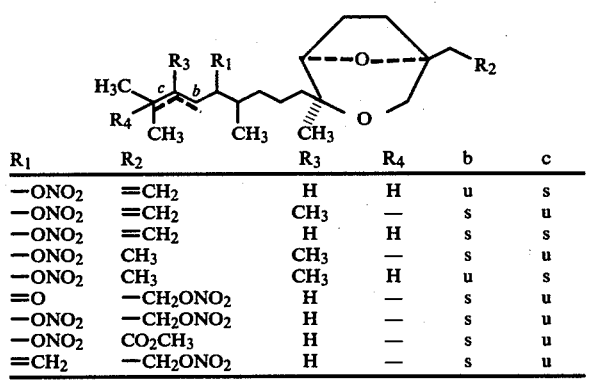

| R₁ | R₂ | R₃ | R₄ | b | c |
|---|---|---|---|---|---|
| —ONO₂ | =CH₂ | H | H | u | s |
| —ONO₂ | =CH₂ | CH₃ | — | s | u |
| —ONO₂ | =CH₂ | H | H | s | s |
| —ONO₂ | CH₃ | CH₃ | — | s | u |
| —ONO₂ | CH₃ | CH₃ | H | u | s |
| =O | —CH₂ONO₂ | H | — | s | u |
| —ONO₂ | —CH₂ONO₂ | H | — | s | u |
| —ONO₂ | CO₂CH₃ | H | — | s | u |
| =CH₂ | —CH₂ONO₂ | H | — | s | u | u - unsaturated
s - saturated

EXAMPLE 138

2S,3R-3-Acetoxy-6-(2-phosphonooxyethylidene)-2-methyl-2-(4,8-dimethyl-5-oxo-7-nonenyl)-oxepane A solution of 2S,3R-3-acetoxy-6-(2-hydroxyethylidene)-2-methyl-2-(4,8-dimethyl-5-oxo-7-nonenyl)-oxepane (380 mg) in dry tetrahydrofuran (10 ml) is added dropwise to a stirred solution of pyrophosphoryl chloride (1 g) in dry tetrahydrofuran (5 ml) at 0°–5° C. After stirring at 0°–5° C. for 3 hours, the reaction mixture is diluted with ice-cold water (75 ml) and the tetrahydrofuran is evaporated in vacuo. The product is extracted with ethyl acetate and after washing with water, the solvent is removed in vacuo to afford 2S,3R-3-acetoxy-6-(2-phosphonooxyethylidene)-2-methyl-2-(4,8-dimethyl-5-oxo-7-nonenyl)-oxepane.

The following compound is prepared according to the procedure of Example 138 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

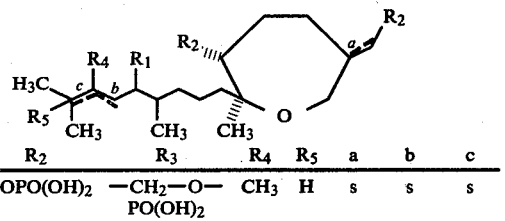

| R₁ | R₂ | R₃ | R₄ | R₅ | a | b | c |
|---|---|---|---|---|---|---|---|
| =O | —OPO(OH)₂ | —CH₂—O—PO(OH)₂ | CH₃ | H | s | s | s | s - saturated
u - unsaturated

The following compound is prepared by the procedure of Example 138 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

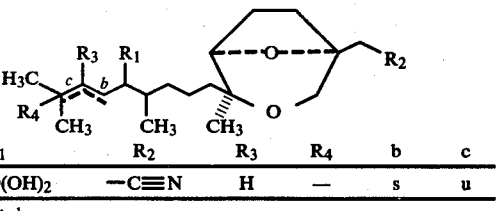

| R₁ | R₂ | R₃ | R₄ | b | c |
|---|---|---|---|---|---|
| —OPO(OH)₂ | —C≡N | H | — | s | u | u - unsaturated
s - saturated

EXAMPLE 139

2S,3R-3-Acetoxy-6-(2-phosphonooxyethylidene)-2-methyl-2-(4,8-dimethyl-5-oxo-7-nonenyl)-oxepane, disodium salt A solution of 2S,3R-3-acetoxy-6-(2-phosphonooxyethylidene)-2-methyl-2-(4,8-dimethyl-5-oxo-7-nonenyl)-oxepane (500 mg) in methanol (10 ml) is adjusted to pH 10.5 by slow addition of cold aqueous sodium hydroxide solution. Addition of ether affords 2S,3R-3-acetoxy-6-(2-phosphonooxyethylidene)-2-methyl-2-(4,8-dimethyl-5-oxo-7-nonenyl)-oxepane, disodium salt, which is collected by filtration.

The following compound is prepared according to the procedure of Example 139 by substituting an equivalent amount of the appropriate starting material for 2S,3R-3-acetoxy-6-(2-phosphonooxyethylidene)-2-methyl-2-(4,8-dimethyl-5-oxo7-nonenyl)-oxepane.

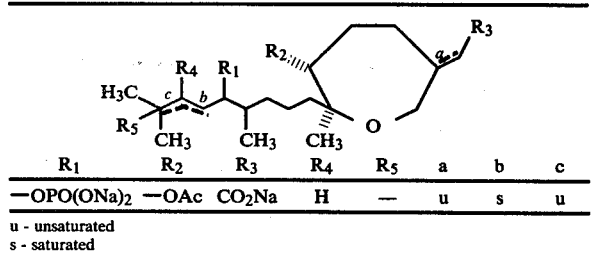

| R₁ | R₂ | R₃ | R₄ | R₅ | a | b | c |
|---|---|---|---|---|---|---|---|
| —OPO(ONa)₂ | —OAc | CO₂Na | H | — | u | s | u | u - unsaturated
s - saturated

The following compounds are prepared according to the procedure of Example 139 by substituting an equivalent amount of the appropriate starting material for 2S,3R-3-acetoxy-6-(2-phosphonooxyethylidene)-2-methyl-2-(4,8-dimethyl-5-oxo-7-nonenyl)-oxepane.

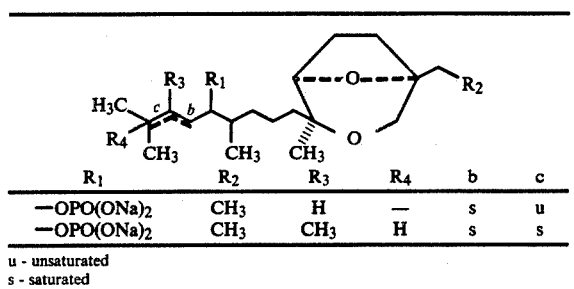

| R₁ | R₂ | R₃ | R₄ | b | c |
|---|---|---|---|---|---|
| —OPO(ONa)₂ | CH₃ | H | — | s | u |
| —OPO(ONa)₂ | CH₃ | CH₃ | H | s | s | u - unsaturated
s - saturated

EXAMPLE 140

2S,3R-3-Acetoxy-6-(2-dimethylphosphonooxyethylidene)-2-methyl-2-(4,8-dimethyl-5-oxo-7-nonenyl)-oxepane To a stirred solution of phosphorous oxychloride (0.2 ml) in dry acetone (2 ml) at 0° is slowly added a solution of 2S,3R-3-acetoxy-6-(2-hydroxyethylidene)-2-methyl-2-(4,8-dimethyl-5-oxo-7-nonenyl)-oxepane (380 mg) and triethylamine (0.5 ml) in dry acetone (2 ml). After 1 hour, anhydrous methanol (1 ml) is slowly introduced and the mixture allowed to stir for 1 hour. Triethylamine hydrochloride is removed by filtration and ether (30 ml) is added to the filtrate. The organic phase is washed with 10% aqueous sodium bicarbonate, dried and evaporated to afford 2S,3R-3-acetoxy-6-(2-dimethylphosphonooxyethylidene)-2-methyl-2-(4,8-dimethyl-5-oxo-7-nonenyl)-oxepane.

The following compounds are prepared according to the procedure of Example 140 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

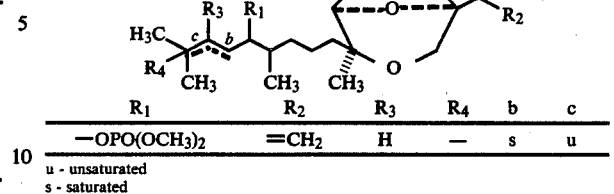

| R₁ | R₂ | R₃ | R₄ | b | c |
|---|---|---|---|---|---|
| —OPO(OCH₃)₂ | =CH₂ | H | — | s | u | u - unsaturated
s - saturated

EXAMPLE 141

2S,3R-3-Acetoxy-6-(2-bromoethylidene)-2-methyl-2-(4,8-dimethyl-5-oxo-7-nonenyl)-oxepane To a mixture of 2S,3R-3-acetoxy-6-(2-hydroxyethylidene)-2-methyl-2-(4,8-dimethyl-5-oxo-7-nonenyl)-oxepane (390 mg.), pyridine (2 ml.) and ether (30 ml.) is added an excess of phosphorous tribromide (540 mg.) at 0° under nitrogen. The resulting mixture is stirred for 2 hours and poured into water (30 ml.). The mixture is then extracted with ether (3×30 ml.), the organic layers are combined, washed with saturated curpic sulfate, dried and evaporated in vacuo to give 2S,3R-3-acetoxy-6-(2-bromoethylidene)-2-methyl-2-(4,8-dimethyl-5-oxo-7-nonenyl)-oxepane.

Similarly, by substituting phosphorous trichloride for phosphorous tribromide in the procedure of Example 141, the corresponding chloride is obtained.

The following compounds are prepared according to the procedure of Example 141 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane and employing the appropriate phosphorous trihalide.

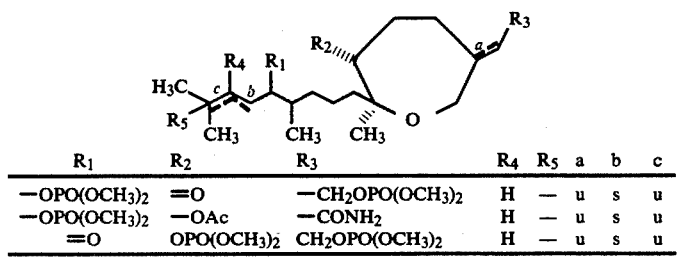

| R₁ | R₂ | R₃ | R₄ | R₅ | a | b | c |
|---|---|---|---|---|---|---|---|
| —OPO(OCH₃)₂ | =O | —CH₂OPO(OCH₃)₂ | H | — | u | s | u |
| —OPO(OCH₃)₂ | —OAc | —CONH₂ | H | — | u | s | u |
| =O | OPO(OCH₃)₂ | CH₂OPO(OCH₃)₂ | H | — | u | s | u | u - unsaturated
s - saturated

The following compound is prepared according to the procedure of Example 140 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane.

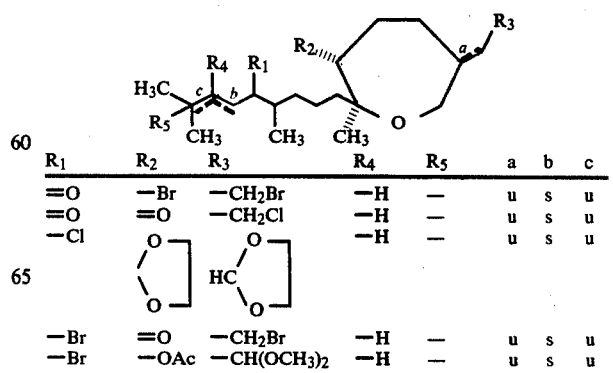

| R₁ | R₂ | R₃ | R₄ | R₅ | a | b | c |
|---|---|---|---|---|---|---|---|
| =O | —Br | —CH₂Br | —H | — | u | s | u |
| =O | =O | —CH₂Cl | —H | — | u | s | u |
| —Cl | O⟩ O | HC⟨ O O | —H | — | u | s | u |
| —Br | =O | —CH₂Br | —H | — | u | s | u |
| —Br | —OAc | —CH(OCH₃)₂ | —H | — | u | s | u |

-continued

[Structure: oxepane ring with substituents R1, R2, R3, R4, R5, CH3, CH3, CH3, with positions a, b, c]

| R1 | R2 | R3 | R4 | R5 | a | b | c |
|---|---|---|---|---|---|---|---|
| —Br | —Br | —CH2Br | —H | — | u | s | u |
| =O | —Cl | —CH2Cl | —CH3 | H | u | u | s |
| =O | —Cl | —CH2Cl | —H | H | s | s | s |
| =O | —Cl | —CH2Cl | —CH3 | H | s | s | s |
| =O | —Br | —CH2Br | —H | — | s | s | u |
| =O | —Br | —CH2Br | —H | H | u | s | s |
| =O | —Cl | —CH2Cl | —CH3 | —H | s | u | s |
| =O | —Cl | —CH2Cl | —CH3 | —H | u | s | s |
| =O | —Br | —CH2Br | —H | —H | u | u | s |
| =O | —Br | —CH2Br | —CH3 | — | u | s | u |
| =O | —Br | —CH2Br | =CH2 | —H | u | s | s |
| =O | —Cl | —CH2Cl | —H | —H | s | u | s |
| =O | —Br | —CH2Br | —CH3 | — | s | s | u |
| =O | —Br | —CH2Br | =CH2 | —H | s | s | s |
| —Br | —OAc | —CO2H | —H | — | u | s | u |
| —Cl | —OAc | —CO2H | —CH3 | —H | u | u | s |
| —Br | —OAc | —CO2H | —H | —H | u | s | u |
| —Cl | —OAc | —CO2CH3 | —H | — | u | s | u |
| —Br | —OAc | —CO2C2H5 | —CH3 | —H | u | u | s |
| —Br | —OAc | —CO2—C2H5 | —H | — | u | s | u |
| —Br | —OAc | —CO2C6H5 | —CH3 | —H | s | u | s |
| —Cl | =O | —CONH2 | —H | — | u | s | u |
| —Br | —OAc | —CONH2 | —CH3 | —H | u | u | s |
| —Cl | —OAc | —C≡N | —H | — | u | s | u |
| —Cl | —OAc | —C≡N | —CH3 | —H | u | u | s |
| —Cl | —OAc | —C≡N | —CH3 | —H | s | u | s |
| =O | —Br | —CH2Br | —H | —OH | u | u | s |
|  | —Br | —CH2Br | —H | — | u | s | u |
| [O/O cyclic] | —Cl | —CH2Cl | —H | H | s | s | s |
| [S/S cyclic] |  |  |  |  |  |  |  |
| =CH2 | —Br | —CH2Br | —H | — | u | s | u |
| —Br | —OAc | [S/CH/S cyclic] | —H | — | u | s | u | u - unsaturated
s - saturated

The following compounds are prepared according to the procedure of Example 141 by substituting an equivalent amount of the appropriate starting material for 2S,3R-3-acetoxy-6-(2-hydroxyethylidene)-2-methyl-2-(4,8-dimethyl-5-oxo-7-nonenyl)-oxepane and employing the appropriate phosphorous trihalide.

[Structure]

| R1 | R2 | R3 | R4 | b | c |
|---|---|---|---|---|---|
| —Br | =CH2 | —H | — | s | u |
| —Cl | —CH3 | —H | — | s | u |
| —Br | —CH2Br | —H | — | s | u |
| —Br | —HC(OCH3)2 | —H | — | s | u |
| —Cl | —CO2H | —H | — | s | u |
| —Cl | —C≡N | —H | — | s | u |
| —Br | —CO2C2H5 | —H | — | s | u |
| —Br | —CO2C4H9 | —H | — | s | u |
| —Cl | —CO—NH2 | —H | — | s | u |
| —Br | =CH2 | —CH3 | —H | s | u |
| —Cl | =CH2 | —CH3 | — | s | u |
| —Cl | —CH2Cl | —CH3 | —H | u | s |
| —Cl | =CH2 | —H | —OH | u | s |
| —Cl | —CONHC2H5 | —H | — | s | u |
| —Br | —CON(CH3)2 | —H | — | s | u |
| =O | —CH2Br | —H | — | s | u |
| [O/O cyclic] | —CH2Br | —H | — | s | u |
| [S/S cyclic] | —CH2Cl | —H | — | s | u |
| =CH2 | —CH2Br | —H | — | s | u |
| Br | —CH2OAc | —H | — | s | u | u - unsaturated
s - saturated

EXAMPLE 142

2S,3R-3-Acetoxy-6-(2-mercaptoethylidene)-2-methyl-2-(4,8-dimethyl-5-oxo-7-nonenyl)-oxepane

A solution of thioacetic acid (78 mg.) in absolute ethanol (20 ml.) is neutralized with potassium hydroxide (56 mg.) and 2S,3R-3-acetoxy-6-(2-bromoethylidene)-2-methyl-2-(4,8-dimethyl-5-oxo-7-nonenyl)-oxepane (440 mg.) is added at 0°. The reaction mixture is allowed to warm to room temperature and stirred for 6 hours. The resulting mixture is treated with water (20 ml.) and the ethanol is removed in vacuo. The residue is extracted with ether; the combined organic phase is dried and evaporated to give 2S,3R-3-acetoxy-6-(2-mercaptoethylidene)-2-methyl-2-(4,8-dimethyl-5-oxo-7-nonenyl)-oxepane.

The following compounds are prepared according to the procedure of Example 142 by substituting an equivalent amount of the appropriate starting material for 2S,3R-3-acetoxy-6-(2-bromoethylidene)-2-methyl-2-(4,8-dimethyl-5-oxo-7-nonenyl)-oxepane.

[Structure]

| R1 | R2 | R3 | R4 | R5 | a | b | c |
|---|---|---|---|---|---|---|---|
| =O | —SH(S) | CH2SH | —H | — | u | s | u |
| =O | =O | CH2SH | —H | — | u | s | u |
| —SH | =O | CHO | —H | — | u | s | u |
| —SH | =O | —CH2SH | —H | — | u | s | u |
| —SH | —SH(S) | —CH2SH | —H | — | u | s | u |
| =O | —SH(S) | —CH2SH | —CH3 | —H | u | u | s |
| =O | —SH(S) | —CH2SH | —H | —H | s | s | s |
| =O | —SH(S) | —CH2SH | —CH3 | —H | s | s | s |
| =O | —SH(S) | —CH2SH | —CH3 | —H | s | u | s |
| =O | —SH(S) | —CH2SH | —CH3 | —H | u | s | s |
| =O | —SH(S) | —CH2SH | —CH3 | — | u | s | u |
| =O | —SH(S) | —CH2SH | —H | —H | s | u | s |
| =O | —SH(S) | —CH2SH | =CH2 | —H | s | s | s |
| —SH | —OAc | —CO2H | —CH3 | —H | u | u | s |
| —SH | —OAc | CO2CH3 | —H | — | u | s | u |
| —SH | —OAc | CON(CH3)2 | —H | — | u | s | u |
| —SH | —OAc | CON(CH3)2 | —CH3 | —H | s | u | s |

-continued

[Structure diagram with R1, R2, R3, R4, R5 substituents on an oxepane ring system with H3C, CH3 groups]

| R₁ | R₂ | R₃ | R₄ | R₅ | a | b | c |
|---|---|---|---|---|---|---|---|
| —SH | =O | CONH₂ | —H | — | | u | s | u |
| —SH | —OAc | C≡N | —H | — | | u | s | u |
| —SH | —OAc | C≡N | —CH₃ | H | u | u | s |
| —SH | —OAc | C≡N | —CH₃ | H | s | u | s |
| —SH | —SH(S) | —CH₂SH | —H | — | u | s | u |
| ⟨O-O⟩ | —SH(S) | —CH₂SH | —H | — | u | s | u |
| =CH₂ | —SH(S) | —CH₂SH | —H | — | u | s | u |
| —SH | —SH(S) | —CH₂OAc | —H | — | u | s | u | u - unsaturated
s - saturated
(S) = configuration at position 3

The following compounds are prepared according to the procedure of Example 142 by substituting an equivalent amount of the appropriate starting material for 2S,3R-3-acetoxy-6-(2-bromoethylidene)-2-methyl-2-(4,8-dimethyl-5-oxo-7-nonenyl)-oxepane.

[Structure diagram with R1, R2, R3, R4 substituents]

| R₁ | R₂ | R₃ | R₄ | b | c |
|---|---|---|---|---|---|
| —SH | —CH₃ | —H | — | s | u |
| —SH | —CHO | —H | — | s | u |
| —SH | —CO₂H | —H | — | s | u |
| —SH | C≡N | —H | — | s | u |
| —SH | CONH₂ | —H | — | s | u |
| —SH | =CH₂ | —CH₃ | — | s | u |
| —SH | —CH₂SH | —CH₃ | —H | u | s |
| —SH | =CH₂ | —H | —OH | u | s |
| —SH | CONHC₂H₅ | —H | — | s | u |
| =O | —CH₂SH | —H | — | s | u |
| ⟨S-S⟩ | —CH₂SH | —H | — | s | u | u - unsaturated
s - saturated

EXAMPLE 143

2S,3R-3-Acetoxy-6-(2-methylthioethylidene)-2-methyl-2-(4,8-dimethyl-5-oxo-7-nonenyl)-oxepane Methyl mercaptan (1 g.) is added to a mixture of sodium hydride (24 mg.) and tetrahydrofuran (10 ml.) at −20°. After 1 hour of stirring, the mixture is allowed to warm to room temperature and stirred for 1 hour. To the resulting suspension 2S,3R-3-acetoxy-6-(2-bromoethylidene)-2-methyl-2-(4,8-dimethyl-5-oxo-7-nonenyl)-oxepane (450 mg.) in tetrahydrofuran is slowly added and the resulting mixture is stirred for 16 hours. The mixture is treated with water (30 ml.) and ether (60 ml.). The organic layer is dried and evaporated to afford 2S,3R-3-acetoxy-6-(2-methylthioethylidene)-2-methyl-2-(4,8-dimethyl-5-oxo-7-nonenyl)-oxepane.

Similarly, by substituting other mercaptans for methyl mercaptan in the procedure of Example 143, the corresponding thioethers are obtained. Thus, cyclopentyl mercaptan, thiophenol and benzylmercaptan afford the cyclopentyl thioether, phenylthioether and benzylthioether respectively.

The following compounds are prepared according to the procedure of Example 143 by substituting an equivalent amount of the appropriate starting material for 2S,3R-3-acetoxy-6-(2-bromoethylidene)-2-methyl-2-(4,8-dimethyl-5-oxo-7-nonenyl)-oxepane.

[Structure diagram with R1, R2, R3, R4, R5 substituents]

| R₁ | R₂ | R₃ | R₄ | R₅ | a | b | c |
|---|---|---|---|---|---|---|---|
| —SCH₃ | —OAc | —CHO | —H | — | u | s | u |
| =O | —SCH₃(S) | —CH₂SCH₃ | —H | — | s | s | u |
| =O | —SCH₃(S) | —CH₂SCH₃ | —H | H | u | s | s |
| =O | —SCH₃(S) | —CH₂SCH₃ | —H | H | u | u | s |
| =O | —SCH₃(S) | —CH₂SCH₃ | —CH₃ | H | u | s | s |
| =O | —SCH₃(S) | —CH₂SCH₃ | —CH₃ | — | s | s | u |
| —SCH₃ | —OAc | —CO₂H | —H | — | u | s | u |
| —SCH₃ | —OAc | —CO₂H | —H | H | u | u | s |
| —SCH₃ | —OAc | —CO₂C₂H₅ | —CH₃ | H | u | u | s |
| —SCH₃ | —OAc | —CONH₂ | —CH₃ | H | u | s | s |
| =O | —SCH₃(S) | —CH₂SCH₃ | —H | OH | u | u | s |
| ⟨S-S⟩ | —SCH₃(S) | —CH₂SCH₃ | —H | H | s | s | s |
| —SCH₃ | —OAc | —CH⟨S-S⟩ | —H | — | u | s | u | u - unsaturated
s - saturated
(S) = configuration at position 3

The following compounds are prepared according to the procedure of Example 143 by substituting an equivalent amount of the appropriate starting material for 2S,3R-3-acetoxy-6-(2-bromoethylidene)-2-methyl-2-(4,8-dimethyl-5-oxo-7-nonenyl)-oxepane.

[Structure diagram with R1, R2, R3, R4 substituents]

| R₁ | R₂ | R₃ | R₄ | b | c |
|---|---|---|---|---|---|
| —SCH₃ | =CH₂ | —H | — | s | u |
| —SCH₃ | —CH₂SCH₃ | —H | — | s | u |
| —SCH₃ | —CON(CH₃)₂ | —H | — | s | u |
| —SCH₃ | —CO₂C₄H₉ | —H | — | s | u |
| —SCH₃ | =CH₂ | —CH₃ | —H | u | s |
| ⟨O-O⟩ | —CH₂SCH₃ | —H | — | s | u |
| =CH₂ | —CH₂SCH₃ | —H | — | s | u |
| —SCH₃ | —CH₂OAc | —H | — | s | u | u - unsaturated
s - saturated

EXAMPLE 144

2S,3R-3-Acetoxy-6-(2-p-nitrophenylcarbamoyloxyethylidene)-2-methyl-2-(4,8-dimethyl-5-oxo-7-nonenyl)-oxepane.

A solution of 2S,3R-3-acetoxy-6-(2-hydroxyethylidene)-2-methyl-2-(4,8-dimethyl-5-oxo-7-nonenyl)-oxepane (380 mg.) in benzene (5 ml.) is treated with p-nitrophenylisocyanate (180 mg.) in benzene (5 ml.) at room temperature under nitrogen for 15 minutes. Removal of the solvent affords 2S,3R-3-acetoxy-6-(2-p-nitrophenylcarbamoyloxyethylidene)-2-methyl-2-(4,8-dimethyl-5-oxo-7-nonenyl)-oxepane.

Similarly, by substituting other isocyanates for p-nitrophenylisocyanate in this procedure, the corresponding urethanes are obtained. Thus, methylisocyanate and phenylisocyanate afford the methyl urethane and phenyl urethane respectively.

EXAMPLE 145

2S,3R-6-[2-(Tetrahydropyran-2-yloxy)-ethylidene]-2-methyl-2-(4,8-dimethyl-5-thioxo-7-nonenyl)-3-tetrahydropyran-2-yloxy)-oxepane.

To a stirred solution of 2S,3R-6-[2-(tetrahydropyran-2-yloxy)-ethylidene]-2-methyl-2-(4,8-dimethyl-5-oxo-7-nonenyl)-3-(tetrahydropyran-2-yloxy)-oxepane (506 mg.) in pyridine (10 ml.), heated under nitrogen to ≈90°, phosphorous pentasulfide (556 mg.) is slowly added over a period of 10 minutes. The reaction mixture is maintained at 90° for 12 hours, then cooled and poured into ice water and extracted with ether. The ether layer is dried and evaporated to afford 2S,3R-6-[2-(tetrahydropyran-2-yloxy)-ethylidene]-2-methyl-2-(4,8-dimethyl-5-thioxo-7-nonenyl)-3-(tetrahydropyran-2-yloxy)-oxepane.

The following compounds are prepared according to the procedure of Example 145 by substituting an equivalent amount of the appropriate starting material for 2S,3R-6-[2-(tetrahydropyran-2-yloxy)-ethylidene]-2-methyl-2-(4,8-dimethyl-5-oxo-7-nonenyl)-3-(tetrahydropyran-2-yloxy)-oxepane.

| $R_1$ | $R_2$ | $R_3$ | $R_4$ | b | c |
|---|---|---|---|---|---|
| =S | =CH$_2$ | H | — | s | u |
| =S | =CH$_2$ | CH$_3$ | H | u | s |
| =S | CH$_3$ | H | H | s | s |
| =S | CH$_3$ | CH$_3$ | H | s | s |
| =S | =CH$_2$ | H | H | u | s |
| =S | =CH$_2$ | =CH$_2$ | H | s | s |
| =S | =CH$_2$ | CH$_3$ | — | s | u |
| =S | CH$_3$ | H | — | s | u |
| =S | =CH$_2$ | H | H | s | s |
| =S | CH$_3$ | H | H | u | s |
| =S | CH$_3$ | =CH$_2$ | H | s | s |
| =S | CH$_3$ | CH$_3$ | H | s | s |
| =S | =CH$_2$ | CH$_3$ | H | s | s |
| =S | CH$_3$ | CH$_3$ | H | u | s | u - unsaturated
s - saturated

EXAMPLE 146

2S,3R-6-(2-Hydroxyethylidene)-2-methyl-2-(4,8-dimethyl-5-thioxo-7-nonenyl)-oxepan-3-ol Following the procedure of Example 12 but substituting an equivalent amount of 2S,3R-6-[2-(tetrahydroyran-2-yloxy)-ethylidene]-2-methyl-2-(4,8-dimethyl-5-thioxo-7-nonenyl)-3-(tetrahydropyran-2-yloxy)-oxepane for 2S-6-[2-(tetrahydropyran-2-yloxy)-ethylidene]-2-methyl-2-[4,8-dimethyl-5-(tetrahydropyran-2-yloxy)-7-nonenyl]-oxepan-3-one, 2S,3R-6-(2-hydroxyethylidene)-2-methyl-2-(4,8-dimethyl-5-thioxo-7-nonenyl)-oxepan-3-ol is obtained.

EXAMPLE 147

2S,3R-3-Acetoxy-6-(2-acetoxyethylidene)-2-methyl-2-(4,8-dimethyl-5,5-ethylenedioxy-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg.) in anhydrous benzene (25 ml.), ethylene glycol (1 g.) and p-toluenesulfonic acid monohydrate (19 mg.) is heated at reflux for 16 hours employing a Dean-Stark trap. The suspension is cooled to room temperature. Solid sodium carbonate (35 mg.) is added followed by water (50 ml.) and other (50 ml.). The phases are separated, the aqueous layer extracted with additional ether and the combined organic extracts are washed with saturated salt solutions, dried and evaporated to give 2S,3R-3-acetoxy-6-(2-acetoxyethylidene)-2-methyl-2-(4,8-dimethyl-5,5-ethylenedioxy-7-nonenyl)-oxepane.

The following compounds are prepared according to the procedure of Example 147 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

| $R_1$ | $R_2$ | $R_3$ | $R_4$ | $R_5$ | a | b | c |
|---|---|---|---|---|---|---|---|
| –O–O (cyclic) | —OH | —CH$_2$OH | —H | — | — | u | s | u |
| –O–O (cyclic) | –O–O (cyclic) | —CH$_2$OH | —H | — | — | u | s | u |
| –O–O (cyclic) | —OAc | CH(–O–O) | —H | — | — | u | s | u |
| –O–O (cyclic) | –O–O (cyclic) | CH(–O–O) | —H | — | — | u | s | u |
| –O–O (cyclic) | —OAc | —CH$_2$OAc | —CH$_3$ | H | u | u | s |
| —OAc | –O–O (cyclic) | —CH$_2$OAc | —H | H | u | s | s |
| –O–O (cyclic) | —OH | —CH$_2$OH | —CH$_3$ | H | s | u | s |
| –O–O (cyclic) | —OH | —CH$_2$OH | —H | H | u | u | s |
| –O–O (cyclic) | —OAc | —CH$_2$OAc | —CH$_3$ | — | s | s | u |
| –O–O (cyclic) | —OAc | —CONH$_2$ | —H | — | u | s | u |
| –O–O (cyclic) | —OAc | C≡N | —CH$_3$ | H | u | u | s |

-continued

[Structure: oxepane ring with substituents R1, R2, R3, R4, R5 and positions a, b, c with CH3 groups]

| R1 | R2 | R3 | R4 | R5 | a | b | c |
|---|---|---|---|---|---|---|---|
| —O—O— (dioxolane) | —OAc | —CH2OAc | —H | OH | u | u | s |
| —O—O— (dioxolane) | —Br | —CH<O—O (dioxolane) | —H | — | u | s | u |
| —O—O— (dioxolane) | —OAc | CH=CH2 | —H | — | u | s | u | u - unsaturated
s - saturated

The following compounds are prepared according to the procedure of Example 147 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

[Structure with R1, R2, R3, R4 substituents on oxepane system]

| R1 | R2 | R3 | R4 | b | c |
|---|---|---|---|---|---|
| —O—O— | =CH2 | —H | — | s | u |
| —O—O— | —CH2OAc | —H | — | s | u |
| —O—O— | C≡N | —H | — | s | u |
| —O—O— | —CONH2 | —H | — | s | u |
| —O—O— | =CH2 | —CH3 | H | u | s |
| —O—O— | =CH2 | —CH3 | — | s | u |
| —O—O— | —CH<O—O | —CH3 | H | u | s |
| —O—O— | —CH2Cl | —H | — | s | u |
| CH3/ \OH | —CH<O—O | —H | — | s | u |
| NH2 | —CH<O—O | —H | — | s | u | u - unsaturated
s - saturated

EXAMPLE 148

2S,3R-3-Acetoxy-6-(2-acetoxyethylidene)-2-methyl-2-(4,8-dimethyl-5,5-ethylenedithio-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg.) and ethanedithiol (0.25 ml.) is treated with boron trifluoride etherate (0.25 ml.) at room temperature. After standing for 24 hours, the excess ethanedithiol is removed in vacuo and the residue is treated with 0.1 N sodium hydroxide and ether containing a trace of pyridine. The two phases are separated, the ethereal layer is washed with saturated salt solution, dried and evaporated to give 2S,3R-3-acetoxy-6-(2-acetoxyethylidene)-2-methyl-2-(4,8-dimethyl-5,5-ethylenedithio-7-nonenyl)-oxepane.

The following compounds are prepared according to the procedure of Example 148 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane

[Structure with R1, R2, R3, R4, R5 substituents]

| R1 | R2 | R3 | R4 | R5 | a | b | c |
|---|---|---|---|---|---|---|---|
| —OH | —S—S— (dithiolane) | —CH<S—S | —H | — | u | s | u |
| —OH | —S—S— | —CH2OH | —H | H | s | s | s |
| —OH | —S—S— | —CH2OAc | —CH3 | — | u | s | u |
| —OH | —S—S— | —CH2OAc | —CH2 | H | u | s | s |
| —OAc | —S—S— | —CO2H | —H | — | u | s | u |
| —OAc | —S—S— | —CO2H | —CH3 | H | u | u | s |
| —OAc | —S—S— | —CO2C2H5 | —CH3 | H | u | u | s |
| —N(CH3)2 | —S—S— | —CONH2 | —H | — | u | s | u |
| —N(CH3)2 | —OAc | —CH<S—S | —H | — | u | s | u | u - unsaturated
s - saturated

The following compounds are prepared according to the procedure of Example 148 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

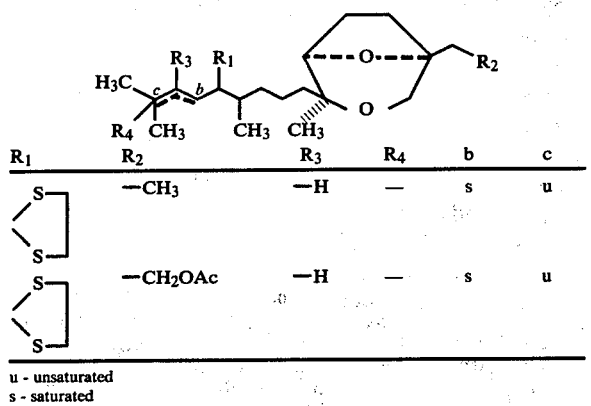

| $R_1$ | $R_2$ | $R_3$ | $R_4$ | b | c |
|---|---|---|---|---|---|
| ⟨S-, S-⟩ | —CH$_3$ | —H | — | s | u |
| ⟨S-, S-⟩ | —CH$_2$OAc | —H | — | s | u | u - unsaturated
s - saturated

EXAMPLE 149

2S,3R-3-Acetoxy-6-(2-acetoxyethylidene)-2-methyl-2-(4,8-dimethyl-5,5-ethylenethiooxy-7-nonenyl)-oxepane A solution of 2S,3R-3-acetoxy-6-(2-acetoxyethylidene)-2-methyl-2-(4,8-dimethyl-5-oxo-7-nonenyl)-oxepane (422 mg.) in dioxane (1.0 ml.) is treated with β-mercaptoethanol (400 mg.) followed by the addition of freshly fused zinc chloride (500 mg.) and anhydrous sodium acetate (500 mg.). The solution is initially cooled in ice and then allowed to warm to room temperature. After 24 hours, the reaction mixture is diluted with water (25 ml.) and extracted with chloroform. The organic extract is then washed with saturated salt solution, dried and evaporated to give 2S,3R-3-acetoxy-6-(2-acetoxyethylidene)-2-methyl-2-(4,8-dimethyl-5,5-ethylenethiooxy-7-nonenyl)-oxepane.

The following compounds are prepared according to the procedure of Example 149 by substituting an equivalent amount of the appropriate starting material for 2S,3R-3-acetoxy-6-(2-acetoxyethylidene-2-methyl-2-(4,8-dimethyl-5-oxo-7-nonenyl)-oxepane.

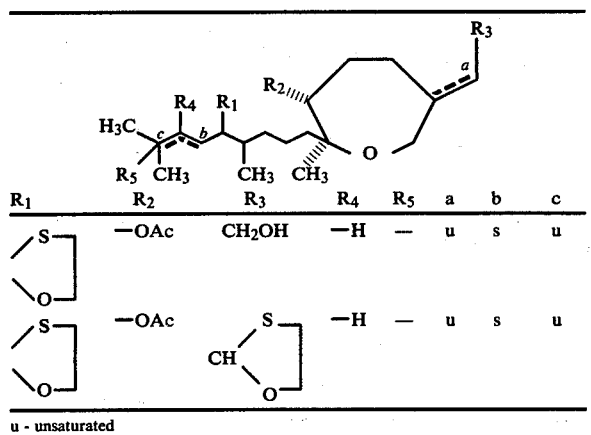

| $R_1$ | $R_2$ | $R_3$ | $R_4$ | $R_5$ | a | b | c |
|---|---|---|---|---|---|---|---|
| ⟨S-, O-⟩ | —OAc | CH$_2$OH | —H | — | u | s | u |
| ⟨S-, O-⟩ | —OAc | ⟨S-, O-⟩CH | —H | — | u | s | u | u - unsaturated
s - saturated

The following compound is prepared according to the procedure of Example 149 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

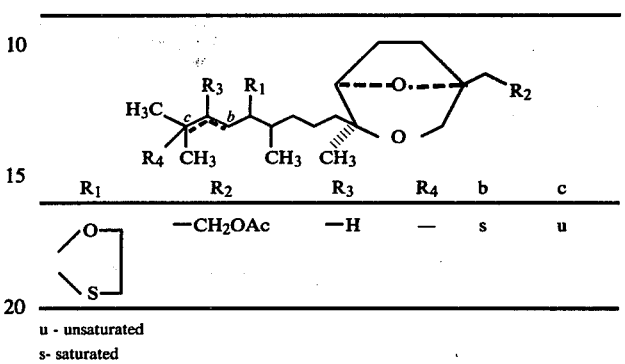

| $R_1$ | $R_2$ | $R_3$ | $R_4$ | b | c |
|---|---|---|---|---|---|
| ⟨O-, S-⟩ | —CH$_2$OAc | —H | — | s | u | u - unsaturated
s - saturated

EXAMPLE 150

2S,3R-3-Acetoxy-6-(2-acetoxyethylidene)-2-methyl-2-(5,5-dimethoxy-4,8-dimethyl-7-nonenyl)-oxepane Following the procedure of Example 74, but substituting an equivalent amount of 2S,3R-3-acetoxy-6-(2-acetoxyethylidene)-2-methyl-2-(4,8-dimethyl-5-oxo-7-nonenyl)-oxepane for 2S-6-(2-hydroxyethylidene)-2-methyl-2-(4,8-dimethyl-5-oxo-7-nonenyl)-oxepan-3-one, there is obtained 2S,3R-3-acetoxy-6-(2-acetoxyethylidene)-2-methyl-2-(5,5-dimethoxy-4,8-dimethyl-7-nonenyl )-oxepane.

The following compounds are prepared according to the procedure of Example 150 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

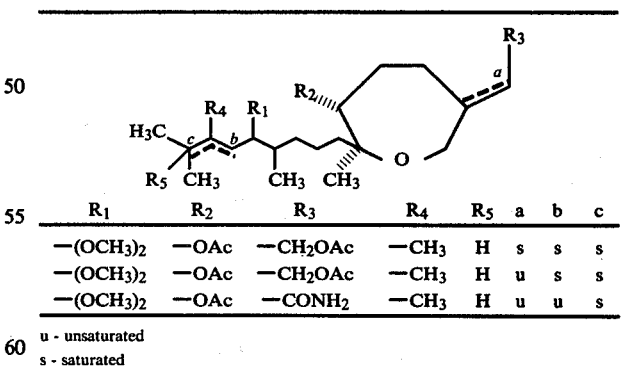

| $R_1$ | $R_2$ | $R_3$ | $R_4$ | $R_5$ | a | b | c |
|---|---|---|---|---|---|---|---|
| —(OCH$_3$)$_2$ | —OAc | —CH$_2$OAc | —CH$_3$ | H | s | s | s |
| —(OCH$_3$)$_2$ | —OAc | —CH$_2$OAc | —CH$_3$ | H | u | s | s |
| —(OCH$_3$)$_2$ | —OAc | —CONH$_2$ | —CH$_3$ | H | u | u | s | u - unsaturated
s - saturated

The following compounds are prepared according to the procedure of Example 150 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

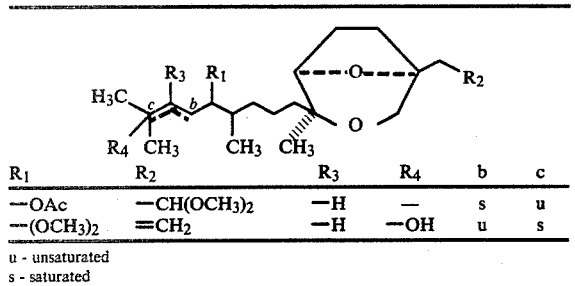

| $R_1$ | $R_2$ | $R_3$ | $R_4$ | b | c |
|---|---|---|---|---|---|
| —OAc | —CH(OCH$_3$)$_2$ | —H | — | s | u |
| —(OCH$_3$)$_2$ | =CH$_2$ | —H | —OH | u | s | u - unsaturated
s - saturated

EXAMPLE 151

2S,3R-3-Acetoxy-6-(2-acetoxyethylidene)-2-methyl-2-[4,8-dimethyl-5,5-di-(ethylthio)-7-nonenyl]-oxepane A solution of 2S,3R-3-acetoxy-6-(2-acetoxyethylidene)-2-methyl-2-(4,8-dimethyl-5-oxo-7-nonenyl)-oxepane (422 mg.) in ethyl mercaptan (17.5 ml.) is treated with anhydrous sodium sulfate (880 mg.) and freshly fused zinc chloride (440 mg.). The reaction flask is stoppered and kept in the cold for 72 hours. The excess mercaptan is removed in vacuo and the residue is treated with 0.1 N sodium hydroxide and ethyl ether containing a trace of pyridine. The phases are separated and the organic layer is washed with saturated salt solution, dried and evaporated to give 2S,3R-3-acetoxy-6-(2-acetoxyethylidene)-2-methyl-2-[4,8-dimethyl-5,5-di-(ethylthio)-7-nonenyl]-oxepane.

The following compound is prepared according to the procedure of Example 151 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

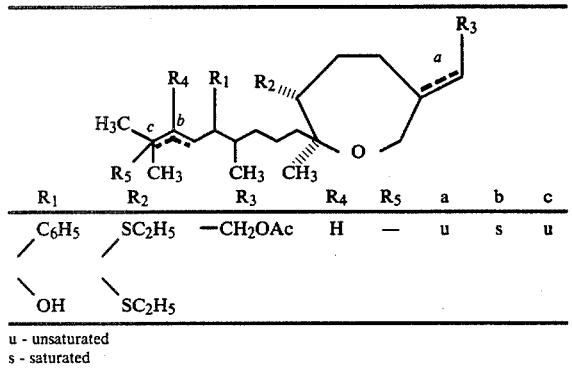

| $R_1$ | $R_2$ | $R_3$ | $R_4$ | $R_5$ | a | b | c |
|---|---|---|---|---|---|---|---|
| —C$_6$H$_5$ / —OH | —SC$_2$H$_5$ / —SC$_2$H$_5$ | —CH$_2$OAc | H | — | u | s | u | u - unsaturated
s - saturated

The following compounds are prepared according to the procedure of Example 151 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

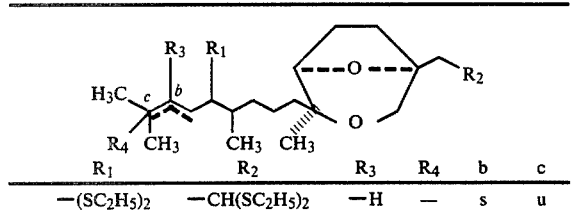

| $R_1$ | $R_2$ | $R_3$ | $R_4$ | b | c |
|---|---|---|---|---|---|
| —(SC$_2$H$_5$)$_2$ | —CH(SC$_2$H$_5$)$_2$ | —H | — | s | u |

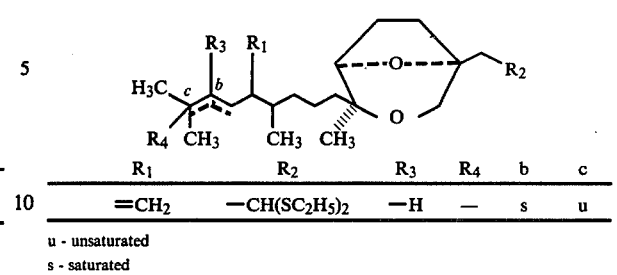

| $R_1$ | $R_2$ | $R_3$ | $R_4$ | b | c |
|---|---|---|---|---|---|
| =CH$_2$ | —CH(SC$_2$H$_5$)$_2$ | —H | — | s | u | u - unsaturated
s - saturated

EXAMPLE 152

2S,3R-3-Acetoxy-6-(2-acetoxyethylidene)-2-methyl-2-[4,8-dimethyl-5-(spiro-2-thiazolidine)-7-nonenyl]-oxepane A solution of 2S,3R-3-acetoxy-6-(2-acetoxyethylidene)-2-methyl-2-(4,8-dimethyl-5-oxo-7-nonenyl)-oxepane (422 mg.) in anhydrous benzene (20 ml.) is treated with 2-mercaptoethylamine (165 mg.) and p-toluenesulfonic acid (5 mg.) under a Dean-Stark trap at reflux in a nitrogen atmosphere for 48 hours. The reaction mixture is washed with cold, saturated salt solution and the organic layer dried and evaporated to give 2S,3R-3-acetoxy-6-(2-acetoxyethylidene)-2-methyl-2-[4,8-dimethyl-5-(spiro-2-thiazolidine)-7-nonenyl]-oxepane.

The following compounds are prepared according to the procedure of Example 152 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

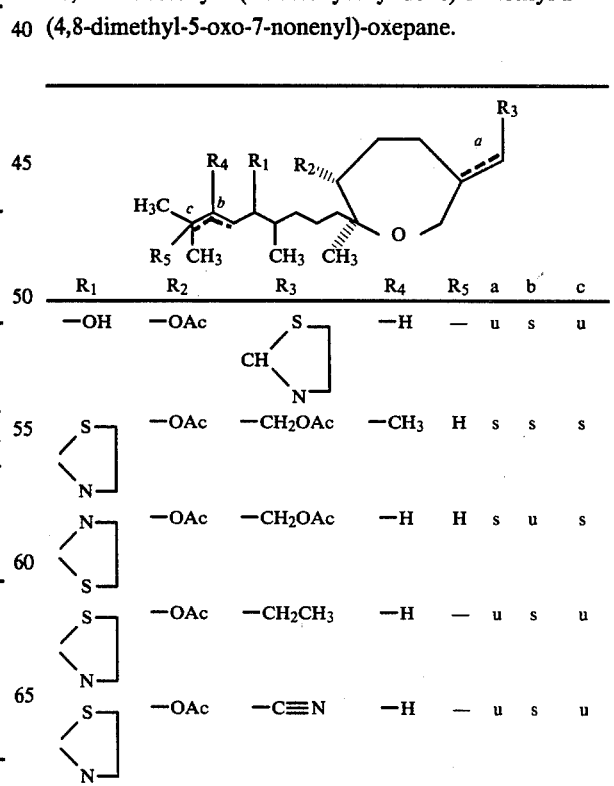

| $R_1$ | $R_2$ | $R_3$ | $R_4$ | $R_5$ | a | b | c |
|---|---|---|---|---|---|---|---|
| —OH | —OAc | S—CH—N (thiazolidine) | —H | — | u | s | u |
| S/N (thiazolidine) | —OAc | —CH$_2$OAc | —CH$_3$ | H | s | s | s |
| N/S (thiazolidine) | —OAc | —CH$_2$OAc | —H | H | s | u | s |
| S/N (thiazolidine) | —OAc | —CH$_2$CH$_3$ | —H | — | u | s | u |
| S/N (thiazolidine) | —OAc | —C≡N | —H | — | u | s | u |

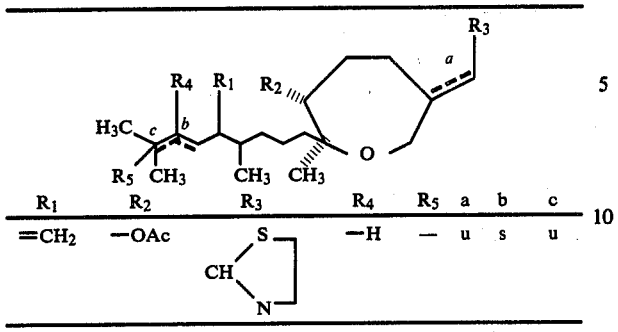

| R1 | R2 | R3 | R4 | R5 | a | b | c |
|---|---|---|---|---|---|---|---|
| =CH2 | —OAc | S—CH—N (ring) | —H | — | u | s | u | u - unsaturated
s - saturated

The following compounds are prepared according to the procedure of Example 152 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

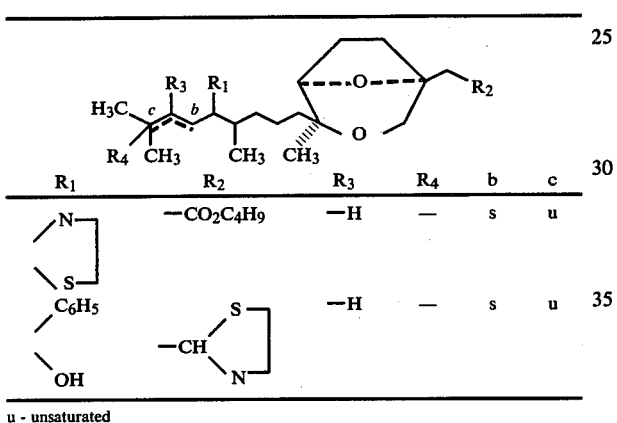

| R1 | R2 | R3 | R4 | b | c |
|---|---|---|---|---|---|
| N—S (ring, /\) | —CO2C4H9 | | —H | s | u |
| C6H5 / \ OH | —CH—S—N (ring) | | —H | s | u | u - unsaturated
s - saturated

EXAMPLE 153

2S,3R-6-(2-Hydroxyethylidene)-2-methyl-2-(5-hydroxy-4,5,8-trimethyl-7-nonenyl)oxepan-3-ol 2S,3R-6-(2-Hydroxyethylidene)-2-methyl-2-(4,8-dimethyl-5-oxo-7-nonenyl)-oxepan-3-ol (407 mg.) is dissolved in tetrahydrofuran (8 ml.). The solution is cooled to −78° under nitrogen and treated slowly with an excess of methyllithium (3 ml., 1.6 M in ether). The reaction mixture is kept at −78° for 10 minutes and then slowly warmed to room temperature by removing the cooling bath. The mixture is then treated with ether (100 ml.) and saturated NH4Cl solution (50 ml.). The organic layer is washed with water (50 ml.), dried (MgSO4) and evaporated in vacuo to give 2S,3R-6-(2-hydroxyethylidene)-2-methyl-2-(5-hydroxy-4,5,8-trimethyl-7-nonenyl)-oxepan-3-ol (410 mg.).

IR (neat) μ: 2.87; NMR $TMS^{CDCl_3}\delta$:

5.3 (m, 2H, —HC=C〈 ,

HC=C), 3.8 (m, 5H, HC—OH, OCH2C, =C—CH2OH).

Similarly, by substituting other organolithium or organomagnesium halides for methyllithium in the procedure of Example 153, the corresponding alcohols are formed. Thus, n-butyllithium, ethyllithium, allyl magnesium bromide and 1-propenyl magnesium bromide afford the n-butyl carbinol, ethyl carbinol, allyl carbinol and 1-propenyl carbinol, respectively.

The following compounds are prepared by the procedure of Example 153 by substituting an equivalent amount of the appropriate starting material for 2S,3R-6E-(2-hydroxyethylidene)-2-methyl-2-(4,8-dimethyl-5-oxo-7-nonenyl)-oxepan-3-ol and employing the appropriate organo-metallic reagent.

| R1 | R2 | R3 | R4 | R5 | a | b | c |
|---|---|---|---|---|---|---|---|
| CH3 / \ OH | —OH | —CH2OH | —H | — | u | s | u |
| CH3 / \ OH | CH3 / \ OH | —CH2OH | —H | — | u | s | u |
| —OH | —OH | —CH〈CH3 / OH | —H | — | u | s | u |
| CH3 / \ OH | —OH | —CH2OH | —H | — | s | s | u |
| CH3 / \ OH | —OH | —CH2OH | =CH2 | H | u | s | s |
| C2H5 / \ OH | —OH | —CH2OH | —H | H | s | u | s |
| CH2CH=CH2 / \ OH | —OH | —CH2OH | H | H | s | s | s |
| CH2CH=CH2 / \ OH | —OH | —CH2OH | —CH3 | — | u | s | s | u - unsaturated
s - saturated

The following compounds are prepared by the procedure of Example 153 by substituting an equivalent amount of the appropriate starting material for 2S,3R-6-(2-hydroxyethylidene)-2-methyl-2-(4,8-dimethyl-5-oxo- 7-nonenyl)-oxepan-3-ol and employing the appropriate organometallic reagent.

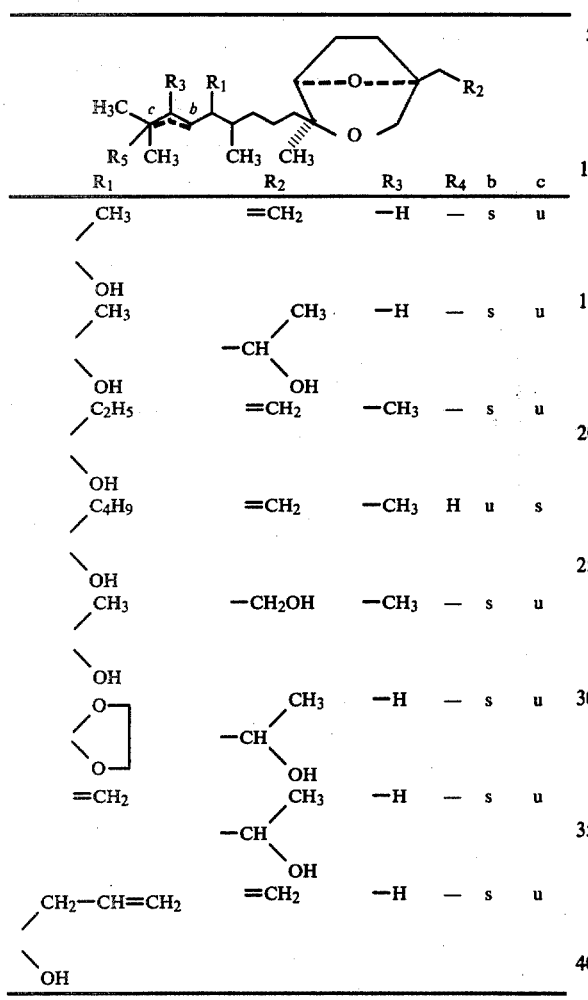

| R₁ | R₂ | R₃ | R₄ | b | c |
|---|---|---|---|---|---|
| ⟨CH₃ / OH | =CH₂ | —H | — | s | u |
| ⟨CH₃ / OH | —CH⟨CH₃/OH | —H | — | s | u |
| ⟨C₂H₅ / OH | =CH₂ | —CH₃ | — | s | u |
| ⟨C₄H₉ / OH | =CH₂ | —CH₃ | H | u | s |
| ⟨CH₃ / OH | —CH₂OH | —CH₃ | — | s | u |
| ⟨O—/O— | —CH⟨CH₃/OH | —H | — | s | u |
| =CH₂ | —CH⟨CH₃/OH | —H | — | s | u |
| ⟨CH₂—CH=CH₂ / OH | =CH₂ | —H | — | s | u | u - unsaturated
s - saturated

EXAMPLE 154

2S,3R-6-(2-Hydroxyethylidene)-2-methyl-2-(4,8-dimethyl-5-ethynyl-5-hydroxy-7-nonenyl)-oxepan-3-ol A solution of 2S,3R-6-(2-hydroxyethylidene)-2-methyl-2-(4,8-dimethyl-5-oxo-7-nonenyl)-oxepan-3-ol (600 mg.) in anhydrous dioxane (10 ml.) is added at room temperature to a stirred mixture of lithium acetylide ethylenediamine complex (2.6 g.) in anhydrous dioxane (30 ml.). A stream of acetylene is passed through this stirred mixture for 24 hours. The reaction mixture is then treated with a saturated ammonium chloride solution (50 ml.) and ether (200 ml.). The organic phase is dried and evaporated in vacuo to give a brown oily residue which is plate chromatographed on silica gel, using ethyl acetate-cyclohexane (1:1) as the developing solvent. The most polar band is eluted with isopropanol-chloroform (1:1) to afford 2S,3R-6-(2-hydroxyethylidene)-2-methyl-2-(4,8-dimethyl-5-ethynyl-5-hydroxy-7-nonenyl)-oxepan-3-ol (246 mg.).

IR (neat) μ: 2.93, 3.0, 4.23;
NMR $T_{MS}^{CDCl_3}\delta$: 1.0 and 1.03

[a pair of d, J = 7Hz, 3H, CH₃—CH—C(OH)—C≡CH], 1.17 (s, 3H, CH₃—C—O—C), 1.55, 1.77 [each s, each 3H, (CH₃)₂C=C<], 2.40 (s, 1H, C≡CH), 2.63 (s, ≈3H, OH exchanged with D₂O), 3.53

(t, 1H, HC—OH), 4.08 (s, 2H, C—O—CH₂—C), 4.17 (d, J=6Hz, 2H, C=CH—CH₂OH), 5.4 [m, 2H, C=CH—CH₂OH and (CH₃)₂—C=CH—].

The following compounds are prepared by the procedure of Example 154 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

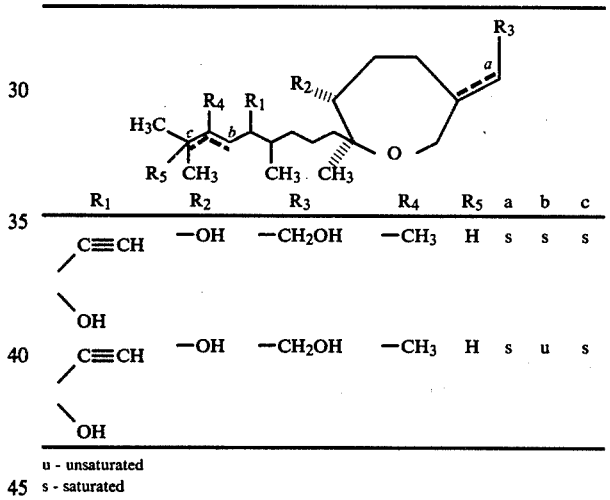

| R₁ | R₂ | R₃ | R₄ | R₅ | a | b | c |
|---|---|---|---|---|---|---|---|
| ⟨C≡CH / OH | —OH | —CH₂OH | —CH₃ | H | s | s | s |
| ⟨C≡CH / OH | —OH | —CH₂OH | —CH₃ | H | s | u | s | u - unsaturated
s - saturated

The following compound is prepared according to the procedure of Example 154 by substituting an equivalent amount of the appropriate starting material for 2S,3R-6-(2-hydroxyethylidene)-2-methyl-2-(4,8-dimetyl-5-oxo-7-nonenyl)-oxepan-3-ol.

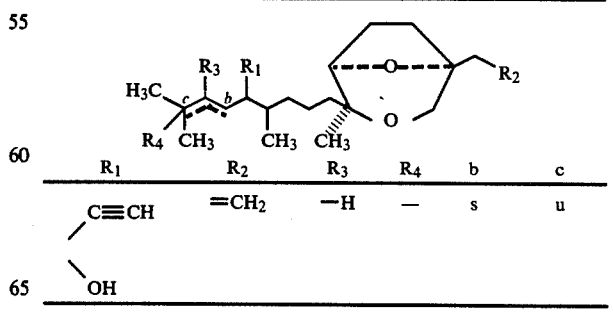

| R₁ | R₂ | R₃ | R₄ | b | c |
|---|---|---|---|---|---|
| ⟨C≡CH / OH | =CH₂ | —H | — | s | u | u - unsaturated
s - saturated

EXAMPLE 155

2S,3R-6-(2-Hydroxyethylidene)-2-methyl-2-(4,8-dimethyl-5-ethenyl-5-hydroxy-7-nonenyl)-oxepan-3-ol Treatment of 2S,3R-6-(2-hydroxyethylidene)-2-methyl-2-(4,8-dimethyl-5-oxo-7-nonenyl)-oxepan-3-ol with an excess of vinyl magnesium bromide as in Example 154 affords 2S,3R-6-(2-hydroxyethylidene)-2-methyl-2-(4,8-dimethyl-5-ethenyl-5-hydroxy-7-nonenyl)-oxepan-3-ol.

The following compounds are prepared according to the method of Example 155 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

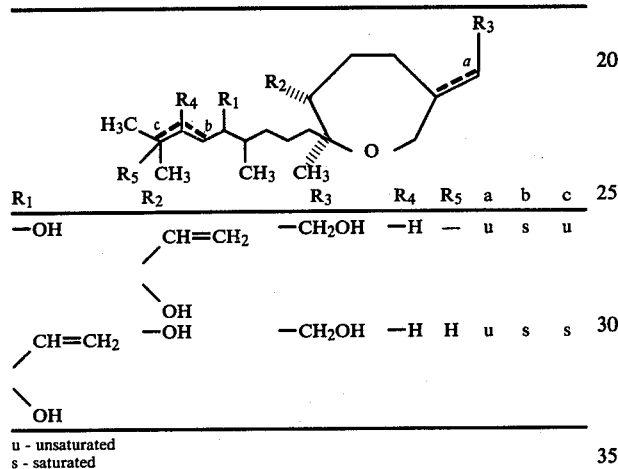

| R$_1$ | R$_2$ | R$_3$ | R$_4$ | R$_5$ | a | b | c |
|---|---|---|---|---|---|---|---|
| —OH | CH=CH$_2$ \ / OH | —CH$_2$OH | —H | — | u | s | u |
| CH=CH$_2$ \ / OH | —OH | —CH$_2$OH | —H | H | u | s | s | u - unsaturated
s - saturated

The following compounds are prepared according to the procedure of Example 155 by substituting an equivalent amount of the appropriate starting material for 2S,3R-6-(2-hydroxyethylidene)-2-methyl-2-(4,8-dimethyl-5-oxo-7-nonenyl)-oxepan-3ol.

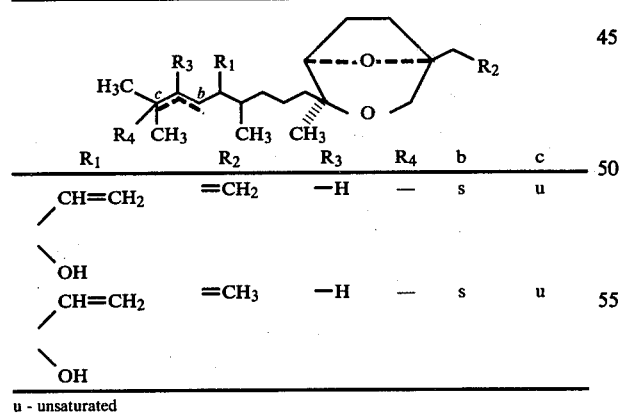

| R$_1$ | R$_2$ | R$_3$ | R$_4$ | b | c |
|---|---|---|---|---|---|
| CH=CH$_2$ \ / OH | =CH$_2$ | —H | — | s | u |
| CH=CH$_2$ \ / OH | =CH$_3$ | —H | — | s | u | u - unsaturated
s - saturated

EXAMPLE 156

2S,3R-6-(2-Hydroxyethylidene)-2-methyl-2-(4,8-dimethyl-5-hydroxy-5-phenyl-7-nonenyl)-oxepan-3-ol Treatment of 2S,3R-6-(2-hydroxyethylidene)-2-methyl-2-(4,8-dimethyl-5-oxo-7-nonenyl)-oxepan-3-ol with phenyllithium as in Example 154 affords 2S,3R-6-(2-hydroxyethylidene)-2-methyl-2-(4,8-dimethyl-5-hydroxy-5-phenyl-7-nonenyl)-oxepan-3-ol.

The following compounds are prepared according to the procedure of Example 156 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

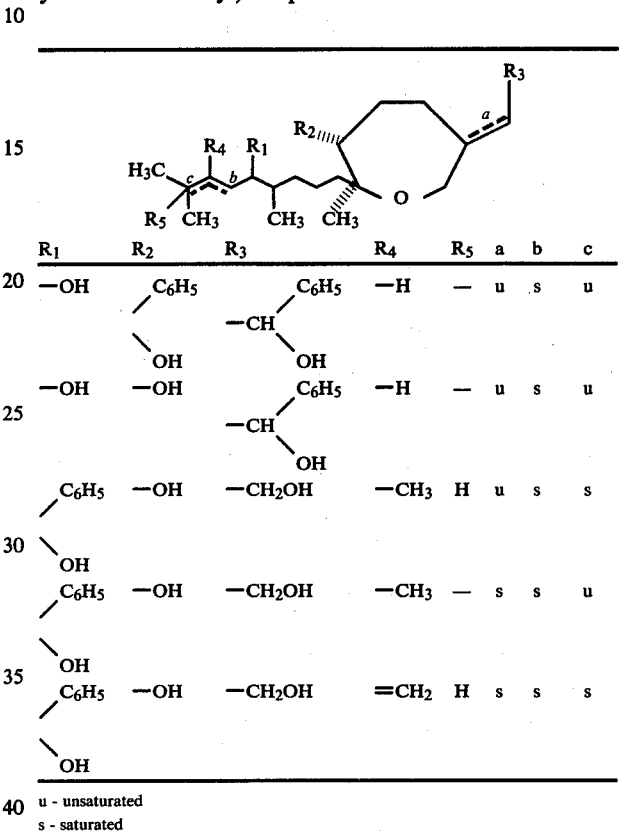

| R$_1$ | R$_2$ | R$_3$ | R$_4$ | R$_5$ | a | b | c |
|---|---|---|---|---|---|---|---|
| —OH | C$_6$H$_5$ \ / —CH \ OH | C$_6$H$_5$ \ / —CH \ OH | —H | — | u | s | u |
| —OH | —OH | C$_6$H$_5$ \ / —CH \ OH | —H | — | u | s | u |
| C$_6$H$_5$ \ / \ OH | —OH | —CH$_2$OH | —CH$_3$ | H | u | s | s |
| C$_6$H$_5$ \ / \ OH | —OH | —CH$_2$OH | —CH$_3$ | — | s | s | u |
| C$_6$H$_5$ \ / \ OH | —OH | —CH$_2$OH | =CH$_2$ | H | s | s | s | u - unsaturated
s - saturated

The following compounds are prepared by the procedure of Example 156 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

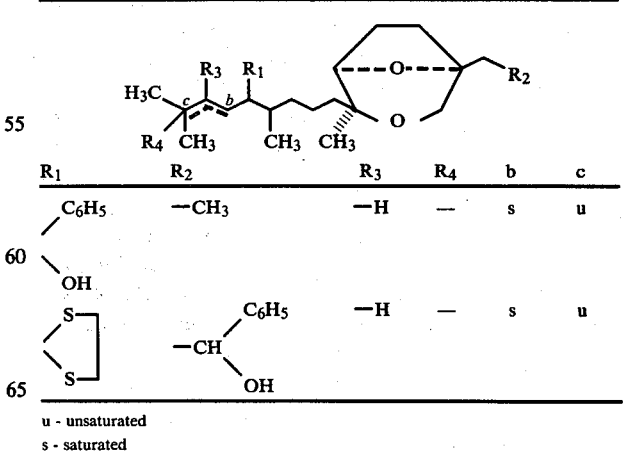

| R$_1$ | R$_2$ | R$_3$ | R$_4$ | b | c |
|---|---|---|---|---|---|
| C$_6$H$_5$ \ / \ OH | —CH$_3$ | —H | — | s | u |
| S—\ \ S—/ | C$_6$H$_5$ \ / —CH \ OH | —H | — | s | u | u - unsaturated
s - saturated

EXAMPLE 157

2S,3R-6-(2-Hydroxyethylidene)-2-methyl-2-(5-benzyl-4,8-dimethyl-5-hydroxy-7-nonenyl)-oxepan-3-ol.

Treatment of 2S,3R-6-(2-hydroxyethylidene)-2-methyl-2-(4,8-dimethyl-5-oxo-7-nonenyl)-oxepan-3-ol with 4 eq. of benzyl magnesium bromide (freshly prepared from benzyl bromide and magnesium in ether) as in Example 155 affords 2S,3R-6-(2-hydroxyethylidene)-2-methyl-2-(5-benzyl-4,8-dimethyl-5-hydroxy-7-nonenyl)-oxepan-3-ol.

The following compounds are prepared according to the procedure of Example 157 by substituting an equivalent amount of the appropriate starting material for 2S,3R-6-(2-hydroxyethylidene)-2-methyl-2-(4,8-dimethyl-5-oxo-7-nonenyl)-oxepan-3-ol.

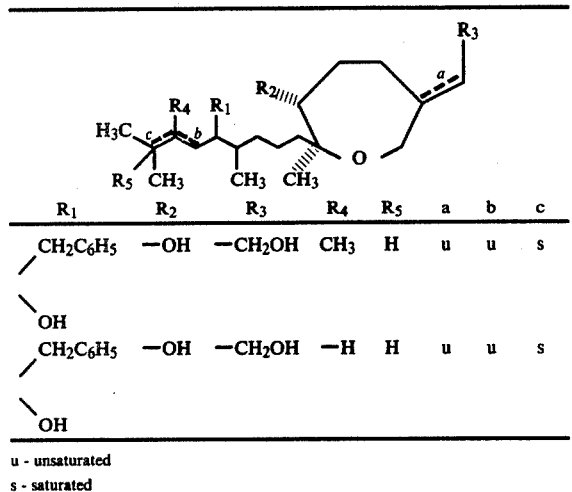

| $R_1$ | $R_2$ | $R_3$ | $R_4$ | $R_5$ | a | b | c |
|---|---|---|---|---|---|---|---|
| CH$_2$C$_6$H$_5$ / \ OH | —OH | —CH$_2$OH | CH$_3$ | H | u | u | s |
| CH$_2$C$_6$H$_5$ / \ OH | —OH | —CH$_2$OH | —H | H | u | u | s | u - unsaturated
s - saturated

The following compounds are prepared according to the procedure of Example 157 by substituting an equivalent amount of the appropriate starting material for 2S,3R-6-(2-hydroxyethylidene)-2-methyl-2-(4,8-dimethyl-5-oxo-7nonenyl)-oxepan-3-ol.

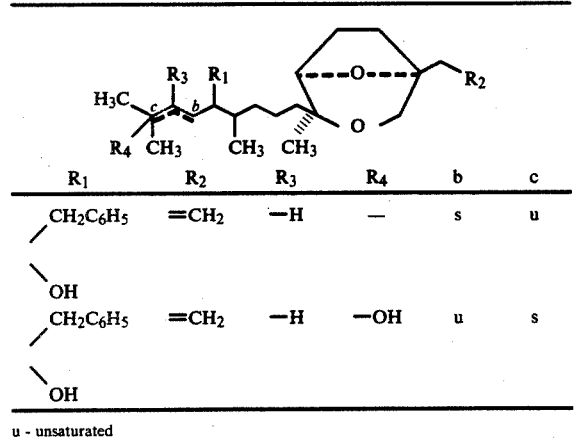

| $R_1$ | $R_2$ | $R_3$ | $R_4$ | b | c |
|---|---|---|---|---|---|
| CH$_2$C$_6$H$_5$ / \ OH | =CH$_2$ | —H | — | s | u |
| CH$_2$C$_6$H$_5$ / \ OH | =CH$_2$ | —H | —OH | u | s | u - unsaturated
s - saturated

EXAMPLE 157A 2S,3R-6-(2-Hydroxyethylidene)-2-methyl-2-(4,8-dimethyl-5-hydroxy-5-propynyl-7-nonenyl)-oxepan-3-ol Lithium propynide is generated by slow addition of n-butyllithium (4 mmole) to a solution of propyne (1 ml.) in tetrahydrofuran (15 ml.) at −78° under argon. To this reagent is added 2S,3R-6-(2-hydroxyethylidene)-2-methyl-2-(4,8-dimethyl-5-oxo-7-nonenyl)-oxepan-3-ol (330 mg.) in tetrahydrofuran (1 ml.) at room temperature and the resulting mixture is stirred for 5 hours. The mixture is treated with ether (50 ml.) and saturated ammonium chloride solution (30 ml.). The organic phase is dried and evaporated in vacuo to afford 2S,3R-6-(2-hydroxyethylidene)-2-methyl-2-(4,8-dimethyl-5-hydroxy-5-propynyl-7-nonenyl)-oxepan-3-ol.

Similarly by substituting other 1-alkynes for propyne in the procedure of Example 157A, the corresponding alcohols are formed. Thus, lithium pentynide and lithium hexynide afford the 1-pentynyl carbinol and 1-hexynyl carbinol respectively.

EXAMPLE 158

2S,3R-6-(2-Trimethylsiloxyethylidene)-2-methyl-2-(4,8-dimethyl-5-methylene-7-nonenyl)-3-trimethylsiloxyoxepane To a mixture of (methyl)-triphenylphosphonium iodide (406 mg.) and tetrahydrofuran (10 ml.) is added n-butyllithium at −20° under argon; 2S,3R-6-(2-trimethylsiloxyethylidene)-2-methyl-2-(4,8-dimethyl-5-oxo-7-nonenyl)-3-trimethylsiloxyoxepane (504 mg.) is added to this reagent and the mixture is stirred for 30 minutes. The resulting mixture is allowed to warm to room temperature and is stirred for another 30 minutes. The mixture is then poured into buffer (pH=7, 30 ml.). The resulting mixture is then extracted with ether. The combined organic phase is dried and evaporated to afford 2S,3R-6-(2-trimethylsiloxyethylidene)-2-methyl-2-(4,8-dimethyl-5-methylene-7-nonenyl)-3-trimethylsiloxyoxepane.

The following compounds are prepared according to the procedure of Example 158 by substituting an equivalent amount of the appropriate starting material for 2S,3R-6-(2-trimethylsiloxyethylidene)-2-methyl-2-(4,8-dimethyl-5-oxo-7-nonenyl)-3-trimethylsiloxyoxepane.

| R1 | R2 | R3 | R4 | R5 | a | b | c |
|---|---|---|---|---|---|---|---|
| =CH2 | —OH | —CH2OH | —H | — | u | s | u |
| =CH2 | =CH2 | —CH2OH | —H | — | u | s | u |
| —OH | =CH2 | —CH=CH2 | —H | — | u | s | u |
| —OH | =CH2 | —CH2OH | —H | — | u | s | u |
| —OH | —OAc | CH=CH2 | —H | — | u | s | u |
| =CH2 | —OH | —CH2OH | —CH3 | H | u | u | s |
| =CH2 | —OH | —CH2OH | —H | H | s | s | s |
| =CH2 | —OH | —CH2OH | —CH3 | H | s | s | s |
| =CH2 | —OH | —CH2OH | —H | H | u | s | s |
| =CH2 | —OH | —CH2OH | —CH3 | H | u | s | s |
| =CH2 | —OH | —CH2OH | —CH3 | — | s | s | u |
| =CH2 | —OAc | —CO2CH3 | —H | — | u | s | u |
| =CH2 | =CH2 | —CO2C2H5 | —CH3 | H | u | u | s |
| =CH2 | =CH2 | —CO2H | —H | — | u | s | u |
| —OH | =CH2 | —CONH2 | —H | — | u | s | u |
| =CH2 | —OAc | —CONH2 | CH3 | —H | u | u | s |
| =CH2 | —OAc | —CN | CH3 | —H | s | u | s |
| =CH2 | —OCOC6H5 | —CH2OCOC6H5 | —H | —OH | u | u | s |
| =CH2 (O-O) | =CH2 | —CH=CH2 | —H | — | u | s | u | u - unsaturated
s - saturated

The following compounds are prepared according to the procedure of Example 158 by substituting an equivalent amount of the appropriate starting material for 2S,3R-6-(2-trimethylsiloxyethylidene)-2-methyl-2-(4,8-dimethyl-5-oxo-7-nonenyl)-3-trimethylsiloxyoxepane.

| R1 | R2 | R3 | R4 | b | c |
|---|---|---|---|---|---|
| =CH2 | =CH2 | —H | — | s | u |
| =CH2 | —CH2OH | —H | — | s | u |
| —OAc | CH=CH2 | —H | — | s | u |
| =CH2 | —CO2H | —H | — | s | u |
| =CH2 | CONH2 | —H | — | s | u |
| =CH2 | =CH2 | —CH3 | —H | u | s |
| =CH2 | —CH2OH | —CH3 | —H | u | s |
| =CH2 | —CH2OAc | —H | — | s | u |
| =CH2 (S-S) | CH=CH2 | —H | — | s | u |
| =CH2 | CH=CH2 | —H | — | s | u |

EXAMPLE 159

2S,3R-6-(2-Trimethylsiloxyethylidene)-2-methyl-2-(4,8-dimethyl-5-ethylidene-7-nonenyl)-3-trimethylsiloxyoxepane Following the procedure of Example 158 but substituting an equivalent amount of (ethyl)-triphenylphosphonium iodide for (methyl)-triphenylphosphonium iodide, 2S,3R-6-(2-trimethylsiloxyethylidene)-2-methyl-2-(4,8-dimethyl-5-ethylidene-7-nonenyl)-3-trimethylsiloxyoxepane is obtained.

Similarly by substituting other phosphonium halides for (ethyl)-triphenylphosphonium iodide in the procedure of Example 159, the corresponding alkylidene derivatives are formed. Thus, (benzyl)-triphenylphosphonium chloride and (butyl)-triphenylphosphonium bromide afford the benzylidene and butylidene derivatives respectively.

The following compounds are prepared according to the procedure of Example 159 by substituting an equivalent amount of the appropriate starting material for 2S,3R-6-(2-trimethylsiloxyethylidene)-2-methyl-2-(4,8-dimethyl-5-oxo-7-nonenyl)-3-trimethylsiloxyoxepane and employing the appropriate phosphonium halide.

| R1 | R2 | R3 | R4 | R5 | a | b | c |
|---|---|---|---|---|---|---|---|
| —OH | —OAc | —CH=CH—CH3 | —H | — | u | s | u |
| =CHCH3 | —OH | —CH2OH | —H | — | s | s | s |

-continued

| R1 | R2 | R3 | R4 | R5 | a | b | c |
|---|---|---|---|---|---|---|---|
| =CHC2H5 | —OH | —CH2OH | —CH3 | H | s | u | s |
| =CH—CH3 | —OH | —CH2OH | —H | H | u | u | s |
| =CH—C6H5 | —OH | —CH2OH | —CH3 | — | u | s | u |
| =CH—CH3 | —OH | —CH2OH | =CH2 | H | u | s | s |
| =CH—C6H5 | —OH | —CH2OH | —H | H | s | u | s |
| =CH—CH3 | —OH | —CH2OH | =CH2 | H | s | s | s |
| =CH—CH=CH2 | —OH | —CH2OH | —H | — | u | s | u |
| =CH—CH=CH2 | —OH | —CH2OH | —CH3 | H | u | u | s |
| =CH—C6H5 | —OAc | —CO2CH3 | —H | — | u | s | u |
| =CH—CH3 | =CH—CH3 | —CO2H | —CH3 | H | s | u | s |
| =CH—C6H5 | —OAc | —C≡N | —H | — | u | s | u |
| =CHCH3 | =CHCH3 | —C≡N | —CH3 | H | u | u | s |
|  | =CHCH3 | —CH=CH—CH3 | —H | H | s | s | s |
| =CH—C6H5 | =CH—C6H5 | —CH2OAc | —H | — | u | s | u |
| —OAc | —OAc | —CH=CH—C2H5 | —H | — | u | s | u | u - unsaturated
s - saturated

The following compounds are prepared according to the procedure of Example 159 by substituting an equivalent amount of the appropriate starting material for 2S,3R-6-(2-trimethylsiloxyethylidene)-2-methyl-2-(4,8-dimethyl-5-oxo-7-nonenyl)-3-trimethylsiloxyoxepane.

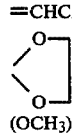

| R1 | R2 | R3 | R4 | b | c |
|---|---|---|---|---|---|
| =CHCH3 | —CH3 | —H | — | s | u |
| =CHC6H5 | —CO2H | —H | — | s | u |
| =CH—CH=CH2 | —CN | —H | — | s | u |
| =CH—CH3 | —CO2CH3 | —H | — | s | u |
| =CH—CH3 | =CH2 | —CH3 | — | s | u |
| =CHCH3 | =CH2 | —H | —OH | u | s |
| =CHC6H5 | —CONHC2H5 | —H | — | s | u |
|  | —CH=CHC6H5 | —H | — | s | u |
| (OCH3)2 | —CH=CHC6H5 | —H | — | s | u |

EXAMPLE 160

2S,3R-6-(2-Trimethylsiloxyethylidene)-2-methyl-2-(4,8-dimethyl-5-hydroxy-7-nonenyl)-3-trimethylsiloxyoxepane Following the procedure of Example 18 but substituting an equivalent amount of 2S,3R-6-(2-trimethylsiloxyethylidene)-2-methyl-2-(4,8-dimethyl-5-oxo-7-nonenyl)-3-trimethylsiloxyoxepane for 2S,3R-6E-(2-hydroxyethylidene)-2-methyl-2-(4,8-dimethyl-5-oxo-7-nonenyl)-oxepan-3-ol,2S,3R-6-(2-trimethylsiloxyethylidene)-2-methyl-2-(4,8-dimethyl-5-hydroxy-7-nonenyl)-3-trimethylsiloxyoxepane is obtained.

EXAMPLE 161

2S,3R-6-(2-Trimethylsiloxyethylidene)-2-methyl-2-(4,8-dimethyl-5-p-toluenesulfonyloxy-7-nonenyl)-3-trimethylsiloxyoxepane To a mixture of 2S,3R-6-(2-trimethylsiloxyethylidene)-2-methyl-2-(4,8-dimethyl-5-hydroxy-7-nonenyl)-3-trimethylsiloxyoxepane (506 mg), pyridine (1 ml) and ether (20 ml) is added p-toluenesulfonyl chloride (195 mg) at 0° under argon. The mixture is stirred for 1 hour and then treated with ether (30 ml) and water (30 ml). The organic layer is washed with saturated cupric sulfate and the organic phase is then dried and evaporated to afford 2S,3P-6-(2-trimethylsiloxyethylidene)-2-methyl-2-(4,8-dimethyl-5-p-toluenesulfonyloxy-7-nonenyl)-3-trimethylsiloxyoxepane.

EXAMPLE 162

2S,3R-6-(2-Trimethylsiloxyethylidene)-2-methyl-2-(4,5,8-trimethyl-7-nonenyl)-3-trimethylsiloxyoxepane Lithium dimethyl copper is generated from cuprous iodide (190 mg) and methyl lithium (2 mmole) in ether (10 ml) at 0° under argon. A solution of 2S,3R-6-(2-trimethylsiloxyethylidene)-2-methyl-2-(4,8-dimethyl-5-p-toluenesulfonyloxy-7-nonenyl)-3-trimethylsiloxyoxepane (300 mg) in ether (5 ml) is added slowly to this reagent at −20° under argon. The mixture is allowed to warm to room temperature and stirred for 5 hours. The mixture is then poured into saturated ammonium chloride solution (30 ml) at 0° and then quickly extracted with ether (100 ml). The organic layer is dried and evaporated in vacuo to afford 2S,3R-6-(2-trimethylsiloxyethylidene)-2-methyl-2-(4,5,8-trimethyl-7-nonenyl)-3-trimethylsiloxyoxepane.

EXAMPLE 163

2S,3R-3-Acetoxy-6-(2-acetoxyethylidene)-2-methyl-2-(5-cyano-4,8-dimethyl-5-hydroxy-7-nonenyl)-oxepane To a mixture of 2S,3R-3-acetoxy-6-(2acetoxyethylidene)-2-methyl-2-(4,8-dimethyl-5-oxo-7-nonenyl)-oxepane (422 mg), sodium cyanide (300 mg), tetrahydrofuran (9 ml), and water (1 ml) is added concentrated hydrochloric acid (1 ml) at −20°. The mixture is stirred overnight and treated with ether (30 ml) and water (10 ml). The organic layer is dried and evaporated to afford 2S,3R-3-acetoxy-6-(2-acetoxyethylidene)-2-methyl-2-(5-cyano-4,8-dimethyl-5-hydroxy-7-nonenyl)- oxepane.

| $R_1$ | $R_2$ | $R_3$ | $R_4$ | $R_5$ | a | b | c |
|---|---|---|---|---|---|---|---|
| /OH \CN | —OH | —CH$_2$OH | —H | — | u | s | u |
| /OH \CN | /OH \CN | —CH$_2$OH | —H | — | u | s | u |
| /OH \CN | —OCH$_3$ | —CH$_2$OCH$_3$ | —H | — | u | s | u |
| —OH \CN | /OH \CN | —CH$_2$OH | —H | — | u | s | u |
| —OH | —OAc | CH/OH \CN | —H | — | u | s | u |
| —Br | —OAc | CH/OH \CN | —H | — | u | s | u |
| /OH \CN | /OH \CN | CH/OH \CN | —H | — | u | s | u |
| /OH \CN | —Cl | CH$_2$Cl | —CH$_3$ | H | u | u | s |
| /OH \CN | —Cl | —CH$_2$Cl | —H | H | s | s | s |
| /OH \CN | —Br | —CH$_2$Br | —H | — | s | s | u |
| /OH \CN | —OAc | —CH$_2$OAc | —H | H | u | s | s |
| /OH \CN | —Cl | —CH$_2$Cl | —CH$_3$ | H | s | u | s |
| /OH \CN | —OAc | —CH$_2$OAc | —CH$_3$ | H | u | s | s |
| /OH \CN | —OAc | —CH$_2$OAc | —H | H | u | u | s |

-continued

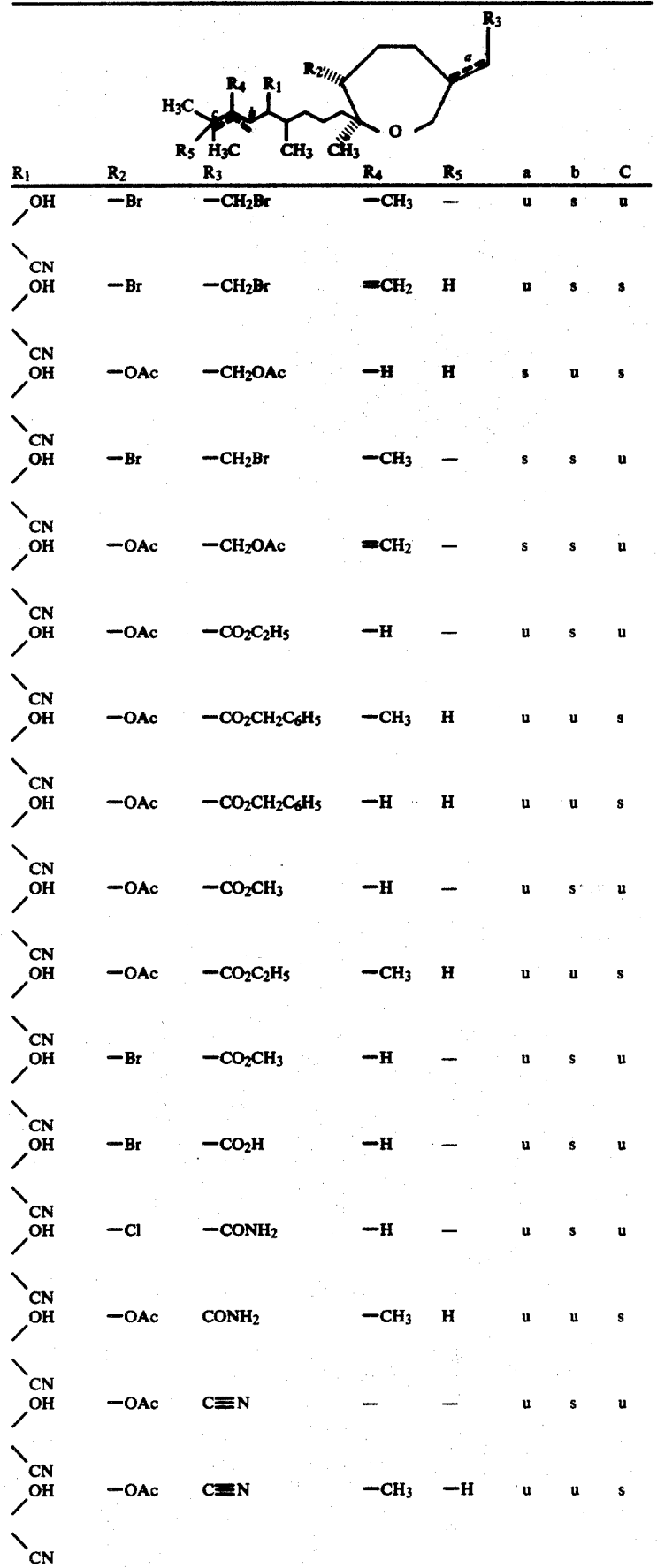

| R₁ | R₂ | R₃ | R₄ | R₅ | a | b | c |
|---|---|---|---|---|---|---|---|
| OH, CN | —Br | —CH₂Br | —CH₃ | — | u | s | u |
| OH, CN | —Br | —CH₂Br | =CH₂ | H | u | s | s |
| OH, CN | —OAc | —CH₂OAc | —H | H | s | u | s |
| OH, CN | —Br | —CH₂Br | —CH₃ | — | s | s | u |
| OH, CN | —OAc | —CH₂OAc | =CH₂ | — | s | s | u |
| OH, CN | —OAc | —CO₂C₂H₅ | —H | — | u | s | u |
| OH, CN | —OAc | —CO₂CH₂C₆H₅ | —CH₃ | H | u | u | s |
| OH, CN | —OAc | —CO₂CH₂C₆H₅ | —H | H | u | u | s |
| OH, CN | —OAc | —CO₂CH₃ | —H | — | u | s | u |
| OH, CN | —OAc | —CO₂C₂H₅ | —CH₃ | H | u | u | s |
| OH, CN | —Br | —CO₂CH₃ | —H | — | u | s | u |
| OH, CN | —Br | —CO₂H | —H | — | u | s | u |
| OH, CN | —Cl | —CONH₂ | —H | — | u | s | u |
| OH, CN | —OAc | CONH₂ | —CH₃ | H | u | u | s |
| OH, CN | —OAc | C≡N | — | — | u | s | u |
| OH, CN | —OAc | C≡N | —CH₃ | —H | u | u | s |

-continued

[Structure: oxepane ring with substituents R1, R2, R3, R4, R5, CH3 groups, showing positions a, b, c]

| R1 | R2 | R3 | R4 | R5 | a | b | c |
|---|---|---|---|---|---|---|---|
| —OH, —CN | —Br | —CH2Br | —H | —OH | u | u | s |
| [thiazine ring S,N] | —OAc | —OH, CH, CN | —H | — | u | s | u |
| [dithiolane ring S,S] | —OAc | —OH, CH, CN | —H | — | u | s | u |
| =CH2 | —OAc | —OH, CH, CN | —H | — | u | s | u |
| =CH2 | —OH, —CN | CH2OAc | —H | — | u | s | u |
| —CH3, —CN | OAc | —OH, CH, CN | —H | — | u | s | u |
| —OH, —C6H5, —CN, —OH | —OAc | —OH, CH, CN | —H | — | u | s | u |

The following compounds are prepared according to the procedure of Example 163 by substituting an equivalent amount of the appropriate starting material for 2S,3R-3-acetoxy-6-(2-acetoxyethylidene)-2-methyl-2-(4,8-dimethyl-5-oxo-7-nonenyl)-oxepane.

[Structure: oxepane with R1, R2, R3, R4 substituents, positions b, c]

| R1 | R2 | R3 | R4 | b | c |
|---|---|---|---|---|---|
| —OH, —CN | =CH2 | —H | — | s | u |
| —OH, —CN | —CH3 | —H | — | s | u |
| —OH, —CN | —CH2OH | —H | — | s | u |
| —OH, —CN | —CH(OH)(CN) | —H | — | s | u |

-continued

[Structure: oxepane with R1, R2, R3, R4 substituents, positions b, c]

| R1 | R2 | R3 | R4 | b | c |
|---|---|---|---|---|---|
| —OH, —CN | —CO2H | —H | — | s | u |
| —OH, —CN | —C≡N | —H | — | s | u |
| —OH, —CN | —CH2Br | —H | — | s | u |
| —OH, —CN | —CO2C4H9 | —H | — | s | u |
| —OH, —CN | —CONH2 | —H | — | s | u |
| —OH, —CN | =CH2 | —CH3 | —H | u | s |

-continued

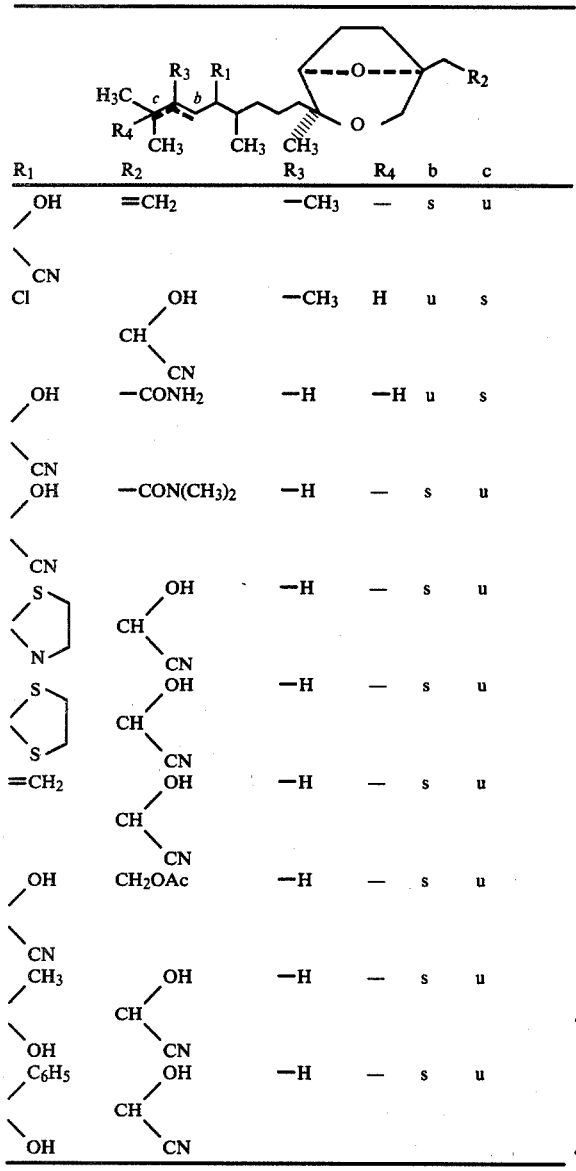

| R₁ | R₂ | R₃ | R₄ | b | c |
|---|---|---|---|---|---|
| /OH \CN | =CH₂ | —CH₃ | — | s | u |
| Cl /  \CH \CN | /OH | —CH₃ | H | u | s |
| /OH \CN | —CONH₂ | —H | —H | u | s |
| /OH \CN | —CON(CH₃)₂ | —H | — | s | u |
| S⟩N | /OH CH \CN | —H | — | s | u |
| S⟩S | /OH CH \CN | —H | — | s | u |
| =CH₂ | /OH CH \CN | —H | — | s | u |
| /OH \CN | CH₂OAc | —H | — | s | u |
| /CH₃ \OH | /OH CH \CN | —H | — | s | u |
| /C₆H₅ \OH | /OH CH \CN | —H | — | s | u |

EXAMPLE 164

2S,3R-3-Acetoxy-6-(2-acetoxyethylidene)-2-methyl-2-(5-acetoxy-4,8-dimethyl-5,7-nonadienyl)-oxepane A mixture of 2S,3R-3-acetoxy-6-(2-acetoxyethylidene)-2-methyl-2-(4,8-dimethyl-5-oxo-7-nonenyl)-oxepane (430 mg), p-toluenesulfonic acid (2 mg) and isopropenyl acetate (10 ml) is refluxed under nitrogen for 16 hours. The solvent is removed in vacuo below 50° to afford 2S,3R-3-acetoxy-6-(2-acetoxyethylidene)-2-methyl-2-(5-acetoxy-4,8-dimethyl-5,7-nonadienyl)-oxepane.

EXAMPLE 165

2S,3R-6-(2-Trimethylsiloxyethylidene)-2-methyl-2-(4,8-dimethyl-5-trimethylsiloxy-5,7-nonadienyl)-3-trimethylsiloxyoxepane Lithium diisopropylamide is generated from diisopropylamine and n-butyllithium at −20° under argon in tetrahydrofuran (10 ml). A solution of 2S,3R-6-(2-trimethylsiloxyethylidene)-2-methyl-2-(4,8-dimethyl-5-oxo-7-nonenyl)-3-trimethylsiloxyoxepane (452 mg) in tetrahydrofuran (5 ml) is added to this reagent and the resulting mixture is stirred for 10 minutes. An excess of trimethylsilyl chloride (150 mg) is added to this mixture and the mixture is allowed to warm to room temperature. The mixture is filtered and the filtrate is treated with pentane (30 ml). The resulting mixture is filtered again and the filtrate is concentrated in vacuo to afford 2S,3R-6-(2-trimethylsiloxyethylidene)-2-methyl-2-(4,8-dimethyl-5-trimethylsiloxy-5,7-nonadienyl)-3-trimethylsiloxyoxepane.

EXAMPLE 166

2S,3R-6-(2-Trimethylsiloxyethylidene)-2-methyl-2-(4,8-dimethyl-5-methoxy-5,7-nonadienyl)-3-trimethylsiloxyoxepane Following the procedure of Example 165 but substituting an equivalent amount of trimethyloxonium tetrafluoroborate for trimethylsilyl chloride, 2S,3R-6-(2-trimethylsiloxyethylidene)-2-methyl-2-(4,8-dimethyl-5-methoxy-5,7-nonadienyl)-3-trimethylsiloxyoxepane is obtained.

EXAMPLE 167

2S,3R-6-(2-Hydroxyethylidene)-2-methyl-2-(4,8-dimethyl-8-hydroperoxy-5-oxo-6-nonenyl)-oxepan-3-ol A solution of 2S,3R-6E-(2-hydroxyethylidene)-2-methyl-2-(4,8-dimethyl-5-oxo-7-nonenyl)-oxepan-3-ol (0.980 g) in methanol (70 ml) containing Rose Bengal saturated anion exchange resin (AG1X8, 2.5 g) is irradiated with a 300 W tungsten lamp for 92 hours while bubbling oxygen through it. The suspension is stirred briskly while being cooled with a cold finger throughout the period of irradiation. The resin is removed by filtration and washed with methanol. The combined filtrate and washings are distilled in vacuo below 40°. The residue is plate chromatographed on silica gel using isopropanol-chloroform (1:9) as the developing solvent. The most polar uv quenching band is eluted with isopropanolchloroform (1:1) to afford 2S,3R-6-(2-hydroxyethylidene)-2-methyl-2-(4,8-dimethyl-8-hydroperoxy-5-oxo-6-nonenyl)-oxepan-3-ol (213 mg).

IR (neat): 2.92 (OH), 5.94, 6.02 (conjugated (C=O), 6.14 (C=C), 11.8 (—O—OH); uv (EtOH): 222 nm (ε5140); NMR (CDCl₃, δ): 1.08 (d, J=6 Hz, ~3H, CH₃—CH), 1.15 (s, 3H, CH₃—C—O—C), 1.36 [s, ~6H (CH₃)₂—C—O—OH], 3.50 (m, ~1H, H—C—OH), 4.06 (s, ~2H, —O—CH₂—C=C), 4.26 (d, J=6 Hz, ~2H, C=CH—CH₂—OH), ~5.4 (m, C=CH—CH₂—OH), 6.20 (d, J=16 Hz, CH=CH—C=O), 6.83 (d, J=16 Hz, CH=CH—C=O).

The following compounds are prepared according to the procedure of Example 167 by substituting an equivalent amount of the appropriate starting material for 2S,3R-6E-(2-hydroxyethylidene)-2-methyl-2-(4,8-dimethyl-5-oxo-7-nonenyl)-oxepan-3-ol.

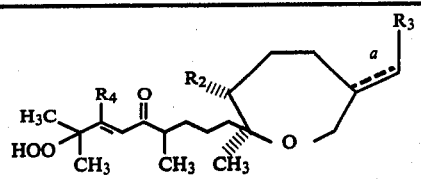

| R2 | R3 | R4 | a |
|---|---|---|---|
| —OH | CH2OH | H | s |
| —OH | CH2OH | CH3 | u |
| —OH | CH2OH | CH3 | s |
| =O | CH2OH | H | s |
| =O | CH2OH | CH3 | u |
| =O | CH2OH | CH3 | s |
| =O | CO2H | H | s |
| =O | CO2H | CH3 | u |
| =O | CO2H | CH3 | s |
| —OAc | CO2H | CH3 | s |
| —OAc | CO2H | CH3 | u |
| —OAc | CO2H | CH3 | s |
| =O | CO2CH3 | H | s |
| =O | CO2CH3 | CH3 | u |
| =O | CO2CH3 | CH3 | s |
| —OAc | CO2H | H | s |
| —OAc | CO2CH3 | CH3 | u |
| —OAc | CO2CH3 | CH3 | s |
| =O | CO2Na | H | s |
| =O | CO2Na | CH3 | u |
| =O | CO2Na | CH3 | s |
| =O | CONHCH2—C6H5 | H | s |
| =O | CON(CH3)CH2C6H5 | CH3 | u |
| =O | CONH2 | CH3 | s |
| —OAc | CON(CH3)2 | H | s |
| —OAc | CONHC4H9 | CH3 | u |
| —OAc | CONHCH3 | CH3 | s |
| =O | C≡N | H | s |
| =O | C≡N | CH3 | u |
| =O | C≡N | CH3 | s |
| —OAc | C≡N | H | s |
| —OAc | C≡N | CH3 | u |
| —OAc | C≡N | CH3 | s |
| =O | CH2OH | H | u |
| =O | CO2H | H | u |
| —OAc | CO2H | H | u |
| =O | CO2CH3 | H | u |
| —OAc | CO2CH3 | H | u |
| =O | CO2Na | H | u |
| =O | CONH2 | H | u |
| —OAc | CON(CH3)2 | H | u |
| =O | C≡N | H | u |
| —OAc | C≡N | H | u |

The following compounds are prepared according to the procedure of Example 167 by substituting an equivalent amount of the appropriate starting material for 2S,3R-6E-(2-hydroxyethylidene)-2-methyl-2-(4,8-dimethyl-5-oxo-7-nonenyl)-oxepan-3-ol.

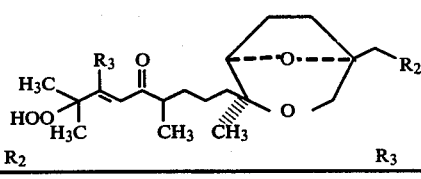

| R2 | R3 |
|---|---|
| =CH2 | H |
| =CH2 | CH3 |
| CH3 | CH3 |
| CH3 | H |
| CH2OH | CH3 |
| COOH | CH3 |
| COOCH3 | CH3 |
| C≡N | CH3 |
| CONHCH2—C6H5 | CH3 |
| COOH | H |

-continued

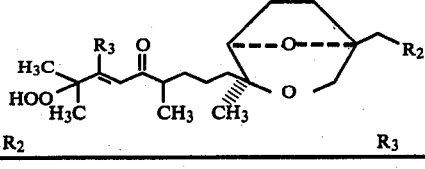

| R2 | R3 |
|---|---|
| COOCH3 | H |
| C≡N | H |
| CONH2 | H |

EXAMPLE 168

2S,3R-6-(2-Hydroxyethylidene)-2-methyl-2-(4,8-dimethyl-8-hydroxy-5-oxo-6-nonenyl)-oxepan-3-ol A solution of 2S,3R-6-(2-hydroxyethylidene)-2-methyl-2-(4,8-dimethyl-8-hydroperoxy-5-oxo-6-nonenyl)-oxepan-3-ol (354 mg) in methanol (30 ml) is stirred overnight with triphenylphosphine. Evaporation of the solvent in vacuo affords a residue which is plate chromatographed on silica gel using isopropanolchloroform (1:9) as the eluting solvent. The major band is eluted with isopropanol to afford 2S,3R-6-(2-hydroxyethylidene)-2-methyl-2-(4,8-dimethyl-8-hydroxy-5-oxo-6-nonenyl)-oxepan-3-ol (173 mg):

NMR (CDCl3,δ): 1.07 (d, J=7 Hz, ~3H, C$\underline{H}_3$—CH), 1.08 (s, 3H, C$\underline{H}_3$—C—O—C), 1.35 [s, 6H, (C$\underline{H}_3$)2—C—OH], 2.50 (broad s, O$\underline{H}$), 3.63

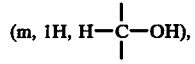

(m, 1H, H—C—OH), 4.05 (s, 2H, —OC$\underline{H}_2$—C=C), 4.1 (d, J=7 Hz, ~2H, C=CH—C$\underline{H}_2$OH), 5.36 (m, 1H, C=C$\underline{H}$—CH2OH), 6.26 (d, J=16 Hz, 1H, CH=C$\underline{H}$—C=O), and 6.85 (d, J=16 Hz, 1H, C$\underline{H}$=CH—C=O); IR (neat) μ: 2.95 (OH), 3.25 (C=C), 5.95, 6.03 (C=C—C=O), 6.15 (C=C): uv (EtOH): 224 nm (ε=9420).

EXAMPLE 169

2S-3-Methoxy-2-methyl-6-carboxymethyl-2-(4,8-dimethyl-5-oxo-7-nonenyl)-3,6-oxidooxepane A solution of 2S,3R-2-methyl-6-carboxymethylene-2-(4,8-dimethyl-5-oxo-7-nonenyl)-oxepan-3-one (350 mg) in methanol (10 ml) is treated with glacial acetic acid (0.1 ml). The resulting solution is refluxed for 3 hours, cooled and evaporated in vacuo to afford 2S-3-methoxy-2-methyl-6-carboxymethyl-2-(4,8-dimethyl-5-oxo-7-nonenyl)-3,6-oxido-oxepane.

Similarly by substituting other hydroxy compounds for methanol in the procedure of Example 169, the corresponding bicyclic derivatives are formed. Thus, ethanol and a water: tetrahydrofuran mixture afford the 3-ethoxy and 3-hydroxy derivative respectively.

EXAMPLE 170

2S,3R-3-Acetoxy-6-(2-acetoxyethylidene)-2-methyl-2-(4,8-dimethyl-5-p-toluenesulfonylhydrazono-7-nonenyl)-oxepane Following the procedure of Example 124 but substituting an equivalent amount of p-toluenesulfonylhydrazide for p-bromobenzenesulfonylhydrazide, 2S,3R-3-acetoxy-6-(2-acetoxyethylidene)-2-methyl-2-(4,8-dimethyl-5-p-toluenesulfonylhydrazono-7-nonenyl)-oxepane is obtained.

EXAMPLE 171

2S,3R-3-Acetoxy-6-(2-acetoxyethylidene)-2-methyl-2-(4,8-dimethyl-7-nonenyl)-oxepane A solution of 2S,3R-3-acetoxy-6-(2-acetoxyethylidene)-2-methyl-2-(4,8-dimethyl-5-p-toluenesulfonylhydrazono-7-nonenyl)-oxepane (590 mg) in methanol (25 ml) is treated with sodium borohydride (825 mg) at reflux under nitrogen. After 18 hours, the resulting solution is evaporated in vacuo and the residue partitioned between ether and water. The organic phase is then washed with a saturated salt solution, dried and evaporated to afford 2S,3R-3-acetoxy-6-(2-acetoxyethylidene)-2-methyl-2-(4,8-dimethyl-7-nonenyl)-oxepane.

EXAMPLE 172

2S,3R-6-[6,1'-Oxido-2'-(tetrahydropyran-2-yloxy)-ethyl]-2-methyl-2-(4,8-dimethyl-7,8-oxido-5-oxo-7-nonyl)-3-(tetrahydropyran-2-yloxy)-oxepane Following the procedure of Example 27 but substituting an equivalent amount of 2S,3R-6-[2-(tetrahydropyran-2-yloxy)-ethylidene]-2-methyl-(4,8-dimethyl-5-oxo-7-nonenyl)-3-(tetrahydropyran-2-yloxy)-oxepane for 2S,3R-3-acetoxy-6-(2-acetoxyethylidene)-2-methyl-2-(4,8-dimethyl-5-oxo-7-nonenyl)-oxepane and two equivalents of m-chloroperbenzoic acid, 2S,3R-6-[6,1'-oxido-2'-(tetrahydropyran-2-yloxy)-ethyl]-2-methyl-2-(4,8-dimethyl-7,8-oxido-5-oxo-7-nonyl)-3-(tetrahydropyran-2-yloxy)-oxepane is obtained.

EXAMPLE 173

2S,3R-6Z-[2-(Tetrahydropyran-2-yloxy)-ethylidene]-2-methyl-2-(4,8-dimethyl-5-oxo-7-nonenyl)-3-(tetrahydropyran-2-yloxy)-oxepane A solution of 2S,3R-6-[6,1'-oxido-2'-(tetrahydropyran-2-yloxy)-ethyl]-2-methyl-2-(4,8-dimethyl-7,8-oxido-5-oxo-7-nonyl)-3-(tetrahydropyran-2-yloxy)-oxepane (0.506 g) in purified tetrahydrofuran (10 ml) is treated with lithium diphenylphosphide (6.8 ml of 0.55 M solution in tetrahydrofuran) for 20 hours at room temperature under nitrogen. Acetic acid (0.056 g) is added followed by methyl iodide (0.284 g) and the mixture is allowed to stand for 0.5 hours at room temperature. after aqueous work up, the organic phase is evaporated to afford 2S,3R-6Z-[2-(tetrahydropyran-2-yloxy)-ethylidene]-2-methyl-2-(4,8-dimethyl-5-oxo-7-nonenyl)-3-(tetrahydropyran-2-yloxy)-oxepane.

EXAMPLE 174

2S,3R-6Z-(2-Hydroxyethylidene)-2-methyl-2-(4,8-dimethyl-5-oxo-7-nonenyl)-oxepan-3-ol Following the procedure of Example 12 but substituting an equivalent amount of 2S,3R-6Z-[2-(tetrahydropyran-2-yloxy)-ethylidene]-2-methyl-2-(4,8-dimethyl-5-oxo-7-nonenyl)-3-(tetrahydropyran-2-yloxy)-oxepane for 2S-6-[2-(tetrahydropyran-2-yloxy)-ethylidene]-2-methyl-2-[4,8-dimethyl-5-(tetrahydropyran-2-yloxy)-7-nonenyl]-oxepan-3-one there is obtained 2S,3R-6Z-(2-hydroxyethylidene)-2-methyl-2-(4,8-dimethyl-5-oxo-7-nonenyl)-oxepan-3-ol.

The compound of Example 174 can be substituted for 2S,3R-6E-(2-hydroxyethylidene)-2-methyl-2-(4,8-dimethyl-5-oxo-7-nonenyl)-oxepan-3-ol and converted to all the corresponding derivatives covered under the generic formula for monocyclic compounds.

EXAMPLES 175

2S,3R-6-(2-Hydroxyethylidene)-2-methyl-2-(5,5-dimethoxy-4,8-dimethyl-7-nonenyl)-oxepan-3-ol Following the procedure of Example 74 but substituting an equivalent amount of 2S,3R-6E-(2-hydroxyethylidene)-2-methyl-2-(4,8-dimethyl-5-oxo-7-nonenyl)-oxepan-3-ol for 2S-6-(2-hydroxyethylidene)-2-methyl-2-(4,8-dimethyl-5-oxo-7 -nonenyl)-oxepan-3-one,2S,3R-6-(2-hydroxyethylidene)-2-methyl-2-(5,5-dimethoxy-4,8-dimethyl-7-nonenyl)-oxepan-3-ol is obtained.

EXAMPLE 176

2S,3R-6-(2-Acetoxyethylidene)-2-methyl-2-(5,5-dimethoxy-4,8-dimethyl-7-nonenyl)-oxepan-3-ol Following the procedure of Example 3 but substituting an equivalent amount of 2S,3R-6-(2-hydroxyethylidene)-2-methyl-2-(5,5-dimethoxy-4,8-dimethyl-7-nonenyl)-oxepan-3-ol for 2S,3R-6E-(2-hydroxyethylidene)-2-methyl-2-(4,8-dimethyl-5-oxo-7-nonenyl)-oxepan-3-ol, 2S,3R-6-(2-acetoxyethylidene)-2-methyl-2-(5,5-dimethoxy-4,8-dimethyl-7-nonenyl)-oxepan-3-ol is obtained.

EXAMPLE 177

2S-6-(2-Acetoxyethylidene)-2-methyl-2-(5,5-dimethoxy-4,8-dimethyl-7-nenonyl)-oxepan-3-one Following the procedure of Example 4 but substituting an equivalent amount of 2S,3R-6-(2-acetoxyethylidene)-2-methyl-2-(5,5-dimethoxy-4,8-dimethyl-7-nonenyl)-oxepan-3-ol for 2S,3R-6-(2-acetoxyethylidene)-2-methyl-2-(4,8-dimethyl-5-oxo-7-nonenyl)-oxepan-3-ol, 2S-6-(2-acetoxyethylidene)-2-methyl-2-(5,5-dimethoxy-4,8-dimethyl-7-nonenyl)-oxepan-3-one is obtained.

EXAMPLE 178

2S,3S-6-(2-Acetoxyethylidene)-2-methyl-2-(5,5-dimethoxy-4,8-dimethyl-7-nonenyl)-oxepan-3-ol Following the procedure of Example 18 but substituting an equivalent amount of 2S-6-(2-acetoxyethylidene)-2-methyl-2-(5,5-dimethoxy-4,8-dimethyl-7-nonenyl)-oxepan-3-one for 2S,3R-6E-(2-hydroxyethylidene)-2-methyl-2-(4,8-dimethyl-5-oxo-7-nonenyl)- oxepan-3-ol affords a mixture of 2S,3R-6-(2-acetoxyethylidene)-2-methyl-2-(5,5-dimethoxy-4,8-dimethyl-7-nonenyl)-oxepan-3-ol and 2S,3S-6-(2-acetoxyethylidene)-2-methyl-2-(5,5-dimethoxy-4,8-dimethyl-7-nonenyl)-oxepan-3-ol. The compounds are separated by chromatography.

EXAMPLE 179

2S,3S-6-(2-Acetoxyethylidene)-2-methyl-2-(4,8-dimethyl-5-oxo-7-nonenyl)-oxepan-3-ol Following the procedure of Example 78 but substituting an equivalent amount of 2S,3S-6-(2-acetoxyethylidene)-2-methyl-2-(5,5-dimethoxy-4,8-dimethyl-7-nonenyl)-oxepan-3-ol for 2S,3,3-dimethoxy-2-methyl-6-cyanomethylene-2-(5,5-dimethoxy-4,8-dimethyl-7-nonenyl)-oxepane, 2S,3S-6-(2-acetoxyethylidene)-2-methyl-2-(4,8-dimethyl-5-oxo-7-nonenyl)-oxepan-3-ol is obtained.

EXAMPLE 180

2S,3S-6-(2-Hydroxyethylidene)-2-methyl-2-(4,8-dimethyl-5-oxo-7-nonenyl)-oxepan-3-ol Following the procedure of Example 21 but substituting an equivalent amount of 2S,3S-6-(2-acetoxyethylidene)-2-methyl-2-(4,8-dimethyl-5-oxo-7-nonenyl)-oxepan-3-ol for 2S,3R-3-acetoxy-6-(2-acetoxyethylidene)-2-methyl-2-(5-acetoxy-4,8-dimethyl-7-nonenyl)-oxepane affords 2S,3S-6-(2-hydroxyethylidene)-2-methyl-2-(4,8-dimethyl-5-oxo-7-nonenyl)-oxepan-3-ol.

The compound of Example 180 can be substituted for 2S,3R-6E-(2-hydroxyethylidene)-2-methyl-2-(4,8-dimethyl-5-oxo-7-nonenyl)-oxepan-3-ol and converted to all the corresponding derivatives covered under the generic formula for monocyclic compounds.

EXAMPLE 181

2S,3R-3-acetoxy-6-(2-fluoroethylidene)-2-methyl-2-(4,8-dimethyl-5-oxo-7-nonenyl)-oxepane A solution of 2S,3R-3-acetoxy-6-(2-hydroxyethylidene)-2-methyl-2-(4,8-dimethyl-5-oxo-7-nonenyl)-oxepane (390 mg) in methylene chloride (15 ml) is treated with N-(2-chloro-1,1,2-trifluoroethyl)-diethylamine (1.0 g) and the resulting mixture stirred at room temperature. After 24 hours the methylene chloride and excess N-(2-chloro-1,1,2-trifluoroethyl)-diethylamine are evaporated in vacuo to afford 2S,3R-3-acetoxy-6-(2-fluoroethylidene)-2-methyl-2-(4,8-dimethyl-5-oxo-7-nonenyl)-oxepane.

EXAMPLE 182

2S,3R-3-Acetoxy-6-(2-iodoethylidene)-2-methyl-2-(4,8-dimethyl-5-oxo-7-nonenyl)-oxepane Sodium iodide (165 mg) is added to methyl ethyl ketone (10 ml) and the resulting suspension is allowed to reflux for 1 hour. The solution is cooled to 50° and a solution of 2S,3R-3-acetoxy-6-(2-bromoethylidene)-2-methyl-2-(4,8-dimethyl-5-oxo-7-nonenyl)-oxepane 454 mg) in methyl ethyl ketone (2 ml) is added and the resulting suspension stirred at 50°. After 12 hours, the mixture is cooled, filtered and the filtrate evaporated in vacuo to give a residue which is partitioned between ether and water. The organic phase is washed with 10% sodium bisulfite, 55 sodium bicarbonate, water, dried and evaporated to afford 2S,3R-3-acetoxy-6-(2-iodoethylidene)-2-methyl-2-(4,8-dimethyl-5-oxo-7-nonenyl)-oxepane.

EXAMPLE 183

2S,3R,6R-2-Methyl-6-carboxymethyl-2-(4,8-dimethyl-5-ethynyl-5-hydroxy-7-nonenyl)-3,6-oxidooxepane Following the procedure of Example 110 but substituting an equivalent amount of 2S,3R-6-(2-hydroxyethylidene)-2-methyl-2-(4,8-dimethyl-5-ethynyl-5-hydroxy-7-nonenyl)-oxepan-3-ol for 2S,3R-6-(2-hydroxyethylidene)-2-methyl-2-(4,8-dimethyl-5-hydroxy-7-nonenyl)-oxepan-3-ol affords a residue which is plate chromatographed on silica gel, using isopropanol-chloroform (1:12) as the eluting solvent. The major band is eluted with isopropanol-chloroform (2:1) to afford 2S,3R,6R-2-methyl-6-carboxymethyl-2-(4,8-dimethyl-5-ethynyl-5-hydroxy-7-nonenyl)-3,6-oxidooxepane (252 mg).

NMR (CDCl$_3$—D$_2$O)δ: 0.98 and 1.03

[a pair of doublets,

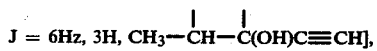

J = 6Hz, 3H, CH$_3$—CH—C(OH)C≡CH], 1.33 (s, 3H, C$\underline{H_3}$—C—O—C), 1.65 and 1.77 [each s, each 3H, (C$\underline{H_3}$)$_2$—C=CH], 2.38 (s, 1H, —C≡C$\underline{H}$), 2.60 (s, 2H, C$\underline{H_2}$—CO$_2$H), 3.37 and 3.75 (each d, J=11 Hz, 2H, —C—C$\underline{H_2}$—O—C), 3.88 (m, 1H, $\underline{H}$—C—O—C), 5.12–5.48 [m, 1H, (CH$_3$)$_2$—C=C$\underline{H}$]; IR (neat) u: 2.89 (OH), 5.80 (COOH).

EXAMPLE 184

2S,3R,6R-6-(2-Oxoethyl)-2-methyl-2-(4,8-dimethyl-5-oxononyl)-3,6-oxidooxepane

A solution of 2S,3R,6R-6-(2-oxoethyl)-2-methyl-2-(4,8-dimethyl-5-oxo-7-nonenyl)-3,6-oxidooxepane (611 mg) in ethyl acetate (300 ml) is hydrogenated in the presence of 10% palladium on carbon (400 mg) at atmospheric pressure for 1 hour. The mixture is filtered through a pad of celite and the solvent is evaporated in vacuo to give an oily residue. The residue is plate chromatographed on silica gel using ethyl acetate-hexane (1:3) as the developing solvent. The major band is eluted with the same solvent system to afford 2S,3R,6R-6-(2-oxoethyl)-2-methyl-2-(4,8-dimethyl-5-oxononyl)-3,6-oxidooxepane (540 mg).

NMR (CDCl$_3$)δ: 0.8 [d, J=6 Hz, 6H, (C$\underline{H_3}$)$_2$—CH), 1.06 (d, J=7 Hz, 3H, CH—C$\underline{H_3}$), 1.30 (s, 3H, O—C—C$\underline{H_3}$), 2.58 (d, J=2 Hz, 2H, C$\underline{H_2}$—CHO), 3.29 and 3.73

(each d, J = 11Hz, 2H, $\diagdown$C—CH$_2$—O—C), 3.82 (m, 1H, H—C—O—C), 9.80 (t, J=2 Hz, 1H, C$\underline{H}$O) IR (neat) μ 3.63 (C—H of CHO), 5.80 (HC=O), 5.82 (>C=O).

EXAMPLE 185

2S,3R,6R-2-Methyl-6-carboxymethyl-2-(4,8-dimethyl-5-oxononyl)-3,6-oxidooxepane

A solution of silver nitrate (1.328 g) in water (18 ml) is treated with 10% sodium hydroxide solution (11 ml) under nitrogen. A 15% ammonium hydroxide solution (12.8 ml) is added dropwise with stirring until the precipitate disappears. To this reagent a solution of 2S,3R,6R-6-(2-oxoethyl)-2-methyl-2-(4,8-dimethyl-5-oxononyl)-3,6-oxidooxepane (300 mg) in methanol (10 ml) is added and the resulting mixture is heated at 85° C. for 5 hours. The mixture is then treated with ice water (160 ml), ethyl acetate (80 ml) and acidified to pH 3-4 with 5% hydrochloric acid. The organic layer is dried and evaporated in vacuo to give an oily residue which is plate chromatographed on silica gel, using isopropanol chloroform (1:11) with a few drops of acetic acid as the eluting solvent. The major band is eluted with isopropanol-chloroform (1:11) to afford 2S,3R,6R-2-methyl-6-carboxymethyl-2-(4,8-dimethyl-5-oxononyl)-3,6-oxidooxepane (167 mg).

NMR (CDCl$_3$)δ: 0.88 (d, J=6 Hz, 6H, (C$\underline{H}_3$)$_2$—CH—), 1.06 (d, J=7 Hz, 3H, CH—C$\underline{H}_3$), 1.30 (s, 3H, O—C—C$\underline{H}_3$), 2.62 (s, 2H, C$\underline{H}_2$—CO$_2$H), 3.36 and 3.78 (each d, J=11 Hz, 2H, —C—C$\underline{H}_2$—O—C), 3.85

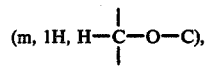

4.67-5.05 (broad s, 1H, COO$\underline{H}$, exchanged with D$_2$O); IR (neat) μ: 5.75 (HO—C=O), 5.93 (>C=O).

EXAMPLE 186

2S,3R-3-Acetoxy-6-(2-acetoxyethylidene)-2-methyl-2-(5-acetoxy-4,8-dimethyl-7-nonenyl)-oxepane A solution of 2S,3R-6-(2-hydroxyethylidene)-2-methyl-2-(4,8-dimethyl-5-hydroxy-7-nonenyl)-oxepan-3-ol (4.74 mg) in pyridine (6.0 ml) is treated with acetic anhydride (4.5 ml) at room temperature under nitrogen for 18 hrs. The pyridine is removed in vacuo and methanol is added to destroy excess acetic anhydride. The solvent is removed in vacuo and the residue (600 mg) is plate chromatographed on silica gel, using ethyl acetate-cyclohexane as the developing solvent. The major band is eluted with ethyl acetate to afford 2S,3R-3-acetoxy-6-(2-acetoxyethylidene)-2-methyl-2-(5-acetoxy-4,8-dimethyl-7-nonenyl)-oxepane (390 mg).

IR (neat): 5.75μ, (C=O);

NMR (CDCl$_3$,δ): 0.89 (d, J=7 Hz, 3H, CH—C$\underline{H}_3$), 1.15 (s, 3H, —O—C—C$\underline{H}_3$), 1.60 and 1.66 (each s, each 3H, (C$\underline{H}_3$)$_2$—(C=C); 2.03 (s, 9H, O—CO—C$\underline{H}_3$); 4.08 (s, 2H, —C$\underline{H}_2$—O—C); 4.56 (d, J=7 Hz, 2H, C$\underline{H}_2$—OAc); 4.67-5.0 (m, 2H, C$\underline{H}$—OAc); 5.0—5.5 (m, 2H, C=C$\underline{H}$—CH$_2$OAc and (CH$_3$)$_2$—C=C$\underline{H}$).

EXAMPLE 187

2S,3R,6R-2-Methyl-6-carboxymethyl-2-(4,8-dimethyl-8-hydroxy-5-oxo-6-nonenyl)-3,6-oxidooxepane Following the procedure of Example 110, but substituting 2S,3R-6E-(2-hydroxyethylidene)-2-methyl-2-(4,8-dimethyl-5-oxo-7-nonenyl)-oxepan-3-ol (660 mg) for 2S, 3R-6-(2-hydroxyethylidene)-2-methyl-2-(4,8-dimethyl-5-hydroxy-7-nonenyl)-oxepan-3-ol affords a residue which is plate chromatographed on silica gel using isopropanol-chloroform-acetic acid (36:363:1) as the eluting solvent. The most polar band is eluted with isopropanol to afford 2S,3R-6R-2-methyl-6-carboxymethyl-2-(4,8-dimethyl-8-hydroxy-5-oxo-6-nonenyl)-3,6-oxidooxepane (238 mg):

IR (CCl$_4$) μ: 2.8–3.3 broad (OH), 5.65 (shoulder), 5.82 (CO and COOH); NMR (CDCl$_3$)δ: 1.08 (d, J=7 Hz, 3H, C$\underline{H}_3$—CH), 1.30

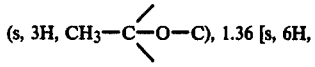

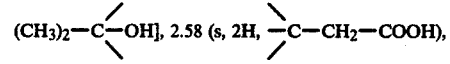

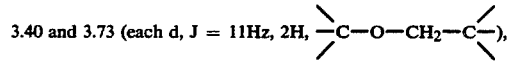

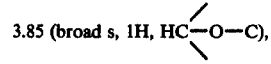

6.25 (d, J=16 Hz, 1H, CH=C$\underline{H}$—C=O), 6.83 (d, J=16 Hz, 1H, C$\underline{H}$=CH—C=O) and 5.1 (broad s, 1H, COO$\underline{H}$).

EXAMPLE 188

2S,3R-6-[2-Tetrahydropyran-2-yloxy)-ethylidene]-2-methyl-2-[4,8-dimethyl-5-hydroxy-5-(3-tetrahydropyran-2'-yloxyprop-1-ynyl)-7-nonenyl]-3-(tetrahydropyran-2-yloxy)-oxepane Following the procedure of Example 157A but substituting an equivalent amount of 2S,3R-6-[2-(tetrahydropyran-2-yloxy)-ethylidene)]-2-methyl-2-(4,8-dimethyl-5-oxo-7-nonenyl)-3-(tetrahydropyran-2-yloxy)-oxepane for 2S,3R-6-(2-hydroxyethylidene)-2-methyl-2-(4,8-dimethyl-5-oxo-7-nonenyl)-oxepan-3-ol and lithium 3-tetrahydropyran-2'-yloxyprop-1-ynide for lithium propynide, 2S,3R-6-[2-(tetrahydropyran-2-yloxy)-ethylidene]-2-methyl-2-[4,8-dimethyl-5-hydroxy-5-(3-tetrahydropyran-2'-yloxyprop-1-ynyl)-7-nonenyl]-3-tetrahydropyran-2-yloxy)-oxepane is obtained.

The following compound is prepared according to the procedure of Example 188 by substituting an equivalent amount of the appropriate starting material for 2S,3R-6-[2-(tetrahydropyran-2-yloxy)-ethylidene)]-2-methyl-2-(4,8-dimethyl-5-oxo-7-nonenyl)-3-(tetrahydropyran-2-yloxy)-oxepane.

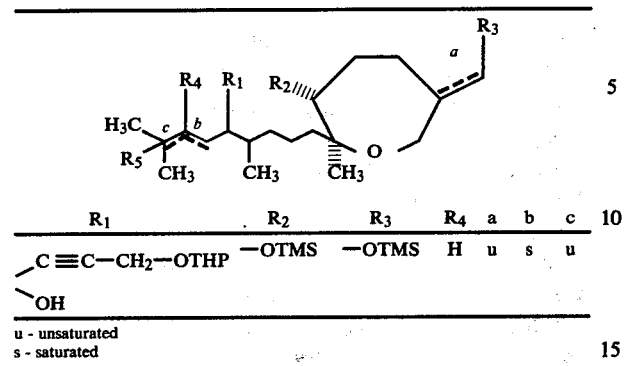

| R₁ | R₂ | R₃ | R₄ | a | b | c |
|---|---|---|---|---|---|---|
| ⟋C≡C—CH₂—OTHP  ⟍OH | —OTMS | —OTMS | H | u | s | u | u - unsaturated
s - saturated

The following compound is prepared according to the procedure of Example 188 by substituting an equivalent amount of the appropriate starting material for 2S,3R-6-[2-(tetrahydropyran-2-yloxy)-ethylidene)]-2-methyl-2-(4,8-dimethyl-5-oxo-7-nonenyl)-3-(tetrahydropyran-2-yloxy)-oxepane.

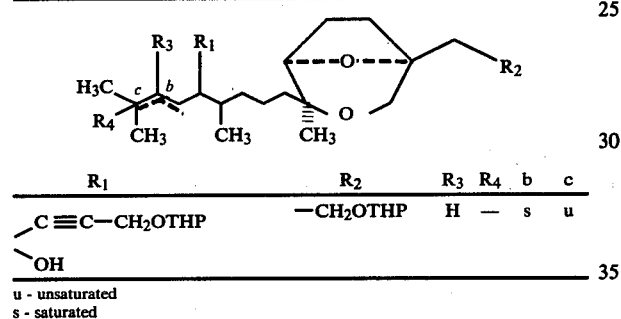

| R₁ | R₂ | R₃ | R₄ | b | c |
|---|---|---|---|---|---|
| ⟋C≡C—CH₂OTHP  ⟍OH | —CH₂OTHP | H | — | s | u | u - unsaturated
s - saturated

EXAMPLE 189

2S,3R-6-[2-(tetrahydropyran-2-yloxy)-ethylidene]-2-methyl-2-(4,8-dimethyl-5-hydroxy-5-propadienyl-7-nonenyl)-3-(tetrahydropyran-2-yloxy)-oxepane A suspension of lithium aluminum hydride (1 g.) in dry ether (20 ml.) is heated under reflux for 1 hr., cooled to room temperature and treated dropwise with stirring with a solution of 2S,3R-6-[2-(tetrahydropyran-2-yloxy)-ethylidene]-2-methyl-2-[4,8-dimethyl-5-hydroxy-5-(3-tetrahydropyran-2'-yloxyprop-1-ynyl)-7-nonenyl]-3-(tetrahydropyran-2-yloxy)-oxepane (1 g.) in dry ether (20 ml.). The resulting suspension is heated under reflux for 2.5 hrs., and after cooling the reaction mixture, the excess metal hydride is decomposed by the addition of acetone. A saturated solution of sodium sulfate and solid sodium sulfate are added to precipitate the metal salts. the mixture is filtered and the solids washed with methylene chloride. Removal of the solvent from the combined filtrate and washings affords 2S,3R-6-[2-(tetrahydropyran-2-yloxy)-ethylidene]-2-methyl-2-(4,8-dimethyl-5-hydroxy-5-propadienyl-7-nonenyl)-3-(tetrahydropyran-2-yloxy)-oxepane.

The following compound is prepared according to the procedure of Example 189 by substituting an equivalent amount of the appropriate starting material for 2S,3R-6-[2-tetrahydropyran-2-yloxy)-ethylidene]-2-methyl-2-[4,8-dimethyl-5-hydroxy-5-(3-tetrahydropyran-2'-yloxyprop-1-ynyl)-7-nonenyl]-3-tetrahydropyran-2-yloxy)-oxepane.

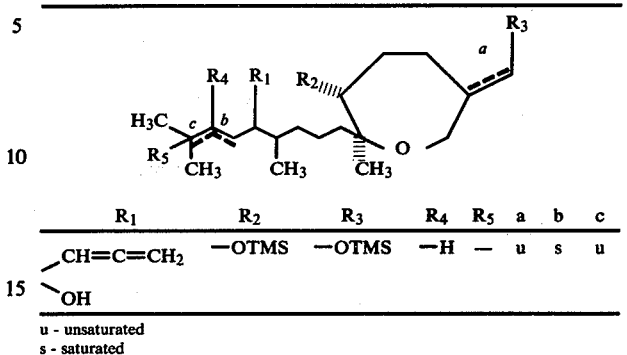

| R₁ | R₂ | R₃ | R₄ | R₅ | a | b | c |
|---|---|---|---|---|---|---|---|
| ⟋CH=C=CH₂  ⟍OH | —OTMS | —OTMS | —H | — | u | s | u | u - unsaturated
s - saturated

The following compounds are prepared according to the procedure of Example 189 by substituting an equivalent amount of the appropriate starting material for 2S,3R-6-[2-tetrahydropyran-2-yloxy)-ethylidene]-2-methyl-2-[4,8-dimethyl-5-hydroxy-5-(3-tetrahydropyran-2'-yloxyprop-1-ynyl)-7-nonenyl]-3-tetrahydropyran-2-yloxy)-oxepane.

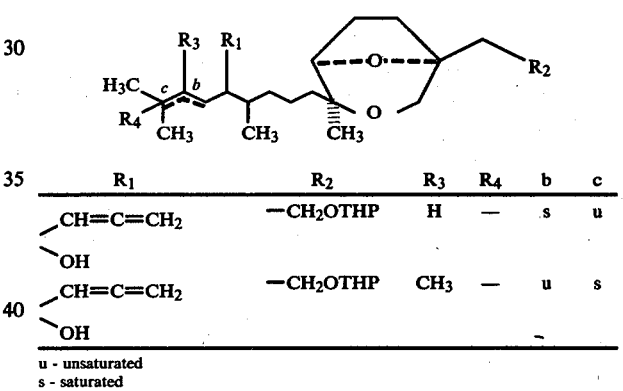

| R₁ | R₂ | R₃ | R₄ | b | c |
|---|---|---|---|---|---|
| ⟋CH=C=CH₂  ⟍OH | —CH₂OTHP | H | — | s | u |
| ⟋CH=C=CH₂  ⟍OH | —CH₂OTHP | CH₃ | — | u | s | u - unsaturated
s - saturated

EXAMPLE 190

2S,3R-6-(2-Hydroxyethylidene)-2-methyl-2-(4,8-dimethyl-5-hydroxy-5-propandienyl-7-noneyl)-oxepan-3-ol Following the procedure of Example 12 but substituting an equivalent amount of 2S,3R-6-[2-tetrahydrpyran-2-yloxy)-ethylidene]-2-methyl-2-(4,8-dimethyl-5-hydroxy-5-propadienyl-7-nonenyl)-3-(tetrahydropyran-2-yloxy)-oxepane for 2S-6-[2-(tetrahydropyran-2-yloxy)-ethylidene]-2-methyl-2-[4,8-dimethyl-5-(tetrahydropyran-2-yloxy)-7-nonenyl]-oxepan-3-one affords 2S,3R-6-(2-hydroxyethylidene)-2-methyl-2-(4,8-dimethyl-5-hydroxy-5-propadienyl-7-nonenyl)-oxepan-3-ol.

EXAMPLE 191

2S,3R-3-Acetoxy-6-(2-acetoxyethylidene)-2-methyl-2-(5-hydroxy-4,5,8-trimethyl-7-nonenyl)-oxepane Following the procedure of Example 2 but substituting an equivalent amount of 2S,3R-6-(2-hydroxyethylidene)-2-methyl-2-(5-hydroxy-4,5,8-trimethyl-7-nonenyl)-oxepan-3-ol for 2S,3R-6-(2-hydroxyethylidene)-2-methyl-2-(4,8-dimethyl-5-oxo-7-nonenyl)-oxepan-3-ol, 2S,3R-3-acetoxy-6-(2-acetoxyethylidene)-2-(5-hydroxy-4,5,8-trimethyl-7-nonenyl)-oxepane is obtained.

The following compounds are prepared according to the method of Example 191 by substituting an equivalent amount of the appropriate starting material for 2S,3R-6-(2-hydroxyethylidene)-2-methyl-2-(5-hydroxy-4,5,8-trimethyl-7-nonenyl)-oxepan-3-ol.

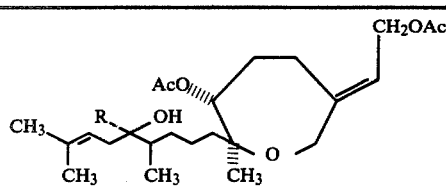

| R |
|---|
| —C≡CH |
| —CH=CH₂ |
| —C₆H₅ |
| —CH₂C₆H₅ |
| —CH₂—CH=CH₂ |
| -n-C₄H₉ |
| —CH=C=CH₂ |

EXAMPLE 192

2S,3R-3-Acetoxy-6-(2-hydroxyethylidene)-2-methyl-2-(5-hydroxy-4,5,8-trimethyl-7-nonenyl)-oxepane Following the procedure of Example 6 but substituting an equivalent amount of 2S,3R-3-acetoxy-6-(2-acetoxyethylidene)-2-methyl-2-(5-hydroxy-4,5,8-trimethyl-7-nonenyl)-oxepane for 2S,3R-3-acetoxy-6-(2-acetoxyethylidene)-2-methyl-2-(4,8-dimethyl-5-oxo-7-nonenyl)-oxepane, 2S,3R-3-acetoxy-6-(2-hydroxyethylidene)-2-methyl-2-(5-hydroxy-4,5,8-trimethyl-7-nonenyl)-oxepane is obtained.

The following compounds are prepared according to the method of Example 192 by substituting an equivalent amount of the appropriate starting material for 2S,3R-3-acetoxy-6-(2-acetoxyethylidene)-2-methyl-2-(5-hydroxy-4,5,8-trimethyl-7-nonenyl)-oxepane.

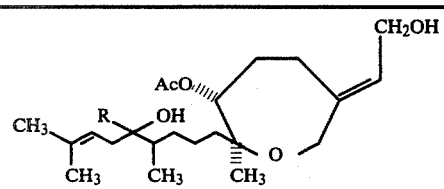

| R |
|---|
| —C≡CH |
| —CH=CH₂ |
| —C₆H₅ |
| —CH₂C₆H₅ |
| —CH₂—CH=CH₂ |
| -n-C₄H₉ |
| —CH=C=CH₂ |

EXAMPLE 193

2S,3R-3-Acetoxy-6-(2-oxoethylidene)-2-methyl-2-(5-hydroxy-4,5,8-trimethyl-7-nonenyl)-oxepane Following the procedure of Example 7 but substituting an equivalent amount of 2S,3R-3-acetoxy-6-(2-hydroxyethylidene)-2-methyl-2-(5-hydroxy-4,5,8-trimethyl-7-nonenyl)-oxepane for 2S,3R-3-acetoxy-6-(2-hydroxyethylidene)-2-methyl-2-(4,8-dimethyl-5-oxo-7-nonenyl)-oxepane, 2S,3R-3-acetoxy-6-(2-oxoethylidene)-2-methyl-2-(5-hydroxy-4,5,8-trimethyl-7-nonenyl)-oxepane is obtained.

The following compounds are prepared according to the method of Example 193 by substituting an equivalent amount of the appropriate starting material for 2S,3R-3-acetoxy-6-(2-hydroxyethylidene)-2-methyl-2-(5-hydroxy-4,5,8-trimethyl-7-nonenyl)-oxepane.

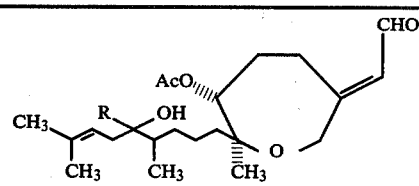

| R |
|---|
| —C≡CH |
| —CH=CH₂ |
| —C₆H₅ |
| —CH₂—C₆H₅ |
| —CH₂—CH=CH₂ |
| -n-C₄H₉ |
| —CH=C=CH₂ |

The following compounds are prepared according to the procedure of Example 193 by substituting the appropriate starting material for 2S,3R-3-acetoxy-6-(2-hydroxyethylidene)-2-methyl-2-(5-hydroxy-4,5,8-trimethyl-7-nonenyl)-oxepane.

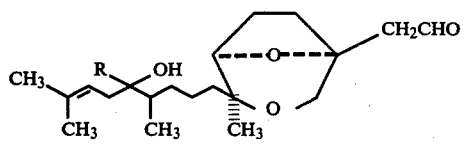

| R |
|---|
| —C≡CH |
| —CH=CH₂ |
| —C₆H₅ |
| —CH₂C₆H₅ |
| —CH₂—CH=CH₂ |
| -n-C₄H₉ |
| —CH=C=CH₂ |
| —CH₃ |

EXAMPLE 194

2S,3R-3-Acetoxy-2-methyl-6-carboxymethylene-2-(5-hydroxy-4,5,8-trimethyl-7-nonenyl)-oxepane Following the procedure of Example 56 but substituting an equivalent amount of 2S,3R-3-acetoxy-6-(2-oxoethylidene)-2-methyl-2-(5-hydroxy-4,5,8-trimethyl-7-nonenyl)-oxepane for 2S-6-(2-oxoethylidene)-2-methyl- 2-(4,8-dimethyl-5-oxo-7-nonenyl)-oxepan-3-one, 2S,3R-3-acetoxy-2-methyl-6-carboxymethylene-2-(5-hydroxy-4,5,8-trimethyl-7-nonenyl)-oxepane is obtained.

The following compounds are prepared according to the method of Example 194 by substituting an equivalent amount of the appropriate starting material for 2S,3R-3-acetoxy-6-(2-oxoethylidene)-2-methyl-2-(5-hydroxy-4,5,8-trimethyl-7-nonenyl)-oxepane.

| R |
| --- |
| —C≡CH |
| —CH=CH₂ |
| —C₆H₅ |
| —CH₂C₆H₅ |
| —CH₂—CH=CH₂ |
| -n-C₄H₉ |

The following compounds are prepared according to the method of Example 194 by substituting an equivalent amount of the appropriate starting material for 2S,3R-3-acetoxy-6-(2-oxoethylidene)-2-methyl-2-(5-hydroxy-4,5,8-trimethyl-7-nonenyl)-oxepane.

| R |
| --- |
| —C≡CH |
| —CH=CH₂ |
| —C₆H₅ |
| —CH₂C₆H₅ |
| —CH₂—CH=CH₂ |
| -n-C₄H₉ |
| —CH₃ |

EXAMPLE 195

2S,3R-3-Acetoxy-2-methyl-6-carbmethoxymethylene-2-(5-hydroxy-4,5,8-trimethyl-7-nonenyl)-oxepane Following the procedure of Example 60 but substituting an equivalent amount of 2S,3R-3-acetoxy-2-methyl-6-carboxymethylene-2-(5-hydroxy-4,5,8-trimethyl-7-nonenyl)-oxepane for 2S-2-methyl-6-carboxymethylene-2-(4,8-dimethyl-5-oxo-7-nonenyl)-oxepan-3-one, 2S,3R-3-acetoxy-2-methyl-6-carbmethoxymethylene-2-(5-hydroxy-4,5,8-trimethyl-7-nonenyl)-oxepane is obtained.

The following compound, are prepared according to the method of Example 195 by substituting an equivalent amount of the appropriate starting material for 2S,3R-3-acetoxy-2-methyl-6-carboxymethylene-2-(5-hydroxy-4,5,8-trimethyl-7-nonenyl)-oxepane.

| R |
| --- |
| —C≡CH |
| —CH=CH₂ |
| —C₆H₅ |
| —CH₂C₆H₅ |
| —CH₂—CH=CH₂ |
| -n-C₄H₉ |

The following compounds are prepared according to the method of Example 195 by substituting an equivalent amount of the appropriate starting material for 2S,3R-3-acetoxy-2-methyl-6-carboxymethylene-2-(5-hydroxy-4,5,8-trimethyl-7-nonenyl)-oxepane.

| R |
| --- |
| —C≡CH |
| —CH=CH₂ |
| —C₆H₅ |
| —CH₂C₆H₅ |
| —CH₂—CH=CH₂ |
| -n-C₄H₉ |
| —CH₃ |

EXAMPLE 196

2S,3R-3-Acetoxy-2-methyl-6-carboxymethylene-2-(5-hydroxy-4,5,8-trimethyl-7-nonenyl)-oxepane, sodium salt Following the procedure of Example 64 but substituting an equivalent amount of 2S,3R-3-acetoxy-2-methyl-6-carboxymethylene-2-(5-hydroxy-4,5,8-trimethyl-7-nonenyl)-oxepane for 2S-2-methyl-6-carboxymethylene-2-(4,8-dimethyl-5-oxo-7-nonenyl)-oxepan-3-one, 2S,3R-3-acetoxy-2-methyl-6-carboxymethylene-2-(5-hydroxy-4,5,8-trimethyl-7-nonenyl)-oxepane, sodium salt is obtained.

The following compounds are prepared according to the method of Example 196 by substituting an equivalent amount of the appropriate starting material for 2S,3R-3-acetoxy-2-methyl-6-carboxymethylene-2-(5-hydroxy-4,5,8-trimethyl-7-nonenyl)-oxepane and the appropriate basic hydroxide.

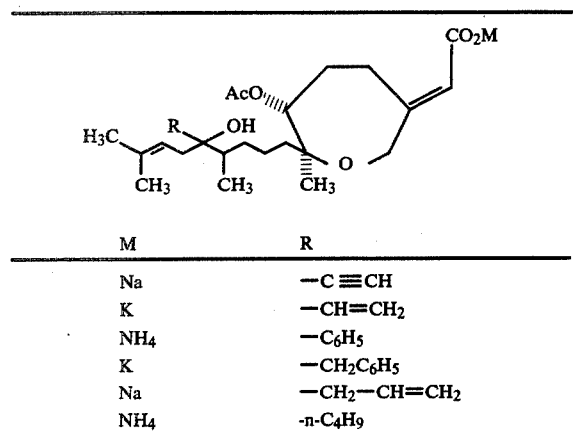

| M | R |
|---|---|
| Na | —C≡CH |
| K | —CH=CH$_2$ |
| NH$_4$ | —C$_6$H$_5$ |
| K | —CH$_2$C$_6$H$_5$ |
| Na | —CH$_2$—CH=CH$_2$ |
| NH$_4$ | -n-C$_4$H$_9$ |

The following compounds are prepared according to the method of Example 196 by substituting an equivalent amount of the appropriate starting material for 2S,3R-3-acetoxy-2-methyl-6-carboxymethylene-2-(5-hydroxy-4,5,8-trimethyl-7-nonenyl)-oxepane.

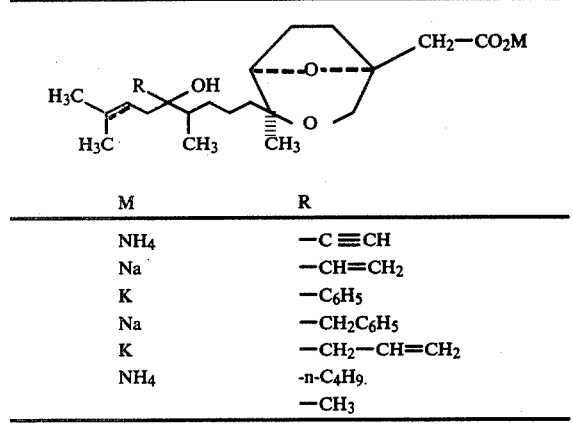

| M | R |
|---|---|
| NH$_4$ | —C≡CH |
| Na | —CH=CH$_2$ |
| K | —C$_6$H$_5$ |
| Na | —CH$_2$C$_6$H$_5$ |
| K | —CH$_2$—CH=CH$_2$ |
| NH$_4$ | -n-C$_4$H$_9$ |
|  | —CH$_3$ |

EXAMPLE 197

2S,3R-3-Acetoxy-6-[2-(hydroxyimino)-ethylidene]-2-methyl-2-(5-hydroxy-4,5,8-trimethyl-7-nonenyl)-oxepane Following the procedure of Example 76 but substituting an equivalent amount of 2S,3R-3-acetoxy-6-(2-oxoethylidene)-2-methyl-2-(5-hydroxy-4,5,8-trimethyl-7-nonenyl)-oxepane for 2S-3,3-dimethoxy-6-(2-oxoethylidene)-2-methyl-2-(5,5-dimethoxy-4,8-dimethyl-7-nonenyl)-oxepane, 2S,3R-3-acetoxy-6-[2-(hydroxyimino)-ethylidene]-2-methyl-2-(5-hydroxy-4,5,8-trimethyl-7-nonenyl)-oxepane is obtained.

The following compounds are prepared according to the method of Example 197 by substituting an equivalent amount of the appropriate starting material for 2S,3R-3-acetoxy-6-(2-oxoethylidene)-2-methyl-2-(5-hydroxy-4,5,8-trimethyl-7-nonenyl)-oxepane.

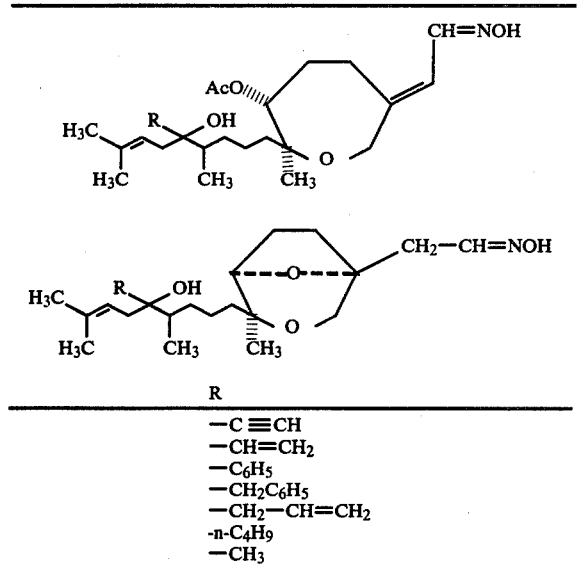

| R |
|---|
| —C≡CH |
| —CH=CH$_2$ |
| —C$_6$H$_5$ |
| —CH$_2$C$_6$H$_5$ |
| —CH$_2$—CH=CH$_2$ |
| -n-C$_4$H$_9$ |
| —CH$_3$ |

EXAMPLE 193

2S,3R-3-Acetoxy-2-methyl-6-cyanomethylene-(5-hydroxy-4,5,8-trimethyl-7-nonenyl)-oxepane Following the procedure of Example 77 but substituting an equivalent amount of 2S,3R-3-acetoxy-6-[2-(hydroxyimino)-ethylene]-2-methyl-2-(5-hydroxy-4,5,8-trimethyl-7-nonenyl)-oxepane for 2S-3,3-dimethoxy-6-[2-(hydroxyimino)-ethylidene]-2-methyl-2-(5,5-dimethoxy-4,8-dimethyl-7-nonenyl)-oxepane, 2S,3R-3-acetoxy-2-methyl-6-cyanomethylene-2-(5-hydroxy-4,5,8-trimethyl-7-nonenyl)-oxepane is obtained.

The following compounds are prepared according to the method of Example 198 by substituting an equivalent amount of the appropriate starting material for 2S,3R-3-acetoxy-6-[2-(hydroxyimino)-ethylidene]-2-methyl-2-(5-hydroxy-4,5,8-trimethyl-7-nonenyl)-oxepane

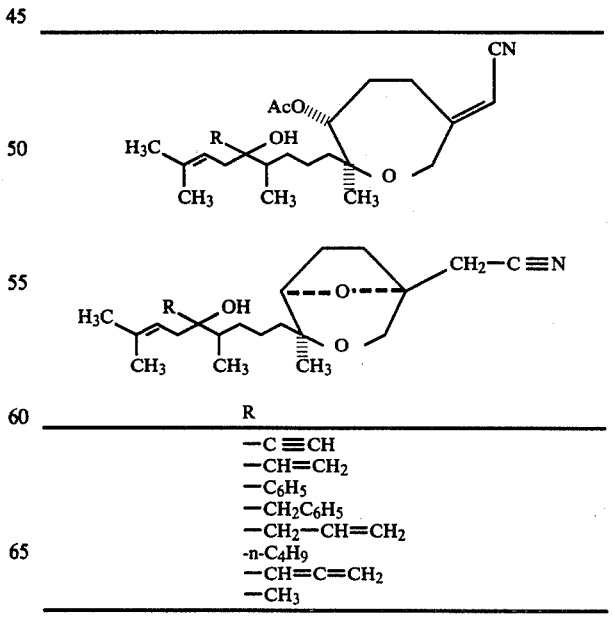

| R |
|---|
| —C≡CH |
| —CH=CH$_2$ |
| —C$_6$H$_5$ |
| —CH$_2$C$_6$H$_5$ |
| —CH$_2$—CH=CH$_2$ |
| -n-C$_4$H$_9$ |
| —CH=C=CH$_2$ |
| —CH$_3$ |

EXAMPLE 199

2S,3R-3-Acetoxy-2-methyl-6-chloroformylmethylene-2-(5-hydroxy-4,5,8-trimethyl-7-nonenyl)-oxepane Following the procedure of Example 65 but substituting an equivalent amount of 2S,3R-3-acetoxy-2-methyl-6-carboxymethylene-2-(5-hydroxy-4,5,8-trimethyl-7-nonenyl)-oxepane for 2S,3R-3-acetoxy-2-methyl-6-carboxymethylene-2-(4,8-dimethyl-5-oxo-7-nonenyl)-oxepane, 2S,3R-3-acetoxy-2-methyl-6-chloroformylmethylene-2-(5-hydroxy-4,5,8-trimethyl-7-nonenyl)-oxepane is obtained.

The following compounds are prepared according to the method of Example 199 by substituting an equivalent amount of the appropriate starting material for 2S,3R-3-acetoxy-2-methyl-6-carboxymethylene-2-(5-hydroxy-4,5,8-trimethyl-7-nonenyl)-oxepane.

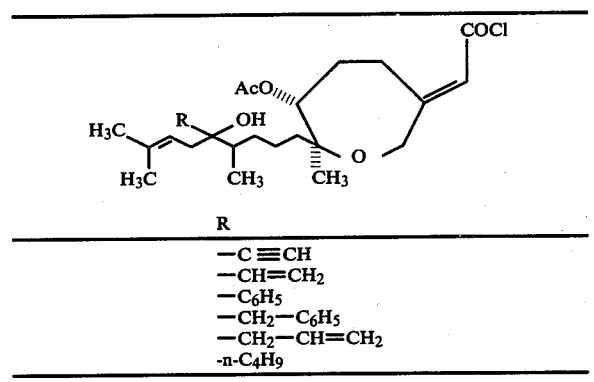

| R |
|---|
| —C≡CH |
| —CH=CH$_2$ |
| —C$_6$H$_5$ |
| —CH$_2$—C$_6$H$_5$ |
| —CH$_2$—CH=CH$_2$ |
| -n-C$_4$H$_9$ |

The following compounds are prepared according to the method of Example 199 by substituting an equivalent amount of the appropriate starting material for 2S,3R-3-acetoxy-2-methyl-6-carboxymethylene-2-(5-hydroxy-4,5,8-trimethyl-7-nonenyl)-oxepane.

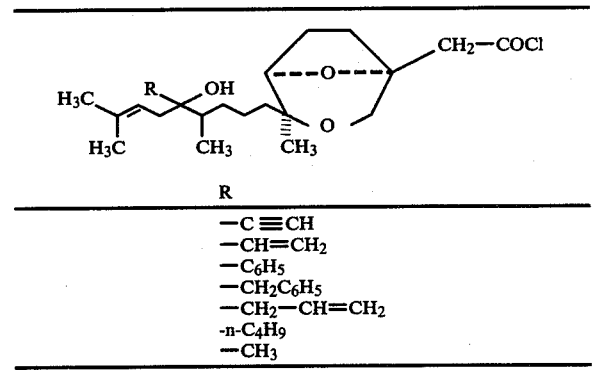

| R |
|---|
| —C≡CH |
| —CH=CH$_2$ |
| —C$_6$H$_5$ |
| —CH$_2$C$_6$H$_5$ |
| —CH$_2$—CH=CH$_2$ |
| -n-C$_4$H$_9$ |
| —CH$_3$ |

EXAMPLE 200

2S,3R-3-Acetoxy-2-methyl-6-carbamoylmethylene-2-(4,5,8-trimethyl-5-oxo-7-nonenyl)-oxepane Following the procedure of Example 66 but substituting an equivalent amount of 2S,3R-3-acetoxy-2-methyl-6-chloroformylmethylene-2-(5-hydroxy-4,5,8-trimethyl-7-nonenyl)-oxepane for 2S,3R-3-acetoxy-2-methyl-6-chloroformylmethylene-2-(4,8-dimethyl-5-oxo-7-nonenyl)-oxepane, 2S,3R-3-acetoxy-2-methyl-6-carbamoylmethylene-2-(4,5,8-trimethyl-5-oxo-7-nonenyl)-oxepane is obtained.

The following compounds are prepared according to the method of Example 200 by substituting an equivalent amount of the appropriate starting material for 2S,3R-3-acetoxy-2-methyl-6-chloroformylmethylene-2-(5-hydroxy-4,5,8-trimethyl-7-nonenyl)-oxepane.

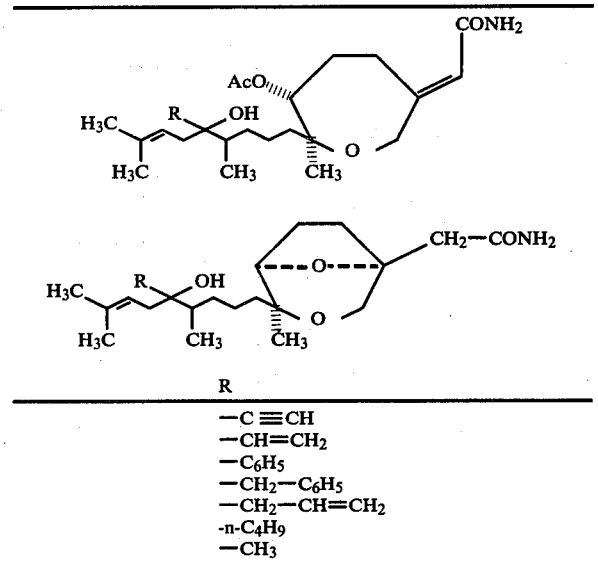

| R |
|---|
| —C≡CH |
| —CH=CH$_2$ |
| —C$_6$H$_5$ |
| —CH$_2$—C$_6$H$_5$ |
| —CH$_2$—CH=CH$_2$ |
| -n-C$_4$H$_9$ |
| —CH$_3$ |

EXAMPLE 201

2S,3R,6S-6-Carboxy-2-methyl-2-(5-oxo-4,7,8-trimethyl-6E-nonenyl)-3,6-oxidooxepane To a mixture of 2S,3R,6E-6-(2-hydroxyethylidene)-2-methyl-2-(5-oxo-4,7,8-trimethyl-6E-nonenyl)-oxepan-3-ol (234.8 mg., 0.66 mmole) and acetone (20 ml.), Jones reagent (3 mmole) is added slowly at 0° under nitrogen. The reaction mixture is kept at 0° C. for 10 min and then is treated with methanol (5 ml), ether (30 ml) and water (15 ml). The organic phase is extracted with 10% sodium bicarbonate (3×20 ml). The aqueous phase is combined and acidified at 0° to pH 2 to 3 with 10% hydrochloric acid. The mixture is extracted with methylene chloride (2×125 ml), the extracts are dried (MgSO$_4$) and evaporated to afford 2S,3R,6S-6-carboxy-2-methyl-2-(5-oxo-4,7,8-trimethyl-6E-nonenyl)-3,6-oxidooxepane (150 mg, 68% yield).

IR (neat) μ: 2.78–4.00(br), 5.78 (s), 5.94 (s), 6.17 (s); NMR$_{TMS}^{CDCl_3}$ δ: 8.6 (br, 1H, —CO$_2$H), 6.02 (br, 1H, (CH$_3$)$_2$—C=CH), 3.8 (m, 3H, C—CH$_2$—O—C, O—C—CH—O), 2.06 (d, J=1 Hz, 3H, CH$_3$—C=CH—).

EXAMPLE 202

2S,3R,6S-6-Carboxy-2-methyl-2-(4,8-dimethyl-5-oxo-7-nonenyl)-3,6-oxidooxepane

Following the procedure of Example 201 but substituting an equivalent amount of 2S,3R,6E-6-(2-hydroxyethylidene)-2-methyl-2-(4,8-dimethyl-5-oxo-7-nonenyl)-oxepan-3-ol for 2S,3R, 6E-6-(2-hydroxyethylidene)-2-methyl-2-(5-oxo-4,7,8-trimethyl-6E-nonenyl)-oxepan-3-ol, there is obtained 2S,3R,6S-6-carboxy- 2-methyl-2-(4,8-dimethyl-5-oxo-7-nonenyl)-3,6-oxidooxepane.

IR (neat) μ: 2.78–4.00 (br), 5.78 (s), 5.86 (s); NMR$_{TMS}^{CDCl_3}$ δ: 8.8 (br, 1H, CO$_2$H), 5.3 [br, 1H, (CH$_3$)$_2$—C=CH], 3.8 (m, 3H, C—CH$_2$—OC, O—C—CH—O), 3.1 (bd, J=7 Hz, 2H, C=C—CH$_2$—CO), 1.75 (bs, 3H, CH$_3$—C=C), 1.62 (bs, 3H, CH$_3$—C=C).

EXAMPLE 203

2S,3R,6S-6-Carboxy-2-methyl-2-(5-hydroxy-4,8-dimethyl-7-nonenyl)-3,6-oxidooxepane Following the procedure of Example 18 but substituting an equivalent amount of 2S,3R,6S-6-carboxy-2-methyl-2-(4,8-dimethyl-5-oxo-7-nonenyl)-3,6-oxidooxepane for 2S,3R,6E-6-(2-hydroxyethylidene)-2-methyl-2-(4,8-dimethyl-5-oxo-7-nonenyl)-oxepan-3-ol, there is obtained 2S,3R-6S-6-carboxy-2-methyl-2-(5-hydroxy-4,8-dimethyl-7-nonenyl)-3,6-oxidooxepane.

IR (neat) μ: 2.78–4.00 (br), 5.78 (s); NMR$_{TMS}^{CDCl_3}$ δ: 5.3 [br, 1H, (CH$_3$)$_2$—C=CH], 3.8 (m, 4H, C—CH$_2$—O—C and —O—C—CH—O, —HOCH—), 1.75 (bs, 3H, CH$_3$—C=C), 1.62 (bs, 3H, CH$_3$—C=C).

EXAMPLE 204

2S,3R,6R-2-Methyl-6-chloroformylmethyl-2-(4,8-dimethyl-5-oxo-7-nonenyl)-3,6-oxidooxepane Following the procedure of Example 65 but substituting an equivalent amount of 2S,3R,6R-2-methyl-6-carboxymethyl-2-(4,8-dimethyl-5-oxo-7-nonenyl)-3,6-oxidooxepane for 2S,3R-3-acetoxy-2-methyl-6-carboxymethylene-2-(4,8-dimethyl-5-oxo-7-nonenyl)-oxepane, there is obtained 2S,3R,6R-2-methyl-6-chloroformylmethyl-2-(4,8-dimethyl-5-oxo-7-nonenyl)-3,6-oxidooxepane.

The following compounds are prepared according to the procedure of Example 204 by substituting an equivalent amount of the appropriate carboxylic acid for 2S,3R,6R-2-methyl-6-carboxymethyl-2-(4,8-dimethyl-5-oxo-7-nonenyl)-3,6-oxidooxepane.

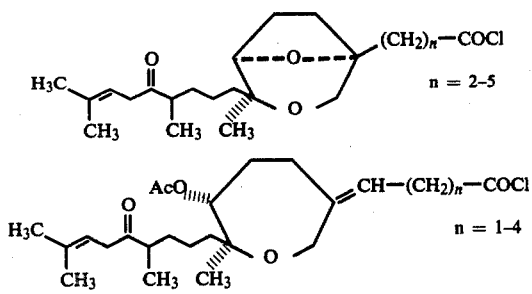

EXAMPLE 205

2S,3R,6R-6-(2-Carboxyethyl)-2-methyl-2-(4,8-dimethyl-5-oxo-7-nonenyl)-3,6-oxidooxepane A solution of 2S,3R,6R-2-methyl-6-chloroformylmethyl-2-(4,8-dimethyl-5-oxo-7-nonenyl)-3,6-oxidooxepane (400 mg.) in ether (30 ml.) is added dropwise to an ethereal solution of diazomethane (1.1 mmole) at 0° under argon. After keeping the reaction mixture overnight at room temperature, the ether is removed under reduced pressure. The residue is redissolved in dioxane (20 ml.) and then added slowly to a mixture of silver oxide (127 mg.) and an aqueous solution of sodium thiosulfate. The mixture is stirred for 3 hrs. at room temperature while an additional quantity of silver oxide is added in portions and the temperature is kept at 50° for 1 hr. The solution is cooled and filtered and the residue washed with a 10% sodium hydroxide solution (3×20 ml.). The aqueous layer is acidified with 10% hydrochloric acid solution at 0° C. to pH 2~3. The mixture is extracted with ethyl acetate (3×15 ml.). The organic phase is dried and evaporated in vacuo to give 2S,3R,6R-6-(2-carboxyethyl)-2-methyl-2-(4,8-dimethyl-5-oxo-7-nonenyl)-3,6-oxidooxepane.

The following compounds are prepared according to the procedure of Example 205 by substituting an equivalent amount of the appropriate starting material for 2S,3R,6R-2-methyl-6-chloroformylmethyl-2-(4,8-dimethyl-5-oxo-7-nonenyl)-3,6-oxidooxepane.

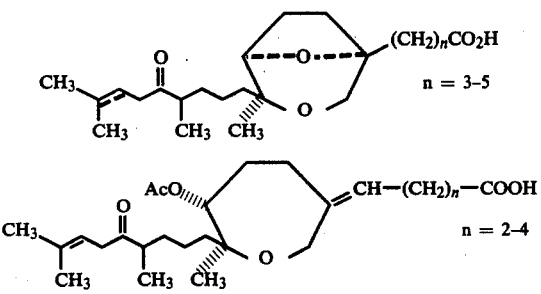

EXAMPLE 206

2S,3R,6S-6-Carbmethoxy-2-methyl-2-(4,8-dimethyl-5-oxo-7-nonenyl)-3,6-oxidooxepane Following the procedure of Example 60 but substituting an equivalent amount of 2S,3R,6S-6-carboxy-2-methyl-2-(4,8-dimethyl-5-oxo-7-nonenyl)-3,6-oxidooxepane for 2S-2-methyl-6-carboxymethylene-2-(4,8-dimethyl-5-oxo-7-nonenyl)-oxepan-3-one, there is obtained 2S,3R,6S-6-carbmethoxy-2-methyl-2-(4,8-dimethyl-5-oxo-7-nonenyl)-3,6-oxidooxepane.

The following compounds are prepared according to the procedure of Example 206 by substituting an equivalent amount of the appropriate carboxylic acid for 2S,3R,6S-6-carboxy-2-methyl-2-(4,8-dimethyl-5-oxo-7-nonenyl)-3,6-oxidooxepane.

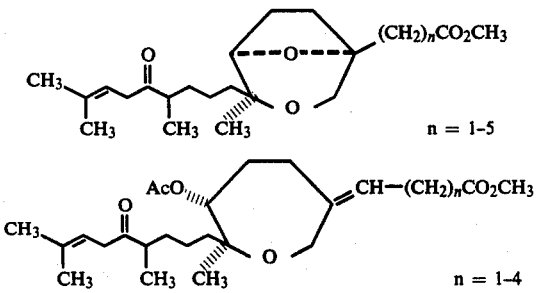

EXAMPLE 207

2S,3R,6S-6-Carboxy-2-methyl-2-(4,8-dimethyl-5-oxo-7-nonenyl)-3,6-oxidooxepane, sodium salt Following the procedure of Example 64 but substituting an equivalent amount of 2S,3R,6S-6-carboxy-2-methyl-2-(4,8-dimethyl-5-oxo-7-nonenyl)-3,6-oxidooxepane for 2S-2-methyl-6-carboxymethylene-2-(4,8-dimethyl-5-oxo-7-nonenyl)-oxepan-3-one, there is obtained 2S,3R,6S-6-carboxy-2-methyl-2-(4,8-dimethyl-5-oxo-7-nonenyl)-3,6-oxidooxepane, sodium salt.

The following compounds are prepared according to the procedure of Example 207 by substituting an equivalent amount of the appropriate carboxylic acid for 2S,3R,6S-6-carboxy-2-methyl-2-(4,8-dimethyl-5-oxo-7nonenyl)-3,6-oxidooxepane.

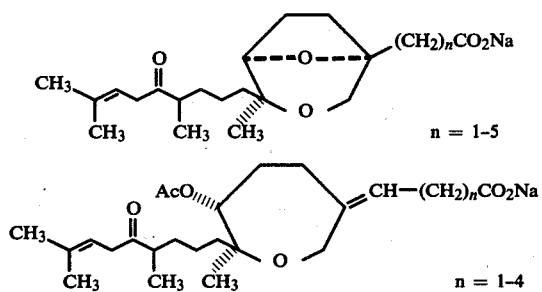

EXAMPLE 208

2S,3R,6S-6-Chloroformyl-2-methyl-2-(4,8-dimethyl-5-oxo-7-nonenyl)-3,6-oxidooxepane Following the procedure of Example 65 but substituting an equivalent amount of 2S,3R,6S-6-carboxy-2-methyl-2-(4,8-dimethyl-5-oxo-7-nonenyl)-3,6-oxidooxepane for 2S,3R-3-acetoxy-2-methyl-6-carboxymethylene-2-(4,8-dimethyl-5-oxo-7-nonenyl)-oxepane, there is obtained 2S,3R,6S-6-chloroformyl-2-methyl-2-(4,8-dimethyl-5-oxo-7-nonenyl)-3,6-oxidooxepane.

EXAMPLE 209

2S,3R,6S-6-Carbamoyl-2-methyl-2-(4,8-dimethyl-5-oxo-7-nonenyl)-3,6-oxidooxepane

Following the procedure of Example 66 but substituting an equivalent amount of 2S,3R,6S-6-chloroformyl-2-methyl-2-(4,8-dimethyl-5-oxo-7-nonenyl)-3,6-oxidooxepane for 2S,3R-3-acetoxy-2-methyl-6-chloroformylmethylene-2-(4,8-dimethyl-5-oxo-7-nonenyl)-oxepane, there is obtained 2S,3R,6S-6-carbamoyl-2-methyl-2-(4,8-dimethyl-5-oxo-7-nonenyl)-3,6-oxidooxepane.

The following compounds are prepared according to the procedure of Example 209 by substituting an equivalent amount of the appropriate acid chloride for 2S,3R,6S-6-chloroformyl-2-methyl-2-(4,8-dimethyl-5-oxo-7-nonenyl)-3,6-oxidooxepane.

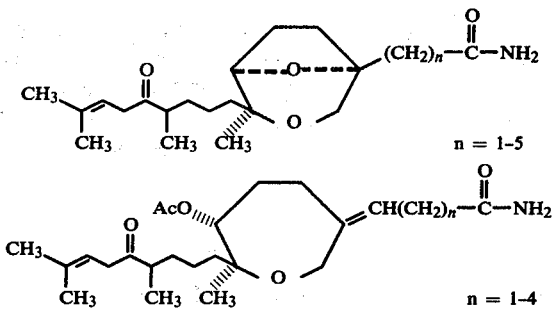

EXAMPLE 210

2S,3R,6S-6-Carbamoyl-2-methyl-2-(4,8-dimethyl-5-hydroxy-7-nonenyl)-3,6-oxidooxepane Following the procedure of Example 18 but substituting an equivalent amount of 2S,3R,6S-6-carbamoyl-2-methyl-2-(4,8-dimethyl-5-oxo-7-nonenyl)-3,6-oxidooxepane for 2S,3R-6E-(2-hydroxyethylidene)-2-methyl-2-(4,8-dimethyl-5-oxo-7-nonenyl)-oxepan-3-ol, there is obtained 2S,3R,6S-6-carbamoyl-2-methyl-2-(4,8-dimethyl-5-hydroxy-7-nonenyl)-3,6-oxidooxepane.

The following compounds are prepared according to the procedure of Example 210 by substituting an equivalent amount of the appropriate keto-amide for 2S,3R,6S-6-carbamoyl-2-methyl-2-(4,8-dimethyl-5-oxo-7-nonenyl)-3,6-oxidooxepane.

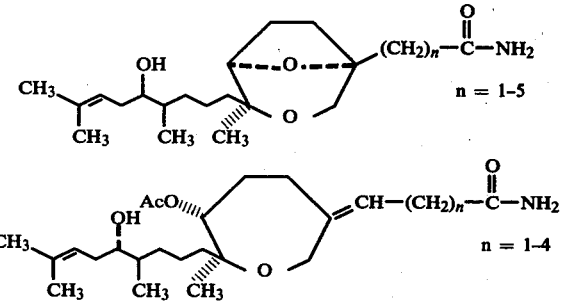

EXAMPLE 211

2S,3R,6S-6-Carbmethoxy-2-methyl-2-(4,8-dimethyl-5-hydroxy-7-nonenyl)-3,6-oxidooxepane Following the procedure of Example 18 but substituting an eqivalent amount of 2S,3R,6S-6-carbmethoxy-2-methyl-2-(4,8-dimethyl-5-oxo-7-nonenyl)-3,6-oxidooxepane for 2S,3R-6E-(2-hydroxyethylidene)-2-methyl-2-(4,8-dimethyl-5-oxo-7-nonenyl)-oxepan-3-ol, there is obtained 2S,3R,6S-6-carbmethoxy-2-methyl-2-(4,8-dimethyl-5-hydroxy-7-nonenyl)-3,6-oxidooxepane.

The following compounds are prepared according to the procedure of Example 211 by substituting an equivalent amount of the appropriate keto-ester for 2S,3R,6S-6-carbmethoxy-2-methyl-2-(4,8-dimethyl-5-oxo-7-nonenyl)-3,6-oxidooxepane.

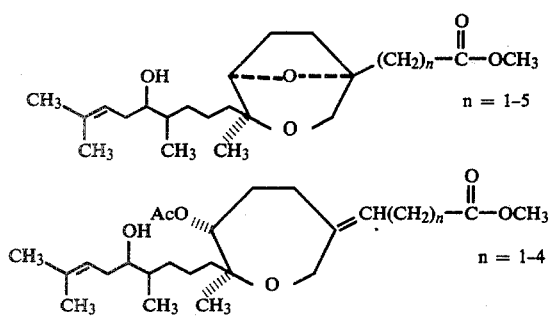

EXAMPLE 212

2S,3R,6S-6-Carboxy-2-methyl-2-(4,8-dimethyl-5-hydroxy-7-nonenyl)-3,6-oxidooxepane, sodium salt Following the procedure of Example 64 but substituting an equivalent amount of 2S,3R,6S-6-carboxy-2-methyl-2-(4,8-dimethyl-5-hydroxy-7-nonenyl)-3,6-oxidooxepane for 2S-2-methyl-6-carboxymethylene-2-(4,8-dimethyl-5-oxo-7-nonenyl)-oxepan-3-one, there is obtained 2S,3R,6S-6-carboxy-2-methyl-2-(4,8-dimethyl-5-hydroxy-7-nonenyl)-3,6-oxidooxepane, sodium salt.

The following compounds are prepared according to the procedure of Example 212 by substituting an equivalent amount of the appropriate carboxylic acid for 2S,3R,6S-6-carboxy-2-methyl-2-(4,8-dimethyl-5-hydroxy-7-nonenyl)-3,6-oxidooxepane.

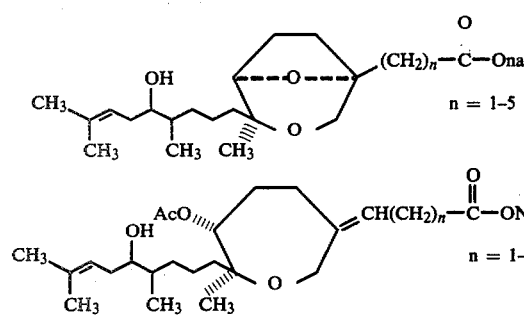

EXAMPLE 213

2S,3R,6R-2-Methyl-6-hydroxymethyl-2(4,8-dimethyl-5-hydroxy-7-nonenyl)-3,6-oxidooxepane To a stirred solution of lithium aluminum hydride (38 mg.) in tetrahydrofuran (10 ml.) is slowly added, under nitrogen, a solution of 2S,3R,6S-6-carboxy-2-methyl-2-(4,8-dimethyl-5-hydroxy-7-nonenyl)-3,6-oxidooxepane (340 mg.) in tetrahydrofuran (10 ml.) and the mixture heated to reflux for 1 hour. The cooled mixture is treated with water (~5 ml.) followed by dilute aqueous hydrochloric acid (10 ml.) and then extracted with ether. Removal of the ether in vacuo affords 2S,3R,6R-2-methyl-6-hydroxymethyl-2-(4,8-dimethyl-5-hydroxy-7-nonenyl)-3,6-oxidooxepane.

The following compounds are prepared according to the procedure of Example 213 by substituting an equivalent amount of the appropriate carboxylic acid for 2S,3R,6S-6-carboxy-2-methyl-2-(4,8-dimethyl-5-hydroxy-7-nonenyl)-3,6-oxidooxepane.

EXAMPLE 214

2S,3R,6S-2-Methyl-6-oxomethyl-2-(4,8-dimethyl-5-hydroxy-7-nonenyl)-3,6-oxidooxepane To a stirred and cooled (−60° C.) solution of 2S,3R-6S-6-carbmethoxy-2-methyl-2-(4,8-dimethyl-5-hydroxy-7-nonenyl)-3,6-oxidooxepane 354 mg.) in toluene (10 ml.) is added, under nitrogen, a solution of diisobutylaluminum hydride in hexane (1.4 M., 1.85 ml.). The mixture is allowed to warm to room temperature, stirred for an additional 2 hrs. and then treated with a saturated aqueous solution of ammonium chloride (~5 ml.). The organic layer is separated, washed, dried and evaporated in vacuo to afford 2S,3R,6S-2-methyl-6-oxomethyl-2-(4,8-dimethyl-5-hydroxy-7-nonenyl)-2,6-oxidooxepane.

The following compounds are prepared according to the procedure of Example 214 by substituting an equivalent amount of the appropriate ester for 2S,3R,6S-6-carbmethoxy-2-methyl-2-(4,8-dimethyl-5-hydroxy-7-nonenyl)-3,6-oxidooxepane.

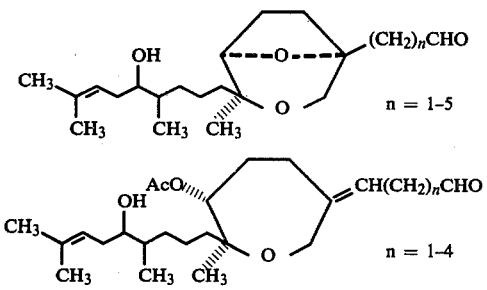

EXAMPLE 215

2S,3R,6S-2-Methyl-6-oxomethyl-2-(4,8-dimethyl-5-oxo-7-nonenyl)-3,6-oxidooxepane

Following the procedure of Example 4 but substituting an equivalent amount of 2S,3R,6S-2-methyl-6-oxomethyl-2-(4,8-dimethyl-5-hydroxy-7-nonenyl)-3,6-oxidooxepane for 2S,3R-6-(2-acetoxyethylidene)-2-methyl-2-(4,8-dimethyl-5-oxo-7-nonenyl)-oxepan-3-ol, there is obtained 2S,3R,6S-2-methyl-6-oxomethyl-2-(4,8-dimethyl-5-oxo-7-nonenyl)-3,6-oxidooxepane.

The following compounds are prepared according to the procedure of Example 215 by substituting an equivalent amount of the appropriate hydroxy aldehyde for 2S,3R,6S-2-methyl-6-oxomethyl-2-(4,8-dimethyl-5-hydroxy-7-nonenyl)-3,6-oxidooxepane.

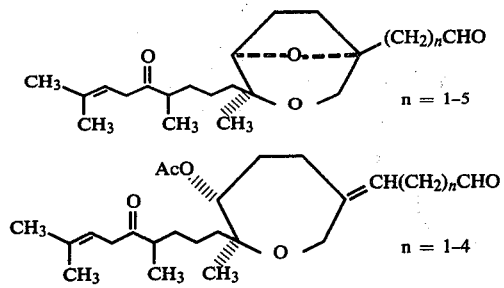

EXAMPLE 216

2S,3R,6R-2-Methyl-6-hydroxymethyl-2-(4,8-dimethyl-5-oxo-7-nonenyl)-3,6-oxidooxepane Following the procedure of Example 106 but substituting an equivalent amount of 2S,3R,6S-2-methyl-6-oxomethyl-2-(4,8-dimethyl-5-oxo-7-nonenyl)-3,6-oxidooxepane for 2S, 3R, 6R-6-(2-oxoethyl)-2-methyl-2-(4,8-dimethyl-5-oxo-7-nonenyl)-3,6-oxidooxepane, there is obtained 2S,3R,6R-2-methyl-6-hydroxymethyl-2-(4,8-dimethyl-5-oxo-7-nonenyl)-3,6-oxidooxepane.

The following compounds are prepared according to the procedure of Example 216 by substituting an equivalent amount of the appropriate keto-aldehyde for 2S,3R,6S-2-methyl-6-oxomethyl-2-(4,8-dimethyl-5-oxo-7-nonenyl)-3,6-oxidooxepane.

EXAMPLE 218

2S,3R,6R-2-Methyl-6-hydroxyiminomethyl-2-(4,8-dimethyl-5-oxo-7-nonenyl)-3,6-oxidooxepane Following the procedure of Example 217 but substituting an equivalent amount of 2S,3R,6S-2-methyl-6-oxomethyl-2-(4,8-dimethyl-5-oxo-7-nonenyl)-3,6-oxidooxepane for 2S,3R,6S-2-methyl-6-oxomethyl-2-(4,8-dimethyl-5-hydroxy-7-nonenyl)-3,6-oxidooxepane and employing 1 mole equivalent of hydroxylamine hydrochloride, there is obtained 2S,3R,6R-2-methyl-6-hydroxyiminomethyl-2-(4,8-dimethyl-5-oxo-7-nonenyl)-3,6-oxidooxepane.

The following compounds are prepared according to the procedure of Example 218 by substituting an equivalent amount of the appropriate keto-aldehyde for 2S,3R,6S-2-methyl-6-oxomethyl-2-(4,8-dimethyl-5-oxo-7-nonenyl)-3,6-oxidooxepane.

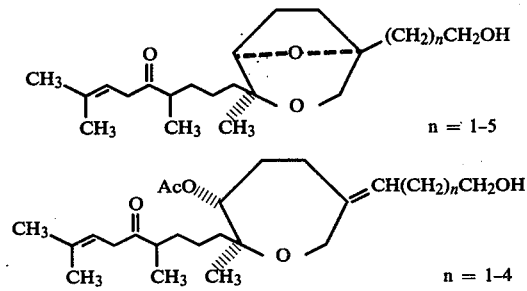

EXAMPLE 217

2S,3R,6R-2-Methyl-6-hydroxyiminomethyl-2-(4,8-dimethyl-5-hydroxy-7-nonenyl)-3,6-oxidooxepane Following the procedure of Example 76 but substituting an equivalent amount of 2S,3R,6S-2-methyl-6-oxomethyl-2-(4,8-dimethyl-5-hydroxy-7-nonenyl)-3,6-oxidooxepane for 2S,3,3-dimethoxy-6(2-oxoethylidene)-2-methyl-2-(5,5-dimethoxy-4,8-dimethyl-7-nonenyl)-oxepane, there is obtained 2S,3R,6R-2-methyl-6-hydroxyiminomethyl-2-(4,8-dimethyl-5-hydroxy-7-nonenyl)-3,6-oxidooxepane.

The following compounds are prepared according to the procedure of Example 217 by substituting an equivalent amount of the appropriate aldehyde for 2S,3R,6S-2-methyl-6-oxomethyl-2-(4,8-dimethyl-5-hydroxy-7-nonenyl)-3,6-oxidooxepane.

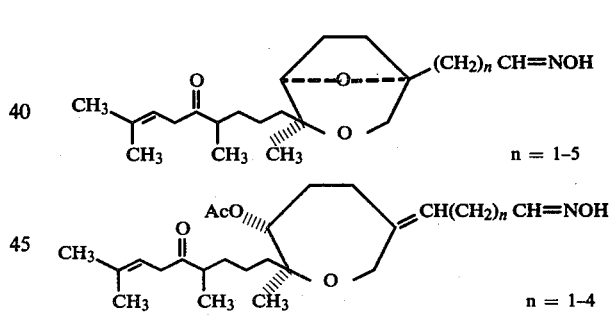

EXAMPLE 219

2S,3R,6R-6-Cyano-2-methyl-2-(4,8-dimethyl-5-oxo-7-nonenyl)-3,6-oxidooxepane

Following the procedure of Example 77 but substituting an equivalent amount of 2S,3R,6R-2-methyl-6-hydroxyiminomethyl-2-(4,8-dimethyl-5-oxo-7-nonenyl)-3,6-oxidooxepane for 2S-3,3-dimethoxy-6-(2-hydroxyiminoethylidene)-2-methyl-2-(5,5-dimethoxy-4,8-dimethyl-7-nonenyl)oxepane, there is obtained 2S,3R,6R-6-cyano-2-methyl-2-(4,8-dimethyl-5-oxo-7-nonenyl)-3,6-oxidooxepane.

The following compounds are prepared according to the procedure of Example 219 by substituting an equivalent amount of the appropriate oxime for 2S,3R,6R-2-methyl-6-hydroxyiminomethyl-2-(4,8-dimethyl-5-oxo-7-nonenyl)-3,6-oxidooxepane.

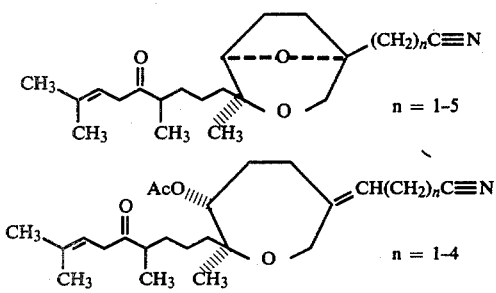

EXAMPLE 220

2S,3R,6R-6-Cyano-2-methyl-2-(4,8-dimethyl-5-hydroxy-7-nonenyl)-3,6-oxidooxepane

Following the procedure of Example 18 but substituting an equivalent amount of 2S,3R,6R-6-cyano-2-methyl-2-(4,8-dimethyl-5-oxo-7-noneyl)-3,6-oxidooxepane for 2S,3R,6E-6-(2-hydroxyethylidene)-2-methyl-2-(4,8-dimethyl-5-oxo-7-nonenyl)-oxepan-3-ol, there is obtained 2S,3R,6R-6-cyano-2-methyl-2-(4,8-dimethyl-5-hydroxy-7-nonenyl)-3,6-oxidooxepane.

The following compounds are prepared according to the procedure of Example 220 by substituting an equivalent amount of the appropriate keto-nitrile for 2S,3R,6R-6-cyano-2-methyl-2-(4,8-dimethyl-5-oxo-7-nonenyl)-3,6-oxidooxepane.

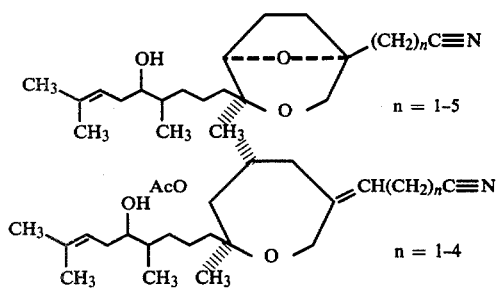

EXAMPLE 221

2S,3R,6R-6-Carbmeyhoxyethyl-2-methyl-2-(5,5-dimethoxy-4,8-dimethyl-7-nonenyl)-3,6-oxidooxepane Following the procedure of Example 74 but substituting an equivalent amount of 2S,3R,6R-6-carbmethoxyethyl-2-methyl-2-(4,8-dimethyl-5-oxo-7-nonenyl)-3,6-oxidooxepane for 2S-6-(2-hydroxyethylidene)-2-methyl-2-(4,8-dimethyl-5-oxo-7-noneyl)-oxepan-3-one, there is obtained 2S,3R,6R-6-carbmethoxyethyl-2-methyl-2-(5,5-dimethoxy-4,8-dimethyl-7-nonenyl)-3,6-oxidooxepane.

EXAMPLE 222

2S,3R,6R-2-Methyl-2-(5,5-dimethoxy-4,8-dimethyl-7-nonenyl)-3,6-oxido-6-(2-carbmethoxypropyl)-oxepane A solution of n-butyl lithium in hexane (2.4 M., 0.417 ml.) is added to a solution of diisopropylamine (95 mg.) in anhydrous tetrahydrofuran (2 ml.) at −78° C. under nitrogen. After stirring for 15 minutes, a solution of 2S,3R,6R-6-carbmethoxyethyl-2-methyl-2-(5,5-dimethoxy-4,8-dimethyl-7-nonenyl)-3,6-oxidooxepane (426 mg.) in anhydrous tetrahydrofuran (1 ml.) is added. After stirring for 0.5 hr., a solution of methyl iodide (0.156 mg.) in anhydrous tetrahydrofuran (1 ml.) is added. The mixture is allowed to attain room temperature, quenched with water and extracted with ether. The ether extract is washed, dried and evaporated to dryness to afford 2S,3R,6R-2-methyl-2-(5,5-dimethoxy-4,8-dimethyl-7-nonenyl)-3,6-oxido-6-(2-carbmethoxypropyl)-oxepane.

When ethyl, propyl, butyl or allyl iodide is employed in place of methyl iodide, the corresponding carbalkoxyalkyl derivative is obtained.

EXAMPLE 223

2S,3R,6R-2-Methyl-2-(4,8-dimethyl-5-oxo-7-nonenyl)-3,6-oxido-6-(2-carboxypropyl)-oxepane A mixture of 2S,3R,6R-2-methyl-2-(5,5-dimethoxy-4,8-dimethyl-7-nonenyl)-3,6-oxido-6-(2-carbmethoxypropyl)-oxepane (440 mg.), methanol (6 ml.) and saturated aqueous potassium carbonate solution (2 ml.) is stirred at 0° for 2 hrs. under argon. The solvent is removed in vacuo and the residue is treated with chloroform (18 ml.) and 20% aqueous trifluoroacetic acid (4 ml.). The resulting mixture is stirred at room temperature for 3 hrs. under argon. The reaction mixture is treated with ethyl acetate (20 ml.) and water (10 ml.). The organic layer is separated and dried ($Na_2SO_4$). The solvent is removed to afford 2S,3R,6R-2-(4,8-dimethyl-5-oxo-7-nonenyl)-3,6-oxido-6-(2-carboxypropyl)-oxepane.

EXAMPLE 224

2S-3-Acetoxy-2-methyl-6-carboxymethyl-2-(4,8-dimethyl-5-oxo-7-nonenyl)-3,6-oxidooxepane A mixture of 2S-3-hydroxy-2-methyl-6-carboxymethyl-2-(4,8-dimethyl-5-oxo-7-nonenyl)-3,6-oxidooxepane (368 mg), ether (10 ml), acetic anhydride (0.2 ml) and pyridine (1 ml) is stirred for 16 hours at room temperature under nitrogen. The resulting mixture is treated with ether (50 ml) and water (10 ml). The organic layer is washed with aqueous cupric sulfate solution (2×50 ml) and dried. The solvent is removed in vacuo to give 2S-3-acetoxy-2-methyl-6-carboxymethyl-2-(4,8-dimethyl-5-oxo-7-nonenyl)-3,6-oxidooxepane.

EXAMPLE 225

2S,3R,6R-2-Methyl-6-carboxymethyl-2-(5-hydroxy-4,5,8-trimethyl-7-nonenyl)-3,6-oxidooxepane To a stirred suspension of pre-reduced platinum oxide (0.50 g) in water (50 ml) is added sodium bicarbonate (0.95 g) and 2S,3R-6-(2-hydroxyethylidene)-2-methyl-2-(5-hydroxy-4,5,8-trimethyl-7-nonenyl)-oxepan-3-ol (0.40 g) in acetone (20 ml) and water (30 ml). The mixture is stirred at room temperature under an oxygen atmosphere for 22 hours. The platinum metal is removed by filtration through a pad of celite. The filtrate is evaporated to dryness in vacuo. The residue is dissolved in water (200 ml) and extracted with ethyl acetate (2×200 ml). The aqueous layer is acidified to pH 3 with dilute aqueous hydrochloric acid and quickly extracted with ethyl acetate (2×200 ml). The organic layer is washed with brine, dried (Na₂SO₄) and evaporated to give an oily residue which is purified on preparative tlc plates (1:9, isopropanol:chloroform) to afford 2S,3R,6R-2-methyl-6-carboxymethyl-2-(5-hydroxy-4,5,8-trimethyl-7-nonenyl)-3,6-oxidooxepane (0.236 g):

IR (neat) μ: 2.90 (OH), 5.80 (C=O); NMR (CDCl₃—TMS) δ: 1.63 and 1.73 [both s, 3H each, (CH₃)₂—C=CH—], 2.60 (s, 2H, CH₂—COOH), 3.36 and 3.73 (each d, J=11 Hz, each 1H, 7—CH₂).

EXAMPLE 226

2S,3R,6R-2-Methyl-6-carboxymethyl-2-[5-oxo-4,7,8-trimethyl-6E-nonenyl]-3,6-oxidooxepane Following the procedure of Example 225 but substituting an equivalent amount of 2S,3R-6-(2-hydroxyethylidene)-2-methyl-2-[5-oxo-4,7,8-trimethyl-6E-nonenyl]-oxepan-3-ol for 2S,3R-6-(2-hydroxyethylidene)-2-methyl-2-(5-hydroxy-4,5,8-trimethyl-7-nonenyl-oxepan-3-ol), 2S,3R,6R-2-methyl-6-carboxymethyl-2-[5-oxo-4,7,8-trimethyl-6E-nonenyl]-3,6-oxidooxepane (64% yield) is obtained.

IR (neat) μ: 5.81 (COOH), 5.90 (C=O), 6.15 (C=C); NMR (CDCl₃—TMS) δ: 1.30 (s, 3H, 2—CH₃), 2.07 (s, 3H, CH₃C=C), 2.60 (s, 2H, CH₃—COOH), 3.35 and 3.75 (each d, J=12 Hz, each 1H, 7—CH₂).

EXAMPLE 227

2S,3R,6R-6-(2-Hydroxyethyl)-2-methyl-2-(4,8-dimethyl-5-hydroxynonyl)-3,6-oxidooxepane A solution of 2S,3R,6R-6-(2-hydroxyethyl)-2-methyl-2-(4,8-dimethyl-5-hydroxy-7-nonenyl)-3,6-oxidooxepane (234 mg) in ethyl acetate (150 ml) is hydrogenated in the presence of 5% palladium-carbon (200 mg) at atmospheric pressure for 2 hours. The mixture is filtered through a pad of celite and the solvent evaporated in vacuo to give an oily residue. This crude product is purified on preparative tlc plates to afford 2S,3R,6R-6-(2-hydroxyethyl-2-methyl-3-(4,8-dimethyl-5-hydroxynonyl)-3,6-oxidooxepane (0.105 g), m.p.=88°-90°:

IR (neat) μ: 2.90 (OH); NMR (CDCl₃—TMS) δ: 0.88 [d, J=6 Hz, 9H, (CH₃)₂—CH and CH₃—CH], 1.30 (s, 3H, CH₃)₂—C—), 3.19 and 3.78 (each d, J=11 Hz, each 1H, CH₂—O).

EXAMPLE 228

2S,3R,6R-6-(2-Oxoethyl)-2-methyl-2-(4,8-dimethyl-5-hydroxynonyl)-3,6-oxidooxepane Following the procedure of Example 227 but substituting an equivalent amount of 2S,3R,6R-6-(2-oxoethyl)-2-methyl-2-(4,8-dimethyl-5-hydroxy-7-nonenyl)-3,6-oxidooxepane for 2S,3R, 6R-6-(2-hydroxyethyl)-2-methyl-2-(4,8-dimethyl-5-hydroxy-7-nonenyl)-3,6-oxidooxepane, 2S,3R,6R-6-(2-oxoethyl)-2-methyl-2-(4,8-dimethyl-5-hydroxynonyl)-3,6-oxidooxepane (54% yield) is obtained.

IR (neat) μ: 2.86 (OH), 3.64 (CHO) and 5.80 (C=O); NMR (CDCl₃—TMS) δ: 0.90 [d, J=6 Hz, 9H, (CH₃)₃—CH and CH₃—CH], 1.33 (s, 3H, CH₃—C—), 2.60 (d, J=2 Hz, 2H, CH₂—CHO), 3.29 and 3.74 (each d, J=11 Hz, each 1H, O—CH₂—), 9.78 (t, J=2 Hz, 1H, CHO).

EXAMPLE 229

2S,3R,6R-2-Methyl-6-carboxymethyl-2-(4,8-dimethyl-5-hydroxynonyl)-3,6-oxidooxepane Following the procedure of Example 227 but substituting an equivalent amount of 2S,3R,6R-2-methyl-6-carboxymethyl-2-(4,8-dimethyl-5-hydroxy-7-nonenyl)-3,6-oxidooxepane for 2S,3R,6R-6-(2-hydroxyethyl)-2-methyl-2-(4,8-dimethyl-5-hydroxy-7-nonenyl)-3,6-oxidooxepane, 2S,3R,6R-2-methyl-6-carboxymethyl-2-(4,8-dimethyl-5-hydroxynonyl)-3,6-oxidooxepane (35% yield) is obtained, mp 93°-94°:

IR (neat) μ: 2.90 (OH), 5.80 (COOH); NMR (CDCl₃—TMS) δ: 0.88 [d, J=6 Hz, 9H, (CH₃)₂CH and CH₃—CH], 1.33 (s, 3H, CH₃—C—), 2.60 (s, 2H, CH₂—COOH), 3.39 and 3.78 (both d, J=11 Hz, each 1H, O—CH₂—).

EXAMPLE 230

2S,3R,6R-6-(2-Hydroxyethyl)-2-methyl-2-(4,8-dimethyl-5-oxononyl)-3,6-oxidooxepane A suspension of sodium borohydride (125 mg) in benzene (25 ml) is treated with acetic acid (165 mg) and refluxed for 1 hour under nitrogen. To this reagent is added 2S,3R,6R-6-(2-oxoethyl)-2-methyl-2-(4,8-dimethyl-5-oxononyl)-3,6-oxidooxepane (286 mg) in benzene (10 ml). The resulting mixture is refluxed for 5 hours under nitrogen. The resulting mixture is treated with water (30 ml) and extracted with methylene chloride (2×150 ml). The organic layer is dried and the solvent removed in vacuo to give a yellow oil which is purified on preparative tlc plates (2:5, ethyl acetate:chloroform) to give 2S,3R,6R-(2-hydroxyethyl)-2-methyl-2-(4,8-dimethyl-5-oxononyl)-3,6-oxidooxepane(0.197 g):

IR (neat) μ: 2.86 (OH) and 5.85 (C=O); NMR (CDCl₃—TMS) δ: 0.88 ]d, J=6 Hz, 6H, (CH₃)₂—CH], 1.06 (d, J=7 Hz, 3H, CH₃—CH), 1.30 (s, 3H, CH₃—C), 3.19 and 3.78 (each d, J=11 Hz, each 1H, O—CH₂—).

EXAMPLE 231

2S,3R-3-Acetoxy-6-(2-hydroxyethylidene)-2-methyl-2(4,8-dimethyl-5-hydroxy-7-nonenyl)-oxepane A solution of 2S,3R-3-acetoxy-6-(2-acetoxyethylidene)-2-methyl-2-(4,8-dimethyl-5-hydroxy-7-nonenyl)-oxepane (940 mg) in methanol (36 ml) is treated at 0° with potassium carbonate (489 mg) in water (25 ml) for 5 hours under nitrogen. The mixture is treated with water (500 ml) and extracted with ether (2×500 ml). The organic layer is dried and the solvent removed in vacuo to give an oily residue which is purified on preparative tlc plates to give 2S,3R-3-acetoxy-6-(2-hydroxyethylidene)-2-methyl-2-(4,8-dimethyl-5-hydroxy-7-nonenyl)-oxepane (0.552 g).

EXAMPLE 232

2S,3R-3-Acetoxy-6-(2-oxoethylidene)-2-methyl-2-(4,8-dimethyl-5-hydroxy-7-nonenyl)-oxepane A mixture of 2S,3R-3-acetoxy-6-(2-hydroxyethylidene)-2-methyl-2-(4,8-dimethyl-5-hydroxy-7-nonenyl)-oxepane (553 mg), manganese dioxide (1 g) and methylene chloride (100 ml) is stirred for 89 hours under nitrogen. The manganese dioxide is filtered, washed with methylene chloride and the solvent removed in vacuo to give an oil which is purified on preparative tlc plates (3:2, ethyl acetate:hexane) to give 2S,3R-3-acetoxy-6-(2-oxoethylidene)-2-methyl-2-(4,8-dimethyl-5-hydroxy-7-nonenyl)-oxepane (0.296 g).

EXAMPLE 233

2S,3R-3-Acetoxy-2-methyl-6-carbmethoxymethylene-2-(4,8-dimethyl-5-hydroxy-7-nonenyl)-oxepane A mixture of 2S,3R-3-acetoxy-6-(2-oxoethylidene)-2-methyl-2-(4,8-dimethyl-5-hydroxy-7-nonenyl)-oxepane (396 mg), sodium cyanide (229.3 mg), acetic acid (100 ml) is stirred at room temperature for 19 hours under nitrogen. The manganese dioxide is filtered, washed with methylene chloride and the solvent removed in vacuo to give an oily residue. This crude product is diluted with water (400 ml) and extracted with ether (2×500 ml). The organic layer is dried and the solvent removed in vacuo to give an oil which is purified on preparative tlc plates (3:2, ethyl acetate:hexane) to give 2S,3R-3-acetoxy-2-methyl-6-carbmethoxymethylene-2-(4,8-dimethyl-5-hydroxy-7-nonenyl)-oxepane (0.145 g):

IR (neat) $\mu$: 2.92 (OH), 5.78 (COOCH$_3$) and 5.80 (OCOCH$_3$); NMR (CDCl$_3$—TMS) $\delta$: 0.90 (d, J=6Hz, 3H, C$\underline{H}_3$—CH), 1.15 (s, 3H, C$\underline{H}_3$—C—), 1.63 and 1.73 [both s, 3H each (C$\underline{H}_3$)$_2$—C=C], 2.03 (s, 3H, OCOC$\underline{H}_3$), 3.68 (s, 3H, COOC$\underline{H}_3$), 5.65 (bs, 1H, =C$\underline{H}$COOCH$_3$).

PREPARATION OF STARTING MATERIAL (CRUDE EXTRACT)

Ten kg. of dried or fresh leaves from the zoapatle plant and 30 gallons of water are added to a 100 gallon steam-jacketed stainless steel tank. The mixture is heated at 98°–100° C. for 2.5 hours with periodic stirring. The hot mixture is filtered through gauze to afford a clear dark tea, about 25 gallons in volume. The solid residue in the tank is washed with 4 gallons of hot water, filtered, and the filtrate combined with the tea obtained above. The combined aqueous extracts are extracted with 30 gallons of ethyl acetate. The mixture is stirred vigorously and allowed to settle. The top frothy layer is siphoned off to break the emulsion, and as much ethyl acetate separated as possible. Another 20 gallons of ethyl acetate are added to the mixture and the above process repeated. The combined ethyl acetate extracts are evaporated at 50° C. under vacuum. The residue is extracted with three portions of hot (75°–80°) benzene (10 liters total). The benzene extracts are evaporated at 50° C. under vacuum and the residue is washed three times with a total of 8 liters of refluxing hexane. The hexane-washed residue is dissolved in 2 liters of acetone, 10 g. of Nuchar is added, and the mixture is stirred 1 hour at room temperature. The charcoal is removed by filtration, and the filtrate evaporated by distillation at 30° C. under vacuum to afford 69 g. of crude extract. This crude extract is used as the starting material in Examples 1 and 25.

The following general procedure is a standard procedure employed to detect uterine contractions in female animals.

PROCEDURE I

Mature female New Zealand rabbits are anesthetized with sodium pentobarbital and ovariectomized. Following a recovery period of one week, the rabbits are treated with 5 $\mu$g./day s.c. of 17$\beta$-estradiol for 6 consecutive days, followed by treatment with 1.0 mg./day s.c. of progesterone for 7 consecutive days. The uterus and oviducts of the rabbits are perfused 72 hours after the last dose of progesterone according to the method of Heilman et al., (Fertil. Steril. 23:221-229) with slight modifications. The oviduct and uterus are perfused at a rate of 53 $\mu$l./min. The uterus is perfused with a tube extending 1.0 cm. into the lumen of the uterus from the oviducal end. The uterus is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

The following general procedure is a standard procedure employed to detect interruption of pregnancy after implantation has occurred.

PROCEDURE II

Mature, Hartley strain, female guinea pigs are continuously cohabited (monogamously) with males until a vaginal plug (copulation plug) is found in the cage. This time is considered to be day 1 of gestation. Groups of 5–6 females are given test materials intraperitoneally in a vehicle comprised of an emulsion of sesame oil and water on day 22 of gestation. The pigs are sacrificed between the 25th and 45th day of gestation and examined for evidence of resorption or abortion.

What is claimed is:

1. A compound selected from the group consisting of:

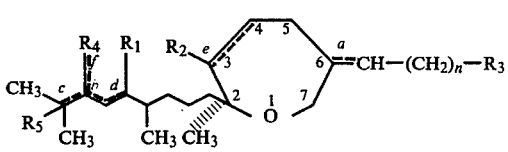

wherein R$_1$ and R$_2$ are each —XY wherein X is hydrogen or hydroxy provided that when X is hydrogen, Y is hydrogen; methyl; hydroxy; lower alkoxy; cycloalkoxy; phenoxy; substituted phenoxy wherein the substituent is nitro, halo or lower alkyl having 1–5 carbon atoms; trialkylsilyloxy; —OCOR' wherein R' is lower alkyl, cycloalkyl, phenyl, and substituted phenyl wherein the substituent is nitro, halo or lower alkyl having 1–5 carbon atoms; a sulfate, nitrate or phosphate radical; thiol; alkylthio; phenylthio and substituted phenylthio wherein the substituent is nitro, halo or lower alkyl having 1–5 carbon atoms; halo; amino; alkylamino; dialkylamino; phenylamino and substituted phenylamino wherein the substituent is nitro, halo or lower alkyl having 1-5 carbon atoms; and the quaternary ammonium and acid addition salts thereof; acylamino wherein the acyl group is derived from a lower alkanoic acid having 1-8 carbon atoms or from benzoic acid or substituted benzoic acid wherein the substituent is nitro, halo or lower alkyl having 1-5 carbon atoms; —OCONHR wherein R is hydrogen or lower alkyl; and when X is hydroxy, Y is cyano; lower alkyl; lower alkenyl; lower alkynyl; propadienyl; benzyl, substituted benzyl wherein the substituent is nitro, halo or lower alkyl having 1-5 carbon atoms; phenyl; substituted phenyl wherein the substituent is nitro, halo or lower alkyl having 1-5 carbon atoms; provided that when d or e is unsaturated $R_1$ and $R_2$ are either X or Y; and $R_1$ and/or $R_2$ are oxo; thioxo; hydroxyimino; alkoxyimino; phenyloxyimino and substituted phenyloxyimino wherein the substituent is nitro, halo or lower alkyl having 1-5 carbon atoms; acyloxyimino wherein the acyl group is derived from a lower alkanoic acid having 1-8 carbon atoms or from benzoic acid or substituted benzoic acid wherein the substituent is nitro, halo, or lower alkyl having 1-5 carbon atoms; hydrazono; alkylhydrazono; phenylhydrazono or substituted phenylhydrazono wherein the substituent is halo, nitro or lower alkyl having 1-5 carbon atoms; phenylsulfonylhydrazono or substituted phenylsulfonylhydrazono wherein the substituent is halo, nitro, or lower alkyl having 1-5 carbon atoms; carbamoylhydrazono; ethylenedioxy; ethylenedithio; ethylenethiooxy; dialkoxy; thiazolidinyl; methylenyl; alkylidenyl; alkylimino; or phenylamino and substituted phenylamino wherein the substituent is halo, nitro, or lower alkyl having 1-5 carbon atoms;

$R_3$ is —CHXY wherein X is hydrogen or hydroxy provided that when X is hydrogen, Y is hydrogen, methyl, hydroxy; lower alkoxy; cycloalkoxy; phenoxy; substituted phenoxy wherein the substituent is halo, nitro or lower alkyl having 1-5 carbon atoms; trialkylsilyloxy; heterocycloalkyloxy wherein the hetero atom is nitrogen, oxygen or sulfur and the cycloalkyl group contains 4-5 carbon atoms; —OCOR' wherein R' is lower alkyl, cycloalkyl, phenyl, or substituted phenyl wherein the substituent is halo, nitro or lower alkyl having 1-5 carbon atoms; a sulfate, nitrate or phosphate radical; thiol; lower alkylthio; phenylthio or substituted phenylthio wherein the substituent is halo, nitro or lower alkyl having 1-5 carbon atoms; halo; amino; lower alkylamino; lower dialkylamino; phenylamino or substituted phenylamino wherein the substituent is halo, nitro or lower alkyl having 1-5 carbon atoms; and the quaternary ammonium and acid addition salts thereof, acylamino wherein the acyl group is derived from a lower alkanoic acid having 1-8 carbon atoms or from benzoic acid or substituted benzoic acid wherein the substituent is nitro, halo or lower alkyl having 1-5 carbon atoms; —OCONHR wherein R is hydrogen or lower alkyl; and when X is hydroxy, Y is cyano; lower alkyl; lower alkenyl; lower alkynyl; propadienyl; benzyl, substituted benzyl wherein the substituent is halo, nitro or lower alkyl having 1-5 carbon atoms; phenyl; substituted phenyl wherein the substituent is halo, nitro or lower alkyl having 1-5 carbon atoms; and $R_3$ is —CHZ wherein Z is oxo, thioxo; hydroxyimino; lower alkoxyimino; phenyloxyimino or substituted phenyloxyimino wherein the substituent is halo, nitro or lower alkyl having 1-5 carbon atoms; acyloxyimino wherein the acyl group is derived from a lower alkanoic acid having 1-8 carbon atoms and benzoic acid or substituted benzoic acid wherein the substituent is nitro, halo or lower alkyl having 1-5 carbon atoms; hydrazono; lower alkylhydrazono; lower dialkylhydrazono; phenylhydrazono or substituted phenylhydrazono wherein the substituent is nitro, halo or lower alkyl having 1-5 carbon atoms; phenylsulfonylhydrazono or substituted phenylsulfonylhydrazono wherein the substituent is nitro, halo or lower alkyl having 1-5 carbon atoms; carbamoylhydrazono; ethylenedioxy; ethylenedithio; ethylenethiooxy; lower dialkoxy; thiazolidinyl; methylenyl; lower alkylidenyl; lower alkylimino; or phenylimino or substituted phenylimino wherein the substituent is halo, nitro or lower alkyl having 1-5 carbon atoms; and $R_3$ is carboxy; —COOR' wherein R' is lower alkyl, cycloalkyl, phenyl or substituted phenyl wherein the substituent is nitro, halo or lower alkyl having 1-5 carbon atoms; —COR" wherein R" is amino, lower alkylamino, lower dialkylamino, phenylamino or substituted phenylamino wherein the substituent is halo, nitro or lower alkyl having 1-5 carbon atoms; halo; hydrazino, lower alkylhydrazino, lower dialkylhydrazino, phenylhydrazino and substituted phenylhydrazino wherein the substituent is halo, nitro or lower alkyl having 1-5 carbon atoms; phenylsulfonylhydrazino and substituted phenylsulfonylhydrazino wherein the substituent is halo, nitro or lower alkyl having 1-5 carbon atoms; cyano; and ammonium, alkali metal and alkaline earth metal salts thereof where $R_3$ is carboxy;

$R_4$ is hydrogen; methyl or methylenyl;

$R_5$ is hydrogen; hydroxy; hydroperoxy or —OCOR'''' wherein R''' is lower alkyl;

and n is an integer from 0-5, provided that $C_3$ does not have the R configuration and the orientation at the a double bond does not have the E configuration when n=0, a and c are unsaturated, b, d, e and f are saturated, $R_1$ is oxo, $R_2$ is —XY wherein X and Y are hydrogen and hydroxy, $R_3$ is —CH$_2$OH and $R_4$ is hydrogen and when n=0, a and b are unsaturated, c, d, e and f are saturated, $R_1$ is oxo, $R_2$ is —XY wherein X and Y are hydrogen and hydroxy, $R_3$ is —CH$_2$OH, $R_4$ is methyl and $R_5$ is hydrogen.

2. A compound of claim 1 wherein double bonds are present at a and c.

3. A compound of claim 1 which compound is 2S,3R-3-acetoxy-6-(2-acetoxyethylidene)-2-methyl-2-(4,8-dimethyl-5-oxo-7-nonenyl)-oxepane.

4. A compond of claim 1 which compound is 2S,3R-6-(2-acetoxyethylidene)-2-methyl-2-(4,8-dimethyl-5-oxo-7-nonenyl)-oxepan-3-ol.

5. A compound of claim 1 which compound is 2S,3R-3-acetoxy-6-(2-hydroxyethylidene)-2-methyl-2-(4,8-dimethyl-5-oxo-7-nonenyl)-oxepane.

6. A compound of claim 1 which compound is 2S,3R-3-acetoxy-6-(2-oxoethylidene)-2-methyl-2-(4,8-dimethyl-5-oxo-7-nonenyl)-oxepane.

7. A compound of claim 1 which compound is 2S,3R-6-(2-hydroxyethylidene)-2-methyl-2-(4,8-dimethyl-5-hydroxy-7-nonenyl)-oxepan-3-ol.

8. A compound of claim 1 which compound is 2S,3R-3-acetoxy-6-(2-acetoxyethylidene)-2-methyl-2-(4,8-dimethyl-5-hydroxy-7-nonenyl)-oxepane.

9. A compound of claim 1 which compound is 2S,3R-6-(2-hydroxyethyl)-2-methyl-2-(4,8-dimethyl-5-oxo-7-nonyl)-oxepan-3-ol.

10. A compound of claim 1 which compound is 2S,3R-6-(2-hydroxyethylidene)-2-methyl-2-(5-hydroxy-4,5,8-trimethyl-7-nonenyl)-oxepan-3-ol.

11. A compound of claim 1 which compound is 2S,3R-6-(2-hydroxyethylidene)-2-methyl-2-(4,8-dimethyl-5-ethynyl-5-hydroxy-7-nonenyl)-oxepan-3-ol.

12. A compound of claim 1 which compound is 2S,3R-6-(2-hydroxyethylidene)-2-methyl-2-(4,8-dimethyl-8-hydroperoxy-5-oxo-6-nonenyl)-oxepan-3-ol.

13. A compound of claim 1 which compound is 2S,3R-6-(2-hydroxyethylidene)-2-methyl-2-(4,8-dimethyl-8-hydroxy-5-oxo-6-nonenyl)-oxepan-3-ol.

14. A compound of claim 1 which compound is 2S,3R-3-acetoxy-6-(2-acetoxyethylidene)-2-methyl-2-(5-acetoxy-4,8-dimethyl-7-nonenyl)-oxepane.

15. A compound of claim 1 which compound is 2S,3R-3-acetoxy-2-methyl-6-carbmethoxymethylene-2-(4,8-dimethyl-5-hydroxy-7-nonenyl)-oxepane.

16. A compound of claim 1 which compound is 2S,3R-3-acetoxy-6-(2-oxoethylidene)-2-methyl-2-(4,8-dimethyl-5-hydroxy-7-nonenyl)-oxepane.

17. A compound of claim 1 which compound is 2S-6-(2-acetoxyethylidene)-2-methyl-2-(4,8-dimethyl-5-oxo-7-nonenyl)-oxepan-3-one.

18. A method of interrupting preqnancy which comprises administering to female animals a compound of claim 1 in an amount sufficient to interrupt pregnancy.

19. A method of inducing uterine contractions which comprises administering to a female animal a compound of claim 1 in an amount sufficient to induce uterine contractions.

* * * * *